US009975963B2

(12) United States Patent
Lin et al.

(10) Patent No.: US 9,975,963 B2
(45) Date of Patent: May 22, 2018

(54) NSP4 INHIBITORS AND METHODS OF USE

(71) Applicant: Genentech, Inc., South San Francisco, CA (US)

(72) Inventors: Shuo-Yen Jack Lin, South San Francisco, CA (US); Daniel K. Kirchhofer, Los Altos, CA (US); Menno Van Lookeren Campagne, South San Francisco, CA (US)

(73) Assignee: Genentech, Inc., South San Franciso, CA (US)

( * ) Notice: Subject to any disclaimer, the term of this patent is extended or adjusted under 35 U.S.C. 154(b) by 0 days. days.

(21) Appl. No.: 15/094,843

(22) Filed: Apr. 8, 2016

(65) Prior Publication Data

US 2016/0215065 A1  Jul. 28, 2016

Related U.S. Application Data

(63) Continuation of application No. PCT/US2014/060182, filed on Oct. 10, 2014.

(60) Provisional application No. 62/053,052, filed on Sep. 19, 2014, provisional application No. 61/893,059, filed on Oct. 18, 2013, provisional application No. 61/890,147, filed on Oct. 11, 2013.

(51) Int. Cl.
*C07K 16/40* (2006.01)
*C07K 16/24* (2006.01)
*A61K 39/00* (2006.01)

(52) U.S. Cl.
CPC .............. *C07K 16/40* (2013.01); *C07K 16/24* (2013.01); *A61K 2039/505* (2013.01); *C07K 2317/14* (2013.01); *C07K 2317/24* (2013.01); *C07K 2317/33* (2013.01); *C07K 2317/54* (2013.01); *C07K 2317/55* (2013.01); *C07K 2317/622* (2013.01); *C07K 2317/76* (2013.01); *C07K 2317/92* (2013.01)

(58) Field of Classification Search
CPC .. C07K 16/40; C07K 16/24; C07K 2317/622; C07K 2317/14; C07K 2317/24; C07K 2317/54; C07K 2317/55; C07K 2317/33; C07K 2317/92; C07K 2317/76; A61K 2039/505
See application file for complete search history.

(56) References Cited

U.S. PATENT DOCUMENTS

| 4,469,863 | A | 9/1984 | Ts'o et al. |
|---|---|---|---|
| 4,676,980 | A | 6/1987 | Segal et al. |
| 4,737,456 | A | 4/1988 | Weng et al. |
| 4,816,567 | A | 3/1989 | Cabilly et al. |
| 5,500,362 | A | 3/1996 | Robinson et al. |
| 5,536,821 | A | 7/1996 | Agrawal et al. |
| 5,541,306 | A | 7/1996 | Agrawal et al. |
| 5,571,894 | A | 11/1996 | Wels et al. |
| 5,587,458 | A | 12/1996 | King et al. |
| 5,591,828 | A | 1/1997 | Bosslet et al. |
| 5,614,622 | A | 3/1997 | Iyer et al. |
| 5,624,821 | A | 4/1997 | Winter et al. |
| 5,637,683 | A | 6/1997 | Usher et al. |
| 5,637,684 | A | 6/1997 | Cook et al. |
| 5,648,237 | A | 7/1997 | Carter |
| 5,648,260 | A | 7/1997 | Winter et al. |
| 5,700,922 | A | 12/1997 | Cook |
| 5,717,083 | A | 2/1998 | Cook et al. |
| 5,719,262 | A | 2/1998 | Buchardt et al. |
| 5,731,168 | A | 3/1998 | Carter et al. |
| 5,739,308 | A | 4/1998 | Kandimalla et al. |
| 5,739,314 | A | 4/1998 | Roy et al. |
| 5,750,373 | A | 5/1998 | Garrard et al. |
| 5,773,601 | A | 6/1998 | Agrawal |
| 5,789,199 | A | 8/1998 | Joly et al. |
| 5,821,337 | A | 10/1998 | Carter et al. |
| 5,840,523 | A | 11/1998 | Simmons et al. |
| 5,869,046 | A | 2/1999 | Presta et al. |
| 5,886,165 | A | 3/1999 | Kandimalla et al. |
| 5,929,226 | A | 7/1999 | Padmapriya et al. |
| 5,955,599 | A | 9/1999 | Iyer et al. |
| 5,959,177 | A | 9/1999 | Hein et al. |
| 5,962,674 | A | 10/1999 | Iyer et al. |
| 5,977,296 | A | 11/1999 | Nielsen et al. |
| 6,040,498 | A | 3/2000 | Stomp et al. |
| 6,075,181 | A | 6/2000 | Kucherlapati et al. |
| 6,117,992 | A | 9/2000 | Iyer |
| 6,140,482 | A | 10/2000 | Iyer et al. |
| 6,150,584 | A | 11/2000 | Kucherlapati et al. |
| 6,171,586 | B1 | 1/2001 | Lam et al. |
| 6,194,551 | B1 | 2/2001 | Idusogie et al. |
| 6,248,516 | B1 | 6/2001 | Winter et al. |

(Continued)

FOREIGN PATENT DOCUMENTS

| EP | 0 404 097 B1 | 9/1996 |
|---|---|---|
| WO | WO-93/01161 A1 | 1/1993 |

(Continued)

OTHER PUBLICATIONS

Vizzi et al., Evaluation of Serum Antibody Responses against the Rotavirus Nonstructural Protein NSP4 in Children after Rhesus Rotavirus Tetravalent Vaccination or Natural Infection. Clin Diagn Lab Immunol. 12(10):1157-1163, 2005.*

Hou et al., Anti-NSP4 Antibody Can Block Rotavirus-induced Diarrhea in Mice. J. Pediatr. Gastroenterol Nutr. 46(4):376-385, 2008.*

Adams et al. "Early Trauma Polymorphonuclear Neutrophil Responses to Chemokines are Associated with Development of Sepsis, Pneumonia, and Organ Failure," *J. Trauma-Injury Infect. Crit. Care* 51:452-456, (2001).

Adams et al. "PHENIX: a Comprehensive Python-Based System for Macromolecular Structure Solution," *Acta Crystallogr. D Biol. Crystallogr.* 66:213-221, (2010).

(Continued)

*Primary Examiner* — Ruixiang Li
(74) *Attorney, Agent, or Firm* — Morrison & Foerster LLP

(57) ABSTRACT

The invention provides NSP4 inhibitors (such as anti-NSP4 antibodies) and methods of using the same.

12 Claims, 38 Drawing Sheets

(56) References Cited

U.S. PATENT DOCUMENTS

| | | |
|---|---|---|
| 6,267,958 B1 | 7/2001 | Andya et al. |
| 6,417,429 B1 | 7/2002 | Hein et al. |
| 6,420,548 B1 | 7/2002 | Vezina et al. |
| 6,455,308 B1 | 9/2002 | Freier |
| 6,602,684 B1 | 8/2003 | Umaña et al. |
| 6,737,056 B1 | 5/2004 | Presta |
| 6,982,321 B2 | 1/2006 | Winter |
| 7,041,870 B2 | 5/2006 | Tomizuka et al. |
| 7,087,409 B2 | 8/2006 | Barbas et al. |
| 7,125,978 B1 | 10/2006 | Vezina et al. |
| 7,189,826 B2 | 3/2007 | Rodman |
| 7,332,581 B2 | 2/2008 | Presta |
| 7,521,541 B2 | 4/2009 | Eigenbrot et al. |
| 7,527,791 B2 | 5/2009 | Adams et al. |
| 2002/0164328 A1 | 11/2002 | Shinkawa et al. |
| 2003/0115614 A1 | 6/2003 | Kanda et al. |
| 2003/0157108 A1 | 8/2003 | Presta |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2005/0014934 A1 | 1/2005 | Hinton et al. |
| 2005/0079574 A1 | 4/2005 | Bond |
| 2005/0119455 A1 | 6/2005 | Fuh et al. |
| 2005/0123546 A1 | 6/2005 | Umaña et al. |
| 2005/0260186 A1 | 11/2005 | Bookbinder et al. |
| 2005/0266000 A1 | 12/2005 | Bond et al. |
| 2006/0025576 A1 | 2/2006 | Miller et al. |
| 2006/0104968 A1 | 5/2006 | Bookbinder et al. |
| 2007/0061900 A1 | 3/2007 | Hudson et al. |
| 2007/0117126 A1 | 5/2007 | Sidhu et al. |
| 2007/0160598 A1 | 7/2007 | Dennis et al. |
| 2007/0237764 A1 | 10/2007 | Birtalan et al. |
| 2007/0292936 A1 | 12/2007 | Barthelemy et al. |
| 2008/0069820 A1 | 3/2008 | Fuh et al. |
| 2009/0002360 A1 | 1/2009 | Chen et al. |
| 2014/0220676 A1 | 8/2014 | Kreuntzer et al. |

FOREIGN PATENT DOCUMENTS

| | | |
|---|---|---|
| WO | WO-93/08829 A1 | 5/1993 |
| WO | WO-93/16185 A2 | 8/1993 |
| WO | WO-93/16185 A3 | 8/1993 |
| WO | WO-94/29351 A2 | 12/1994 |
| WO | WO-94/29351 A3 | 12/1994 |
| WO | WO-1997/30087 A1 | 8/1997 |
| WO | WO-1998/58964 A1 | 12/1998 |
| WO | WO-1999/22764 A1 | 5/1999 |
| WO | WO-99/32619 A1 | 7/1999 |
| WO | WO-99/51642 A1 | 10/1999 |
| WO | WO-00/44895 A1 | 8/2000 |
| WO | WO-00/56746 A2 | 9/2000 |
| WO | WO-00/56746 A3 | 9/2000 |
| WO | WO-2000/61739 A1 | 10/2000 |
| WO | WO-00/75372 A1 | 12/2000 |
| WO | WO-01/14398 A1 | 3/2001 |
| WO | WO-01/29058 A1 | 4/2001 |
| WO | WO-2001/29246 A1 | 4/2001 |
| WO | WO-01/36646 A1 | 5/2001 |
| WO | WO-02/031140 A1 | 4/2002 |
| WO | WO-2003/011878 A2 | 2/2003 |
| WO | WO-2003/011878 A3 | 2/2003 |
| WO | WO-03/084570 A1 | 10/2003 |
| WO | WO-03/085107 A1 | 10/2003 |
| WO | WO-03/085119 A1 | 10/2003 |
| WO | WO-2004/056312 A2 | 7/2004 |
| WO | WO-2004/056312 A3 | 7/2004 |
| WO | WO-2005/035586 A1 | 4/2005 |
| WO | WO-2005/035778 A1 | 4/2005 |
| WO | WO-2005/053742 A1 | 6/2005 |
| WO | WO-2005/100402 A1 | 10/2005 |
| WO | WO-2006/029879 A2 | 3/2006 |
| WO | WO-2006/029879 A3 | 3/2006 |
| WO | WO-2006/044908 A2 | 4/2006 |
| WO | WO-2006/044908 A3 | 4/2006 |
| WO | WO-2008/077546 A1 | 7/2008 |
| WO | WO-2009/089004 A1 | 7/2009 |

OTHER PUBLICATIONS

Adkison et al."Dipeptidyl Peptidase I Activates Neutrophil-Derived Serine Proteases and Regulates the Development of Acute Experimental Arthritis," *J. Clin. Invest.* 109:363-371, (2002).

Almagro and Fransson. "Humanization of Antibodies," *Front. Biosci.* 13: 1619-1633, (2008).

Asami et al. "Trypsin Resistance of a Decapeptide KISS1R Agonist Containing an Nω-Methylarginine Substitution," *Bioorg Med Chem Lett.* 22:6328-6332, (2012).

Baca et al. "Antibody Humanization Using Monovalent Phage Display," *J. Biol. Chem.* 272:10678-10684, (1997).

Baldwin et al. "Specific Enzymic Methylation of an Arginine in the Experimental Allergic Encephalomyelitis Protein From Human Myelin," *Science* 171:579-581, (1971).

Belaaouaj et al. "Mice Lacking Neutrophil Elastase Reveal Impaired Host Defense Against Gram Negative Bacterial Sepsis," *Nat Med*, 4:615-618, (1998).

Binstadt et al. "Particularities of the Vasculature can Promote the Organ Specificity of Autoimmune Attack," *Nat Immunol.* 7:284-292, (2006).

Boerner et al., "Production of Antigen-Specific Human Monoclonal Antibodies From In Vitro-Primed Human Splenocytes," *J. Immunol.*, 147: 86-93, (Jul. 6, 1991).

Brennan et al. "Preparation of Bispecific Antibodies by Chemical Recombination of Monoclonal Immunoglobulin $G_1$ Fragments," *Science* 229:81-83, (Jul. 5, 1985).

Brodeur et al. "Mouse-Human Myeloma Partners for the Production of Heterohybridomas," Chapter 4 in *Monoclonal Antibody Production Techniques and Applications*, Marcel Dekker, Inc., New York, New York, pp. 51-63, (1987).

Bruggemann et al. "Comparison of the Effector Functions of Human Immunoglobulins Using a Matched Set of Chimeric Antibodies," *J. Exp. Med.* 166:1351-1361, (1987).

Carter et al. "Humanization of an Anti-p185$^{HER2}$ Antibody for Human Cancer Therapy," *Proc. Natl. Acad. Sci. USA* 89:4285-4289, (May 1992).

Charlton. "Expression and Isolation of Recombinant Antibody Fragments in *E. coli*" Chapter 14 in *Methods in Molecular Biology*, B.K.C. Lo, ed., Humana Press, Totowa, NJ, vol. 248, pp. 245-254, (2003).

Chen et al. "Selection and Analysis of an Optimized Anti-VEGF Antibody: Crystal Structure of an Affinity-matured Fab in Complex with Antigen," *J. Mal. Biol.* 293:865-881,(1999).

Chothia and Lesk. "Canonical Structures for the Hypervariable Regions of Immunoglobulins," *J. Mol. Biol.* 196:901-917, (1987).

Chowdhury. "Engineering Hot Spots for Affinity Enhancement of Antibodies," *Methods Mal. Biol.* 207:179-196, (2008).

Clackson et al. "Making Antibody Fragments Using Phage Display Libraries," Nature 352:624-628, (1991).

Clark et al. "The Secreted Protein Discovery Initiative (SPDI), a Large-Scale Effort to Identify Novel Human Secreted and Transmembrane Proteins: a Bioinformatics Assessment," *Genome Res*.13:2265-2270, (2003).

Clynes et al. "Fc Receptors are Required in Passive and Active Immunity to Melanoma," *Proc. Natl. Acad. Sci. USA* 95:652-656, (1998.).

Cragg et al. "Complement-Mediated Lysis by Anti-CD20 mAb Correlates with Segregation Into Lipid Rafts," *Blood* 101:1045-1052 ,(2003.).

Cragg, et al. "Antibody Specificity Controls In Vivo Effector Mechanisms of Anti-CD20 Reagents," *Blood* 103:2738-2743, (2004).

Cunningham and Wells. "High-Resolution Epitope Mapping of hGH-Receptor Interactions by Alanine-Scanning Mutagenesis," *Science* 244:1081-1085, (1989).

Dall' Acqua et al. "Antibody Humanization by Framework Shuffling," *Methods* 36:43-60, (2005).

(56) References Cited

OTHER PUBLICATIONS

Debela et al."Structural Basis of the Zinc Inhibition of Human Tissue Kallikrein 5," *J Mol Biol.* 373:1017-1031, (2007).
Duncan and Winter. "The Binding Site for Clq on IgG," *Nature* 322:738-40, (1988).
Dyer et al. "Functionailly Competent Eosinophils Differentiated Ex Vivo in High Purity from Normal Mouse Bone Marrow," *J Immunol.* 181 (6):4004-4009, (2008).
Eigenbrot et al."Structural and Functional Analysis of HtrA1 and its Subdomains," *Structure* 20:1040-1050, (2012).
Fellouse. "Synthetic Antibodies From a Four-Amino-Acid Code: A Dominant Role for Tyrosine in Antigen Recognition," *Proc. Natl. Acad. Sci. USA* 101(34):12467-12472, (2004).
Ferrara et al. "Modulation of Therapeutic Antibody Effector Functions by Glycosylation Engineering: Influence of Golgi Enzyme Localization Domain and Co-Expression of Heterologous 131, 4-N-acetylglucosaminyltransferase III and Golgi a-mannosidase II," *Biotechnology and Bioengineering*, 93(5):851-861, (2006).
Flatman et al. "Process Analytics for Purification of Monoclonal Antibodies," *J. Chromatogr. B* 848:79-87, (2007).
Fujinaga et al. "The Crystal Structure of PR3, a Neutrophil Serine Proteinase Antigen of Wegener's Granulomatosis Antibodies," *J Mol. Biol.* 261:267-278, (1996).
Gallop et al. "Applications of Combinatorial Technologies to Drug Discovery. 1. Background and Peptide Combinatorial Libraries," *Journal of Medicinal Chemistry* 37(9):1233-1251 (Apr. 29, 1994).
Ganesan et al. "Unraveling the Allosteric Mechanism of Serine Protease Inhibition by an Antibody," *Structure* 17:1614-1624, (2009).
Gazzano-Santoro et al. "A non-radioactive complement-dependent cytotoxicity assay for anti-CD20 monoclonal antibody," *J. Immunol. Methods* 202: 163-171, (1996).
Gerngross. "Advances in the Production of Human Therapeutic Proteins in Yeasts and filamentous fungi," *Nat. Biotech.* 22: 1409-1414, (2004).
Gouy et al. "SeaView Version 4: A Multiplatform Graphical User Interface for Sequence Alignment and Phylogenetic Tree Building," *Mol Biol Evol.* 27:221-224, (2010).
Graham et al. "Characteristics of a Human Cell Line Transformed by DNA from Human Adenovirus Type 5," *J. Gen Viral.* 36:59-74, (1977).
Griffiths et al. "Human Anti-Self Antibodies with High Specificity From Phage Display Libraries," *EMBO J.* 12:725-734, (1993).
Gross et al. "Bioluminescence Imaging of Myeloperoxidase Activity in vivo," *Nat. Med.* 15::455-461, (2009).
Gruber et al. "Efficient Tumor Cell Lysis Mediated by a Bispecific Single Chain Antibody Expressed in *Escherichia coli,*" *J. Immunol.*, 152:5368-5374, (1994).
Guyer et al. "Immunoglobulin Binding by Mouse Intestinal Epithelial Cell Receptors," *J. Immunol.* 117(2):587-593, (1976).
Hedstrom et al. "Serine Protease Mechanism and Specificity," *Chem Rev.* 102:4501-4524, (2002).
Hellstrom et al. "Antitumor Effects of L6, an IgG2a Antibody That Reacts with Most Human Carcinomas," *Proc. Nat'lAcad. Sci. USA* 83:7059-7063, (1986).
Hellstrom et al. "Strong Antitumor Activities of IgG3 Antibodies to a Human Melanoma-Associated Ganglioside," *Proc. Nat'lAcad. Sci. USA* 82:1499-1502, (Mar. 1985).
Henrich et al. "The Crystal Structure of the Proprotein Processing Proteinase Furin Explains its Stringent Specificity," *Nat Struct Biol.* 10:520-526, (2003).
Hinkofer et al. "A Monoclonal Antibody (MCPR3-7) Interfering with the Activity of Proteinase 3 by an Allosteric Mechanism," *J. Biol. Chem.* 288:26635-26648, (2013).
Hof et al. "The 1.8 A Crystal Structure of Human Cathepsin G in Complex with Suc-Val-Pro-PheP-(OPh)z: A Janus-Faced Proteinase with two Opposite Specificities," *EMBO J.* 15:5481-5491, (1996).
Holliger et al. "Diabodies: Small Bivalent and Bispecific Antibody Fragments," *Proc. Natl. Acad. Sci. USA* 90: 6444-6448, (1993).

Hoogenboom and Winter. "By-Passing Immunisation Human Antibodies from Synthetic Repertoires of Germline $V_H$ Gene Segments Rearranged in Vitro," *J. Mal. Biol.*, 227:381-388, (1992).
Hoogenboom et al. "Overview of Antibody Phage-Display Technology and Its Applications," Chapter 1 in *Methods in Molecular Biology*, O'Brien et al., ed., Human Press, Totowa, NJ, 178:1-37, (2001).
Hudson et al. "Engineered antibodies," *Nat. Med.* 9: 129-134, (2003).
Idusogie et al. "Mapping of the Clq Binding Site on Rituxan, a Chimeric Antibody with a Human IgGl Fe," *J. Immunol.* 164:4178-4184, (2000).
Kam et al. "Carbon Nanotubes as Multifunctional Biological Transporters and Near-Infrared Agents for Selective Cancer Cell Destruction," *Proc. Natl. Acad. Sci. USA* 102:11600-11605, (2005).
Kanda et al. "Comparison of Cell Lines for Stable Production of Fucose-Negative Antibodies With Enhanced ADCC," *Biotechnol. Bioeng.* 94(4):680-688, (2006).
Kashmiri et al. "SDR Grafting-a New Approach to Antibody Humanization," *Methods* 36:25-34, (2005).
Keegan et al. "Automated Search-Model Discovery and Preparation for Structure Solution by Molecular Replacement," *Acta Crystallogr D Biol Crystallogr.*63:447-457, (2007).
Kessenbrock et al. "Proteinase 3 and Neutrophil Elastase Enhance Inflammation in Mice by Inactivating Antiinflammatory Progranulin," *J Clin Invest.* 118:2438-2447, (2008).
Kim et al. "Localization of the Site of the Murine IgG1 Molecule that is Involved in Binding to the Murine Intestbtal Fe Receptor," *Eur. J. Immunol.* 24:2429-2434, (1994).
Kindt et al. "Antigens and Antibodies," Chapter 4 in Kuby Immunology, 6th ed., W.H. Freeman and Co., p. 91, (2007).
Klimka et al. "Human Anti-CD30 Recombinant Antibodies by Guided Phage Antibody Selection Using Cell Panning," *Br. J. Cancer*, 83:252-260, (2000).
Korkmaz et al. "Neutrophil Elastase, Proteinase 3, and Cathepsin G as Therapeutic Targets in Human Diseases," *Pharmacological Reviews American Society for Pharamacology and Experimental Therapeutics, US* 62(2):726-759, (Dec. 1, 2010).
Kostelny et al. "Formation of a Bispecific Antibody by the Use of Leucine Zippers," *J. Immunol.*, 148(5):1547-1553, (1992).
Kozbor et al. "A Human Hybrid Myeloma for Production of Human Monoclonal Antibodies," *J. Immunol.*, 133: 3001-3005, (1984).
Kuhl et al. "Mapping of Conformational Epitopes on Human Proteinase 3, the Autoantigen of Wegener's Granulomatosis," *J. Immunol.*, 185, 387-399, (2010).
Larkin et al. "Clustal W and Clustal X Version 2.0," *Bioinformatics* 23:2947-2948, (2007).
Lee et al. "High-Affinity Human Antibodies from Phage-Displayed Synthetic Fab Libraries with a Single Framework Scaffold," *J. Mol. Biol.* 340(5): 1073-1093, (2004).
Lee et al. "Bivalent Antibody Phage Display Mimics Natural Immunoglobulin," *J. Immunol. Methods* 284(1-2):119-132,(2004).
Lefrancais et al. "IL-33 is Processed Into Mature Bioactive Forms by Neutrophil Elastase and Cathepsin G," *Proc. Natl. Acad. Sci. USA* 109:1673-1678, (2012).
Li et al. "Human Antibodies for Immunotherapy Development Generated via a Human B Cell Hybridoma Technology," *Proc. Natl. Acad. Sci. USA*, 103:3557-3562, (2006).
Li et al. "Optimization of Humanized IgGs in Glycoengineered *Pichia pastoris,*" *Nat. Biotech.* 24:210-215, (2006).
Lindsey et al. "Matrix-Dependent Mechanism of Neutrophil-Mediated Release and Activation of Matrix Metalloproteinase 9 in Myocardial Ischemia/Reperfusion," *Circulation*103:2181-2187, (2001).
Lonberg. "Fully Human Antibodies From Transgenic Mouse and Phage Display Platforms," *Curr. Opin. Immunol.* 20:450-459, (2008).
Lonberg. "Human Antibodies from Transgenic Animals," *Nat. Biotech.* 23:1117-1125, (2005).
Lukacs et al. "The Role of Stem Cell Factor (c-kit Ligand) and Inflammatory Cytokines in Pulmonary Mast Cell Activation," *Blood* 87(6):2262-2268, (1996).

(56) References Cited

OTHER PUBLICATIONS

MacCallum et al. "Antibody-antigen Interactions: Contact Analysis and Binding Site Topography," *J. Mol. Biol.* 262:732-745, (1996).
Magrone et al. "Mechanisms of Neutrophil-mediated Disease: Innovative Therapeutic Interventions," *Curr Pharm Des*.18(12):1609-19, (2012).
Marks et al. "By-passing Immunization Human Antibodies from V~gene Libraries Displayed on Phage," *J. Mal. Biol.* 222: 581-597 (1991).
Marks and Bradbury. "Selection of Human Antibodies From Phage Display Libraries," Chapter 8 in *Antibody EngineeringMethods in Molecular Biolog*, Lo, ed., Human Press, Totowa, NJ, 248: 161-175, (2003).
Mather. "Establishment and Characterization of Two Distinct Mouse Testicular Epithelial Cell Lines," *Biol. Reprod.* 23:243-251, (1980).
Mather et al. "Culture of Testicular Cells in Hormone-Supplemented Serum-Free Medium," *Annals N.Y. Acad. Sci.* 383:44-68, (1982).
McCafferty et al. "Phage Antibodies: Filamentous Phage Displaying Antibody Variable Domains," *Nature* 348:552-554, (Dec. 6, 1990).
Milstein et al. "Hybrid Hybridomas and Their use in Immunohistochemistry," *Nature* 305: 537-540, (Oct. 6, 1983).
Morrison et al. "Chimeric Human Antibody Molecules: Mouse Antigen-Binding Domains With Human Constant Region Domains," *Proc. Natl. Acad. Sci. USA* 81:6851-6855, (Nov. 1984).
Navia et al. "Structure of Human Neutrophil Elastase in Complex With a Peptide Chloromethyl Ketone Inhibitor at 1.84—A Resolution," *Proc. Natl. Acad. Sci. USA* 86:7-11, (Jan. 1989).
Ni. "Research Progress and Future Perspectives in Anitobodomics and Antibodomic drugs," *Xiandai Mianyixue*, 26(4):265-268, (2006), (Translation of the Abstract).
Okazaki et al. "Fucose Depletion from Human IgG1 Oligosaccharide Enhances Binding Enthalpy and Association Rate Between IgG1 and FcγRIIIa," *J. Mol. Biol.* 336:1239-1249, (2004).
Okonechnikov et al. "Unipro UGENE: A Unified Bioinformatics Toolkit," *Bioinformatics* 28(8):1166-1167, (2012).
Osbourn et al."From Rodent Reagents to Human Therapeutics Using Antibody Guided Selection," *Methods* 36:61-68, (2005).
Otwinowski et al. "Processing of X-Ray Diffraction Data Collected in Oscillation Mode," *Methods in Enzymology* 276:307-326, (1997).
Padlan. "A Possible Procedure for Reducing the Immunogenicity of Antibody Variable Domains While Preserving Their Ligand-Binding Properties," *Mol.Immunol.* 28(4/5):489-498, (1991).
Perera et al. "NSP4, an elastase-related protease in human neutrophilis with arginine specificity," *Proc. Natl. Acad. Sci. USA* 109(16):6229-6234, (Apr. 17, 2012).
Perera et al. "Perspectives and Potential Roles for the Newly Discovered NSP4 in the Immune System," *Expert Rev. Clin. Immunol.* 8:501-503, (2012).
Perera et al. "NSP4 is Stored in Azurophil Granules and Released by Activated Neutrophils as Active Endoprotease with Restricted Specificity," *The Jounal of Immunology* 191(5):2700-2707, (Jul. 31, 2013).
Petkova et al. "Enhanced Half-Life of Genetically Engineered Human IgG1 Antibodies in a Humanized FcRn Mouse Model: Potential Application in Humorally Mediated Autoimmune Disease," *Int'l. Immunol.* 18(12):1759- 1769, (2006).
Pham. "Neutrophil Serine Proteases: Specific Regulators of Inflammation," *Nature Review Immunology* 6(7):541-550, (Jul. 2006).
Pham et al. "Neutrophil Serine Proteases Fine-Tune the Inflammatory Response," *Int. J Biochem Cell Biol.* 40(6-7):1317-1333, (2008).
Plückthun. "Antibodies From *Escherichia coli*," Chapter 11 in *The Pharmacology of Monoclonal Antibodies*, Rosenburg and Moore eds., Springer-Verlag, New York, vol. 113, pp. 269-315, (1994).
Portolano et al. "Lack of Promiscuity in Autoantigen-Specific H and L Chain Combinations as Revealed by Human H and L Chain Roulette," *J. Immunol.* 150:880-887, (Feb. 1, 1993).
Presta et al "Humanization of an Anti-Vascular Endothelial Growth Factor Monoclonal Antibody for the Therapy of Solid Tumors and Other Disorders," *Cancer Res.* 57:4593-4599, (Oct. 15, 1997).
Presta et al. "Humanization of an Antibody Directed Against IgE," *J. Immunol.*, 151(5):2623-2632, (Sep. 1, 1993).
Queen et al. "A Humanized Antibody that Binds to the Interleukin 2 Receptor," *Proc. Nat'l Acad. Sci. USA* 86:10029-10033, (Dec. 1989).
Ravetch and Kinet. "Fc Receptors,"*Annu. Rev. Immunol.* 9: 457-92, (1991).
Reeves et al. "Killing Activity of Neutrophils is Mediated Through Activation of Proteases byK$^+$ Flux," *Nature* 416:291-297, (2002).
Riechmann et al. "Reshaping Human Antibodies for Therapy," *Nature* 332:323-329, (Mar. 24, 1988).
Ripka et al. "Two Chinese Hamster Ovary Glycosylation Mutants Affected in the Conversion of GDP-Mannose to GDP-Fucose," *Arch. Biochem. Biophys.* 249:533-545, (1986).
Rosok et al. "A Combinatorial Library Strategy for the Rapid Humanization of Anticarcinoma BR96 Fab," *J. Biol. Chem.* 271:22611-22618, (1996).
Shields et al. "High Resolution Mapping of the Binding Site on Human IgGI for Fcγ RI, FcγRII, FeγRIII, and FcRn and Design of IgG1 Variants with Improved Binding to the FcγR," *J. Biol. Chem.* 9(2): 6591-6604, (Mar. 2, 2001).
Sidhu et al. "Phage-displayed Antibody Libraries of Synthetic Heavy Chain Complementarity Determining Regions," *J. Mal. Biol.* 338(2): 299-310, (2004).
Sims et al. "A Humanized CD18 Antibody Can Block Function without Cell Destruction," *J. Immunol.* 151(4):2296-2308, (Aug. 8, 1993).
Tang et al. "The Growth Factor Progranulin Binds to TNF Receptors and is Therapeutic Against Inflammatory Arthritis in Mice," *Science* 332:478-484, (Apr. 22, 2011).
Tang et al. "A Mouse Knockout Library for Secreted and Transmembrane Proteins," *Nat Biotechnol.* 28(7):749-755, (Jul. 2010).
Theilgaard-Monch et al. "The Transcriptional Program of Terminal Granulocytic Differentiation," *Blood* 105:1785-1796, (Feb. 15, 2005).
Traunecker et al. "Bispecific Single Chain Molecules (Janusins) Target Cytotoxic Lymphocytes on HIV Infected Cells," *EMBO J.* 10(12): 3655-3659, (1991).
Tutt et al. "Trispecific F(ab')$_3$ Derivatives That Use Cooperative Signaling Via the TCR/CD3 Complex and CD2 to Activate and Redirect Resting Cytotoxic T Cells," *J. Immunol.* 147(1):60-69, (Jul. 1, 1991).
Urlaub et al. "Isolation of Chinese Hamster Cell Mutants Deficient in Dihydrofolate Reductase Activity," *Proc. Natl. Acad. Sci. USA* 77(7):4216-4220, (Jul. 1980).
Vaguliene et al. "Local and Systemic Neutrophilic Inflammation in Patients with Lung Cancer and Chronic Obstructive Pulmonary Disease," *BMC Immunology* 14(36):1-11, (2013).
Van Dijk and Van De Winkel. "Human Antibodies as Next Generation Therapeutics," *Curr. Opin. Pharmacol.* 5: 368-74, (2001).
Vollmers and Brandlein. "The "Early Birds": Natural IgM Antibodies and Immune Surveillance," *Histology and Histopathology*, 20(3):927-937, (2005).
Vollmers and Brandlein. "Death by Stress: Natural IgM-Induced Apoptosis," *Methods and Findings in Experimental and Clinical Pharmacology* 27(3):185-91, (2005).
Weinrauch et al. "Neutrophil Elastase Targets Virulence Factors of Enterobacteria," *Nature* 417:91-94, (May 2, 2002).
Winter et al. "Making Antibodies by Phage Display Technology," *Ann. Rev. Immunol.* 12: 433-455, (1994).
Wright et al. "Effect of Glycosylation on Antibody Function: Implications for Genetic Engineering," *TIBTECH* 15:26-32 (Jan. 1997).
Wright et al. "Neutrophil Function in Inflammation and Inflammatory Diseases," *Rheumatology* 49(9):1618-1631, (Sep. 2010, e-pub. Mar. 24, 2010).
Xu et al. "IL-33 Exacerbates Antigen-Induced Arthritis by Activating Mast Cells," *Proc. Natl. Acad. Sci. USA* 105:10913-10918, (Aug. 5, 2008, e-pub. Jul. 30, 2008).

(56) References Cited

OTHER PUBLICATIONS

Yamane-Ohnuki et al. "Establishment of FUT8 Knockout Chinese Hamster Ovary Cells: An Ideal Host Cell Line for Producing Completely Defucosylated Antibodies With Enhanced Antibody-Dependent Cellular Cytotoxicity," *Biotech. Bioeng.* 87: 614-622, (2004, e-pub. Aug. 6, 2004).

Yazaki and Wu. "Expression of Recombinant Antibodies in Mammalian Cell Lines," Chapter 15 in *Methods in Molecular Biology*, B.K.C. Lo, ed., Humana Press, Totowa, NJ, vol. 248, pp. 255-268, (2003).

Zhang et al. "The Isolation and Characterization of Murine Macrophages," Unit 14.1 in *Curr Protoc Immunol*, 83:14.1.1-14.1.14, (2008).

International Search Report dated Feb. 2, 2015, for PCT Application No. PCT/US2014/060182, filed on Oct. 10, 2014, 6 pages.

Written Opinion dated Feb. 2, 2015, for PCT Application No. PCT/US2014/060182, filed on Oct. 10, 2014, 9 pages.

\* cited by examiner

NSP4

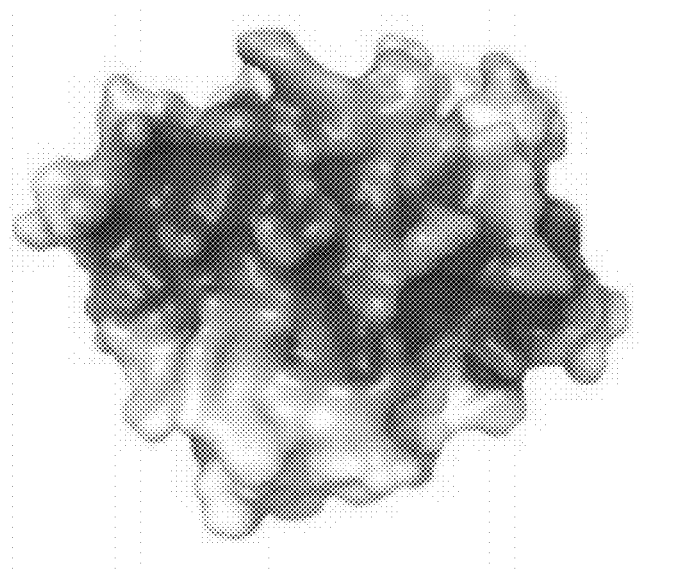
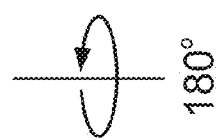
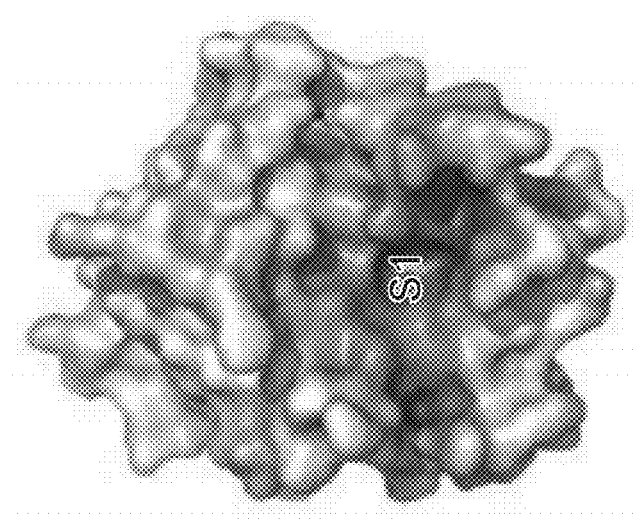
FIG. 4A

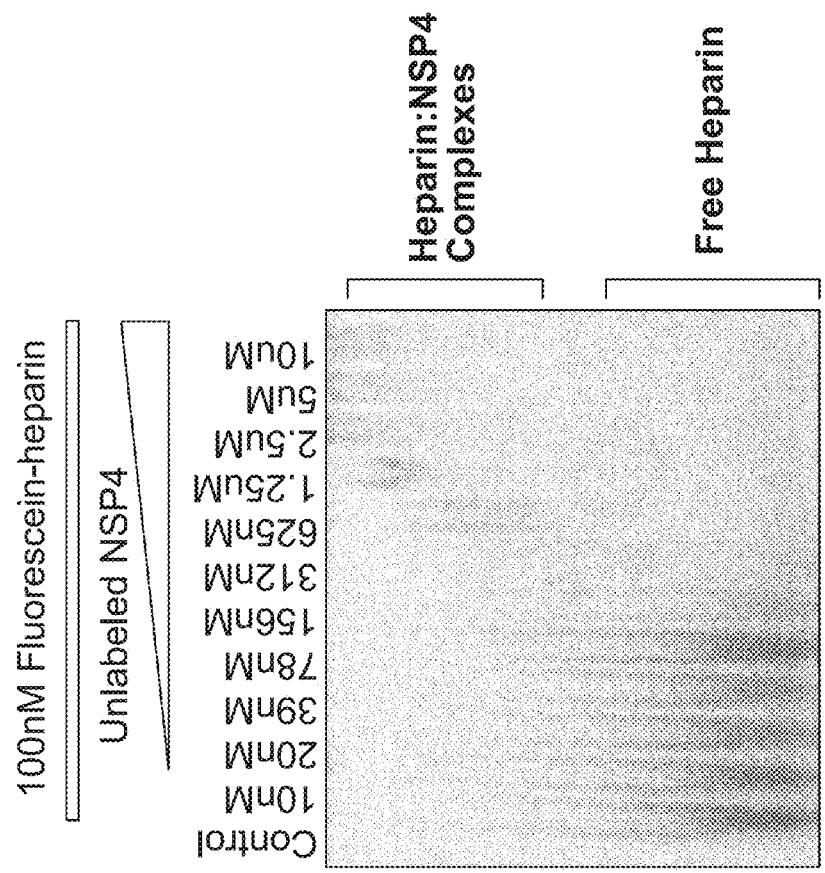
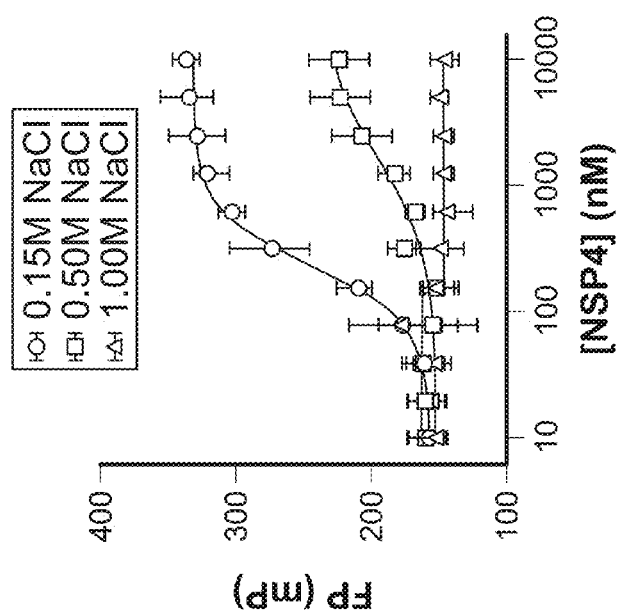
FIG. 4B

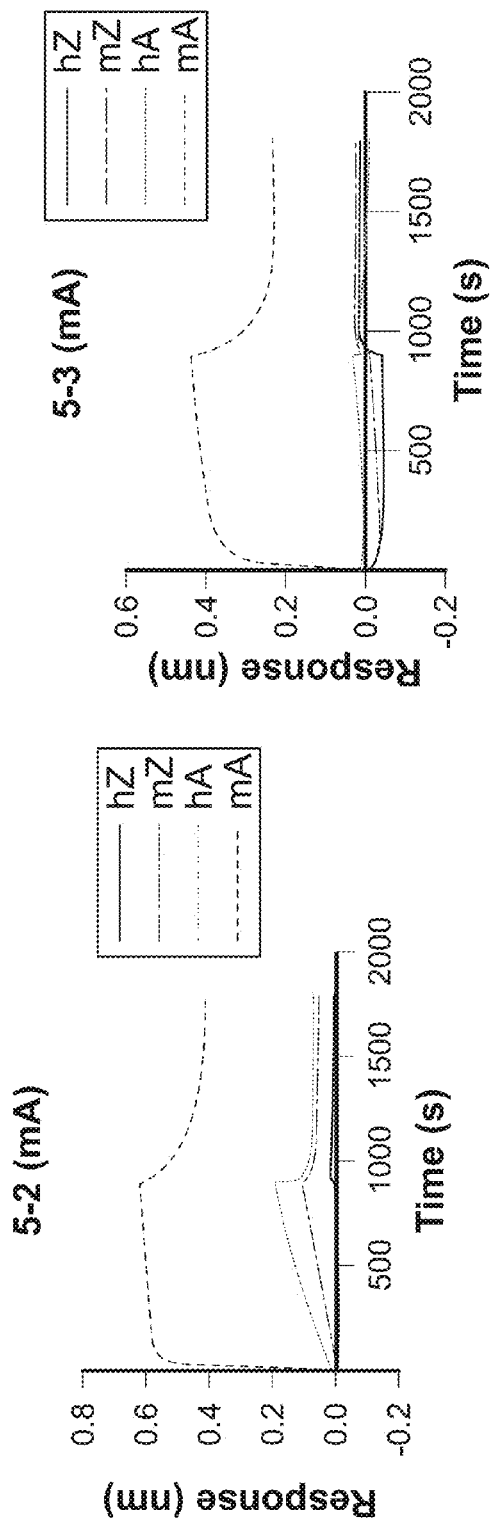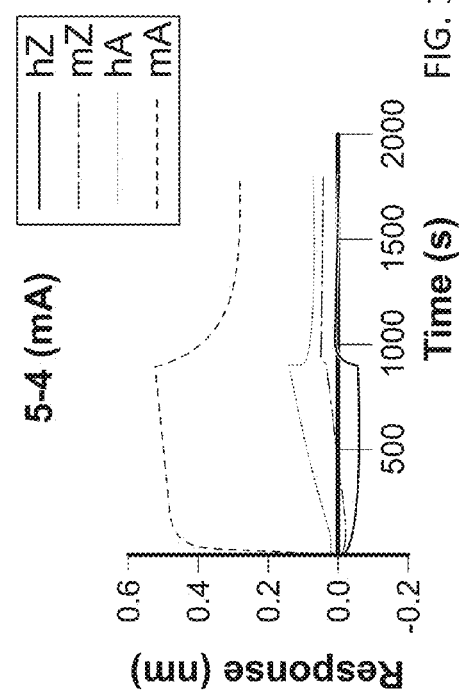
FIG. 14A
FIG. 14B
FIG. 14C

FIG. 19 (Cont.)

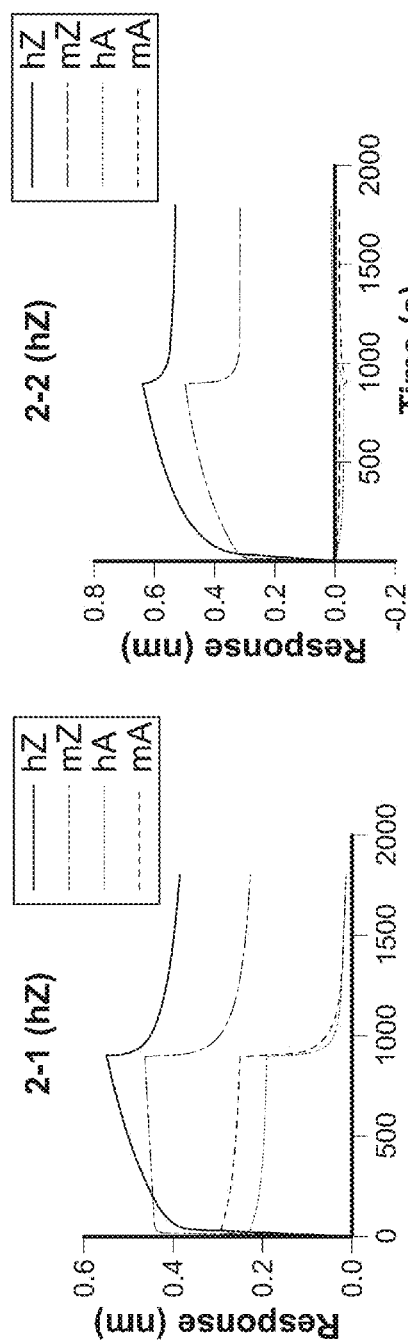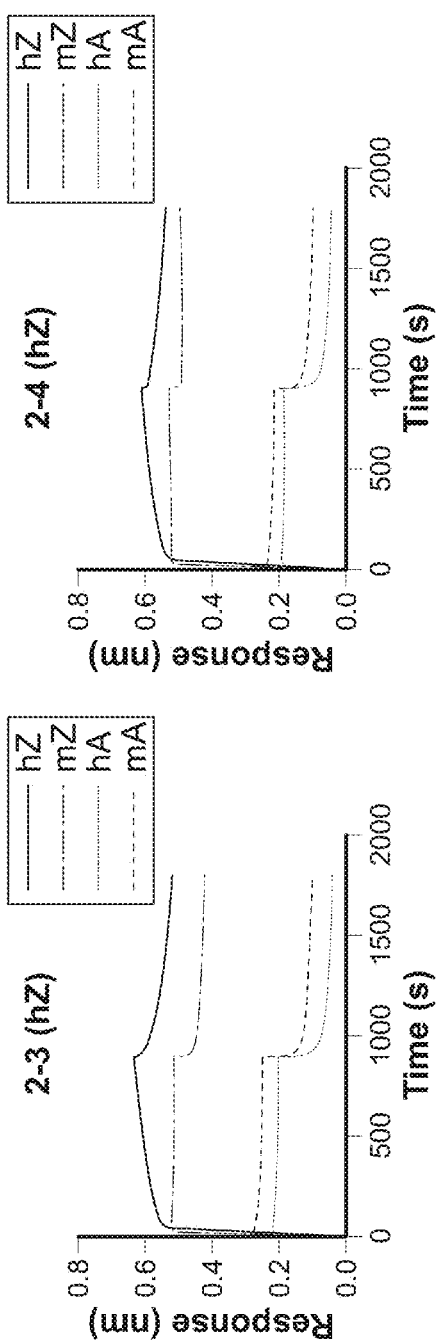
FIG.22A  FIG.22B  FIG.22C  FIG.22D

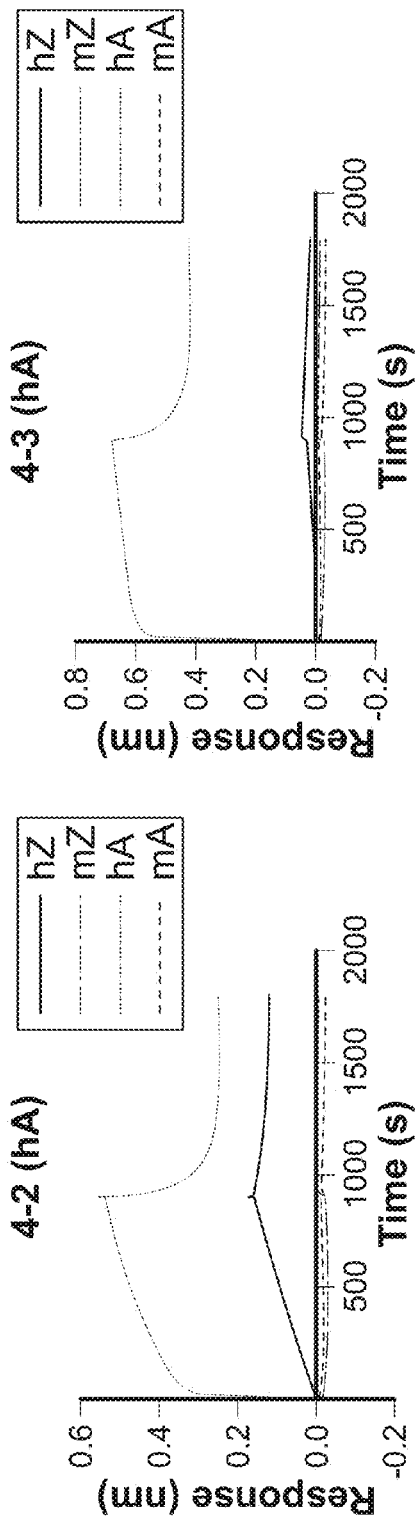
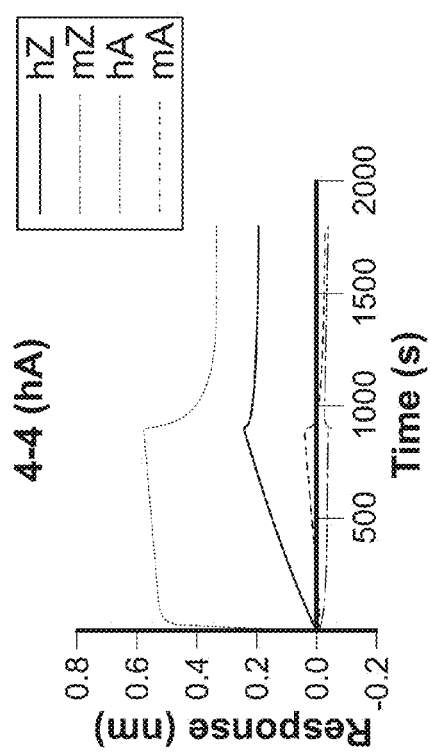
FIG.25A FIG.25B FIG.25C

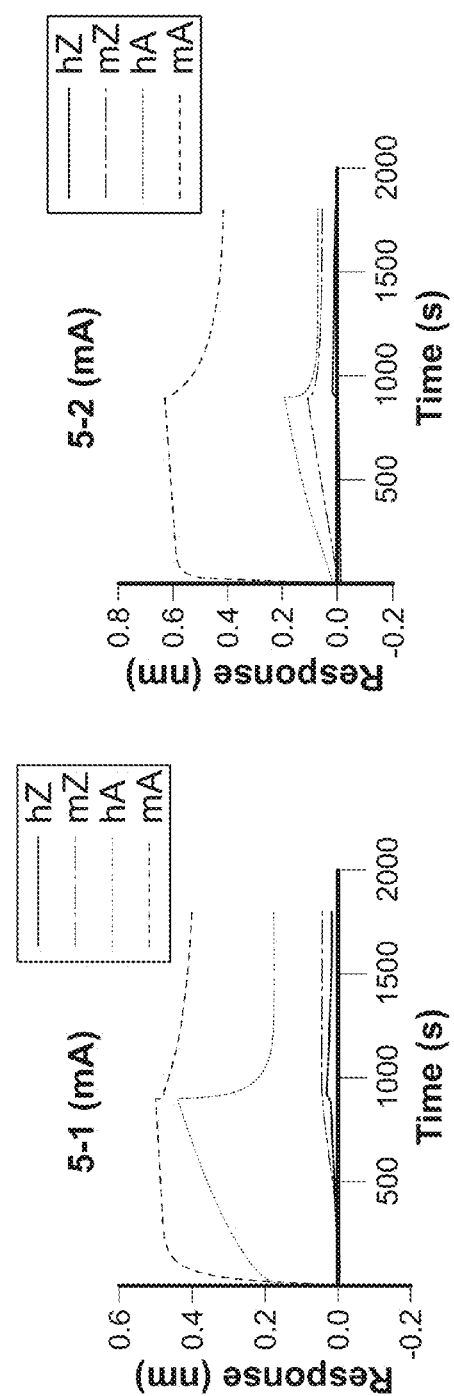
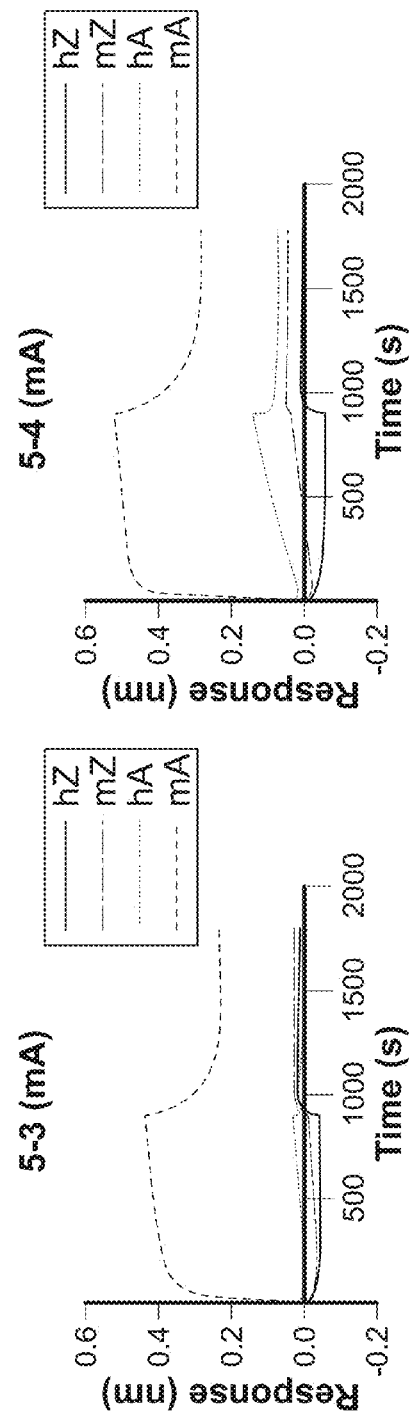
FIG. 26A  FIG. 26B  FIG. 26C  FIG. 26D

| Antibody Specificity to Different NSP4 Variants | | | | Specificity | Specificity Class | Blocking Ab |
|---|---|---|---|---|---|---|
| hZ | hA | mZ | mA | | | |
| 1-series (Panned Against hZ-NSP4) | | | | | | |
| 1-1 | + | | | | hZ-NSP4 | Species + Conformation-specific | No |
| 1-2 | ++ | | | | | | No |
| 1-3 | + | | | | | | No |
| 1-5 | + | | | | | | No |
| 2-series (Panned Against hZ-NSP4) | | | | | | |
| 2-1 | ++ | ++ | | | Zymogen NSP4 | Conformation-specific | No |
| 2-2 | ++ | ++ | | | | | No |
| 2-3 | ++ | ++ | ++ | | | | No |
| 2-4 | ++ | ++ | ++ | | | | No |
| 2-5 | ++ | ++ | ++ | | Zymogen NSP4 | Conformation-specific | No |
| 3-series (Panned Against mZ-NSP4) | | | | | | |
| 3-2 | | | ++ | ++ | Mouse NSP4 | Species-specific | No |
| 3-5 | ++ | ++ | ++ | ++ | Pan-NSP4 | Universal | No |
| 4-series (Panned Against hA-NSP4) | | | | | | |
| 4-2 | + | ++ | | | Human NSP4 | Species-specific | No |
| 4-3 | | ++ | | | hA-NSP4 | Species + Conformation-specific | Yes |
| 4-4 | | ++ | | | Human NSP4 | Species-specific | Yes |
| 5-series (Panned Against mA-NSP4) | | | | | | |
| 5-1 | | | | ++ | Active NSP4 | Conformation-specific | Yes |
| 5-2 | + | + | + | ++ | Mixed | Inhibits mA-NSP4 | Yes |
| 5-3 | | | | ++ | mA-NSP4 | Species + Conformation-specific | Yes |
| 5-4 | | + | | ++ | Mixed | Inhibits mA-NSP4 | Yes |

High Binding, KD < 50 nM    Low Affinity, KD 50 - 1000 nM    No Affinity, KD > 1 μM

FIG. 29

Ab51 Affinity Improved Clones Affinity to mNSP4

NSP4 INHIBITORS AND METHODS OF USE

CROSS REFERENCES TO RELATED APPLICATIONS

This application is a continuation of International Application No. PCT/US2014/060182, filed internationally on Oct. 10, 2014, which claims the priority benefit of U.S. Provisional Application Ser. No. 61/890,147, filed Oct. 11, 2013; 61/893,059, filed Oct. 18, 2013; and 62/053,052, filed Sep. 19, 2014; each of which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392022700SEQLIST.TXT, date recorded: Apr. 7, 2016, size: 63 KB).

FIELD OF THE INVENTION

The present invention relates to NSP4 inhibitors and methods of using the same.

BACKGROUND

Neutrophil serine proteases are a family of effector molecules of the innate immune system that are important for protecting against invading pathogens. Members of this trypsin-fold protease family, neutrophil elastase (NE), cathepsin G (CG), and proteinase 3 (PR3), not only play critical roles in neutrophil-mediated clearance of invading microbes (Reeves et al., *Nature*, 2002, 416:291-297; Weinrauch et al., *Nature*, 2002, 417:91-94; Belaaouaj et al., *Nat Med*, 1998, 4:615-618) and inflammation (Pham et al., *Nat Rev Immunol*, 2006, 6:541-550) but can also participate in the pathogenesis of various diseases (Magrone et al., *Curr Pharm Des.*, 2012, 18(12):1609-19 and Pham et al., *Int J Biochem Cell Biol.*, 2008, 40(6-7):1317-1333). Recently, the serine protease PRSS57, originally discovered by yeast signal trap screening and computational mining of human cDNA libraries (Clark et al., *Genome Res.*, 2003, 13:2265-2270), was identified as the fourth NSP member and subsequently referred to as neutrophil serine protease 4 (NSP4) (Perera et al., *Proc Natl Acad Sci USA*, 2012, 109:6229-6234; Perera et al., *J Immunol.*, 2013). Remarkably, NSP4 is highly conserved from bony fishes to human and predates the emergence of other NSPs, indicating that NSP4 likely plays fundamental roles in neutrophil biology (Perera et al., *Proc Natl Acad Sci USA*, 2012, 109:6229-6234; Perera et al., *Expert Rev Clin Immunol*, 2012, 8:501-503).

The relatively broad substrate specificities of NE, CG, and PR3 are well understood based on the detailed knowledge of their active site structures (Navia et al., *Proc Natl Acad Sci USA*, 1989, 86:7-11; Hof et al., *EMBO J*, 1996, 15:5481-5491; Fujinaga et al., *J Mol Biol*, 1996, 261:267-278.). However, NSP4 poses a conundrum in that, like trypsin, it cleaves substrates after arginine residues (Perera et al., *Proc Natl Acad Sci USA*, 2012, 109:6229-6234; Perera et al., *J Immunol.*, 2013), but paradoxically has a primary sequence that predicts a very different elastase-like active site with preference for small aliphatic amino acids and is seemingly incompatible with the long P1-arginine side chain. Due to NSP4's long evolutionary lineage, and its distinctive active site, it is possible that NSP4 is an important protease for neutrophil function and may contribute to neutrophil-mediated disease or disorders. However, relative to other members of the neutrophil serine protease family, the role of NSP4 in neutrophil-mediated diseases, such as arthritis, is unknown. For instance, the combined deficiencies of NE and CG was required to confer full protection in the mouse collagen antibody-induced arthritis model (Adkison et al., *J Clin Invest*, 2002, 109:363-371). NE and CG are also each capable of processing and activating IL-33 (Lefrancais et al., *Proc Natl Acad Sci USA*, 2012, 109:1673-1678), which is a pro-inflammatory cytokine that promotes inflammatory arthritis (Xu et al., *Proc Natl Acad Sci USA*, 2008, 105: 10913-10918). Similarly, the combined ablation of NE and PR3 was required to prevent the inactivation of progranulin (Kessenbrock et al., *J Clin Invest*, 2008, 118:2438-2447), an anti-inflammatory cytokine that alleviates inflammatory arthritis (Tang et al., *Science*, 2011, 332:478-484).

Resolving the paradox between the predicted elastase-like active site with the actual trypsin-like active site that is exhibited by NSP4 has the potential to provide structural features of the enzyme active site that could facilitate the development of specific NSP4 inhibitors. These NSP4 inhibitors may serve a need for treatment of neutrophil-mediated diseases or disorders where the underlying pathology is completely or partially due to the activity of NSP4.

All references cited herein, including patent applications, patent publications, scientific literature, and National Center for Biotechnology Information (NCBI) Accession numbers are herein incorporated by reference in their entirety, as if each individual reference were specifically and individually indicated to be incorporated by reference.

BRIEF SUMMARY

The invention broadly provides neutrophil serine protease 4 (NSP4) inhibitors and methods of using the same.

In one aspect, provided herein is a method for treating or preventing a disease or disorder mediated by granulocytes in an individual comprising administering to the individual an effective amount of an NSP4 inhibitor. In some embodiments, the disease or disorder is an eosinophil-mediated, basophil-mediated, or a neutrophil-mediated disease or disorder. In some embodiments of the methods described herein, the disease or disorder that can be treated by a NSP4 inhibitor is a vascular disease, an inflammatory disease or an autoimmune disease. In some embodiments of the methods described herein, the disease or disorder is selected from the group consisting of stroke, diabetic retinopathy, edema, diabetic macular edema, hereditary angioedema, idiopathic angioedema, leakage of vasculature, cerebral ischemia, acute lung injury, anaphylaxis, systemic anaphylaxis, allergic lung inflammation, asthma (e.g., allergic asthma, virus-induced asthma), chronic obstructive pulmonary disease (COPD), acute respiratory distress syndrome (ARDS), idiopathic pulmonary fibrosis, systemic lupus erythematosus (SLE), autoimmune vasculitides, blistering skin diseases (e.g., bullous pemphigoid), inflammatory skin diseases (e.g., atopic dermatitis, urticarial, eosinophilic cellulitis), cancer (e.g., lung cancer), kidney diseases (e.g., glomerulonephritis), osteoarthritis, rheumatoid arthritis, psoriatic arthritis, psoriasis, septic shock, inflammatory bowel disease (e.g., ulcerative colitis, Crohn's disease). In some embodiments of the methods described herein, the individual has the disease or disorder or has been diagnosed with the disease or disorder. In some embodiments of the methods described herein, the individual is at risk of developing the disease or disorder. In some embodiments, the individual is a human.

In one aspect, provided herein is a method for treating or preventing a neutrophil-mediated disease or disorder in an individual comprising administering to the individual an effective amount of an NSP4 inhibitor. In some embodiments, the neutrophil-mediated disease or disorder is selected from the group consisting of vascular disease and inflammatory disease. In a further embodiment, the vascular disease is selected from the group consisting of stroke, diabetic retinopathy, edema, diabetic macular edema, hereditary angioedema, idiopathic angioedema, leakage of vasculature, and cerebral ischemia. In another further embodiment, the inflammatory disease is selected from the group consisting of acute lung injury, asthma, chronic obstructive pulmonary disease (COPD), acute respiratory distress syndrome (ARDS), osteoarthritis, rheumatoid arthritis, and septic shock. In any of the embodiments herein, the individual can be a human.

In another aspect, provided herein is an NSP4 inhibitor that can be used in any of the methods described herein. In some embodiments, the NSP4 inhibitor is selected from the group consisting of an antibody, an antisense molecule, a siRNA, a small molecule inhibitor, a protease inhibitor, and a peptide inhibitor. In a further embodiment, the protease inhibitor is a serine protease inhibitor. In another further embodiment, the protease inhibitor is al-antitrypsin, heparin-activated antithrombin, C1 inhibitor, or α2-antiplasmin.

In any of the embodiments herein, the NSP4 inhibitor can be an anti-NSP4 antibody that specifically binds to a NSP4. In any of the embodiments herein, the NSP4 inhibitor can be an anti-NSP4 antibody that specifically binds to a mature form of NSP4. In any of the embodiments herein, the NSP4 inhibitor can be an anti-NSP4 antibody that specifically binds to a mature form of NSP4 but does not bind to a precursor form of NSP4. In any of the embodiments herein, the NSP4 inhibitor can be an anti-NSP4 antibody that specifically binds to a human NSP4. In any of the embodiments herein, the NSP4 inhibitor can be an anti-NSP4 antibody that specifically binds to a mouse NSP4. In any of the embodiments herein, the NSP4 inhibitor can be an anti-NSP4 antibody that specifically binds to both a human NSP4 and a mouse NSP4. In any of the embodiments herein, the anti-NSP4 antibody can be a monoclonal antibody. In any of the embodiments herein, the anti-NSP4 antibody can be an antibody fragment selected from the group consisting of Fab, Fab'-SH, Fv, scFv, and (Fab')$_2$ fragments. In any of the embodiments herein, the anti-NSP4 antibody can be a humanized antibody or a chimeric antibody. In any of the embodiments herein, the anti-NSP4 antibody can comprise at least one, two, three, four, five, or six HVRs selected from (i) HVR-L1 comprising the amino acid sequence of SEQ ID NO:10; (ii) HVR-L2 comprising the amino acid sequence of SEQ ID NO:11; (iii) HVR-L3 comprising the amino acid sequence of SEQ ID NO:12; (iv) HVR-H1 comprising the amino acid sequence of SEQ ID NO:1, 4, or 7; (v) HVR-H2 comprising the amino acid sequence of SEQ ID NO:2, 5, or 8; (vi) HVR-H3 comprising the amino acid sequence of SEQ ID NO:3, 6, or 9. In any of the embodiments herein, the anti-NSP4 antibody can comprise a light chain variable region comprising the amino acid sequence of SEQ ID NO:16, and a heavy chain variable region comprising the amino acid sequence of SEQ ID NO:13, 14 or 15.

In some of the embodiments herein, the NSP4 inhibitor can be administered intravenously, intramuscularly, subcutaneously, topically, orally, transdermally, intraperitoneally, intraorbitally, by implantation, by inhalation, intrathecally, intraventricularly, or intranasally. In any of the embodiments herein, the NSP4 inhibitor can be formulated in a pharmaceutical composition comprising the NSP4 inhibitor and a pharmaceutically acceptable carrier.

In yet another aspect, provided herein is an article of manufacture comprising a NSP4 inhibitor and a package insert comprising instructions for using the NSP4 inhibitor to treat or prevent a disease or disorder mediated by granulocytes in an individual. In some embodiments, the disease or disorder is an eosinophil-mediated, basophil-mediated, or a neutrophil-mediated disease or disorder. In some embodiments, the disease or disorder that can be treated by a NSP4 inhibitor is a vascular disease, an inflammatory disease, or an autoimmune disease. In some embodiments, the disease or disorder is selected from the group consisting of stroke, diabetic retinopathy, edema, diabetic macular edema, hereditary angioedema, idiopathic angioedema, leakage of vasculature, cerebral ischemia, acute lung injury, anaphylaxis, systemic anaphylaxis, allergic lung inflammation, asthma (e.g., allergic asthma, virus-induced asthma), chronic obstructive pulmonary disease (COPD), acute respiratory distress syndrome (ARDS), idiopathic pulmonary fibrosis, systemic lupus erythematosus (SLE), autoimmune vasculitides, blistering skin diseases (e.g., bullous pemphigoid), inflammatory skin diseases (e.g., atopic dermatitis, urticarial, eosinophilic cellulitis), cancer (e.g., lung cancer), kidney diseases (e.g., glomerulonephritis), osteoarthritis, rheumatoid arthritis, psoriatic arthritis, psoriasis, septic shock, inflammatory bowel disease (e.g., ulcerative colitis, Crohn's disease). In some embodiments, the individual has the disease or disorder or has been diagnosed with the disease or disorder. In some embodiments, the individual is at risk of developing the disease or disorder. In some embodiments, the individual is a human.

In yet another aspect, provided herein is an article of manufacture comprising a NSP4 inhibitor and a package insert comprising instructions for using the NSP4 inhibitor to treat or prevent a neutrophil-mediated disease or disorder in an individual. In some embodiments, the neutrophil-mediated disease or disorder is selected from the group consisting of vascular disease and inflammatory disease. In a further embodiment, the vascular disease is selected from the group consisting of stroke, diabetic retinopathy, edema, diabetic macular edema, hereditary angioedema, idiopathic angioedema, leakage of vasculature, and cerebral ischemia. In another further embodiment, the inflammatory disease is selected from the group consisting of acute lung injury, asthma, chronic obstructive pulmonary disease (COPD), acute respiratory distress syndrome (ARDS), osteoarthritis, rheumatoid arthritis, and septic shock. In any of the embodiments herein, the individual can be a human.

In another aspect, provided here is an anti-NSP4 antibody comprising at least one, two, three, four, five or six hypervariable region (HVR) sequences selected from the group consisting of: (a) HVR-H1 comprising the sequence of GFTFSDNDIS (SEQ ID NO:50); (b) HVR-H2 comprising the sequence of GSISPDNGDTNYADSVKG (SEQ ID NO:51); (c) HVR-H3 comprising the sequence of RDDV-PAVFTSAMDY (SEQ ID NO:52); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSX$_1$X$_2$X$_3$PX$_4$T (SEQ ID NO:95), wherein X$_1$ is Y or A; X$_2$ is T, G, or D; X$_3$ is T or F; and X$_4$ is P or L. In yet another aspect, provided herein is an anti-NSP4 antibody comprising a heavy chain and a light chain, wherein (a) the heavy chain comprises an HVR-H1 comprising the sequence of GFTF- SDNDIS (SEQ ID NO:50), an HVR-H2 comprising the sequence of GSISPDNGDTNYADSVKG (SEQ ID NO:51), and an HVR-H3 comprising the sequence of RDDVPAVFT-SAMDY (SEQ ID NO:52); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSX$_1$X$_2$X$_3$PX$_4$T (SEQ ID NO:95), wherein X$_1$ is Y or A; X$_2$ is T, G, or D; X$_3$ is T or F; and X$_4$ is P or L. In certain embodiments, the HVR-L3 comprises the sequence selected from the group consisting of SEQ ID NO:12 and 92-94.

In certain embodiments, the anti-NSP4 antibody comprises at least one, two, three, four, five or six hypervariable region (HVR) sequences selected from the group consisting of: (a) HVR-H1 comprising the sequence of GFTFSDNDIS (SEQ ID NO:50); (b) HVR-H2 comprising the sequence of GSISPDNGDTNYADSVKG (SEQ ID NO:51); (c) HVR-H3 comprising the sequence of RDDVPAVFTSAMDY (SEQ ID NO:52); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSYTTPPT (SEQ ID NO:12). In certain embodiments, the anti-NSP4 antibody comprises a heavy chain and a light chain, wherein (a) the heavy chain comprises an HVR-H1 comprising the sequence of GFTF-SDNDIS (SEQ ID NO:50), an HVR-H2 comprising the sequence of GSISPDNGDTNYADSVKG (SEQ ID NO:51), and an HVR-H3 comprising the sequence of RDDVPAVFT-SAMDY (SEQ ID NO:52); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSYTTPPT (SEQ ID NO:12). In certain embodiments, the antibody comprises a heavy chain variable region comprising the sequence of SEQ ID NO:78 and/or a light chain variable region comprising the sequence of SEQ ID NO:16. In certain embodiments, the antibody comprises a variable domain comprising at least one, two, three, four, five or six hypervariable region (HVR) sequences of antibody 35.WT (e.g., as shown in Tables 5-7). In certain embodiments, the antibody comprises a heavy chain variable region sequence and/or a light chain variable region sequence of antibody 35.WT (e.g., as shown in Table 7).

In certain embodiments, the anti-NSP4 antibody comprises at least one, two, three, four, five or six hypervariable region (HVR) sequences selected from the group consisting of: (a) HVR-H1 comprising the sequence of GFTFSDNDIS (SEQ ID NO:50); (b) HVR-H2 comprising the sequence of GSISPDNGDTNYADSVKG (SEQ ID NO:51); (c) HVR-H3 comprising the sequence of RDDVPAVFTSAMDY (SEQ ID NO:52); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSYGFPLT (SEQ ID NO:92). In certain embodiments, the antibody comprises a heavy chain and a light chain, wherein (a) the heavy chain comprises an HVR-H1 comprising the sequence of GFTFSDN-DIS (SEQ ID NO:50), an HVR-H2 comprising the sequence of GSISPDNGDTNYADSVKG (SEQ ID NO:51), and an HVR-H3 comprising the sequence of RDDVPAVFTS-AMDY (SEQ ID NO:52); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSYGFPLT (SEQ ID NO:92). In certain embodiments, the antibody comprises a heavy chain variable region comprising the sequence of SEQ ID NO:78 and/or a light chain variable region comprising the sequence of SEQ ID NO:102. In certain embodiments, the antibody comprises at least one, two, three, four, five or six hypervariable region (HVR) sequences of antibody 35.14 (e.g., as shown in Tables 5-7). In certain embodiments, the antibody comprises a heavy chain variable region sequence and/or a light chain variable region sequence of antibody 35.14 (e.g., as shown in Table 7).

In certain embodiments, the anti-NSP4 antibody comprises at least one, two, three, four, five or six hypervariable region (HVR) sequences selected from the group consisting of: (a) HVR-H1 comprising the sequence of GFTFSDNDIS (SEQ ID NO:50); (b) HVR-H2 comprising the sequence of GSISPDNGDTNYADSVKG (SEQ ID NO:51); (c) HVR-H3 comprising the sequence of RDDVPAVFTSAMDY (SEQ ID NO:52); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSYDFPLT (SEQ ID NO:93). In certain embodiments, the antibody comprises a heavy chain and a light chain, wherein (a) the heavy chain comprises an HVR-H1 comprising the sequence of GFTFSDN-DIS (SEQ ID NO:50), an HVR-H2 comprising the sequence of GSISPDNGDTNYADSVKG (SEQ ID NO:51), and an HVR-H3 comprising the sequence of RDDVPAVFTS-AMDY (SEQ ID NO:52); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSYDFPLT (SEQ ID NO:93). In certain embodiments, the antibody comprises a heavy chain variable region comprising the sequence of SEQ ID NO:78 and/or a light chain variable region comprising the sequence of SEQ ID NO:103. In certain embodiments, the antibody comprises at least one, two, three, four, five or six hypervariable region (HVR) sequences of antibody 35.50 (e.g., as shown in Tables 5-7). In certain embodiments, the antibody comprises a heavy chain variable region sequence and/or a light chain variable region sequence of antibody 35.50 (e.g., as shown in Table 7).

In certain embodiments, the anti-NSP4 antibody comprises at least one, two, three, four, five or six hypervariable region (HVR) sequences selected from the group consisting of: (a) HVR-H1 comprising the sequence of GFTFSDNDIS (SEQ ID NO:50); (b) HVR-H2 comprising the sequence of GSISPDNGDTNYADSVKG (SEQ ID NO:51); (c) HVR-H3 comprising the sequence of RDDVPAVFTSAMDY (SEQ ID NO:52); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSAGFPLT (SEQ ID NO:94). In certain embodiments, the antibody comprises a heavy chain and a light chain, wherein (a) the heavy chain comprises an HVR-H1 comprising the sequence of GFTFSDN-DIS (SEQ ID NO:50), an HVR-H2 comprising the sequence of GSISPDNGDTNYADSVKG (SEQ ID NO:51), and an HVR-H3 comprising the sequence of RDDVPAVFTS-AMDY (SEQ ID NO:52); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSAGFPLT (SEQ ID NO:94). In certain embodiments, the antibody comprises a heavy chain variable region comprising the sequence of SEQ ID NO:78 and/or a light chain variable region comprising the sequence of SEQ ID NO:104. In certain embodiments, the antibody comprises at least one, two, three, four, five or six hypervariable region (HVR) sequences of antibody 35.62 (e.g., as shown in Tables 5-7). In certain embodiments, the antibody comprises a heavy chain variable region sequence and/or a light chain variable region sequence of antibody 35.62 (e.g., as shown in Table 7).

In yet another aspect, provided herein is an anti-NSP4 antibody comprising (a) an HVR-H2 comprising the sequence of GSISPDNGDTNYADSVKG (SEQ ID NO:51); (b) an HVR-H3 comprising the sequence of RDDVPAVFT-SAMDY (SEQ ID NO:52); and (c) an HVR-L3 comprising the sequence of QQSX$_1$X$_2$X$_3$PX$_4$T (SEQ ID NO:95), wherein X$_1$ is Y or A; X$_2$ is T, G, or D; X$_3$ is T or F; and X$_4$ is P or L. In certain embodiments, the antibody comprises (a) an HVR-H2 comprising the sequence of GSISPDNGDT-NYADSVKG (SEQ ID NO:51); (b) an HVR-H3 comprising the sequence of RDDVPAVFTSAMDY (SEQ ID NO:52); and (c) an HVR-L3 comprising the sequence of QQSYTTPPT (SEQ ID NO:12). In certain embodiments, the antibody comprises (a) an HVR-H2 comprising the sequence of GSISPDNGDTNYADSVKG (SEQ ID NO:51); (b) an HVR-H3 comprising the sequence of RDDVPAVFT-SAMDY (SEQ ID NO:52); and (c) an HVR-L3 comprising the sequence of QQSYGFPLT (SEQ ID NO:92). In certain embodiments, the antibody comprises (a) an HVR-H2 comprising the sequence of GSISPDNGDTNYADSVKG (SEQ ID NO:51); (b) an HVR-H3 comprising the sequence of RDDVPAVFTSAMDY (SEQ ID NO:52); and (c) an HVR-L3 comprising the sequence of QQSYDFPLT (SEQ ID NO:93). In certain embodiments, the antibody comprises (a) an HVR-H2 comprising the sequence of GSISPDNGDT-NYADSVKG (SEQ ID NO:51); (b) an HVR-H3 comprising the sequence of RDDVPAVFTSAMDY (SEQ ID NO:52); and (c) an HVR-L3 comprising the sequence of QQSAGF-PLT (SEQ ID NO:94).

In another aspect, provided herein is an anti-NSP4 antibody comprising at least one, two, three, four, five or six hypervariable region (HVR) sequences selected from the group consisting of: (a) HVR-H1 comprising the sequence of GFTFSGSGIH (SEQ ID NO:65); (b) HVR-H2 comprising the sequence of AWISPTGGNTYYADSVKG (SEQ ID NO:66); (c) HVR-H3 comprising the sequence of KRHLH-NVAFDY (SEQ ID NO:87); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQAYSAPPT (SEQ ID NO:96). In some embodiments, the antibody comprises a heavy chain and a light chain, wherein (a) the heavy chain comprises an HVR-H1 comprising the sequence of GFTFSGSGIH (SEQ ID NO:65), an HVR-H2 comprising the sequence of AWISPTGGNTYYADSVKG (SEQ ID NO:66), and an HVR-H3 comprising the sequence of KRHLHNVAFDY (SEQ ID NO:87); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQAYSAPPT (SEQ ID NO:96). In certain embodiments, the antibody comprises a heavy chain variable region comprising the sequence of SEQ ID NO:105 and/or a light chain variable region comprising the sequence of SEQ ID NO:106. In certain embodiments, the antibody comprises at least one, two, three, four, five or six hypervariable region (HVR) sequences of antibody 35.77 (e.g., as shown in Tables 5-7). In certain embodiments, the antibody comprises a heavy chain variable region sequence and/or a light chain variable region sequence of antibody 35.77 (e.g., as shown in Table 7).

In yet another aspect, provided herein is an anti-NSP4 antibody comprising (a) an HVR-H2 comprising the sequence of AWISPTGGNTYYADSVKG (SEQ ID NO:66); (b) an HVR-H3 comprising the sequence of KRHLHN-VAFDY (SEQ ID NO:87); and (c) an HVR-L3 comprising the sequence of QQAYSAPPT (SEQ ID NO:96).

In another aspect, provided herein an anti-NSP4 antibody comprising at least one, two, three, four, five or six hypervariable region (HVR) sequences selected from the group consisting of: (a) HVR-H1 comprising the sequence of GFTFSGSGIH (SEQ ID NO:65); (b) HVR-H2 comprising the sequence of AWISPTGGNTYYADSVKG (SEQ ID NO:66) or the sequence of AWIPTAGGNTYYADSVKG (SEQ ID NO:88); (c) HVR-H3 comprising the sequence of X$_1$X$_2$X$_3$FHNVAFDY (SEQ ID NO:91), wherein X$_1$ is K or R; X$_2$ is S, G, or V; and X$_3$ is L or F; (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQX$_1$X$_2$X$_3$X$_4$PPT (SEQ ID NO:101), wherein X$_1$ is S, A, N, or T; X$_2$ is Y, N, or F; X$_3$ is T, S, or N; and X$_4$ is T, A, or S. In certain embodiments, the antibody comprises a heavy chain and a light chain, wherein (a) the heavy chain comprises an HVR-H1 comprising the sequence of GFTF-SGSGIH (SEQ ID NO:65), an HVR-H2 comprising the sequence of AWISPTGGNTYYADSVKG (SEQ ID NO:66) or the sequence of AWIPTAGGNTYYADSVKG (SEQ ID NO:88), and an HVR-H3 comprising the sequence of X$_1$X$_2$X$_3$FHNVAFDY (SEQ ID NO:91), wherein X$_1$ is K or R; X$_2$ is S, G, or V; and X$_3$ is L or F; and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQX$_1$X$_2$X$_3$X$_4$PPT (SEQ ID NO:101), wherein X$_1$ is S, A, N, or T; X$_2$ is Y, N, or F; X$_3$ is T, S, or N; and X$_4$ is T, A, or S. In certain embodiments, the HVR-H3 comprises the sequence selected from the group consisting of SEQ ID NO:67, 89, and 90. In certain embodiments, the HVR-L3 comprises the sequence selected from the group consisting of SEQ ID NO:12 and 97-100. In certain embodiments, the HVR-H3 comprises the sequence selected from the group consisting of SEQ ID NO:67, 89, and 90, and the HVR-L3 comprises the sequence selected from the group consisting of SEQ ID NO:12 and 97-100.

In certain embodiments, the anti-NSP4 antibody comprises at least one, two, three, four, five or six hypervariable region (HVR) sequences selected from the group consisting of: (a) HVR-H1 comprising the sequence of GFTFSGSGIH (SEQ ID NO:65); (b) HVR-H2 comprising the sequence of AWISPTGGNTYYADSVKG (SEQ ID NO:66); (c) HVR-H3 comprising the sequence of KSLFHNVAFDY (SEQ ID NO:67); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSYTTPPT (SEQ ID NO:12). In certain embodiments, the antibody comprises a heavy chain and a light chain, wherein (a) the heavy chain comprises an HVR-H1 comprising the sequence of GFTFSGS-GIH (SEQ ID NO:65), an HVR-H2 comprising the sequence of AWISPTGGNTYYADSVKG (SEQ ID NO:66), and an HVR-H3 comprising the sequence of KSLFHNVAFDY (SEQ ID NO:67); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSYTTPPT (SEQ ID NO:12). In certain embodiments, the antibody comprises a heavy chain variable region comprising the sequence of SEQ ID NO:83 and/or a light chain variable region comprising the sequence of SEQ ID NO:16. In certain embodiments, the antibody comprises at least one, two, three, four, five or six hypervariable region (HVR) sequences of antibody 51.WT (e.g., as shown in Tables 5-7). In certain embodiments, the antibody comprises a heavy chain variable region sequence and/or a light chain variable region sequence of antibody 51.WT (e.g., as shown in Table 7).

In certain embodiments, the anti-NSP4 antibody comprises at least one, two, three, four, five or six hypervariable region (HVR) sequences selected from the group consisting of: (a) HVR-H1 comprising the sequence of GFTFSGSGIH (SEQ ID NO:65); (b) HVR-H2 comprising the sequence of AWIPTAGGNTYYADSVKG (SEQ ID NO:88); (c) HVR-H3 comprising the sequence of KSLFHNVAFDY (SEQ ID NO:67); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSYTAPPT (SEQ ID NO:97). In certain embodiments, the antibody comprises a heavy chain and a light chain, wherein (a) the heavy chain comprises an HVR-H1 comprising the sequence of GFTFSGSGIH (SEQ ID NO:65), an HVR-H2 comprising the sequence of AWIPTAGGNTYYADSVKG (SEQ ID NO:88), and an HVR-H3 comprising the sequence of KSLFHNVAFDY (SEQ ID NO:67); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSYTAPPT (SEQ ID NO:97). In certain embodiments, the antibody comprises a heavy chain variable region comprising the sequence of SEQ ID NO:107 and/or a light chain variable region comprising the sequence of SEQ ID NO:108. In certain embodiments, the antibody comprises at least one, two, three, four, five or six hypervariable region (HVR) sequences of antibody 51.30 (e.g., as shown in Tables 5-7). In certain embodiments, the antibody comprises a heavy chain variable region sequence and/or a light chain variable region sequence of antibody 51.30 (e.g., as shown in Table 7).

In certain embodiments, the anti-NSP4 antibody comprises a variable domain comprising at least one, two, three, four, five or six hypervariable region (HVR) sequences selected from the group consisting of: (a) HVR-H1 comprising the sequence of GFTFSGSGIH (SEQ ID NO:65); (b) HVR-H2 comprising the sequence of AWISPTGGNTYYADSVKG (SEQ ID NO:66); (c) HVR-H3 comprising the sequence of KSLFHNVAFDY (SEQ ID NO:67); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQANSTPPT (SEQ ID NO:98). In certain embodiments, the antibody comprises a heavy chain and a light chain, wherein (a) the heavy chain comprises an HVR-H1 comprising the sequence of GFTFSGSGIH (SEQ ID NO:65), an HVR-H2 comprising the sequence of AWISPTGGNTYYADSVKG (SEQ ID NO:66), and an HVR-H3 comprising the sequence of KSLFHNVAFDY (SEQ ID NO:67); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQANSTPPT (SEQ ID NO:98). In certain embodiments, the antibody comprises a heavy chain variable region comprising the sequence of SEQ ID NO:83 and/or a light chain variable region comprising the sequence of SEQ ID NO:109. In certain embodiments, the antibody comprises a variable domain comprising at least one, two, three, four, five or six hypervariable region (HVR) sequences of antibody 51.50 (e.g., as shown in Tables 5-7). In certain embodiments, the antibody comprises a heavy chain variable region sequence and/or a light chain variable region sequence of antibody 51.50 (e.g., as shown in Table 7).

In certain embodiments, the anti-NSP4 antibody comprises at least one, two, three, four, five or six hypervariable region (HVR) sequences selected from the group consisting of: (a) HVR-H1 comprising the sequence of GFTFSGSGIH (SEQ ID NO:65); (b) HVR-H2 comprising the sequence of AWISPTGGNTYYADSVKG (SEQ ID NO:66); (c) HVR-H3 comprising the sequence of RGLFHNVAFDY (SEQ ID NO:89); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSYTAPPT (SEQ ID NO:97). In certain embodiments, the antibody comprises a heavy chain and a light chain, wherein (a) the heavy chain comprises an HVR-H1 comprising the sequence of GFTFSGSGIH (SEQ ID NO:65), an HVR-H2 comprising the sequence of AWISPTGGNTYYADSVKG (SEQ ID NO:66), and an HVR-H3 comprising the sequence of RGLFHNVAFDY (SEQ ID NO:89); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSYTAPPT (SEQ ID NO:97). In certain embodiments, the antibody comprises a heavy chain variable region comprising the sequence of SEQ ID NO:110 and/or a light chain variable region comprising the sequence of SEQ ID NO:108. In certain embodiments, the antibody comprises at least one, two, three, four, five or six hypervariable region (HVR) sequences of antibody 51.51 (e.g., as shown in Tables 5-7). In certain embodiments, the antibody comprises a heavy chain variable region sequence and/or a light chain variable region sequence of antibody 51.51 (e.g., as shown in Table 7).

In certain embodiments, the NSP4 antibody comprises at least one, two, three, four, five or six hypervariable region (HVR) sequences selected from the group consisting of: (a) HVR-H1 comprising the sequence of GFTFSGSGIH (SEQ ID NO:65); (b) HVR-H2 comprising the sequence of AWISPTGGNTYYADSVKG (SEQ ID NO:66); (c) HVR-H3 comprising the sequence of RVFFHNVAFDY (SEQ ID NO:90); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQNFSSPPT (SEQ ID NO:99). In certain embodiments, the antibody comprises a heavy chain and a light chain, wherein (a) the heavy chain comprises an HVR-H1 comprising the sequence of GFTFSGSGIH (SEQ ID NO:65), an HVR-H2 comprising the sequence of AWISPTGGNTYYADSVKG (SEQ ID NO:66), and an HVR-H3 comprising the sequence of RVFFHNVAFDY (SEQ ID NO:90); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQNFSSPPT (SEQ ID NO:99). In certain embodiments, the antibody comprises a heavy chain variable region comprising the sequence of SEQ ID NO:111 and/or a light chain variable region comprising the sequence of SEQ ID NO:112. In certain embodiments, the antibody comprises at least one, two, three, four, five or six hypervariable region (HVR) sequences of antibody 51.59 (e.g., as shown in Tables 5-7). In certain embodiments, the antibody comprises a heavy chain variable region sequence and/or a light chain variable region sequence of antibody 51.59 (e.g., as shown in Table 7).

In certain embodiments, the anti-NSP4 antibody comprises at least one, two, three, four, five or six hypervariable region (HVR) sequences selected from the group consisting of: (a) HVR-H1 comprising the sequence of GFTFSGSGIH (SEQ ID NO:65); (b) HVR-H2 comprising the sequence of AWISPTGGNTYYADSVKG (SEQ ID NO:66); (c) HVR-H3 comprising the sequence of KSLFHNVAFDY (SEQ ID NO:67); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSYTAPPT (SEQ ID NO:97). In certain embodiments, the antibody comprises a heavy chain and a light chain, wherein (a) the heavy chain comprises an HVR-H1 comprising the sequence of GFTFSGSGIH (SEQ ID NO:65), an HVR-H2 comprising the sequence of AWISPTGGNTYYADSVKG (SEQ ID NO:66), and an HVR-H3 comprising the sequence of KSLFHNVAFDY (SEQ ID NO:67); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSYTAPPT (SEQ ID NO:97). In certain embodiments, the antibody comprises a heavy chain variable region comprising the sequence of SEQ ID NO:83 and/or a light chain variable region comprising the sequence of SEQ ID NO:108. In certain embodiments, the antibody comprises at least one, two, three, four, five or six hypervariable region (HVR) sequences of antibody 51.72 (e.g., as shown in Tables 5-7). In certain embodiments, the antibody comprises a heavy chain variable region sequence and/or a light chain variable region sequence of antibody 51.72 (e.g., as shown in Table 7).

In certain embodiments, the anti-NSP4 antibody comprises at least one, two, three, four, five or six hypervariable region (HVR) sequences selected from the group consisting of: (a) HVR-H1 comprising the sequence of GFTFSGSGIH (SEQ ID NO:65); (b) HVR-H2 comprising the sequence of AWISPTGGNTYYADSVKG (SEQ ID NO:66); (c) HVR-H3 comprising the sequence of RGLFHNVAFDY (SEQ ID NO:89); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQTYNAPPT (SEQ ID NO:100). In certain embodiments, the antibody comprises a heavy chain and a light chain, wherein (a) the heavy chain comprises an HVR-H1 comprising the sequence of GFTFSGSGIH (SEQ ID NO:65), an HVR-H2 comprising the sequence of AWISPTGGNTYYADSVKG (SEQ ID NO:66), and an HVR-H3 comprising the sequence of RGLFHNVAFDY (SEQ ID NO:89); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQTYNAPPT (SEQ ID NO:100). In certain embodiments, the antibody comprises a heavy chain variable region comprising the sequence of SEQ ID NO:110 and/or a light chain variable region comprising the sequence of SEQ ID NO:113. In certain embodiments, the antibody comprises at least one, two, three, four, five or six hypervariable region (HVR) sequences of antibody 51.82 (e.g., as shown in Tables 5-7). In certain embodiments, the antibody comprises a heavy chain variable region sequence and/or a light chain variable region sequence of antibody 51.82 (e.g., as shown in Table 7).

In yet another aspect, provided herein is an anti-NSP4 antibody comprising (a) an HVR-H2 comprising the sequence of AWISPTGGNTYYADSVKG (SEQ ID NO:66) or the sequence of AWIPTAGGNTYYADSVKG (SEQ ID NO:88); (b) an HVR-H3 comprising the sequence of $X_1X_2X_3$FHNVAFDY (SEQ ID NO:91), wherein $X_1$ is K or R; $X_2$ is S, G, or V; and $X_3$ is L or F; and (c) an HVR-L3 comprising the sequence of QQX$_1$X$_2$X$_3$X$_4$PPT (SEQ ID NO:101), wherein $X_1$ is S, A, N, or T; $X_2$ is Y, N, or F; $X_3$ is T, S, or N; and $X_4$ is T, A, or S. In certain embodiments, the antibody comprises (a) an HVR-H2 comprising the sequence of AWISPTGGNTYYADSVKG (SEQ ID NO:66); (b) an HVR-H3 comprising the sequence of KSLFHNVAFDY (SEQ ID NO:67); and (c) an HVR-L3 comprising the sequence of QQSYTTPPT (SEQ ID NO:12). In certain embodiments, the antibody comprises (a) an HVR-H2 comprising the sequence of AWIPTAGGNTYYADSVKG (SEQ ID NO:88); (b) an HVR-H3 comprising the sequence of KSLFHNVAFDY (SEQ ID NO:67); and (c) an HVR-L3 comprising the sequence of QQSYTAPPT (SEQ ID NO:97). In certain embodiments, the antibody comprises (a) an HVR-H2 comprising the sequence of AWISPTGGNTYYADSVKG (SEQ ID NO:66); (b) an HVR-H3 comprising the sequence of KSLFHNVAFDY (SEQ ID NO:67); and (c) an HVR-L3 comprising the sequence of QQANSTPPT (SEQ ID NO:98). In certain embodiments, the antibody comprises (a) an HVR-H2 comprising the sequence of AWISPTGGNTYYADSVKG (SEQ ID NO:66); (b) an HVR-H3 comprising the sequence of RGLFHNVAFDY (SEQ ID NO:89); and (c) an HVR-L3 comprising the sequence of QQSYTAPPT (SEQ ID NO:97). In certain embodiments, the antibody comprises (a) an HVR-H2 comprising the sequence of AWISPTGGNTYYADSVKG (SEQ ID NO:66); (b) an HVR-H3 comprising the sequence of RVFFHNVAFDY (SEQ ID NO:90); and (c) an HVR-L3 comprising the sequence of QQNFSSPPT (SEQ ID NO:99). In certain embodiments, the antibody comprises (a) an HVR-H2 comprising the sequence of AWISPTGGNTYYADSVKG (SEQ ID NO:66); (b) an HVR-H3 comprising the sequence of KSLFHNVAFDY (SEQ ID NO:67); and (c) an HVR-L3 comprising the sequence of QQSYTAPPT (SEQ ID NO:97). In certain embodiments, the antibody comprises (a) an HVR-H2 comprising the sequence of AWISPTGGNTYYADSVKG (SEQ ID NO:66); (b) an HVR-H3 comprising the sequence of RGLFHNVAFDY (SEQ ID NO:89); and (c) an HVR-L3 comprising the sequence of QQTYNAPPT (SEQ ID NO:100).

In another aspect, provided herein is an anti-NSP4 antibody comprising at least one, two, three, four, five or six hypervariable region (HVR) sequences selected from the group consisting of: (a) HVR-H1 comprising the sequence of GFTFSGSWIS (SEQ ID NO:20); (b) HVR-H2 comprising the sequence of GTISPYNGSTYYADSVKG (SEQ ID NO:21); (c) HVR-H3 comprising the sequence of RVLRPKVYASVMDY (SEQ ID NO:22); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSYTTPPT (SEQ ID NO:12). In certain embodiments, the antibody comprises (a) HVR-H2 comprising the sequence of GTISPYNGSTYYADSVKG (SEQ ID NO:21); (b) HVR-H3 comprising the sequence of RVLRPKVYASVMDY (SEQ ID NO:22); and (c) an HVR-L3 comprising the sequence of QQSYTTPPT (SEQ ID NO:12). In certain embodiments, the antibody comprises a heavy chain and a light chain, wherein (a) the heavy chain comprises an HVR-H1 comprising the sequence of GFTFSGSWIS (SEQ ID NO:20), an HVR-H2 comprising the sequence of GTISPYNGSTYYADSVKG (SEQ ID NO:21), and an HVR-H3 comprising the sequence of RVLRPKVYAS-VMDY (SEQ ID NO:22); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSYTTPPT (SEQ ID NO:12). In certain embodiments, the antibody comprises a heavy chain variable region comprising the sequence of SEQ ID NO:68 and/or a light chain variable region comprising the sequence of SEQ ID NO:16. In certain embodiments, the antibody comprises at least one, two, three, four, five, or six hypervariable region (HVR) sequences of antibody 1-1 (e.g., as shown in Tables 3 and 4 and SEQ ID NO:19, 11, and 12). In certain embodiments, the antibody comprises a heavy chain variable region sequence and/or a light chain variable region sequence of antibody 1-1 (e.g., as shown in Table 4 and SEQ ID NO:19, 11, and 12).

In yet another aspect, provided herein is an anti-NSP4 antibody comprising at least one, two, three, four, five or six hypervariable region (HVR) sequences selected from the group consisting of: (a) HVR-H1 comprising the sequence of GFTFSGYSIH (SEQ ID NO:23); (b) HVR-H2 comprising the sequence of AGISPTNGYTDYADSVKG (SEQ ID NO:24); (c) HVR-H3 comprising the sequence of RLVFYRGVMDY (SEQ ID NO:25); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSYTTPPT (SEQ ID NO:12). In certain embodiments, the antibody comprises (a) an HVR-H2 comprising the sequence of AGISPTNGYTDYADSVKG (SEQ ID NO:24); (b) an HVR-H3 comprising the sequence of RLVFYRGVMDY (SEQ ID NO:25); and (c) an HVR-L3 comprising the sequence of QQSYTTPPT (SEQ ID NO:12). In certain embodiments, the antibody comprises a heavy chain and a light chain, wherein (a) the heavy chain comprises an HVR-H1 comprising the sequence of GFTFSGYSIH (SEQ ID NO:23), an HVR-H2 comprising the sequence of AGISPTNGYTDYADSVKG (SEQ ID NO:24), and an HVR-H3 comprising the sequence of RLVFYRGVMDY (SEQ ID NO:25); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSYTTPPT (SEQ ID NO:12). In certain embodiments, the antibody comprises a heavy chain variable region comprising the sequence of SEQ ID NO:69 and/or a light chain variable region comprising the sequence of SEQ ID NO:16. In certain embodiments, the antibody comprises at least one, two, three, four, five, or six hypervariable region (HVR) sequences of antibody 1-2 (e.g., as shown in Tables 3 and 4 and SEQ ID NO:19, 11, and 12). In certain embodiments, the antibody comprises a heavy chain variable region sequence and/or a light chain variable region sequence of antibody 1-2 (e.g., as shown in Table 4 and SEQ ID NO:19, 11, and 12).

In yet another aspect, provided herein is an anti-NSP4 antibody comprising at least one, two, three, four, five or six hypervariable region (HVR) sequences selected from the group consisting of: (a) HVR-H1 comprising the sequence of GFTFSDNWIS (SEQ ID NO:26); (b) HVR-H2 comprising the sequence of GYIYPASGYTDYADSVKG (SEQ ID NO:27); (c) HVR-H3 comprising the sequence of SDSPHAYWYAMDY (SEQ ID NO:28); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSYTTPPT (SEQ ID NO:12). In certain embodiments, the antibody comprises (a) an HVR-H2 comprising the sequence of GYIYPASGYTDYADSVKG (SEQ ID NO:27); (b) an HVR-H3 comprising the sequence of SDSPHAYWY-AMDY (SEQ ID NO:28); and (c) an HVR-L3 comprising the sequence of QQSYTTPPT (SEQ ID NO:12). In certain embodiments, the antibody comprises a heavy chain and a light chain, wherein (a) the heavy chain comprises an HVR-H1 comprising the sequence of GFTFSDNWIS (SEQ ID NO:26), an HVR-H2 comprising the sequence of GYIYPASGYTDYADSVKG (SEQ ID NO:27), and an HVR-H3 comprising the sequence of SDSPHAYWYAMDY (SEQ ID NO:28); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSYTTPPT (SEQ ID NO:12). In certain embodiments, the antibody comprises a heavy chain variable region comprising the sequence of SEQ ID NO:70 and/or a light chain variable region comprising the sequence of SEQ ID NO:16. In certain embodiments, the antibody comprises at least one, two, three, four, five, or six hypervariable region (HVR) sequences of antibody 1-3 (e.g., as shown in Tables 3 and 4 and SEQ ID NO:19, 11, and 12). In certain embodiments, the antibody comprises a heavy chain variable region sequence and/or a light chain variable region sequence of antibody 1-3 (e.g., as shown in Table 4 and SEQ ID NO:19, 11, and 12).

In yet another aspect, provided herein is an anti-NSP4 antibody comprising at least one, two, three, four, five or six hypervariable region (HVR) sequences selected from the group consisting of: (a) HVR-H1 comprising the sequence of GFTFTNNSIS (SEQ ID NO:29); (b) HVR-H2 comprising the sequence of GAISPNNGSTYYADSVKG (SEQ ID NO:30); (c) HVR-H3 comprising the sequence of RNAWHYSWVGVMDY (SEQ ID NO:31); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSYTTPPT (SEQ ID NO:12). In certain embodiments, the antibody comprises (a) an HVR-H2 comprising the sequence of GAISPNNGSTYYADSVKG (SEQ ID NO:30); (b) an HVR-H3 comprising the sequence of RNAWHYSWVGVMDY (SEQ ID NO:31); and (c) an HVR-L3 comprising the sequence of QQSYTTPPT (SEQ ID NO:12). In certain embodiments, the antibody comprises a heavy chain and a light chain, wherein (a) the heavy chain comprises an HVR-H1 comprising the sequence of GFTFTNNSIS (SEQ ID NO:29), an HVR-H2 comprising the sequence of GAISPNNGSTYYADSVKG (SEQ ID NO:30), and an HVR-H3 comprising the sequence of RNAWHYSWVGVMDY (SEQ ID NO:31); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSYTTPPT (SEQ ID NO:12). In certain embodiments, the antibody comprises a heavy chain variable region comprising the sequence of SEQ ID NO:71 and/or a light chain variable region comprising the sequence of SEQ ID NO:16. In certain embodiments, the antibody comprises at least one, two, three, four, five, or six hypervariable region (HVR) sequences of antibody 1-5 (e.g., as shown in Tables 3 and 4 and SEQ ID NO:19, 11, and 12). In certain embodiments, the antibody comprises a heavy chain variable region sequence and/or a light chain variable region sequence of antibody 1-5 (e.g., as shown in Table 4 and SEQ ID NO:19, 11, and 12).

In yet another aspect, provided herein is an anti-NSP4 antibody comprising at least one, two, three, four, five or six hypervariable region (HVR) sequences selected from the group consisting of: (a) HVR-H1 comprising the sequence of GFTFTDYSIH (SEQ ID NO:32); (b) HVR-H2 comprising the sequence of AEIYPYSGDTYYADSVKG (SEQ ID NO:33); (c) HVR-H3 comprising the sequence of RDGDGWFDWAMDY (SEQ ID NO:34); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSYTTPPT (SEQ ID NO:12). In certain embodiments, the antibody comprises (a) an HVR-H2 comprising the sequence of AEIYPYSGDTYYADSVKG (SEQ ID NO:33); (b) an HVR-H3 comprising the sequence of RDGDGWFDWAMDY (SEQ ID NO:34); and (c) an HVR-L3 comprising the sequence of QQSYTTPPT (SEQ ID NO:12). In certain embodiments, the antibody comprises a heavy chain and a light chain, wherein (a) the heavy chain comprises an HVR-H1 comprising the sequence of GFTFTDYSIH (SEQ ID NO:32), an HVR-H2 comprising the sequence of AEIYPYSGDTYYADSVKG (SEQ ID NO:33), and an HVR-H3 comprising the sequence of RDGDGWFDWAMDY (SEQ ID NO:34); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSYTTPPT (SEQ ID NO:12). In certain embodiments, the antibody comprises a heavy chain variable region comprising the sequence of SEQ ID NO:72 and/or a light chain variable region comprising the sequence of SEQ ID NO:16. In certain embodiments, the antibody comprises at least one, two, three, four, five, or six hypervariable region (HVR) sequences of antibody 2-1 (e.g., as shown in Tables 3 and 4 and SEQ ID NO:19, 11, and 12). In certain embodiments, the antibody comprises a heavy chain variable region sequence and/or a light chain variable region sequence of antibody 2-1 (e.g., as shown in Table 4 and SEQ ID NO:19, 11, and 12).

In yet another aspect, provided herein is an anti-NSP4 antibody comprising at least one, two, three, four, five or six hypervariable region (HVR) sequences selected from the group consisting of: (a) HVR-H1 comprising the sequence of GFTFSSTAIS (SEQ ID NO:35); (b) HVR-H2 comprising the sequence of GEIYPSDGYTDYADSVKG (SEQ ID NO:36); (c) HVR-H3 comprising the sequence of RVKWAVSSLGVMDY (SEQ ID NO:37); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSYTTPPT (SEQ ID NO:12). In certain embodiments, the antibody comprises (a) an HVR-H2 comprising the sequence of GEIYPSDGYTDYADSVKG (SEQ ID NO:36); (b) an HVR-H3 comprising the sequence of RVKWAVSSLGVMDY (SEQ ID NO:37); and (c) an HVR-L3 comprising the sequence of QQSYTTPPT (SEQ ID NO:12). In certain embodiments, the antibody comprises a heavy chain and a light chain, wherein (a) the heavy chain comprises an HVR-H1 comprising the sequence of GFTFSSTAIS (SEQ ID NO:35), an HVR-H2 comprising the sequence of GEIYPSDGYTDYADSVKG (SEQ ID NO:36), and an HVR-H3 comprising the sequence of RVKWAVSSLGVMDY (SEQ ID NO:37); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSYTTPPT (SEQ ID NO:12). In certain embodiments, the antibody comprises a heavy chain variable region comprising the sequence of SEQ ID NO:73 and/or a light chain variable region comprising the sequence of SEQ ID NO:16. In certain embodiments, the antibody comprises at least one, two, three, four, five, or six hypervariable region (HVR) sequences of antibody 2-2 (e.g., as shown in Tables 3 and 4 and SEQ ID NO:19, 11, and 12). In certain embodiments, the antibody comprises a heavy chain variable region sequence and/or a light chain variable region sequence of antibody 2-2 (e.g., as shown in Table 4 and SEQ ID NO:19, 11, and 12).

In yet another aspect, provided herein is an anti-NSP4 antibody comprising at least one, two, three, four, five or six hypervariable region (HVR) sequences selected from the group consisting of: (a) HVR-H1 comprising the sequence of GFTFTDSDIS (SEQ ID NO:38); (b) HVR-H2 comprising the sequence of AWISPSDGATDYADSVKG (SEQ ID NO:39); (c) HVR-H3 comprising the sequence of HEASDDDYAIDY (SEQ ID NO:40); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSYTTPPT (SEQ ID NO:12). In certain embodiments, the antibody comprises (a) an HVR-H2 comprising the sequence of AWISPSDGATDYADSVKG (SEQ ID NO:39); (b) an HVR-H3 comprising the sequence of HEASDDDYAIDY (SEQ ID NO:40); and (c) an HVR-L3 comprising the sequence of QQSYTTPPT (SEQ ID NO:12). In certain embodiments, the antibody comprises a heavy chain and a light chain, wherein (a) the heavy chain comprises an HVR-H1 comprising the sequence of GFTFTDSDIS (SEQ ID NO:38), an HVR-H2 comprising the sequence of AWISPSDGATDYADSVKG (SEQ ID NO:39), and an HVR-H3 comprising the sequence of HEASDDDYAIDY (SEQ ID NO:40); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSYTTPPT (SEQ ID NO:12). In certain embodiments, the antibody comprises a heavy chain variable region comprising the sequence of SEQ ID NO:74 and/or a light chain variable region comprising the sequence of SEQ ID NO:16. In certain embodiments, the antibody comprises at least one, two, three, four, five, or six hypervariable region (HVR) sequences of antibody 2-3 (e.g., as shown in Tables 3 and 4 and SEQ ID NO:19, 11, and 12). In certain embodiments, the antibody comprises a heavy chain variable region sequence and/or a light chain variable region sequence of antibody 2-3 (e.g., as shown in Table 4 and SEQ ID NO:19, 11, and 12).

In yet another aspect, provided herein is an anti-NSP4 antibody comprising at least one, two, three, four, five or six hypervariable region (HVR) sequences selected from the group consisting of: (a) HVR-H1 comprising the sequence of GFTFSDYWIS (SEQ ID NO:41); (b) HVR-H2 comprising the sequence of AGISPNNGDTYYADSVKG (SEQ ID NO:42); (c) HVR-H3 comprising the sequence of REDDERDYAMDY (SEQ ID NO:43); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSYTTPPT (SEQ ID NO:12). In certain embodiments, the antibody comprises (a) an HVR-H2 comprising the sequence of AGISPNNGDTYYADSVKG (SEQ ID NO:42); (b) an HVR-H3 comprising the sequence of REDDDERDYAMDY (SEQ ID NO:43); and (c) an HVR-L3 comprising the sequence of QQSYTTPPT (SEQ ID NO:12). In certain embodiments, the antibody comprises a heavy chain and a light chain, wherein (a) the heavy chain comprises an HVR-H1 comprising the sequence of GFTFSDYWIS (SEQ ID NO:41), an HVR-H2 comprising the sequence of AGISPNNGDTYYADSVKG (SEQ ID NO:42), and an HVR-H3 comprising the sequence of REDDDERDYAMDY (SEQ ID NO:43); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSYTTPPT (SEQ ID NO:12). In certain embodiments, the antibody comprises a heavy chain variable region comprising the sequence of SEQ ID NO:75 and/or a light chain variable region comprising the sequence of SEQ ID NO:16. In certain embodiments, the antibody comprises at least one, two, three, four, five, or six hypervariable region (HVR) sequences of antibody 2-4 (e.g., as shown in Tables 3 and 4 and SEQ ID NO:19, 11, and 12). In certain embodiments, the antibody comprises a heavy chain variable region sequence and/or a light chain variable region sequence of antibody 2-4 (e.g., as shown in Table 4 and SEQ ID NO:19, 11, and 12).

In yet another aspect, provided herein is an anti-NSP4 antibody comprising at least one, two, three, four, five or six hypervariable region (HVR) sequences selected from the group consisting of: (a) HVR-H1 comprising the sequence of GFTFTGYGIS (SEQ ID NO:44); (b) HVR-H2 comprising the sequence of GWIYPASGATYYADSVKG (SEQ ID NO:45); (c) HVR-H3 comprising the sequence of RHRAFDWYPYYIGSSVMDY (SEQ ID NO:46); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSYTTPPT (SEQ ID NO:12). In certain embodiments, the antibody comprises (a) an HVR-H2 comprising the sequence of GWIYPASGATYYADSVKG (SEQ ID NO:45); (b) an HVR-H3 comprising the sequence of RHRAFDWYPYYIGSSVMDY (SEQ ID NO:46); and (c) an HVR-L3 comprising the sequence of QQSYTTPPT (SEQ ID NO:12). In certain embodiments, the antibody comprises a heavy chain and a light chain, wherein (a) the heavy chain comprises an HVR-H1 comprising the sequence of GFTFTGYGIS (SEQ ID NO:44), an HVR-H2 comprising the sequence of GWIYPASGATYYADSVKG (SEQ ID NO:45), and an HVR-H3 comprising the sequence of RHRAFDWYPYYIGSSVMDY (SEQ ID NO:46); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSYTTPPT (SEQ ID NO:12). In certain embodiments, the antibody comprises a heavy chain variable region comprising the sequence of SEQ ID NO:76 and/or a light chain variable region comprising the sequence of SEQ ID NO:16. In certain embodiments, the antibody comprises at least one, two, three, four, five, or six hypervariable region (HVR) sequences of antibody 2-5 (e.g., as shown in Tables 3 and 4 and SEQ ID NO:19, 11, and 12). In certain embodiments, the antibody comprises a heavy chain variable region sequence and/or a light chain variable region sequence of antibody 2-5 (e.g., as shown in Table 4 and SEQ ID NO:19, 11, and 12).

In yet another aspect, provided herein is an anti-NSP4 antibody comprising at least one, two, three, four, five or six hypervariable region (HVR) sequences selected from the group consisting of: (a) HVR-H1 comprising the sequence of GFTFSDYSIS (SEQ ID NO:47); (b) HVR-H2 comprising the sequence of GEINPAGGATYYADSVKG (SEQ ID NO:48); (c) HVR-H3 comprising the sequence of RGDFPFWSDAYYVMDY (SEQ ID NO:49); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSYTTPPT (SEQ ID NO:12). In certain embodiments, the antibody comprises (a) an HVR-H2 comprising the sequence of GEINPAGGATYYADSVKG (SEQ ID NO:48); (b) an HVR-H3 comprising the sequence of RGDFPFWSDAYYVMDY (SEQ ID NO:49); and (c) an HVR-L3 comprising the sequence of QQSYTTPPT (SEQ ID NO:12). In certain embodiments, the antibody comprises a heavy chain and a light chain, wherein (a) the heavy chain comprises an HVR-H1 comprising the sequence of GFTFSDYSIS (SEQ ID NO:47), an HVR-H2 comprising the sequence of GEINPAGGATYYADSVKG (SEQ ID NO:48), and an HVR-H3 comprising the sequence of RGDFPFWSDAYYVMDY (SEQ ID NO:49); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSYTTPPT (SEQ ID NO:12). In certain embodiments, the antibody comprises a heavy chain variable region comprising the sequence of SEQ ID NO:77 and/or a light chain variable region comprising the sequence of SEQ ID NO:16. In certain embodiments, the antibody comprises at least one, two, three, four, five, or six hypervariable region (HVR) sequences of antibody 3-2 (e.g., as shown in Tables 3 and 4 and SEQ ID NO:19, 11, and 12). In certain embodiments, the antibody comprises a heavy chain variable region sequence and/or a light chain variable region sequence of antibody 3-2 (e.g., as shown in Table 4 and SEQ ID NO:19, 11, and 12).

In yet another aspect, provided herein is an anti-NSP4 antibody comprising at least one, two, three, four, five or six hypervariable region (HVR) sequences selected from the group consisting of: (a) HVR-H1 comprising the sequence of GFTFSDNDIS (SEQ ID NO:50); (b) HVR-H2 comprising the sequence of GSISPDNGDTNYADSVKG (SEQ ID NO:51); (c) HVR-H3 comprising the sequence of RDDVPAVFTSAMDY (SEQ ID NO:52); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSYTTPPT (SEQ ID NO:12). In certain embodiments, the antibody comprises (a) an HVR-H2 comprising the sequence of GSISPDNGDTNYADSVKG (SEQ ID NO:51); (b) an HVR-H3 comprising the sequence of RDDVPAVFTSAMDY (SEQ ID NO:52); and (c) an HVR-L3 comprising the sequence of QQSYTTPPT (SEQ ID NO:12). In certain embodiments, the antibody comprises a heavy chain and a light chain, wherein (a) the heavy chain comprises an HVR-H1 comprising the sequence of GFTFSDNDIS (SEQ ID NO:50), an HVR-H2 comprising the sequence of GSISPDNGDTNYADSVKG (SEQ ID NO:51), and an HVR-H3 comprising the sequence of RDDVPAVFTSAMDY (SEQ ID NO:52); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSYTTPPT (SEQ ID NO:12). In certain embodiments, the antibody comprises a heavy chain variable region comprising the sequence of SEQ ID NO:78 and/or a light chain variable region comprising the sequence of SEQ ID NO:16. the antibody comprises at least one, two, three, four, five, or six hypervariable region (HVR) sequences of antibody 3-5 (e.g., as shown in Tables 3 and 4 and SEQ ID NO:19, 11, and 12). In certain embodiments, the antibody comprises a heavy chain variable region sequence and/or a light chain variable region sequence of antibody 3-5 (e.g., as shown in Table 4 and SEQ ID NO:19, 11, and 12).

In yet another aspect, provided herein is an anti-NSP4 antibody comprising at least one, two, three, four, five or six hypervariable region (HVR) sequences selected from the group consisting of: (a) HVR-H1 comprising the sequence of GFTFSGSDIS (SEQ ID NO:53); (b) HVR-H2 comprising the sequence of GEIYPSNGDTYYADSVKG (SEQ ID NO:54); (c) HVR-H3 comprising the sequence of RSVRPSWWAMDY (SEQ ID NO:55); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSYTTPPT (SEQ ID NO:12). In certain embodiments, the antibody comprises (a) an HVR-H2 comprising the sequence of GEIYPSNGDTYYADSVKG (SEQ ID NO:54); (b) an HVR-H3 comprising the sequence of RSVRPSWWAMDY (SEQ ID NO:55); and (c) an HVR-L3 comprising the sequence of QQSYTTPPT (SEQ ID NO:12). In certain embodiments, the antibody comprises a heavy chain and a light chain, wherein (a) the heavy chain comprises an HVR-H1 comprising the sequence of GFTFSGSDIS (SEQ ID NO:53), an HVR-H2 comprising the sequence of GEIYPSNGDTYYADSVKG (SEQ ID NO:54), and an HVR-H3 comprising the sequence of RSVRPSWWAMDY (SEQ ID NO:55); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSYTTPPT (SEQ ID NO:12). In certain embodiments, the antibody comprises a heavy chain variable region comprising the sequence of SEQ ID NO:79 and/or a light chain variable region comprising the sequence of SEQ ID NO:16. In certain embodiments, the antibody comprises at least one, two, three, four, five, or six hypervariable region (HVR) sequences of antibody 4-2 (e.g., as shown in Tables 3 and 4 and SEQ ID NO:19, 11, and 12). In certain embodiments, the antibody comprises a heavy chain variable region sequence and/or a light chain variable region sequence of antibody 4-2 (e.g., as shown in Table 4 and SEQ ID NO:19, 11, and 12).

In yet another aspect, provided herein is an anti-NSP4 antibody comprising at least one, two, three, four, five or six hypervariable region (HVR) sequences selected from the group consisting of: (a) HVR-H1 comprising the sequence of GFTFSSYDIS (SEQ ID NO:56); (b) HVR-H2 comprising the sequence of GTISPYDGYTDYADSVKG (SEQ ID NO:57); (c) HVR-H3 comprising the sequence of RYIRRYSVHYGMDY (SEQ ID NO:58); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSYTTPPT (SEQ ID NO:12). In certain embodiments, the antibody comprises (a) an HVR-H2 comprising the sequence of GTISPYDGYTDYADSVKG (SEQ ID NO:57); (b) an HVR-H3 comprising the sequence of RYIRRYSVHYGMDY (SEQ ID NO:58); and (c) an HVR-L3 comprising the sequence of QQSYTTPPT (SEQ ID NO:12). In certain embodiments, the antibody comprises a heavy chain and a light chain, wherein (a) the heavy chain comprises an HVR-H1 comprising the sequence of GFTFSSYDIS (SEQ ID NO:56), an HVR-H2 comprising the sequence of GTISPYDGYTDYADSVKG (SEQ ID NO:57), and an HVR-H3 comprising the sequence of RYIRRYSVHYGMDY (SEQ ID NO:58); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSYTTPPT (SEQ ID NO:12). In certain embodiments, the antibody comprises a heavy chain variable region comprising the sequence of SEQ ID NO:80 and/or a light chain variable region comprising the sequence of SEQ ID NO:16. In certain embodiments, the antibody comprises at least one, two, three, four, five, or six hypervariable region (HVR) sequences of antibody 4-3 (e.g., as shown in Tables 3 and 4 and SEQ ID NO:19, 11, and 12). In certain embodiments, the antibody comprises a heavy chain variable region sequence and/or a light chain variable region sequence of antibody 4-3 (e.g., as shown in Table 4 and SEQ ID NO:19, 11, and 12).

In yet another aspect, provided herein is an anti-NSP4 antibody comprising at least one, two, three, four, five or six hypervariable region (HVR) sequences selected from the group consisting of: (a) HVR-H1 comprising the sequence of GFTFTSTSIH (SEQ ID NO:59); (b) HVR-H2 comprising the sequence of AEITPHGGYTNYADSVKG (SEQ ID NO:60); (c) HVR-H3 comprising the sequence of RGRTKWGWLYGMDY (SEQ ID NO:61); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSYTTPPT (SEQ ID NO:12). In certain embodiments, the antibody comprises (a) an HVR-H2 comprising the sequence of AEITPHGGYTNYADSVKG (SEQ ID NO:60); (b) an HVR-H3 comprising the sequence of RGRTKWGWLYGMDY (SEQ ID NO:61); and (c) an HVR-L3 comprising the sequence of QQSYTTPPT (SEQ ID NO:12). In certain embodiments, the antibody comprises a heavy chain and a light chain, wherein (a) the heavy chain comprises an HVR-H1 comprising the sequence of GFTFTSTSIH (SEQ ID NO:59), an HVR-H2 comprising the sequence of AEITPHGGYTNYADSVKG (SEQ ID NO:60), and an HVR-H3 comprising the sequence of RGRTKWGWLYGMDY (SEQ ID NO:61); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSYTTPPT (SEQ ID NO:12). In certain embodiments, the antibody comprises a heavy chain variable region comprising the sequence of SEQ ID NO:81 and/or a light chain variable region comprising the sequence of SEQ ID NO:16. In certain embodiments, the antibody comprises at least one, two, three, four, five, or six hypervariable region (HVR) sequences of antibody 4-4 (e.g., as shown in Tables 3 and 4 and SEQ ID NO:19, 11, and 12). In certain embodiments, the antibody comprises a heavy chain variable region sequence and/or a light chain variable region sequence of antibody 4-4 (e.g., as shown in Table 4 and SEQ ID NO:19, 11, and 12).

In yet another aspect, provided herein is an anti-NSP4 antibody comprising at least one, two, three, four, five or six hypervariable region (HVR) sequences selected from the group consisting of: (a) HVR-H1 comprising the sequence of GFTFTNNSIH (SEQ ID NO:62); (b) HVR-H2 comprising the sequence of AEIAPDDGYTYYADSVKG (SEQ ID NO:63); (c) HVR-H3 comprising the sequence of RGVIRYAYLYAMDY (SEQ ID NO:64); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSYTTPPT (SEQ ID NO:12). In certain embodiments, the antibody comprises (a) an HVR-H2 comprising the sequence of AEIAPDDGYTYYADSVKG (SEQ ID NO:63); (b) an HVR-H3 comprising the sequence of RGVIRYAYLYAMDY (SEQ ID NO:64); and (c) an HVR-L3 comprising the sequence of QQSYTTPPT (SEQ ID NO:12). In certain embodiments, the antibody comprises a heavy chain and a light chain, wherein (a) the heavy chain comprises an HVR-H1 comprising the sequence of GFTFTNNSIH (SEQ ID NO:62), an HVR-H2 comprising the sequence of AEIAPDDGYTYYADSVKG (SEQ ID NO:63), and an HVR-H3 comprising the sequence of RGVIRYAYLYAMDY (SEQ ID NO:64); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSYTTPPT (SEQ ID NO:12). In certain embodiments, the antibody comprises a heavy chain variable region comprising the sequence of SEQ ID NO:82 and/or a light chain variable region comprising the sequence of SEQ ID NO:16. In certain embodiments, the antibody comprises at least one, two, three, four, five, or six hypervariable region (HVR) sequences of antibody 4-5 (e.g., as shown in Tables 3 and 4 and SEQ ID NO:19, 11, and 12). In certain embodiments, the antibody comprises a heavy chain variable region sequence and/or a light chain variable region sequence of antibody 4-5 (e.g., as shown in Table 4 and SEQ ID NO:19, 11, and 12).

In yet another aspect, provided herein is an anti-NSP4 antibody comprising at least one, two, three, four, five or six hypervariable region (HVR) sequences selected from the group consisting of: (a) HVR-H1 comprising the sequence of GFTFSGSGIH (SEQ ID NO:65); (b) HVR-H2 comprising the sequence of AWISPTGGNTYYADSVKG (SEQ ID NO:66); (c) HVR-H3 comprising the sequence of KSLFHNVAFDY (SEQ ID NO:67); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSYTTPPT (SEQ ID NO:12). In certain embodiments, the antibody comprises (a) an HVR-H2 comprising the sequence of AWISPTGGNTYYADSVKG (SEQ ID NO:66); (b) an HVR-H3 comprising the sequence of KSLFHNVAFDY (SEQ ID NO:67); and (c) an HVR-L3 comprising the sequence of QQSYTTPPT (SEQ ID NO:12). In certain embodiments, the antibody comprises a heavy chain and a light chain, wherein (a) the heavy chain comprises an HVR-H1 comprising the sequence of GFTFSGSGIH (SEQ ID NO:65), an HVR-H2 comprising the sequence of AWISPTGGNTYYADSVKG (SEQ ID NO:66), and an HVR-H3 comprising the sequence of KSLFHNVAFDY (SEQ ID NO:67); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSYTTPPT (SEQ ID NO:12). In certain embodiments, the antibody comprises a heavy chain variable region comprising the sequence of SEQ ID NO:83 and/or a light chain variable region comprising the sequence of SEQ ID NO:16. In certain embodiments, the antibody comprises at least one, two, three, four, five, or six hypervariable region (HVR) sequences of antibody 5-1 (e.g., as shown in Tables 3 and 4 and SEQ ID NO:19, 11, and 12). In certain embodiments, the antibody comprises a heavy chain variable region sequence and/or a light chain variable region sequence of antibody 5-1 (e.g., as shown in Table 4 and SEQ ID NO:19, 11, and 12).

In yet another aspect, provided herein is an anti-NSP4 antibody comprising at least one, two, three, four, five or six hypervariable region (HVR) sequences selected from the group consisting of: (a) HVR-H1 comprising the sequence of GFTFSNTYIS (SEQ ID NO:1); (b) HVR-H2 comprising the sequence of GFIYPANGATYYADSVKG (SEQ ID NO:2); (c) HVR-H3 comprising the sequence of RRYRLSFDY (SEQ ID NO:3); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSYTTPPT (SEQ ID NO:12). In certain embodiments, the antibody comprises (a) an HVR-H2 comprising the sequence of GFIYPANGATYYADSVKG (SEQ ID NO:2); (b) an HVR-H3 comprising the sequence of RRYRLSFDY (SEQ ID NO:3); and (c) an HVR-L3 comprising the sequence of QQSYTTPPT (SEQ ID NO:12). In certain embodiments, the antibody comprises a heavy chain and a light chain, wherein (a) the heavy chain comprises an HVR-H1 comprising the sequence of GFTFSNTYIS (SEQ ID NO:1), an HVR-H2 comprising the sequence of GFIYPANGATYYADSVKG (SEQ ID NO:2), and an HVR-H3 comprising the sequence of RRYRLSFDY (SEQ ID NO:3); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSYTTPPT (SEQ ID NO:12). In certain embodiments, the antibody comprises a heavy chain variable region comprising the sequence of SEQ ID NO:84 and/or a light chain variable region comprising the sequence of SEQ ID NO:16. In certain embodiments, the antibody comprises at least one, two, three, four, five, or six hypervariable region (HVR) sequences of antibody 5-2 (e.g., as shown in Tables 3 and 4 and SEQ ID NO:19, 11, and 12). In certain embodiments, the antibody comprises a heavy chain variable region sequence and/or a light chain variable region sequence of antibody 5-2 (e.g., as shown in Table 4 and SEQ ID NO:19, 11, and 12).

In yet another aspect, provided herein is an anti-NSP4 antibody comprising at least one, two, three, four, five or six hypervariable region (HVR) sequences selected from the group consisting of: (a) HVR-H1 comprising the sequence of GFTFSGNDIS (SEQ ID NO:4); (b) HVR-H2 comprising the sequence of AGISPYGGSTYYADSVKG (SEQ ID NO:5); (c) HVR-H3 comprising the sequence of RRVSFYSRHAGMDY (SEQ ID NO:6); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSYTTPPT (SEQ ID NO:12). In certain embodiments, the antibody comprises (a) an HVR-H2 comprising the sequence of AGISPYGGSTYYADSVKG (SEQ ID NO:5); (b) an HVR-H3 comprising the sequence of RRVSFYSRHAGMDY (SEQ ID NO:6); and (c) an HVR-L3 comprising the sequence of QQSYTTPPT (SEQ ID NO:12). In certain embodiments, the antibody comprises a heavy chain and a light chain, wherein (a) the heavy chain comprises an HVR-H1 comprising the sequence of GFTFSGNDIS (SEQ ID NO:4), an HVR-H2 comprising the sequence of AGISPYGGSTYYADSVKG (SEQ ID NO:5), and an HVR-H3 comprising the sequence of RRVSFYSRHAGMDY (SEQ ID NO:6); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSYTTPPT (SEQ ID NO:12). In certain embodiments, the antibody comprises a heavy chain variable region comprising the sequence of SEQ ID NO:85 and/or a light chain variable region comprising the sequence of SEQ ID NO:16. In certain embodiments, the antibody comprises at least one, two, three, four, five, or six hypervariable region (HVR) sequences of antibody 5-3 (e.g., as shown in Tables 3 and 4 and SEQ ID NO:19, 11, and 12). In certain embodiments, the antibody comprises a heavy chain variable region sequence and/or a light chain variable region sequence of antibody 5-3 (e.g., as shown in Table 4 and SEQ ID NO:19, 11, and 12).

In yet another aspect, provided herein is an anti-NSP4 antibody comprising at least one, two, three, four, five or six hypervariable region (HVR) sequences selected from the group consisting of: (a) HVR-H1 comprising the sequence of GFTFTSYAIS (SEQ ID NO:7); (b) HVR-H2 comprising the sequence of AGISPSNGYTNYADSVKG (SEQ ID NO:8); (c) HVR-H3 comprising the sequence of RAGRWTHSDIDY (SEQ ID NO:9); (d) HVR-L1 comprising the sequence of RASQDVS (SEQ ID NO:19); (e) HVR-L2 comprising the sequence of SASFLYS (SEQ ID NO:11); and (f) HVR-L3 comprising the sequence of QQSYTTPPT (SEQ ID NO:12). In certain embodiments, the antibody comprises (a) an HVR-H2 comprising the sequence of AGISPSNGYTNYADSVKG (SEQ ID NO:8); (b) an HVR-H3 comprising the sequence of RAGRWTHSDIDY (SEQ ID NO:9); and (c) an HVR-L3 comprising the sequence of QQSYTTPPT (SEQ ID NO:12). In certain embodiments, the antibody comprises a heavy chain and a light chain, wherein (a) the heavy chain comprises an HVR-H1 comprising the sequence of GFTFTSYAIS (SEQ ID NO:7), an HVR-H2 comprising the sequence of AGISPSNGYTNYADSVKG (SEQ ID NO:8), and an HVR-H3 comprising the sequence of RAGRWTHSDIDY (SEQ ID NO:9); and/or (b) the light chain comprises an HVR-L1 comprising the sequence of RASQDVS (SEQ ID NO:19), an HVR-L2 comprising the sequence of SASFLYS (SEQ ID NO:11), and an HVR-L3 comprising the sequence of QQSYTTPPT (SEQ ID NO:12). In certain embodiments, the antibody comprises a heavy chain variable region comprising the sequence of SEQ ID NO:86 and/or a light chain variable region comprising the sequence of SEQ ID NO:16. In certain embodiments, the antibody comprises at least one, two, three, four, five, or six hypervariable region (HVR) sequences of antibody 5-4 (e.g., as shown in Tables 3 and 4 and SEQ ID NO:19, 11, and 12). In certain embodiments, the antibody comprises a heavy chain variable region sequence and/or a light chain variable region sequence of antibody 5-4 (e.g., as shown in Table 4 and SEQ ID NO:19, 11, and 12).

In certain embodiments that may be combined with any of the above embodiments, the antibody comprises a heavy chain constant region comprising the sequence of SEQ ID NO:114. In certain embodiments that may be combined with any of the above embodiments, the antibody comprises a light chain constant region comprising the sequence of SEQ ID NO:115.

In yet another aspect, provided herein is an anti-NSP4 antibody that specifically binds an NSP4 active site. In another aspect, provided herein is an anti-NSP4 antibody that inhibits catalytic activity of NSP4. In another aspect, provided herein is an anti-NSP4 antibody that specifically binds an NSP4 active site and inhibits catalytic activity of NSP4.

In yet another aspect, provided herein is an anti-NSP4 antibody that specifically binds an NSP4 heparin binding site. In another aspect, provided herein is an anti-NSP4 antibody that competes with heparin for binding to NSP4. In another aspect, provided herein is an anti-NSP4 antibody that specifically binds an NSP4 heparin binding site and competes with heparin for binding to NSP4.

In certain embodiments that may be combined with any of the above embodiments, the antibody is a monoclonal antibody. In certain embodiments that may be combined with any of the preceding embodiments, the antibody is an antibody fragment selected from the group consisting of a Fab, Fab'-SH, Fv, scFv, and (Fab')₂ fragment. In certain embodiments that may be combined with any of the preceding embodiments, the antibody comprises a constant region of human IgG1, IgG2, IgG3, or IgG4. In certain embodiments that may be combined with any of the preceding embodiments, the antibody specifically binds to a mature form of a NSP4. In certain embodiments that may be combined with any of the preceding embodiments, the antibody specifically binds to a mature form of NSP4 but does not bind to a precursor form of NSP4. In certain embodiments that may be combined with any of the preceding embodiments, the antibody specifically binds to a human NSP4. In certain embodiments that may be combined with any of the preceding embodiments, the antibody specifically binds to a mouse NSP4. In certain embodiments that may be combined with any of the preceding embodiments, the antibody specifically binds to both a human NSP4 and a mouse NSP4.

In another aspect, provided herein is an isolated nucleic acid encoding any of the antibodies described herein. In another aspect, provided herein is a vector comprising the nucleic acid described herein. In another aspect, provided herein is a host cell comprising the nucleic acid described herein. In another aspect, provided herein is a method for producing an antibody described herein comprising culturing the host cell described herein under conditions suitable for production of the antibody. In certain embodiments, the method for producing an antibody described herein further comprises recovering the antibody described herein produced by the host cell described herein. In another aspect, provided herein is an antibody produced by the method for producing an antibody described herein. In another aspect, provided herein is a pharmaceutical composition comprising any of the antibodies described herein and a pharmaceutically acceptable carrier.

In yet another aspect, provided herein is a method for treating or preventing a disease or disorder mediated by granulocytes in an individual comprising administering to the individual an effective amount of any of the antibodies described herein. In certain embodiments, the antibody specifically binds an NSP4 active site and/or inhibits catalytic activity of NSP4. In certain embodiments, the antibody specifically binds an NSP4 heparin binding site and/or competes with heparin for binding to NSP4. In certain embodiments, an effective amount of an antibody that specifically binds an NSP4 active site and/or inhibits catalytic activity of NSP4 and an antibody that specifically binds an NSP4 heparin binding site and/or competes with heparin for binding to NSP4 is administered to the individual. In certain embodiments that may be combined with any of the preceding embodiments, the disease or disorder is a neutrophil-mediated, an eosinophil-mediated, or a basophil-mediated disease or disorder. In certain embodiments, the neutrophil-mediated disease or disorder is selected from vascular disease and inflammatory disease. In certain embodiments, the vascular disease is selected from stroke, diabetic retinopathy, edema, diabetic macular edema, hereditary angioedema, idiopathic angioedema, leakage of vasculature, and cerebral ischemia. In certain embodiments, the inflammatory disease is selected from acute lung injury, asthma, chronic obstructive pulmonary disease (COPD), acute respiratory distress syndrome (ARDS), osteoarthritis, rheumatoid arthritis, and septic shock. In certain embodiments, the disease or disorder is selected from stroke, diabetic retinopathy, edema, diabetic macular edema, hereditary angioedema, idiopathic angioedema, leakage of vasculature, systemic lupus erythematosus (SLE), autoimmune vasculitides, cerebral ischemia, acute lung injury, anaphylaxis, systemic anaphylaxis, allergic lung inflammation, idiopathic lung fibrosis, asthma, allergic asthma, virus-induced asthma, chronic obstructive pulmonary disease (COPD), acute respiratory distress syndrome (ARDS), osteoarthritis, rheumatoid arthritis, psoriasis, psoriatic arthritis, blistering skin disease, bullous pemphigoid, inflammatory skin disease, atopic dermatitis, urticaria, eosinophilic cellulitis, cancer, lung cancer, kidney disease, glomerulonephritis, septic shock, inflammatory bowel disease, ulcerative colitis, and Crohn's disease. In certain embodiments that may be combined with any of the preceding embodiments, the individual is a human. In certain embodiments that may be combined with any of the preceding embodiments, the antibody is administered intravenously, intramuscularly, subcutaneously, topically, orally, transdermally, intraperitoneally, intraorbitally, by implantation, by inhalation, intrathecally, intraventricularly, or intranasally. In certain embodiments that may be combined with any of the preceding embodiments, the anti-NSP4 antibody is formulated in a pharmaceutical composition comprising the antibody and a pharmaceutically acceptable carrier.

In yet another aspect, provided herein is an article of manufacture comprising any of the antibodies described herein. In certain embodiments, the article of manufacture further comprises a package insert comprising instructions for using the antibody to treat or prevent a disease or disorder mediated by granulocytes in an individual. In some embodiments, the disease or disorder is an eosinophil-mediated, basophil-mediated, or a neutrophil-mediated disease or disorder. In some embodiments, the disease or disorder that can be treated by an antibody described herein is a vascular disease, an inflammatory disease, or an autoimmune disease. In some embodiments, the disease or disorder is selected from the group consisting of stroke, diabetic retinopathy, edema, diabetic macular edema, hereditary angioedema, idiopathic angioedema, leakage of vasculature, cerebral ischemia, acute lung injury, anaphylaxis, systemic anaphylaxis, allergic lung inflammation, asthma (e.g., allergic asthma, virus-induced asthma), chronic obstructive pulmonary disease (COPD), acute respiratory distress syndrome (ARDS), idiopathic pulmonary fibrosis, systemic lupus erythematosus (SLE), autoimmune vasculitides, blistering skin diseases (e.g., bullous pemphigoid), inflammatory skin diseases (e.g., atopic dermatitis, urticarial, eosinophilic cellulitis), cancer (e.g., lung cancer), kidney diseases (e.g., glomerulonephritis), osteoarthritis, rheumatoid arthritis, psoriatic arthritis, psoriasis, septic shock, inflammatory bowel disease (e.g., ulcerative colitis, Crohn's disease). In some embodiments, the individual has the disease or disorder or has been diagnosed with the disease or disorder. In some embodiments, the individual is at risk of developing the disease or disorder. In some embodiments, the individual is a human.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

DESCRIPTION OF THE FIGURES

FIGS. 4A-4B demonstrate that NSP4 possesses a basic patch that binds heparin via ionic interactions. A) Surface representation of NSP4 as shaded by Poisson-Boltzmann electrostatic calculations contoured from −5 to 5 kT/e. S1 denotes the occluded S1 pocket. B) NSP4 binding to fluorescein-conjugated heparin determined by fluorescence polarization at different ionic conditions (left) and by native polyacrylamide gel electrophoresis at the 0.15M NaCl condition (right).

FIGS. 14A-14C show a series of graphs showing specific binding of antibodies A) 5-2, B) 5-3, and C) 5-4 to the mature form of mouse NSP4 in biolayer interferometry experiments. hZ indicates precursor form of human NSP4; mZ indicates precursor form of mouse NSP4; hA indicates mature form of human NSP4; and mA indicates mature form of mouse NSP4.

FIGS. 16A-16C show a series of graphs showing the mRNA measurement of four distinct sorted bone marrow cell fractions isolated from four wild-type (WT) and four NSP4-deficient mice (NSP4 PRSS57 KO). The transcript levels in wild-type mice are denoted by circles and the transcript levels in NSP4-deficient mice are denoted by squares. Three different NSP4/Prss57 primer/probe sets that span three different exon junctions were used: A) spans exons 1-2, B) spans exons 2-3, and C) spans exons 3-4.

Figure 17:
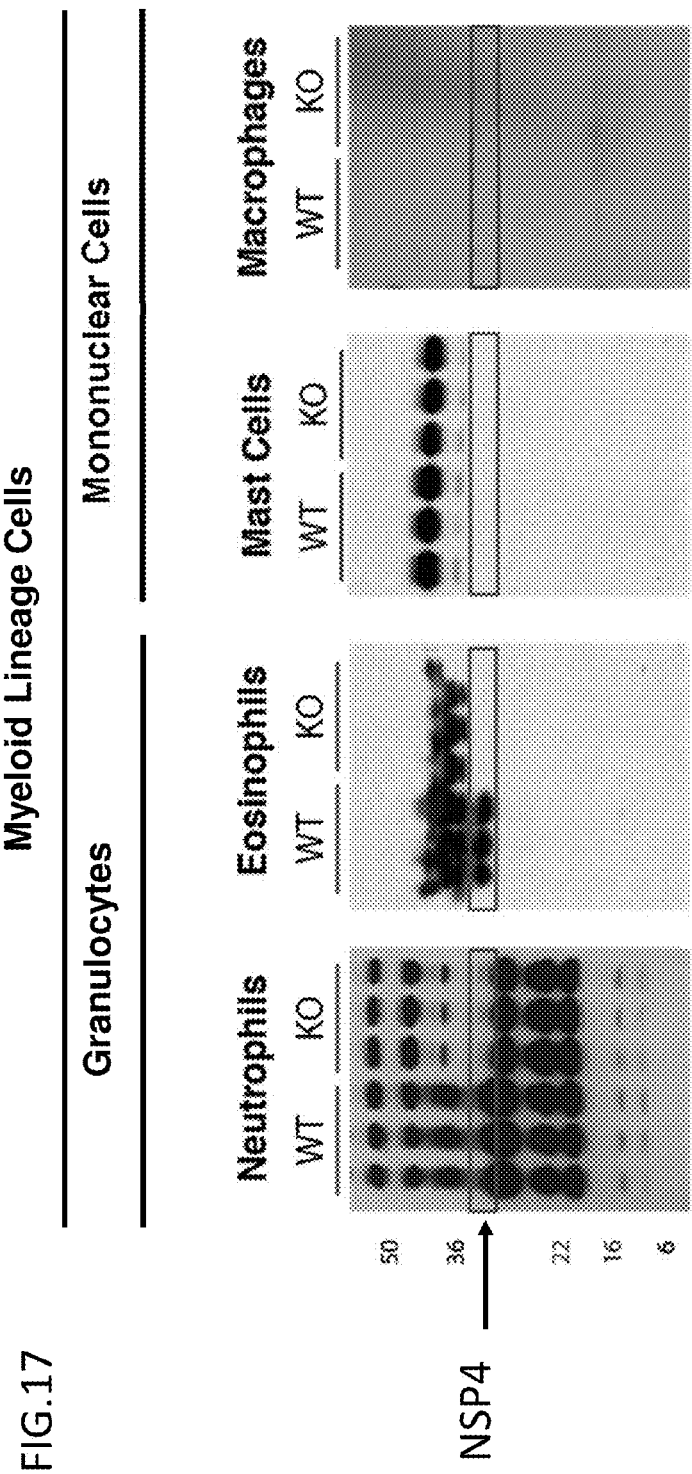

FIG. 17 is a series of Western blots performed to detect the presence of NSP4 protein in four different mouse myeloid lineage cell types (neutrophils, eosinophils, mast cells, and macrophages). Equal amounts of protein lysates (10 ug/lane) were loaded and NSP4 was detected using a rabbit anti-mouse NSP4 polyclonal antibody. Mouse bone marrow-derived neutrophil, eosinophil, mast cells, and macrophages were isolated from three wild-type (WT) and three NSP4 (Prss57)-deficient (KO) mice bone marrows.

Figure 18:
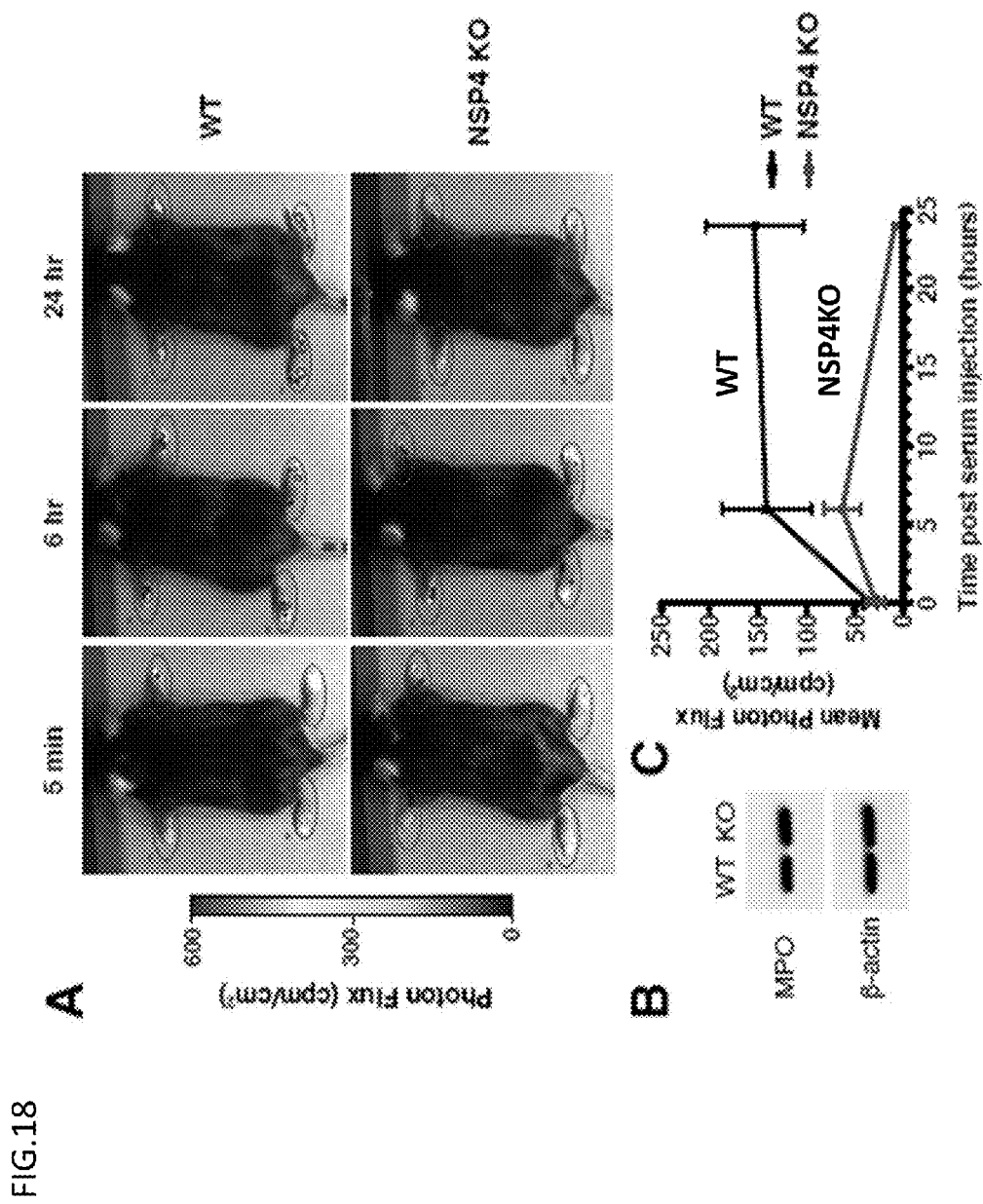

FIGS. 18A-18C show that NSP4 is necessary for neutrophil recruitment. A) Luminol-based bioluminescence imaging of myeloperoxidase (MPO) activity of mouse paws following systemic K/BxN serum injection at the indicated time points. Wildtype (WT) or NSP4-deficient (KO) mice were tested, as indicated, and quantified as photon counts per minute (cpm) per $cm^2$. B) Western blot of MPO and control protein beta actin using total mouse bone marrow-derived neutrophil lysates isolated from wild-type (WT) and NSP4-deficient (KO) mice. Each lane represented pooled lysates from three mice per genotype. C) Representative graph of luminol-based bioluminescence of mouse paws following K/BxN serum injection in wildtype (WT) or NSP4-deficient (NSP4KO) mice (n=3).

Figure 19:
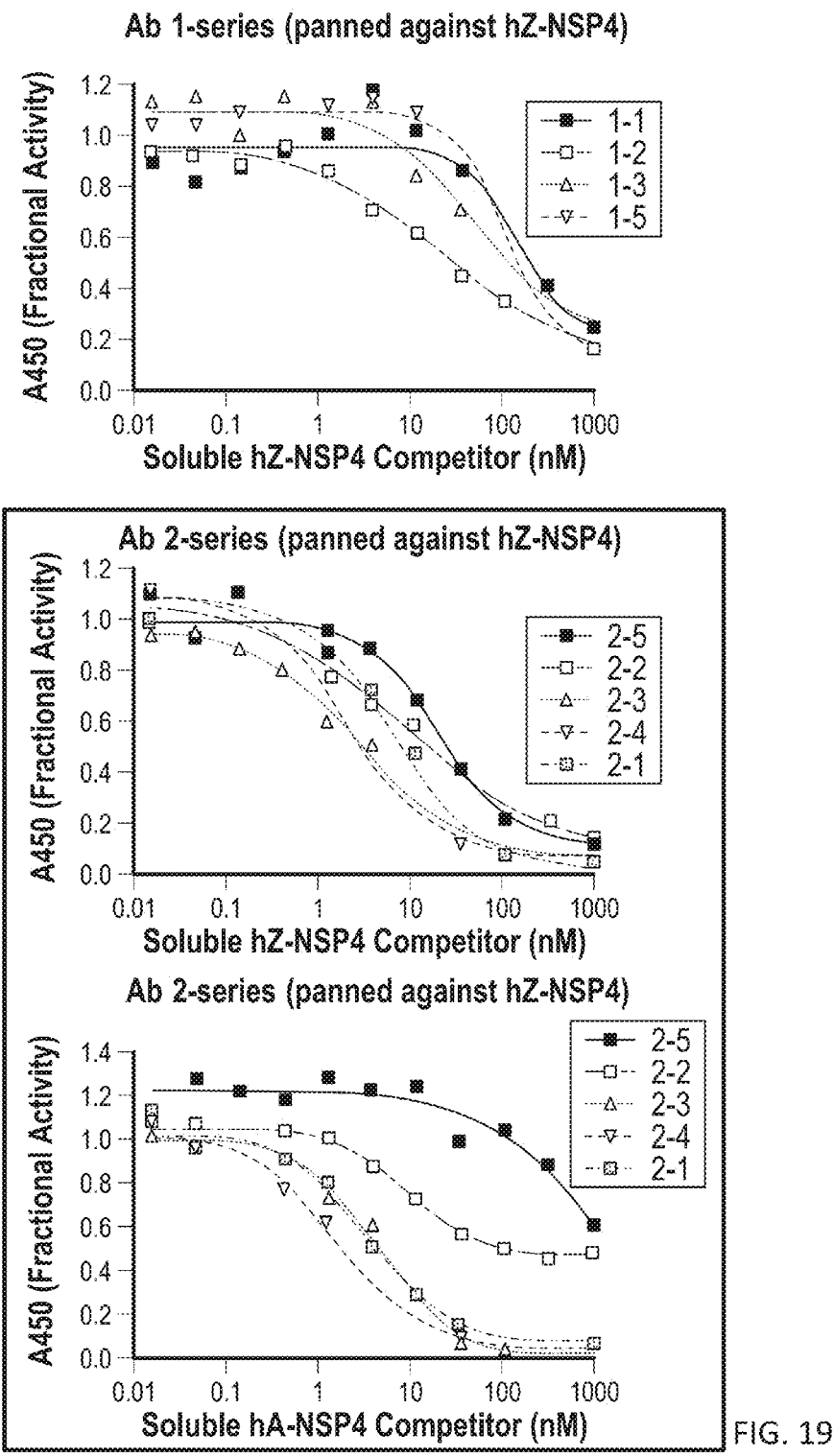

FIG. 19 shows the estimation of NSP4 antibody clone affinity by phage IC50 assay. Detection of phage clones preincubated with soluble NSP4 protein before placement into wells coated with 2 ug/ml of NSP4 and subsequent washing of wells with phosphate buffered saline supplemented with 0.02% Tween-20. hZ, human zymogen NSP4; mZ, mouse zymogen NSP4; hA, human active NSP4; mA, mouse active NSP4. Higher affinity clones bind to soluble NSP4 at lower soluble NSP4 concentrations and thus have curves shifted to the left.

Figure 20A:
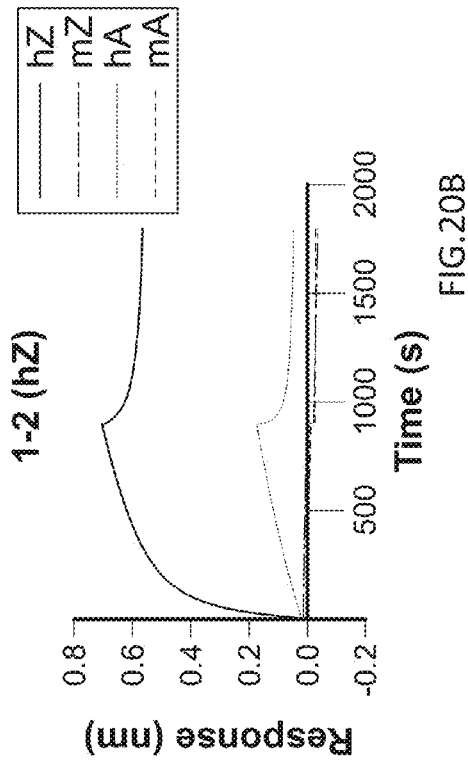
Figure 20B:
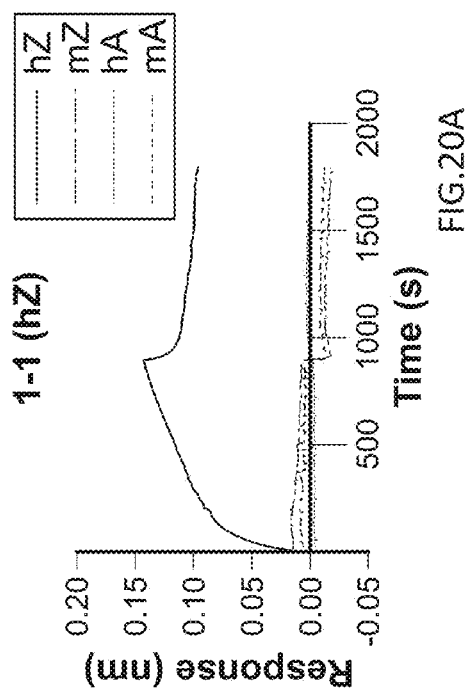

FIGS. 20A-20B show the determination of NSP4 antibody clone affinity by biolayer interferometry. Biolayer interferometry measurement of purified NSP4-specific antibodies 1-1 (A) and 1-2 (B) (both in human IgG1 format) binding to different variants of purified NSP4 protein. hZ, human zymogen NSP4; mZ, mouse zymogen NSP4; hA, human active NSP4; mA, mouse active NSP4; all as labeled.

Figure 21A:
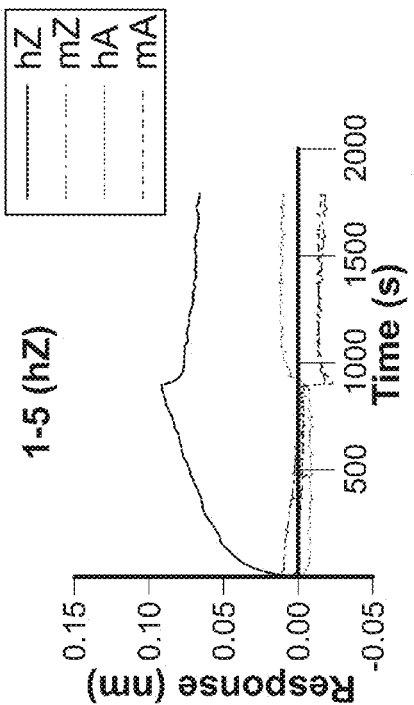
Figure 21B:
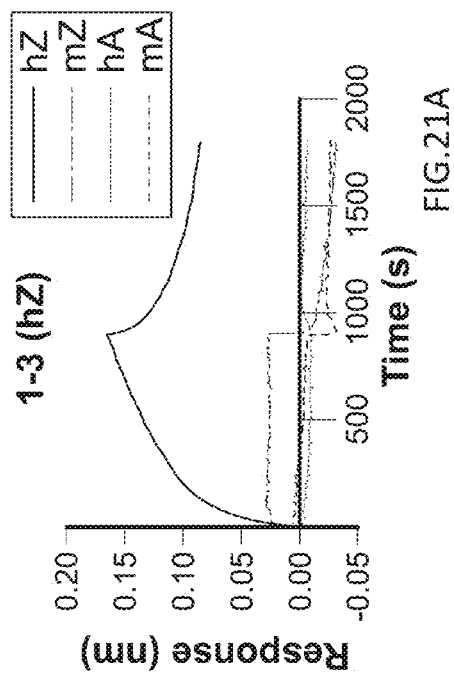

FIGS. 21A-21B show the determination of NSP4 antibody clone affinity by biolayer interferometry. Biolayer interferometry measurement of purified NSP4-specific antibodies 1-3 (A) and 1-5 (B) (both in human IgG1 format) binding to different variants of purified NSP4 protein. hZ, human zymogen NSP4; mZ, mouse zymogen NSP4; hA, human active NSP4; mA, mouse active NSP4; all as labeled.

FIGS. 22A-22D show the determination of NSP4 antibody clone affinity by biolayer interferometry. Biolayer interferometry measurement of purified NSP4-specific antibodies 2-1 (A), 2-2 (B), 2-3 (C), and 2-4 (D) (all in human IgG1 format) binding to different variants of purified NSP4 protein. hZ, human zymogen NSP4; mZ, mouse zymogen NSP4; hA, human active NSP4; mA, mouse active NSP4; all as labeled.

Figure 23:
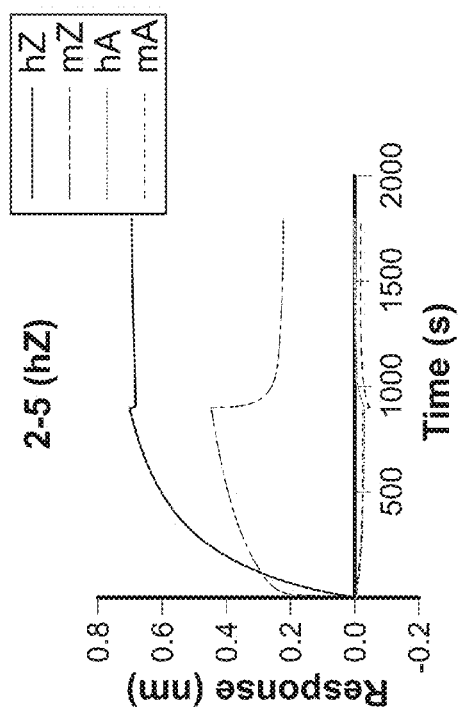

FIG. 23 shows the determination of NSP4 antibody clone affinity by biolayer interferometry. Biolayer interferometry measurement of purified NSP4-specific antibody 2-5 (in human IgG1 format) binding to different variants of purified NSP4 protein. hZ, human zymogen NSP4; mZ, mouse zymogen NSP4; hA, human active NSP4; mA, mouse active NSP4; all as labeled.

Figure 24B:
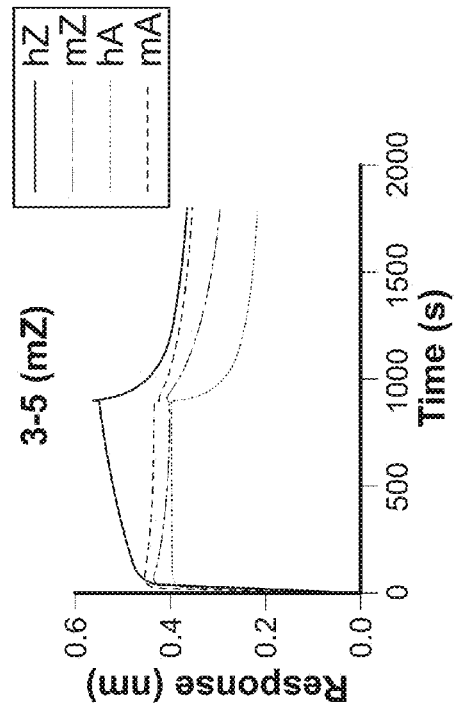
Figure 24A:
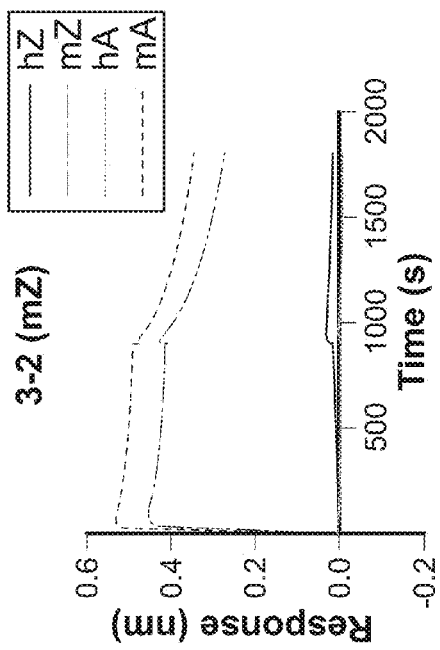

FIGS. 24A-24B show the determination of NSP4 antibody clone affinity by biolayer interferometry. Biolayer interferometry measurement of purified NSP4-specific antibodies 3-2 (A) and 3-5 (B) (both in human IgG1 format) binding to different variants of purified NSP4 protein. hZ, human zymogen NSP4; mZ, mouse zymogen NSP4; hA, human active NSP4; mA, mouse active NSP4; all as labeled.

FIGS. 25A-25C show the determination of NSP4 antibody clone affinity by biolayer interferometry. Biolayer interferometry measurement of purified NSP4-specific antibodies 4-2 (A), 4-3 (B), and 4-4 (C) (all in human IgG1 format) binding to different variants of purified NSP4 protein. hZ, human zymogen NSP4; mZ, mouse zymogen NSP4; hA, human active NSP4; mA, mouse active NSP4; all as labeled.

FIGS. 26A-26D show the determination of NSP4 antibody clone affinity by biolayer interferometry. Biolayer interferometry measurement of purified NSP4-specific antibodies 5-1 (A), 5-2 (B), 5-3 (C), and 5-4 (D) (all in human IgG1 format) binding to different variants of purified NSP4 protein. hZ, human zymogen NSP4; mZ, mouse zymogen NSP4; hA, human active NSP4; mA, mouse active NSP4; all as labeled.

Figure 27:
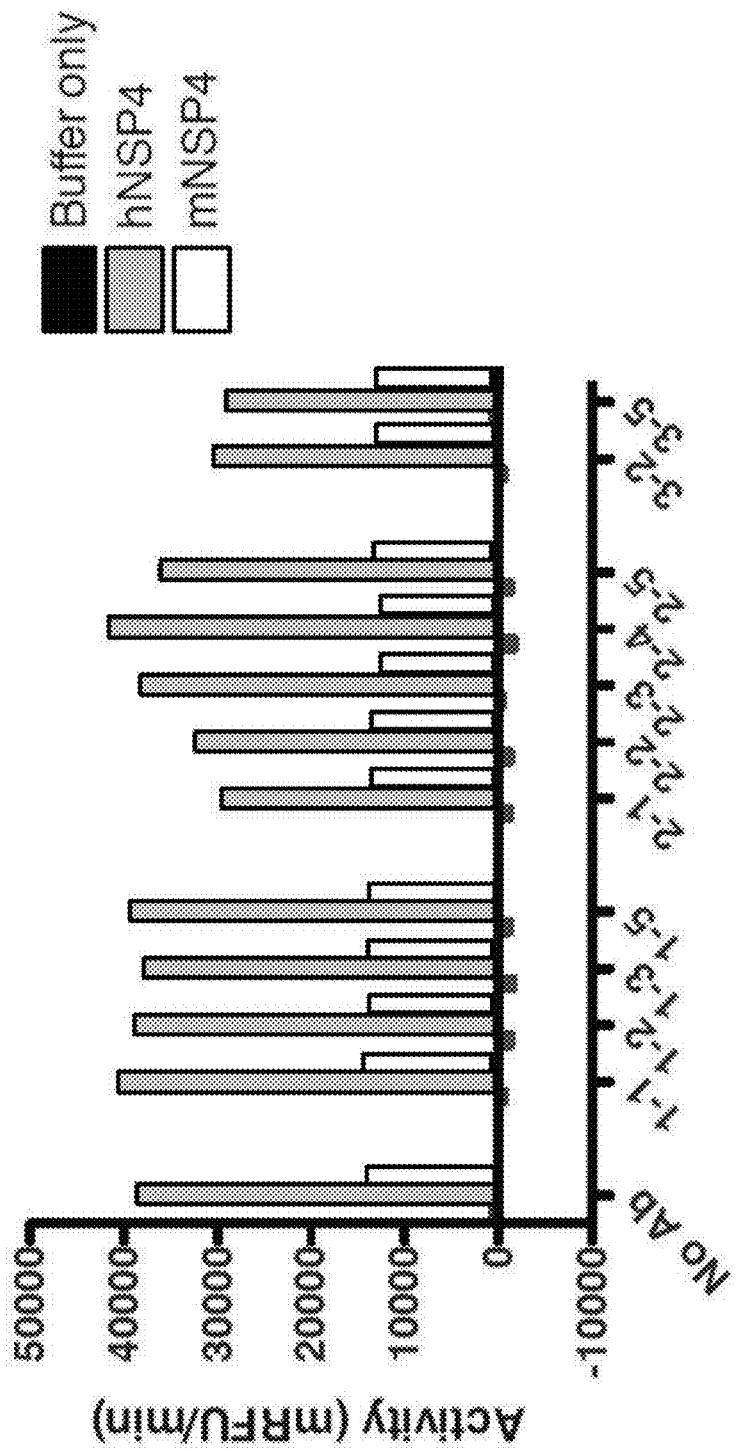

FIG. 27 shows the screening of antibodies panned against zymogen NSP4 by fluorogenic activity assay using active NSP4. Fluorogenic peptide cleavage assay of purified human active NSP4 (gray bars), mouse active NSP4 (white bars), or buffer alone (no enzyme; black bars) preincubated with either buffer alone ("No Ab") or different purified anti-NSP4 antibodies.

Figure 28:
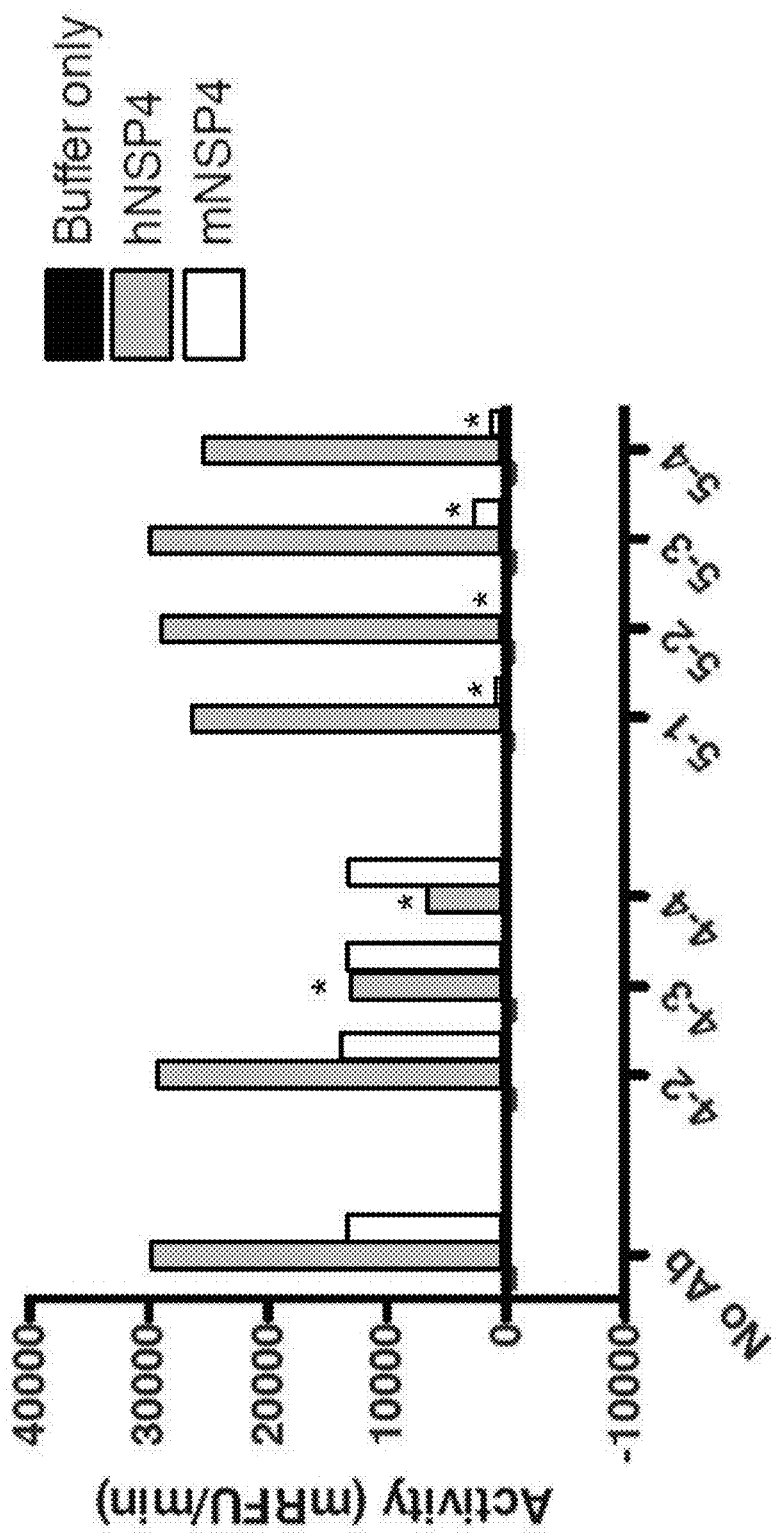

FIG. 28 shows the screening for NSP4 blocking antibodies by fluorogenic activity assay using active NSP4. Fluorogenic peptide cleavage assay of purified human active NSP4 (gray bars), mouse active NSP4 (white bars), or buffer alone (no enzyme; black bars) preincubated with either buffer alone ("No Ab") or different purified NSP4-specific antibodies. Asterisks denote antibodies that inhibit NSP4 enzyme activity.

FIG. 29 is a summary of NSP4 antibody characterization. Provided is a summary of in vitro characterization of purified NSP4-specific antibody as determined by (from left to right): affinity to purified NSP4 variants by biolayer interferometry, specificity classification as determined by biolayer interferometry, and blocking antibody screen by fluorogenic enzyme activity assay.

Figure 30:
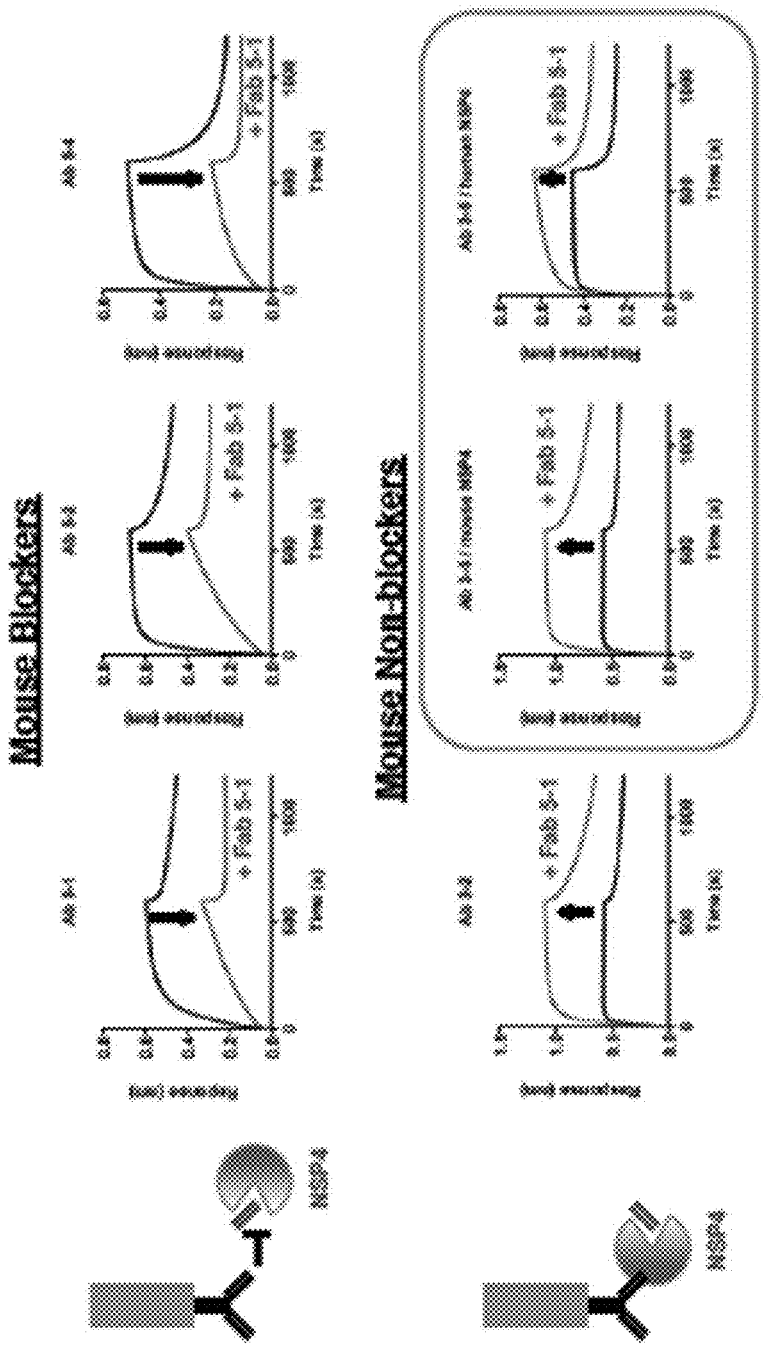

FIG. 30 shows epitope mapping of NSP4 antibodies with Fab 5-1. Epitope mapping of mouse-specific NSP4 antibodies by biolayer interferometry measurements of purified NSP4-specific antibodies binding to purified mouse NSP4 in the presence of Fab 5-1.

Figure 31:
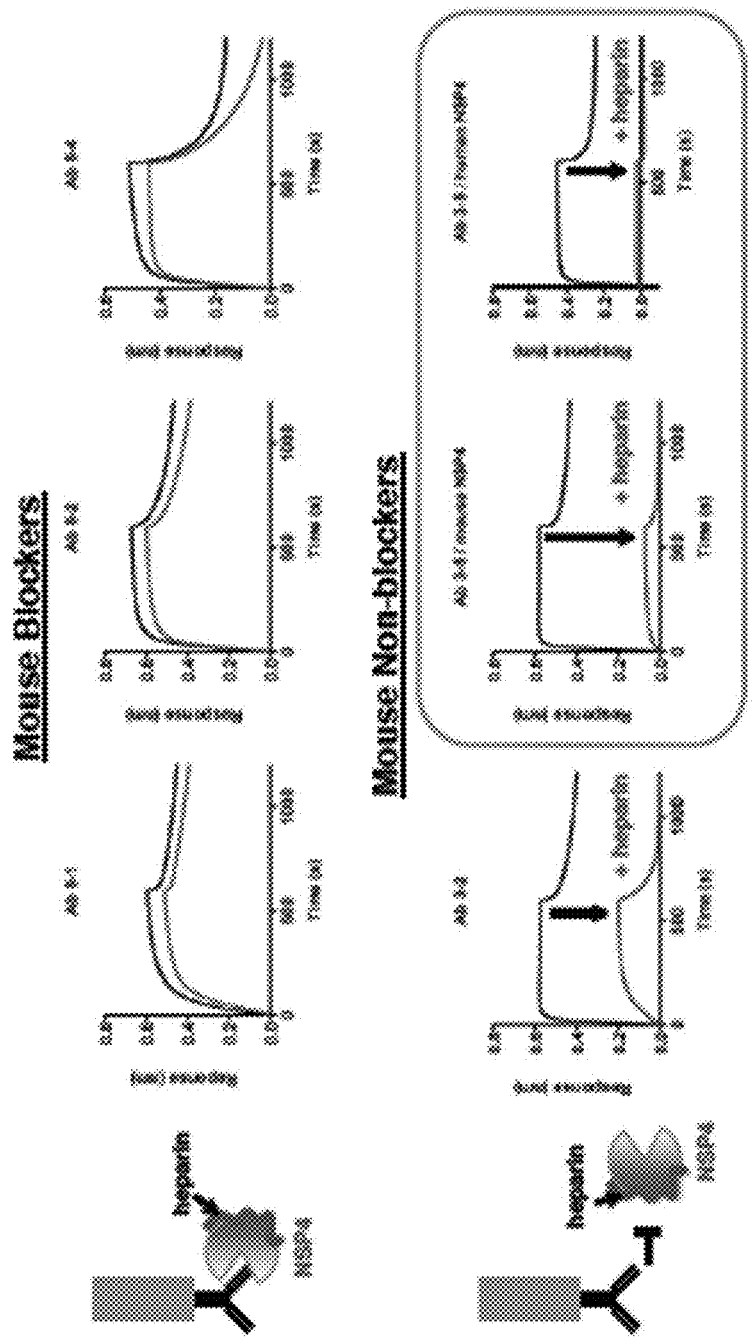

FIG. 31 shows epitope mapping of NSP4 antibodies with heparin. Epitope mapping of mouse-specific NSP4 antibodies by biolayer interferometry measurements of purified NSP4-specific antibodies binding to purified mouse NSP4 in the presence of heparin sulfate.

Figure 32:
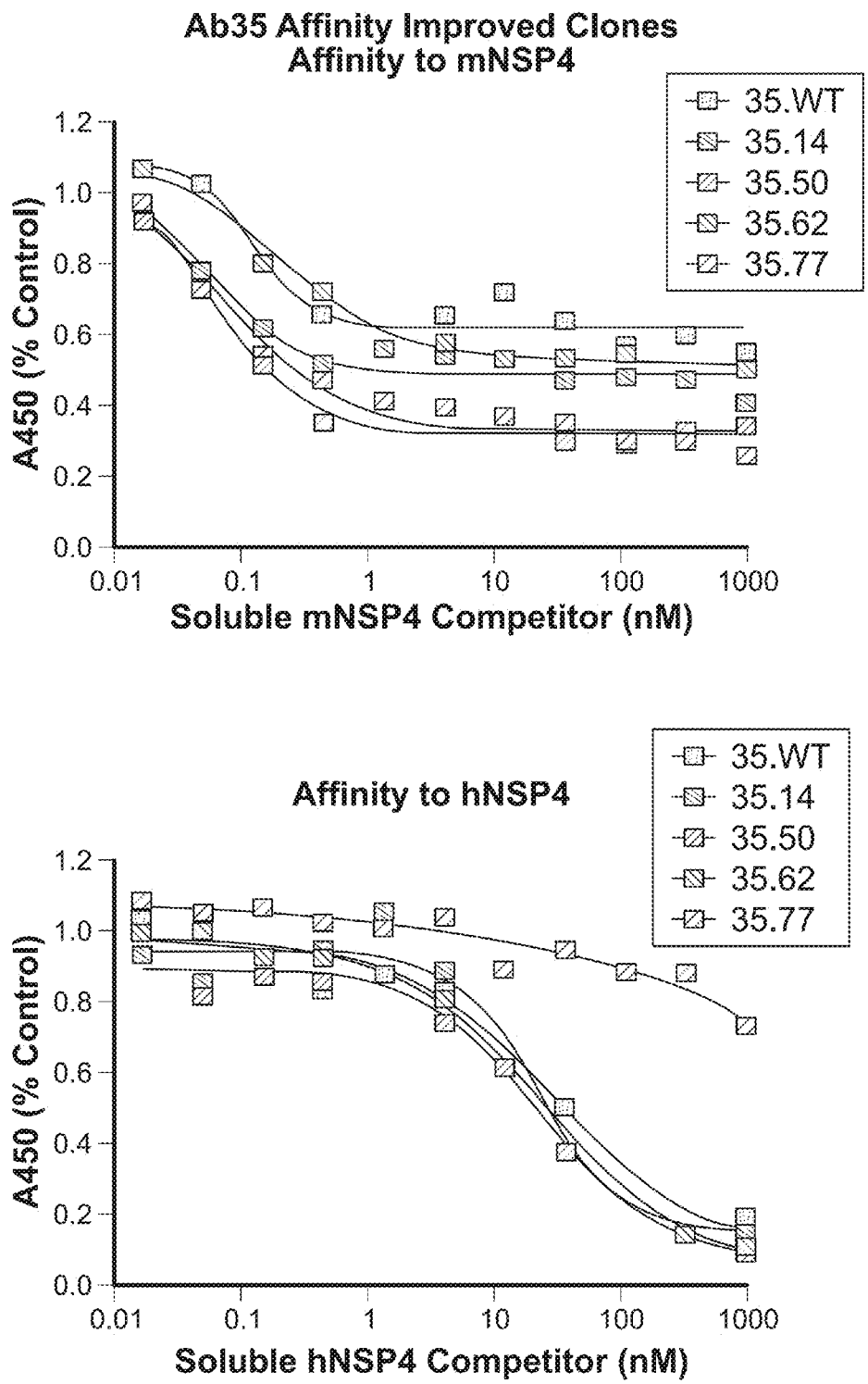

FIG. 32 shows the affinity maturation of the pan NSP4 Ab35 antibody clone. Affinity improvements of antibodies based on Ab 3-5 ("35.WT") as determined by phage IC50 assay using soluble mNSP4 (top) or soluble hNSP4 (bottom) competitor.

FIG. 33 shows the affinity maturation of the conformation-specific NSP4 Ab51 antibody clone. Affinity improvements of antibodies based on Ab 5-1 ("51.WT") as determined by phage IC50 assay using soluble mNSP4 competitor.

DETAILED DESCRIPTION

I. Definitions

The terms "neutrophil serine protease 4" of "NSP4" as used herein, refer to any native NSP4 from any mammals such as primates (e.g., human, rhesus, chimpanzee NSP4) and rodents (e.g., mice and rats), unless otherwise indicated. The term encompasses "full-length," unprocessed NSP4 such as a precursor or zymogen form of NSP4 as well as any form of NSP4 that results from proteolytic cleavage such as a mature or active form of NSP4. The term also encompasses naturally occurring variants of NSP4, e.g., splice variants or allelic variants. The amino acid sequence of an exemplary human NSP4 is shown in SEQ ID NO:17. The amino acid sequence of another exemplary human NSP4 is shown in SEQ ID NO:18.

```
Human NSP4 sequence
                                         (SEQ ID NO: 17)
MGLGLRGWGRPLLTVATALMLPVKPPAGSWGAQIIGGHEVTPHSRP

YMASVRFGGQHHCGGFLLRARWVVSAAHCFSHRDLRTGLVVLGAHV

LSTAEPTQQVFGIDALTTHPDYHPMTHANDICLLRLNGSAVLGPAV

GLLRLPGRRARPPTAGTRCRVAGWGFVSDFEELPPGLMEAKVRVLD

PDVCNSSWKGHLTLTMLCTRSGDSHRRGFCSADSGGPLVCRNRAHG

LVSFSGLWCGDPKTPDVYTQVSAFVAWIWDVVRRSSPQPGPLPGTT

RPPGEAA

Human NSP4 sequence
                                         (SEQ ID NO: 18)
MGLGLRGWGRPLLTVATALMLPVKPPAGSWGAQIIGGHEVTPHSRP

YMASVRFGGQHHCGGFLLRARWVVSAAHCFSHRDLRTGLVVLGAHV

LSTAEPTQQVFGIDALTTHPDYHPMTHANDICLLRLNGSAVLGPAV

GLLRPPGRRARPPTAGTRCRVAGWGFVSDFEELPPGLMEAKVRVLD

PDVCNSSWKGHLTLTMLCTRSGDSHRRGFCSADSGGPLVCRNRAHG

LVSFSGLWCGDPKTPDVYTQVSAFVAWIWDVVRRSSPQPGPLPGTT

RPPGEAA
```

The term "neutrophil serine protease 4 inhibitor" or "NSP4 inhibitor," as used herein, refers to a molecule that blocks, inhibits, reduces (including significantly), or interferes with a NSP4 (mammalian, such as a human NSP4) biological activity in vitro, in situ, and/or in vivo. The term "inhibitor" implies no specific mechanism of biological action whatsoever, and expressly includes and encompasses all possible pharmacological, physiological, and biochemical interactions with a NSP4 whether direct or indirect, and whether interacting with a NSP4, its substrate, or through another mechanism, and its consequences which can be achieved by a variety of different, and chemically divergent, compositions. Exemplary NSP4 inhibitors include, but are not limited to, an anti-NSP4 antibody that specifically binds to a NSP4 or one or both the precursor form and mature form of a NSP4, an anti-sense molecule directed to a nucleic acid encoding a NSP4, a short interfering RNA ("siRNA") molecule directed to a nucleic acid encoding a NSP4, a NSP4 inhibitory compound, an RNA or DNA aptamer that binds to a NSP4 or one or both the precursor form and mature form of a NSP4, and a NSP4 structural analog. In some embodiments, a NSP4 inhibitor (e.g., an antibody) binds (physically interacts with) a NSP4, binds to a NSP4 substrate, and/or inhibits (reduces) NSP4 synthesis, production or release. In other embodiments, a NSP4 inhibitor binds a NSP4 and prevents its binding to its substrate. In still other embodiments, a NSP4 inhibitor reduces or eliminates expression (i.e., transcription or translation) or proteolytic processing of a NSP4. Examples of types of NSP4 inhibitors are provided herein.

As used herein, the term "RNA interference" or "RNAi" refers generally to a process in which a double-stranded RNA molecule or a short hairpin RNA molecule reducing or inhibiting the expression of a nucleic acid sequence with which the double-stranded or short hairpin RNA molecule shares substantial or total homology. The term "short interfering RNA" or "siRNA" or "RNAi agent" refers to an RNA sequence that elicits RNA interference. See Kreutzer et al., WO 00/44895; Zernicka-Goetz et al., WO 01/36646; Fire, WO 99/32619; Mello and Fire, WO 01/29058. As used herein, siRNA molecules include RNA molecules encompassing chemically modified nucleotides and non-nucleotides. The term "ddRNAi agent" refers to a DNA-directed RNAi agent that is transcribed from an exogenous vector. The terms "short hairpin RNA" or "shRNA" refer to an RNA structure having a duplex region and a loop region. In certain embodiments, ddRNAi agents are expressed initially as shRNAs.

As used herein, the term "aptamer" refers to a heterologous oligonucleotide capable of binding tightly and specifically to a desired molecular target, such as, for example, common metabolic cofactors (e.g., Coenzyme A, S-adenosyl methionine, and the like), proteins (e.g., complement protein C5, antibodies, and the like), or conserved structural elements in nucleic acid molecules (e.g., structures important for binding of transcription factors and the like). Aptamers typically comprise DNA or RNA nucleotide sequences ranging from about 10 to about 100 nucleotides in length, from about 10 to about 75 nucleotides in length, from about 10 to about 50 nucleotides in length, from about 10 to about 35 nucleotides in length, and from about 10 to about 25 nucleotides in length. Synthetic DNA or RNA oligonucleotides can be made using standard solid phase phosphoramidite methods and equipment, such as by using a 3900 High Throughput DNA Synthesizer™ available from Applied Biosystems (Foster City, Calif.). Aptamers frequently incorporate derivatives or analogs of the commonly occurring nucleotides found in DNA and RNA (e.g., A, G, C, and T/U), including backbone or linkage modifications (e.g., peptide nucleic acid (PNA) or phosphothioate linkages) to increase resistance to nucleases, binding avidity, or to otherwise alter their pharmacokinetic properties. Exemplary modifications are set forth in U.S. Pat. Nos. 6,455,308; 4,469,863; 5,536,821; 5,541,306; 5,637,683; 5,637,684; 5,700,922; 5,717,083; 5,719,262; 5,739,308; 5,773,601; 5,886,165; 5,929,226; 5,977,296; 6,140,482; and in WIPO publications WO 00/56746 and WO 01/14398. Methods for synthesizing oligonucleotides comprising such analogs or derivatives are disclosed, for example, in the patent publications cited above, and in U.S. Pat. Nos. 6,455,308; 5,614,622; 5,739,314; 5,955,599; 5,962,674; 6,117,992; and in WO 00/75372.

A "blocking" antibody is one that inhibits or reduces a biological activity of the antigen it binds. In some embodiments, blocking antibodies substantially or completely inhibit the biological activity of the antigen. In some embodiments, the antigen is a NSP4.

The terms "anti-NSP4 antibody" and "an antibody that binds to NSP4" refer to an antibody that is capable of binding a NSP4 with sufficient affinity such that the antibody is useful as a diagnostic and/or therapeutic agent in targeting a NSP4. In one embodiment, the extent of binding of an anti-NSP4 antibody to an unrelated, non-NSP4 protein is less than about 10% of the binding of the antibody to NSP4 as measured, e.g., by a radioimmunoassay (RIA) or enzyme-linked immunosorbent assay (ELISA). In certain embodiments, an antibody that binds to a NSP4 has a dissociation constant (Kd) of $\leq 1$ μM, $\leq 100$ nM, $\leq 10$ nM, $\leq 1$ nM, $\leq 0.1$ nM, $\leq 0.01$ nM, or $\leq 0.001$ nM (e.g., $10^{-8}$M or less, e.g. from $10^{-8}$M to $10^{-13}$M, e.g., from $10^{-9}$M to $10^{-13}$ M). In certain embodiments, an anti-NSP4 antibody binds to an epitope of NSP4 that is conserved among NSP4 from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2, diabodies, linear antibodies, single-chain antibody molecules (e.g., scFv), and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. An HVR region as used herein comprise any number of residues located within positions 24-36 (for L1), 46-56 (for L2), 89-97 (for L3), 26-35B (for H1), 47-65 (for H2), and 93-102 (for H3). Therefore, an HVR includes residues in positions described previously:

A) 24-34 (L1), 50-52 (L2), 91-96 (L3), 26-32 (H1), 53-55 (H2), and 96-101 (H3) (Chothia and Lesk, J. Mol. Biol. 196:901-917 (1987);

B) 24-34 of L1, 50-56 of L2, 89-97 of L3, 31-35B of H1, 50-65 of H2, and 95-102 of H3 (Kabat et al., Sequences of Proteins of Immunological Interest, 5th Ed. Public Health Service, National Institutes of Health, Bethesda, Md. (1991).

C) 30-36 (L1), 46-55 (L2), 89-96 (L3), 30-35 (H1), 47-58 (H2), 93-100a-j (H3) (MacCallum et al. J. Mol. Biol. 262: 732-745 (1996).

With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, Front. Biosci. 13:1619-1633 (2008).) Unless otherwise indicated, HVR residues and other residues in the variable domain (e.g., FR residues) are numbered herein according to Kabat et al., supra.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-NSP4 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. An individual is successfully "treated", for example, if one or more symptoms associated with the disorder are mitigated or eliminated. For example, an individual is successfully "treated" if one or more symptoms associated with an inflammatory disease are mitigated or eliminated, including, but are not limited to, decreasing symptoms resulting from the disease, increasing the quality of life of those suffering from the disease, decreasing the dose of other medications required to treat the disease, delaying the progression of the disease, and/or prolonging survival of individuals As used herein, "in conjunction with" refers to administration of one treatment modality in addition to another treatment modality. As such, "in conjunction with" refers to administration of one treatment modality before, during or after administration of the other treatment modality to the individual.

As used herein, the term "prevention" includes providing prophylaxis with respect to occurrence or recurrence of a disorder in an individual. An individual may be predisposed to a disorder, susceptible to a disorder, or at risk of developing a disorder, but has not yet been diagnosed with the disorder. In some embodiments, NSP4 inhibitors described herein are used to delay development of the disorder. In some embodiments, the NSP4 inhibitors described herein prevent inflammation and/or vascular leakage.

As used herein, an individual "at risk" of developing a disorder may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of the disorder, as known in the art. An individual having one or more of these risk factors has a higher probability of developing the disorder than an individual without one or more of these risk factors.

An "effective amount" refers to at least an amount effective, at dosages and for periods of time necessary, to achieve the desired or indicated effect, including a therapeutic or prophylactic result. An effective amount can be provided in one or more administrations.

A "therapeutically effective amount" is at least the minimum concentration required to effect a measurable improvement of a particular disorder. A therapeutically effective amount herein may vary according to factors such as the disease state, age, sex, and weight of the patient, and the ability of the antibody to elicit a desired response in the individual. A therapeutically effective amount is also one in which any toxic or detrimental effects of the antibody are outweighed by the therapeutically beneficial effects. A "prophylactically effective amount" refers to an amount effective, at the dosages and for periods of time necessary, to achieve the desired prophylactic result. Typically but not necessarily, since a prophylactic dose is used in subjects prior to or at the earlier stage of disease, the prophylactically effective amount can be less than the therapeutically effective amount.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

"Antibody-dependent cell-mediated cytotoxicity" or "ADCC" refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII. Fc expression on hematopoietic cells is summarized in Table 3 on page 464 of Ravetch and Kinet, Annu. Rev. Immunol. 9: 457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and natural killer (NK) cells. Alternatively, or additionally, ADCC activity of the molecule of interest may be assessed in vivo, e.g., in an animal model such as that disclosed in Clynes et al., PNAS USA 95:652-656 (1998).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., J. Immunol. Methods 202: 163 (1996), may be performed.

The term "about" as used herein refers to the usual error range for the respective value readily known to the skilled person in this technical field. Reference to "about" a value or parameter herein includes (and describes) embodiments that are directed to that value or parameter per se.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

It is understood that aspect and embodiments of the invention described herein include "comprising," "consisting," and "consisting essentially of" aspects and embodiments.

II. Compositions and Methods

A. NSP4 Inhibitors

Provided herein are NSP4 inhibitors which block, inhibit, reduce, or interfere with the enzymatic activity of a NSP4 in vitro, in situ, and/or in vivo. A NSP4 inhibitor is a molecule having one or more of the following characteristics: (1) inhibits or reduces NSP4 enzymatic activity; (2) the ability to inhibit or reduce binding of a NSP4 to its substrate(s); (3) the ability to increase clearance of a NSP4 (e.g., decrease extracellular levels of released NSP4); (4) the ability to inhibit or reduce NSP4 release from neutrophils, basophils and/or eosinophils; (5) the ability to reduce NSP4 expression (such as at the mRNA level and/or at protein level) in neutrophils, basophils and/or eosinophils; (6) the ability to interact, bind, or recognize a precursor and/or mature form of a NSP4; (7) the ability to enhance inactivation of a NSP4 by a protease inhibitor (e.g., a1-antitrypsin); (8) the ability to specifically interact with or bind to a NSP4 and not with neutrophil elastase (NE), cathepsin G (CG), or proteinase 3 (PR3) activity; (9) the ability to treat, ameliorate, or prevent any aspect of a neutrophil-mediated disease or disorder described or contemplated herein; and (10) the ability to treat, ameliorate, or prevent any aspect of a disease or disorder mediated by granulocytes described or contemplated herein.

Exemplary NSP4 inhibitors that inhibit the production of a NSP4 include agents such as, but not limited to, compounds that specifically inhibit NSP4 synthesis and/or release, antisense molecules directed to a NSP4, or a short interfering RNA (siRNA) molecule directed to a nucleic acid encoding a NSP4. Additional exemplary NSP4 inhibitors that inhibit NSP4 protease activity include agents such as, but not limited to, anti-NSP4 antibodies that specifically bind to a NSP4 (e.g., a precursor NSP4 and/or a mature NSP4), protease inhibitors (e.g., serine protease inhibitors), compounds that specifically inhibit NSP4 catalytic activity such as small molecule inhibitors and/or peptide inhibitors, compounds that specifically inhibit a NSP4 binding to its substrate(s), a NSP4 structural analog, or an RNA or DNA aptamer that binds a NSP4. In some embodiments, a NSP4 inhibitor is an allosteric inhibitor. In some embodiments, a NSP4 inhibitor is an orthosteric inhibitor.

In certain embodiments, a NSP4 inhibitor is a protease inhibitor that reduces the catalytic activity of a NSP4. In certain embodiments, a protease inhibitor contemplated herein reduces levels of NSP4 protease activity by reducing active NSP4 protein concentrations. In some embodiments, the NSP4 inhibitor is a serine protease inhibitor, referred to as a serpin, well known in the art as a group of proteins capable of inhibiting protease activity. For example serpin proteins include, but are not limited to, α1-antitrypsin, C1 inhibitor, heparin-activated antithrombin, and α2-antiplasmin. Methods for making or purifying serpin inhibitors are well known in the art, including, but are not limited to, recombinant protein expression, or immunoaffinity purification.

In certain embodiments, the NSP4 inhibitor is a small molecule inhibitor (e.g., peptide inhibitor), including, but not limited to, small peptides or peptide-like molecules, soluble peptides, and synthetic non-peptidyl organic or inorganic compounds. A small molecule inhibitor may have a molecular weight of any of about 100 to about 20,000 daltons (Da), about 500 to about 15,000 Da, about 1000 to about 10,000 Da. For example, small molecule inhibitors contemplated herein include, but are not limited to, amastatin hydrochloride hydrate, antipain dihydrochloride, aprotinin, elastatinal, epiamastatin hydrochloride, histatin 5, leupeptin hemisulfate, leupeptin trifluoroacetate, leupeptin hydrochloride, pepstatin, or phenylmethanesulfonylfluoride. In some embodiments, the small molecule inhibitor is a macrocyclic inhibitor such as, but not limited to, macrocyclic acylsulfonamides or small molecule inhibitors that are known to inhibit the HCV NS3/4A protease. Methods for making and testing the inhibitory effect a small molecule has on catalytic activity is well known in the art and such methods can be used to assess the effect of the small molecule inhibitor on NSP4 activity. For example, a library of NSP4 inhibitor candidates can be screened for decreasing NSP4 protease activity by incubating each inhibitor candidate with active NSP4 in the presence of a fluorogenic peptide substrate in a buffer. Upon NSP4 cleavage, said fluorogenic peptide substrate will fluoresce and NSP4 activity in the presence of each inhibitor candidate can be measured by techniques well known in the art. Exemplary fluorogenic peptide substrates that can used in assays described herein include, but are not limited to, a fluorogenic peptide substrate with the amino acid sequence $^1$IR{Arg(Me)}SSYSFKK$^{10}$ or $^1$IR{Arg}SSYSFKK$^{10}$.

In certain embodiments, the NSP4 inhibitor is an anti-NSP4 antibody that binds or physically interacts with a NSP4. The antibody may have nanomolar or even picomolar affinities for the target antigen (e.g., NSP4). In certain embodiments, the Kd of the antibody is about 0.05 to about 100 nM. For example, Kd of the antibody is any of about 100 nM, about 50 nM, about 10 nM, about 1 nM, about 500 pM, about 100 pM, or about 50 pM to any of about 2 pM, about 5 pM, about 10 pM, about 15 pM, about 20 pM, or about 40 pM. Methods for the preparation and selection of antibodies that interact and/or bind with specificity to a NSP4 are described herein.

In certain embodiments, the NSP4 inhibitor comprises at least one antisense molecule capable of blocking or decreasing the expression of a functional NSP4 by targeting nucleic acids encoding a NSP4. Nucleic acid sequences of NSP4 are known in the art. For example, a human NSP4 can have a nucleic acid sequence as shown in NCBI Accession number NM_214710 and a mouse NSP4 can have a nucleic acid sequence as shown in NCBI Accession number NM_001042710. Methods are known for the preparation of antisense oligonucleotide molecules and such methods can be used to prepare antisense oligonucleotides that will specifically bind one or more of a NSP4 mRNA without cross-reacting with other polynucleotides. Exemplary sites of targeting include, but are not limited to, the initiation codon, the 5' regulatory regions, the coding sequence, including any conserved consensus regions, and the 3' untranslated region. In certain embodiments, the antisense oligonucleotides are about 10 to about 100 nucleotides in length, about 15 to about 50 nucleotides in length, about 18 to about 25 nucleotides in length, or more. In certain embodiments, the oligonucleotides further comprise chemical modifications to increase nuclease resistance and the like, such as, for example, phosphorothioate linkages and 2'-O-sugar modifications known to those of ordinary skill in the art.

In certain embodiments, the NSP4 inhibitor comprises at least one siRNA molecule capable of blocking or decreasing the expression of a functional NSP4 by targeting nucleic acids encoding a NSP4. Methods for preparation of siRNA molecules are well known in the art and such methods can be used to prepare siRNA molecules that will specifically target a NSP4 mRNA without cross-reacting with other polynucleotides. siRNA molecules may be generated by methods such as by typical solid phase oligonucleotide synthesis, and often will incorporate chemical modifications to increase half-life and/or efficacy of the siRNA agent, and/or to allow for a more robust delivery formulation. Alternatively, siRNA molecules are delivered using a vector encoding an expression cassette for intracellular transcription of siRNA.

In certain embodiments, the NSP4 inhibitor is an RNA or DNA aptamer that binds or physically interacts with a NSP4, and blocks interactions between a NSP4 and its substrate(s). In certain embodiments, the aptamer comprises at least one RNA or DNA aptamer that binds to a mature form of NSP4. In certain embodiments, the aptamer comprises at least one RNA or DNA aptamer that binds to a precursor form of NSP4.

Figure 1:
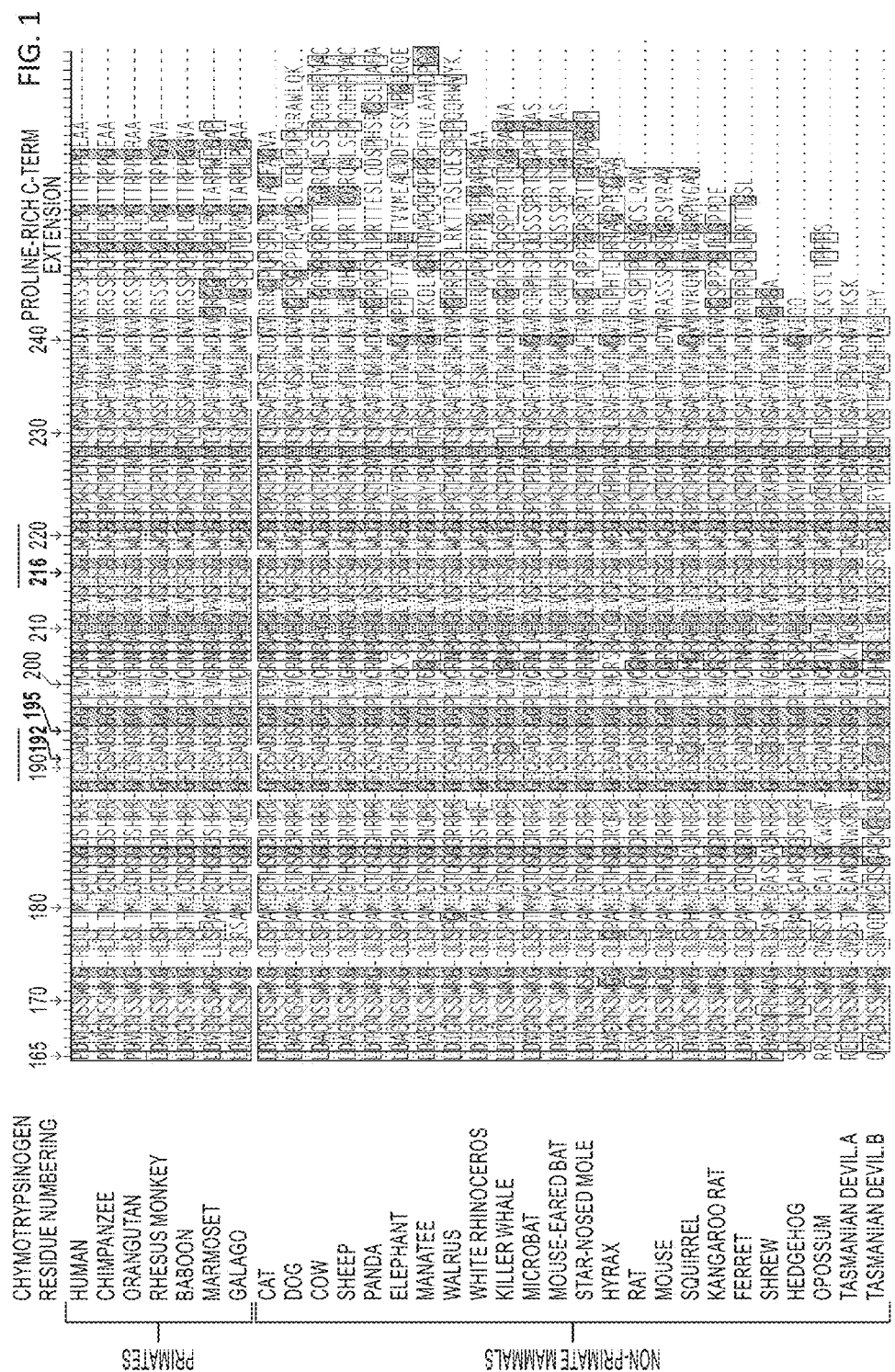
FIG. 1 is a sequence alignment of the active region of NSP4 orthologs. Residues are numbered at the top using the chymotrypsinogen numbering system. The disulfide bonds are denoted at the bottom with lines. Conserved residues are colored using the ClustalX scheme. NSP4 primary substrate specificity determinants at the 190, 192, and 216 positions are labeled and outlined. The length of the 180-loop ($^{190}$FCS$^{192}$) and 220-loop ($^{214}$SFSGxxC$^{220}$) segments that coordinate the P1-arginine side chain is also conserved in NSP4 orthologs and is denoted with black bars at the top. Two or more NSP4 paralogs are found in the Tasmanian devil, frogs (*X. laevis* and *X. tropicalis*), and coelacanth; some paralogs have substitutions at the 192 position, but all species have at least one paralog that have all the requisite H-bond acceptors. Reptilian and avian species have heterophils instead of bona fide neutrophils, and their NSP4 orthologs have a F190V substitution. Avian NSP4 orthologs are predicted to have reduced activity due to a S192A substitution and have a lone unpaired C136 because of a C201F substitution. NSP4 ortholog sequences were compiled from National Center of Biotechnology Information (NCBI) and ENSEMBL databases and aligned using ClustalW (Larkin et al., *Bioinformatics*, 2007, 23:2947-2948). The preliminary alignment was then manually curated and analyzed using SeaView (Gouy et al., *Mol Biol Evol*, 2010, 27:221-224) and Unipro UGENE (Okonechnikov et al., *Bioinformatics*, 2012, 28:1166-1167).
Figure 1:
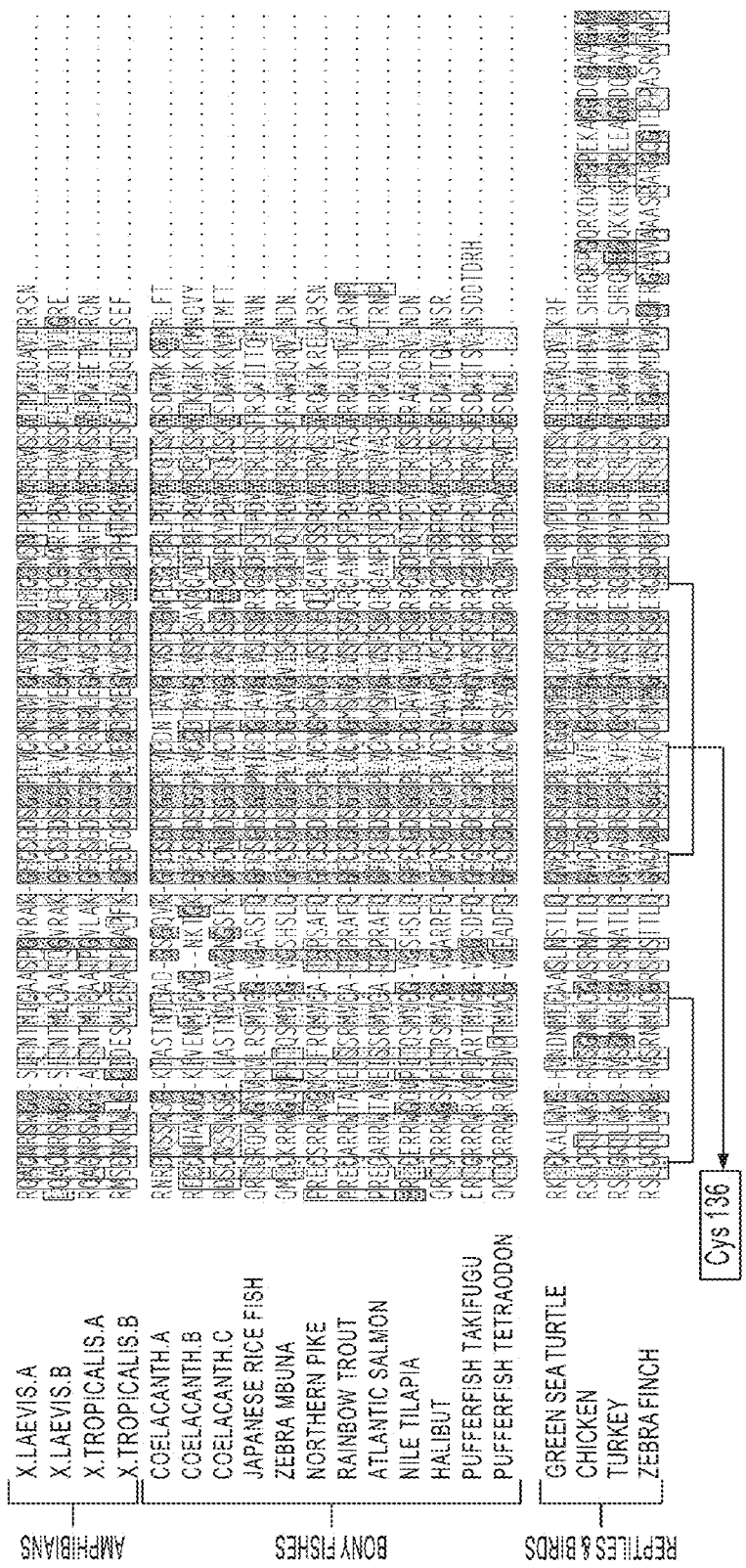

In certain embodiments, the NSP4 inhibitor comprises at least one NSP4 structural analog. The term NSP4 structural analog refers to compounds that have a similar three dimensional structure as part of that of a NSP4 (e.g., a precursor and/or mature form of NSP4) and which bind to a NSP4 substrate under physiological conditions in vitro or in vivo, wherein the binding at least partially inhibits a NSP4 biological activity. Suitable NSP4 structural analogs can be designed and synthesized through molecular modeling of NSP4 binding to its substrate. The NSP4 structural analogs can be monomers, dimers, or higher order multimers in any desired combination of the same or different structures to obtain improved affinities and biological effects. In some embodiments, the NSP4 inhibitor binds to or interacts with an amino acid sequence of a NSP4 as shown in FIG. 1.

Assays

NSP4 inhibitors may be identified and/or characterized using methods well known in the art, such as, for example, radiolabeled inhibitor assays, optical assays, protein binding assays, biochemical screening assays, immunoassays, mass shift measurement assays, fluorescence assays, and/or fluorogenic peptide cleavage assays.

Binding Assays and Other Assays

In certain embodiments, NSP4 inhibitors can be identified by techniques well known in the art for detecting the presence of a NSP4 inhibitor candidate's interaction and/or binding affinity to a NSP4.

In certain embodiments, NSP4 inhibitors that interact with a NSP4 can be identified using a radiolabeled inhibitor assay. For example, a known amount of a radiolabeled inhibitor candidate may be incubated with a known amount of immobilized NSP4 and a buffer. Subsequently, the immobilized NSP4 may be washed with a buffer and the immobilized NSP4 may be measured for the remaining presence of the radiolabeled NSP4 inhibitor candidate using techniques known in the art, such as, for example, a gamma counter. A measurement indicating the presence of a radiolabeled substance may indicate the radiolabeled inhibitor candidate is capable of interacting with and/or binding to NSP4.

In certain embodiments, a NSP4 inhibitor that interacts with a NSP4 may be identified using an optical technique. An exemplary optical technique to detect an inhibitor of a NSP4 may include, e.g., attaching NSP4 to a colorimetric resonant grafting surface, thereby shifting the wavelength of reflected light due to changes in the optical path the light must take, and subsequently measuring additional changes in the wavelength of reflected light when an inhibitor candidate is allowed to interact with NSP4. For example, no change in the measured wavelength of reflected light when an inhibitor is incubated with NSP4 may indicate that the inhibitor candidate is unable to interact with NSP4. Changes in the measured wavelength of reflected light when an inhibitor candidate is incubated with NSP4 may indicate that the inhibitor candidate is capable of binding and/or interacting with NSP4.

In certain embodiments, a NSP4 inhibitor that interacts with a NSP4 may be identified using a protein binding assay. An exemplary protein binding assay to detect a NSP4 inhibitor may include, e.g., co-immunoprecipitation of a NSP4 in the presence of the inhibitor candidate. For example, a NSP4 may be incubated with the inhibitor candidate in buffer, and subsequently an immobilized molecule specific to capture a NSP4, such as, for example, an anti-NSP4 antibody, may be used to capture NSP4 in the presence of the inhibitor candidate and bind the NSP4, potentially with an interacting inhibitor candidate, during wash procedures known in the art. Subsequently, NSP4, potentially with an interacting inhibitor candidate, can be released and the presence of an inhibitor candidate may be detected, based on the inhibitor candidate characteristics, by techniques, such as, for example, mass spectrometry and/or Western blot.

In certain embodiments, a NSP4 inhibitor that interacts with a NSP4 may be identified using a biochemical and/or an immunoassay assay well known in the art. An exemplary technique may include, e.g., an assay to quantitatively measure changes in NSP4 concentration and/or protein half-life using techniques, such as, for example, Western blot. For example, an inhibitor candidate may be incubated with a sample containing a NSP4, and subsequently NSP4 protein quantity may be measured at points during a time course study. Changes in protein quantity and/or protein half-life in comparison to a control treatment may indicate that the NSP4 inhibitor candidate may be capable of altering NSP4 half-life and/or activity.

In certain embodiments, a mass shift measurement assay may be used to identify a NSP4 inhibitor that interacts with a NSP4. An exemplary mass shift measurement assay may include, e.g., detecting the presence of a strongly and/or covalently bound NSP4 inhibitor by measuring a change in NSP4 mass when the inhibitor candidate is interacting with NSP4 by using instruments, such as, but not limited to, a mass spectrometer. For example, a mass shift assay may be performed on a whole protein and/or a peptide-based analysis, depending on the nature of the inhibitor candidate interaction. Detection of a mass shift correlating with the addition of said inhibitor candidate to NSP4 may indicate that the inhibitor candidate may be capable of inhibiting a NSP4. Additionally, an exemplary mass shift measurement assay may include, e.g., detecting the addition of mass to NSP4 correlating with the respective inhibitor candidate mass when the inhibitor candidate is interacting with NSP4 using techniques, such as, for example, surface plasmon resonance. For example, the change in the refractive index of light may be measured and correlated with a change in mass of NSP4 attached to a sensor surface.

In certain embodiments, a chemical cross-linking assay may be used to identify a NSP4 inhibitor that interacts with a NSP4. For example, an inhibitor candidate may be incubated with a NSP4, in vivo or in vitro, with a molecule cross-linker capable of covalently linking an inhibitor candidate interacting with NSP4 to said NSP4 molecule. Subsequently, techniques, such as, but not limited to, mass spectrometry and/or Western blot, may be used to identify an inhibitor candidate that may be capable of inhibiting NSP4. For example, detection of NSP4 covalently cross-linked with the inhibitor candidate may indicate that the inhibitor candidate may be capable of inhibiting NSP4.

In certain embodiments, NSP4 inhibitors that interact with a NSP4 may be identified using a fluorescence inhibitor assay. For example, a known amount of a fluorescent inhibitor candidate may be incubated with a known amount of immobilized NSP4 and a buffer. Subsequently, the immobilized NSP4 may be washed with a buffer and the immobilized NSP4 may be measured for the remaining presence of a fluorescent NSP4 inhibitor candidate using techniques known in the art, such as, but not limited to, fluorescence detection. A measurement indicating the presence of a fluorescent substance may indicate the fluorescent inhibitor candidate is capable of interacting with and/or binding to NSP4.

Activity Assays

Assays known in the art and described herein (e.g., Example 3) can be used for identifying and testing biological activities of NSP4 inhibitors. In some embodiments, assays for testing NSP4 inhibitors ability for blocking a NSP4 activity are provided. An exemplary test for biological activity may include, e.g., providing a NSP4 (e.g., human NSP4) in a mixture with a NSP4 inhibitor and incubating the mixture with one or more internally-quenched fluorogenic peptide substrate and measuring the fluorescence intensity with an instrument, such as, for example, a spectrophotometer. An increase in fluorescence in the presence of a NSP4 inhibitor would indicate the NSP4 inhibitor is unable to block NSP4 activity, while a lack of increase in fluorescence in the presence of a NSP4 inhibitor would indicate the NSP4 inhibitor blocks NSP4 activity. Exemplary fluorogenic peptide substrates that can used in assays described herein include, but are not limited to, a fluorogenic peptide substrate with the amino acid sequence $^1$IR{Arg(Me)}SSYSFKK$^{10}$ or $^1$IR{Arg}SSYSFKK$^{10}$.

In some embodiments, the NSP4 inhibitor may block at least about any of 50%, 60%, 70%, 80%, 85%, 90%, 95% and 100% of NSP4 activity in any of these assays.

Anti-NSP4 Antibodies

In one aspect, the invention provides isolated antibodies that bind to a NSP4. In certain embodiments, an anti-NSP4 antibody has one or more of the following characteristics: (1) binds a NSP4 (e.g., a human NSP4) and inhibits or reduces NSP4 protease activity; (2) blocks binding of a NSP4 to its peptide substrate(s); (3) binds to a NSP4 of a mouse and/or a human; (4) binds to an inactive and/or mature form of NSP4; (5) binds to a complex formed between a NSP4 and a protease inhibitor (e.g., al-antitrypsin); (6) enhances inactivation of a NSP4 by a protease inhibitor (e.g., al-antitrypsin); and (7) reacts specifically with a NSP4 and not with neutrophil elastase (NE), cathepsin G (CG), or proteinase 3 (PR3).

In another aspect, the invention provides an isolated anti-NSP4 antibody that can be classified into one of the following subclasses: 1) Binds to mature and precursor forms of a mouse NSP4 but not to mature and precursor forms of a human NSP4; 2) Binds to mature and precursor forms of a human NSP4 but not to mature and precursor forms of a mouse NSP4; 3) Binds to a mature form of a mouse NSP4 but not to a precursor form of a mouse NSP4; 4) Binds to a mature form of a human NSP4 but not to a precursor form of a human NSP4; 5) Binds to mature forms of a mouse NSP4 and a human NSP4 but not to precursor forms of a mouse NSP4 and a human NSP4; and 6) Binds to mature and precursor forms of a mouse NSP4 and a human NSP4.

Described herein is the finding that NSP4 includes an active site and a heparin binding site (see, e.g., FIG. 4A). Further described herein are antibodies that specifically bind to one of these sites (see, e.g., FIGS. 30-31). In another aspect, the invention provides an isolated anti-NSP4 antibody that can be classified into one of the following subclasses: (1) specifically binds an NSP4 active site or near an NSP4 active site; (2) inhibits catalytic activity of NSP4; (3) specifically binds an NSP4 active site or near an NSP4 active site and inhibits catalytic activity of NSP4; (4) specifically binds an NSP4 heparin binding site; (5) competes with heparin for binding to NSP4; and (6) specifically binds an NSP4 heparin binding site and competes with heparin for binding to NSP4.

In one aspect, the invention provides an isolated anti-NSP4 antibody comprising at least one, two, three, four, five, or six HVRs selected from (i) an HVR-L1 comprising the amino acid sequence of SEQ ID NO:10; (ii) an HVR-L2 comprising the amino acid sequence of SEQ ID NO:11; (iii) an HVR-L3 comprising the amino acid sequence of SEQ ID NO:12; (iv) an HVR-H1 comprising the amino acid sequence of SEQ ID NO:1, 4, or 7; (v) an HVR-H2 comprising the amino acid sequence of SEQ ID NO:2, 5, or 8; and (vi) an HVR-H3 comprising the amino acid sequence of SEQ ID NO:3, 6, or 9.

In one embodiment, the isolated anti-NSP4 antibody comprises a heavy chain variable region comprising an HVR-H1, an HVR-H2, and an HVR-H3 sequence, wherein:
  (a) the HVR-H1 sequence is GFTFSNTYIS (SEQ ID NO:1);
  (b) the HVR-H2 sequence is GFIYPANGATYYADSVKG (SEQ ID NO:2); and
  (c) the HVR-H3 sequence is RRYRLSFDY (SEQ ID NO:3).

In one embodiment, the isolated anti-NSP4 antibody comprises a heavy chain variable region comprising an HVR-H1, an HVR-H2, and an HVR-H3 sequence, wherein:
  (a) the HVR-H1 sequence is GFTFSGNDIS (SEQ ID NO:4);
  (b) the HVR-H2 sequence is AGISPYGGSTYYADSVKG (SEQ ID NO:5); and
  (c) the HVR-H3 sequence is RRVSFYSRHAGMDY (SEQ ID NO:6).

In one embodiment, the isolated anti-NSP4 antibody comprises a heavy chain variable region comprising an HVR-H1, an HVR-H2, and an HVR-H3 sequence, wherein:
  (a) the HVR-H1 sequence is GFTFTSYAIS (SEQ ID NO:7);
  (b) the HVR-H2 sequence is AGISPSNGYTNYADSVKG (SEQ ID NO:8); and
  (c) the HVR-H3 sequence is RAGRWTHSDIDY (SEQ ID NO:9).

In some embodiments, a heavy chain polypeptide provided herein is further combined with a variable region light chain comprising an HVR-L1, an HVR-L2, and an HVR-L3, wherein:
  (a) the HVR-L1 sequence is RASQDVSTAVA (SEQ ID NO:10);
  (b) the HVR-L2 sequence is SASFLYS (SEQ ID NO:11); and
  (c) the HVR-L3 sequence is QQSYTTPPT (SEQ ID NO:12).

In another embodiment, provided is an isolated anti-NSP4 antibody or antigen binding fragment comprising a heavy chain variable region and a light chain variable region, wherein:
  (a) the heavy chain comprises an HVR-H1, an HVR-H2, and an HVR-H3, wherein:
    (i) the HVR-H1 sequence is GFTFSNTYIS (SEQ ID NO:1);
    (ii) the HVR-H2 sequence is GFIYPANGATYYADSVKG (SEQ ID NO:2);
    (iii) the HVR-H3 sequence is RRYRLSFDY (SEQ ID NO:3); and/or
  (b) the light chain comprises an HVR-L1, an HVR-L2, and an HVR-L3, wherein:
    (i) the HVR-L1 sequence is RASQDVSTAVA (SEQ ID NO:10);
    (ii) the HVR-L2 sequence is SASFLYS (SEQ ID NO:11); and
    (iii) the HVR-L3 sequence is QQSYTTPPT (SEQ ID NO:12).

In another embodiment, provided is an isolated anti-NSP4 antibody or antigen binding fragment comprising a heavy chain variable region and a light chain variable region, wherein:
  (c) the heavy chain comprises an HVR-H1, an HVR-H2, and an HVR-H3, wherein:
    (i) the HVR-H1 sequence is GFTFSGNDIS (SEQ ID NO:4);
    (ii) the HVR-H2 sequence is AGISPYGGSTYYADSVKG (SEQ ID NO:5);
    (iii) the HVR-H3 sequence is RRVSFYSRHAGMDY (SEQ ID NO:6); and/or
  (d) the light chain comprises an HVR-L1, an HVR-L2, and an HVR-L3, wherein:
    (i) the HVR-L1 sequence is RASQDVSTAVA (SEQ ID NO:10);
    (ii) the HVR-L2 sequence is SASFLYS (SEQ ID NO:11); and
    (iii) the HVR-L3 sequence is QQSYTTPPT (SEQ ID NO:12).

In another embodiment, provided is an isolated anti-NSP4 antibody or antigen binding fragment comprising a heavy chain variable region and a light chain variable region, wherein:
  (e) the heavy chain comprises an HVR-H1, an HVR-H2, and an HVR-H3, wherein:
    (i) the HVR-H1 sequence is GFTFTSYAIS (SEQ ID NO:7);
    (ii) the HVR-H2 sequence is AGISPSNGYTNYADSVKG (SEQ ID NO:8);
    (iii) the HVR-H3 sequence is RAGRWTHSDIDY (SEQ ID NO:9); and/or
  (f) the light chain comprises an HVR-L1, an HVR-L2, and an HVR-L3, wherein:
    (i) the HVR-L1 sequence is RASQDVSTAVA (SEQ ID NO:10);
    (ii) the HVR-L2 sequence is SASFLYS (SEQ ID NO:11); and
    (iii) the HVR-L3 sequence is QQSYTTPPT (SEQ ID NO:12).

In a still further specific aspect, the antibody further comprises a human or murine constant region. In a still further aspect, the human constant region is selected from the group consisting of IgG1, IgG2, IgG2, IgG3, and IgG4. In a still further specific aspect, the human constant region is IgG1. In a still further aspect, the murine constant region is selected from the group consisting of IgG1, IgG2A, IgG2B, and IgG3. In a still further aspect, the murine constant region is IgG2A. In a still further specific aspect, the antibody has reduced or minimal effector function.

In yet another embodiment, provided is an isolated anti-NSP4 antibody or antigen binding fragment comprising a heavy chain variable region and a light chain variable region, wherein:
  (a) the heavy chain further comprises an HVR-H1, an HVR-H2, and an HVR-H3 sequence having at least 85% sequence identity to GFTFSNTYIS (SEQ ID NO:1), GFIYPANGATYYADSVKG (SEQ ID NO:2), and RRYRLSFDY (SEQ ID NO:3), respectively, and/or
  (b) the light chain further comprises an HVR-L1, an HVR-L2, and an HVR-L3 sequence having at least 85% sequence identity to RASQDVSTAVA (SEQ ID NO:10), SASFLYS (SEQ ID NO:11), and QQSYTTPPT (SEQ ID NO:12), respectively.

In yet another embodiment, provided is an isolated anti-NSP4 antibody or antigen binding fragment comprising a heavy chain variable region and a light chain variable region, wherein:
  (a) the heavy chain further comprises an HVR-H1, an HVR-H2, and an HVR-H3 sequence having at least 85% sequence identity to GFTFSGNDIS (SEQ ID NO:4), AGISPYGGSTYYADSVKG (SEQ ID NO:5), and RRVSFYSRHAGMDY (SEQ ID NO:6), respectively, and/or
  (b) the light chain further comprises an HVR-L1, an HVR-L2, and an HVR-L3 sequence having at least 85% sequence identity to RASQDVSTAVA (SEQ ID NO:10), SASFLYS (SEQ ID NO:11), and QQSYTTPPT (SEQ ID NO:12), respectively.

In yet another embodiment, provided is an isolated anti-NSP4 antibody or antigen binding fragment comprising a heavy chain variable region and a light chain variable region, wherein:
  (a) the heavy chain further comprises an HVR-H1, an HVR-H2, and an HVR-H3 sequence having at least 85% sequence identity to GFTFTSYAIS (SEQ ID NO:7), AGISPSNGYTNYADSVKG (SEQ ID NO:8), and RAGRWTHSDIDY (SEQ ID NO:9), respectively, and/or
  (b) the light chain further comprises an HVR-L1, an HVR-L2, and an HVR-L3 sequence having at least 85% sequence identity to RASQDVSTAVA (SEQ ID NO:10), SASFLYS (SEQ ID NO:11), and QQSYTTPPT (SEQ ID NO:12), respectively.

In a still further embodiment, provided is an isolated anti-NSP4 antibody or antigen binding fragment comprising a heavy chain variable region and a light chain variable region, wherein:
  (a) the heavy chain sequence has at least 85% sequence identity to the heavy chain sequence:

```
                                                  (SEQ ID NO: 13)
EVQLVESGGGLVQPGGSLRLSCAASGFTFSNTYISWVRQAPGKGLE

WVGFIYPANGATYYADSVKGRFTISADTSKNTAYLQMNSLRAEDTA

VYYCSRRYRLSFDYWGQGTLVTVSS,
```
and/or
  (b) the light chain sequence has at least 85% sequence identity to the light chain sequence:

```
                                                  (SEQ ID NO: 16)
DIQMTQSPSSLSASVGDRVTITCRASQDVSTAVAWYQQKPGKAPKL

LIYSASFLYSGVPSRFSGSGSGTDFTLTISSLQPEDFATYYCQQSY

TTPPTFGQGTKVEIKR.
```

In a still another embodiment, provided is an isolated anti-NSP4 antibody or antigen binding fragment comprising a heavy chain variable region and a light chain variable region, wherein:
  (a) the heavy chain sequence has at least 85% sequence identity to the heavy chain sequence:

```
                                                  (SEQ ID NO: 14)
EVQLVESGGGLVQPGGSLRLSCAASGFTFSGNDISWVRQAPGKGLE

WVAGISPYGGSTYYADSVKGRFTISADTSKNTAYLQMNSLRAEDTA

VYYCSRRVSFYSRHAGMDYWGQGTLVTVSS,
```
and/or
  (b) the light chain sequence has at least 85% sequence identity to the light chain sequence:

```
                                                  (SEQ ID NO: 16)
DIQMTQSPSSLSASVGDRVTITCRASQDVSTAVAWYQQKPGKAPKL

LIYSASFLYSGVPSRFSGSGSGTDFTLTISSLQPEDFATYYCQQSY

TTPPTFGQGTKVEIKR.
```

In a still another embodiment, provided is an isolated anti-NSP4 antibody or antigen binding fragment comprising a heavy chain variable region and a light chain variable region, wherein:
  (a) the heavy chain sequence has at least 85% sequence identity to the heavy chain sequence:

```
                                                  (SEQ ID NO: 15)
EVQLVESGGGLVQPGGSLRLSCAASGFTFTSYAISWVRQAPGKGLE

WVAGISPSNGYTNYADSVKGRFTISADTSKNTAYLQMNSLRAEDTA

VYYCSRAGRWTHSDIDYWGQGTLVTVSS,
```
and/or
  (b) the light chain sequence has at least 85% sequence identity to the light chain sequence:

```
                                                  (SEQ ID NO: 16)
DIQMTQSPSSLSASVGDRVTITCRASQDVSTAVAWYQQKPGKAPKL

LIYSASFLYSGVPSRFSGSGSGTDFTLTISSLQPEDFATYYCQQSY

TTPPTFGQGTKVEIKR.
```

In any of the above embodiments, an anti-NSP4 antibody is an isolated antibody. In any of the above embodiments, an anti-NSP4 antibody is humanized. In one embodiment, an anti-NSP4 antibody comprises HVRs as in any of the above embodiments and HVRs (including HVRs comprising Kabat CDR, Chothia CDR, or Contact CDR sequences) shown in FIG. 13, and further comprises an acceptor human framework, e.g. a human immunoglobulin framework or a human consensus framework.

In certain embodiments, an anti-NSP4 antibody described herein comprises HVRs as defined by Kabat, e.g., an anti-NSP4 antibody comprising CDR-H1, CDR-H2, CDR-H3, CDR-L1, CDR-L2, and CDR-L3, wherein each of the CDRs is defined by Kabat as further described herein. In certain embodiments, an anti-NSP4 antibody described herein comprises HVRs as defined by Chothia, e.g., an anti-NSP4 antibody comprising CDR-H1, CDR-H2, CDR-H3, CDR-L1, CDR-L2, and CDR-L3, wherein each of the CDRs is defined by Chothia as further described herein. In certain embodiments, an anti-NSP4 antibody described herein comprises HVRs as defined by Contact CDR sequences, e.g., an anti-NSP4 antibody comprising CDR-H1, CDR-H2, CDR-H3, CDR-L1, CDR-L2, and CDR-L3, wherein each of the CDRs is defined by Contact CDR sequences as further described herein.

In another aspect, an anti-NSP4 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:16. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-NSP4 antibody comprising that sequence retains the ability to bind to a NSP4. In certain embodiments, a total of 1, 2, 3, 4, 5, 6, 7, 8, 9, or 10 amino acids have been substituted, inserted and/or deleted in SEQ ID NO:16. In certain embodiments, the substitutions, insertions, or deletions occur in regions outside the HVRs (i.e., in the FRs). Optionally, the anti-NSP4 antibody comprises the VL sequence of SEQ ID NO:16, including post-translational modifications of that sequence.

In another aspect, an anti-NSP4 antibody comprises a heavy chain variable domain (VH) sequence having at least 90%, 91%, 92%, 93%, 94%, 95%, 96%, 97%, 98%, 99%, or 100% sequence identity to the amino acid sequence selected from the group consisting of SEQ ID NOS:13-15. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-NSP4 antibody comprising that sequence retains the ability to bind to NSP4. In certain embodiments, a total of 1, 2, 3, 4, 5, 6, 7, 8, 9, or 10 amino acids have been substituted, inserted and/or deleted in any of SEQ ID NO: 13-15. In certain embodiments, substitutions, insertions, or deletions occur in regions outside the HVRs (i.e., in the FRs). Optionally, the anti-NSP4 antibody comprises the VH sequence in any of SEQ ID NOS:13-15, including post-translational modifications of that sequence.

In some embodiments, provided herein is an anti-NSP4 antibody comprising a heavy chain and a light chain, wherein
(a) the heavy chain comprises an HVR-H1, an HVR-H2, and an HVR-H3 sequence having at least 85% sequence identity to GFTFSDNDIS (SEQ ID NO:50), GSISPDNGDTNYADSVKG (SEQ ID NO:51), and RDDVPAVFTSAMDY (SEQ ID NO:52), respectively; and/or
(b) the light chain comprises an HVR-L1, an HVR-L2, and an HVR-L3 sequence having at least 85% sequence identity to RASQDVS (SEQ ID NO:19), SASFLYS (SEQ ID NO:11), and QQSX$_1$X$_2$X$_3$PX$_4$T (SEQ ID NO:95), wherein X$_1$ is Y or A; X$_2$ is T, G, or D; X$_3$ is T or F; and X$_4$ is P or L, respectively.

In some embodiments, the anti-NSP4 antibody of the preceding paragraph comprises a light chain comprising an HVR-L3 sequence having at least 85% sequence identity to a sequence selected from SEQ ID NO:12 and 92-94.

In some embodiments, the antibody comprises a heavy chain and a light chain, wherein
(a) the heavy chain comprises an HVR-H1, an HVR-H2, and an HVR-H3 sequence having at least 85% sequence identity to GFTFSDNDIS (SEQ ID NO:50), GSISPDNGDTNYADSVKG (SEQ ID NO:51), and (SEQ ID NO:52), respectively; and/or
(b) the light chain comprises an HVR-L1, an HVR-L2, and an HVR-L3 sequence having at least 85% sequence identity to RASQDVS (SEQ ID NO:19), SASFLYS (SEQ ID NO:11), QQSYTTPPT (SEQ ID NO:12), respectively.

In some embodiments, the antibody comprises a heavy chain variable region comprising a sequence having at least 85% sequence identity to SEQ ID NO:78 and/or a light chain variable region comprising a sequence having at least 85% sequence identity to SEQ ID NO:16.

In some embodiments, the antibody comprises a heavy chain and a light chain, wherein
(a) the heavy chain comprises an HVR-H1, an HVR-H2, and an HVR-H3 sequence having at least 85% sequence identity to GFTFSDNDIS (SEQ ID NO:50), GSISPDNGDTNYADSVKG (SEQ ID NO:51), and RDDVPAVFTSAMDY (SEQ ID NO:52), respectively; and/or
(b) the light chain comprises an HVR-L1, an HVR-L2, and an HVR-L3 sequence having at least 85% sequence identity to RASQDVS (SEQ ID NO:19), SASFLYS (SEQ ID NO:11), and QQSYGFPLT (SEQ ID NO:92), respectively.

In some embodiments, the antibody comprises a heavy chain variable region comprising a sequence having at least 85% sequence identity to SEQ ID NO:78 and/or a light chain variable region comprising a sequence having at least 85% sequence identity to SEQ ID NO:102.

In some embodiments, the antibody comprises a heavy chain and a light chain, wherein
(a) the heavy chain comprises an HVR-H1, an HVR-H2, and an HVR-H3 sequence having at least 85% sequence identity to GFTFSDNDIS (SEQ ID NO:50), GSISPDNGDTNYADSVKG (SEQ ID NO:51), and RDDVPAVFTSAMDY (SEQ ID NO:52), respectively; and/or
(b) the light chain comprises an HVR-L1, an HVR-L2, and an HVR-L3 sequence having at least 85% sequence identity to RASQDVS (SEQ ID NO:19), SASFLYS (SEQ ID NO:11), and QQSYDFPLT (SEQ ID NO:93), respectively.

In some embodiments, the antibody comprises a heavy chain variable region comprising a sequence having at least 85% sequence identity to SEQ ID NO:78 and/or a light chain variable region comprising a sequence having at least 85% sequence identity to SEQ ID NO:103.

In some embodiments, the antibody comprises a heavy chain and a light chain, wherein
(a) the heavy chain comprises an HVR-H1, an HVR-H2, and an HVR-H3 sequence having at least 85% sequence identity to GFTFSDNDIS (SEQ ID NO:50), GSISPDNGDTNYADSVKG (SEQ ID NO:51), and (SEQ ID NO:52), respectively; and/or
(b) the light chain comprises an HVR-L1, an HVR-L2, and an HVR-L3 sequence having at least 85% sequence identity to RASQDVS (SEQ ID NO:19), SASFLYS (SEQ ID NO:11), and QQSAGFPLT (SEQ ID NO:94), respectively.

In some embodiments, the antibody comprises a heavy chain variable region comprising the sequence of SEQ ID NO:78 and/or a light chain variable region comprising the sequence of SEQ ID NO:104.

In some embodiments, provided herein is an anti-NSP4 antibody comprising an HVR-H2, an HVR-H3, and an HVR-L3 sequence having at least 85% sequence identity to GSISPDNGDTNYADSVKG (SEQ ID NO:51), RDDVPAVFTSAMDY (SEQ ID NO:52), and QQSX$_1$X$_2$X$_3$PX$_4$T (SEQ ID NO:95), wherein X$_1$ is Y or A; X$_2$ is T, G, or D; X$_3$ is T or F; and X$_4$ is P or L, respectively.

In some embodiments, the antibody comprises an HVR-H2, an HVR-H3, and an HVR-L3 sequence having at least 85% sequence identity to GSISPDNGDTNYADSVKG (SEQ ID NO:51), RDDVPAVFTSAMDY (SEQ ID NO:52), and QQSYTTPPT (SEQ ID NO:12), respectively. In some embodiments, the antibody comprises an HVR-H2, an HVR-H3, and an HVR-L3 sequence having at least 85% sequence identity to GSISPDNGDTNYADSVKG (SEQ ID NO:51), RDDVPAVFTSAMDY (SEQ ID NO:52), and QQSYGFPLT (SEQ ID NO:92), respectively. In some embodiments, the antibody comprises an HVR-H2, an HVR-H3, and an HVR-L3 sequence having at least 85% sequence identity to GSISPDNGDTNYADSVKG (SEQ ID NO:51), RDDVPAVFTSAMDY (SEQ ID NO:52), and QQSYDFPLT (SEQ ID NO:93), respectively. In some embodiments, the antibody comprises an HVR-H2, an HVR-H3, and an HVR-L3 sequence having at least 85% sequence identity to GSISPDNGDTNYADSVKG (SEQ ID NO:51), RDDVPAVFTSAMDY (SEQ ID NO:52), and QQSAGFPLT (SEQ ID NO:94), respectively.

In some embodiments, provided herein is an anti-NSP4 antibody comprising a heavy chain and a light chain, wherein
  (a) the heavy chain comprises an HVR-H1, an HVR-H2, and an HVR-H3 sequence having at least 85% sequence identity to GFTFSGSGIH (SEQ ID NO:65), AWISPTGGNTYYADSVKG (SEQ ID NO:66), and KRHLHNVAFDY (SEQ ID NO:87), respectively; and/or
  (b) the light chain comprises an HVR-L1, an HVR-L2, and an HVR-L3 sequence having at least 85% sequence identity to RASQDVS (SEQ ID NO:19), SASFLYS (SEQ ID NO:11), and QQAYSAPPT (SEQ ID NO:96), respectively.

In some embodiments, the antibody comprises a heavy chain variable region comprising a sequence having at least 85% sequence identity to SEQ ID NO:105 and/or a light chain variable region comprising a sequence having at least 85% sequence identity to SEQ ID NO:106.

In some embodiments, provided herein is an anti-NSP4 antibody comprising an HVR-H2, an HVR-H3, and an HVR-L3 sequence having at least 85% sequence identity to AWISPTGGNTYYADSVKG (SEQ ID NO:66), KRHLHNVAFDY (SEQ ID NO:87), and QQAYSAPPT (SEQ ID NO:96), respectively.

In some embodiments, provided herein is an anti-NSP4 antibody comprising a heavy chain and a light chain, wherein
  (a) the heavy chain comprises an HVR-H1, an HVR-H2, and an HVR-H3 sequence having at least 85% sequence identity to GFTFSGSGIH (SEQ ID NO:65), AWISPTGGNTYYADSVKG (SEQ ID NO:66) or AWIPTAGGNTYYADSVKG (SEQ ID NO:88), and X$_1$X$_2$X$_3$FHNVAFDY (SEQ ID NO:91), wherein X$_1$ is K or R; X$_2$ is S, G, or V; and X$_3$ is L or F, respectively; and/or
  (b) the light chain comprises an HVR-L1, an HVR-L2, and an HVR-L3 sequence having at least 85% sequence identity to RASQDVS (SEQ ID NO:19), SASFLYS (SEQ ID NO:11), and QQX$_1$X$_2$X$_3$X$_4$PPT (SEQ ID NO:101), wherein X$_1$ is S, A, N, or T; X$_2$ is Y, N, or F; X$_3$ is T, S, or N; and X$_4$ is T, A, or S, respectively.

In some embodiments, the anti-NSP4 antibody of the preceding paragraph comprises a heavy chain comprising an HVR-H3 sequence having at least 85% sequence identity to a sequence selected from SEQ ID NO:67, 89, and 90. In some embodiments, the anti-NSP4 antibody of the preceding paragraph comprises a light chain comprising an HVR-L3 sequence having at least 85% sequence identity to a sequence selected from SEQ ID NO:12 and 97-100.

In some embodiments, the antibody comprises a heavy chain and a light chain, wherein
  (a) the heavy chain comprises an HVR-H1, an HVR-H2, and an HVR-H3 sequence having at least 85% sequence identity to GFTFSGSGIH (SEQ ID NO:65), AWISPTGGNTYYADSVKG (SEQ ID NO:66), KSLFHNVAFDY (SEQ ID NO:67), respectively; and/or
  (b) the light chain comprises an HVR-L1, an HVR-L2, and an HVR-L3 sequence having at least 85% sequence identity to RASQDVS (SEQ ID NO:19), SASFLYS (SEQ ID NO:11), and QQSYTTPPT (SEQ ID NO:12), respectively.

In some embodiments, the antibody comprises a heavy chain variable region comprising a sequence having at least 85% sequence identity to SEQ ID NO:83 and/or a light chain variable region comprising a sequence having at least 85% sequence identity to SEQ ID NO:16.

In some embodiments, the antibody comprises a heavy chain and a light chain, wherein
  (a) the heavy chain comprises an HVR-H1, an HVR-H2, and an HVR-H3 sequence having at least 85% sequence identity to GFTFSGSGIH (SEQ ID NO:65), AWIPTAGGNTYYADSVKG (SEQ ID NO:88), and KSLFHNVAFDY (SEQ ID NO:67), respectively; and/or
  (b) the light chain comprises an HVR-L1, an HVR-L2, and an HVR-L3 sequence having at least 85% sequence identity to RASQDVS (SEQ ID NO:19), SASFLYS (SEQ ID NO:11), and QQSYTAPPT (SEQ ID NO:97), respectively.

In some embodiments, the antibody comprises a heavy chain variable region comprising a sequence having at least 85% sequence identity to SEQ ID NO:107 and/or a light chain variable region comprising a sequence having at least 85% sequence identity to SEQ ID NO:108.

In some embodiments, the antibody comprises a heavy chain and a light chain, wherein
  (a) the heavy chain comprises an HVR-H1, an HVR-H2, and an HVR-H3 sequence having at least 85% sequence identity to GFTFSGSGIH (SEQ ID NO:65), AWISPTGGNTYYADSVKG (SEQ ID NO:66), and KSLFHNVAFDY (SEQ ID NO:67), respectively; and/or
  (b) the light chain comprises an HVR-L1, an HVR-L2, and an HVR-L3 sequence having at least 85% sequence identity to RASQDVS (SEQ ID NO:19), SASFLYS (SEQ ID NO:11), and QQANSTPPT (SEQ ID NO:98), respectively.

In some embodiments, the antibody comprises a heavy chain variable region comprising a sequence having at least 85% sequence identity to SEQ ID NO:83 and/or a light chain variable region comprising a sequence having at least 85% sequence identity to SEQ ID NO:109.

In some embodiments, the antibody comprises a heavy chain and a light chain, wherein
(a) the heavy chain comprises an HVR-H1, an HVR-H2, and an HVR-H3 sequence having at least 85% sequence identity to GFTFSGSGIH (SEQ ID NO:65), AWISPTGGNTYYADSVKG (SEQ ID NO:66), and RGLFHNVAFDY (SEQ ID NO:89), respectively; and/or
(b) the light chain comprises an HVR-L1, an HVR-L2, and an HVR-L3 sequence having at least 85% sequence identity to RASQDVS (SEQ ID NO:19), SASFLYS (SEQ ID NO:11), and QQSYTAPPT (SEQ ID NO:97), respectively.

In some embodiments, the antibody comprises a heavy chain variable region comprising a sequence having at least 85% sequence identity to SEQ ID NO:110 and/or a light chain variable region comprising a sequence having at least 85% sequence identity to SEQ ID NO:108.

In some embodiments, the antibody comprises a heavy chain and a light chain, wherein
(a) the heavy chain comprises an HVR-H1, an HVR-H2, and an HVR-H3 sequence having at least 85% sequence identity to GFTFSGSGIH (SEQ ID NO:65), AWISPTGGNTYYADSVKG (SEQ ID NO:66), and RVFFHNVAFDY (SEQ ID NO:90), respectively; and/or
(b) the light chain comprises an HVR-L1, an HVR-L2, and an HVR-L3 sequence having at least 85% sequence identity to RASQDVS (SEQ ID NO:19), SASFLYS (SEQ ID NO:11), and QQNFSSPPT (SEQ ID NO:99), respectively.

In some embodiments, the antibody comprises a heavy chain variable region comprising a sequence having at least 85% sequence identity to SEQ ID NO:111 and/or a light chain variable region comprising a sequence having at least 85% sequence identity to SEQ ID NO:112.

In some embodiments, the antibody comprises a heavy chain and a light chain, wherein
(a) the heavy chain comprises an HVR-H1, an HVR-H2, and an HVR-H3 sequence having at least 85% sequence identity to GFTFSGSGIH (SEQ ID NO:65), AWISPTGGNTYYADSVKG (SEQ ID NO:66), and KSLFHNVAFDY (SEQ ID NO:67), respectively; and/or
(b) the light chain comprises an HVR-L1, an HVR-L2, and an HVR-L3 sequence having at least 85% sequence identity to RASQDVS (SEQ ID NO:19), SASFLYS (SEQ ID NO:11), and QQSYTAPPT (SEQ ID NO:97), respectively.

In some embodiments, the antibody comprises a heavy chain variable region comprising a sequence having at least 85% sequence identity to SEQ ID NO:83 and/or a light chain variable region comprising a sequence having at least 85% sequence identity to SEQ ID NO:108.

In some embodiments, the antibody comprises a heavy chain and a light chain, wherein
(a) the heavy chain comprises an HVR-H1, an HVR-H2, and an HVR-H3 sequence having at least 85% sequence identity to GFTFSGSGIH (SEQ ID NO:65), AWISPTGGNTYYADSVKG (SEQ ID NO:66), RGLFHNVAFDY (SEQ ID NO:89), respectively; and/or
(b) the light chain comprises an HVR-L1, an HVR-L2, and an HVR-L3 sequence having at least 85% sequence identity to RASQDVS (SEQ ID NO:19), SASFLYS (SEQ ID NO:11), and QQTYNAPPT (SEQ ID NO:100), respectively.

In some embodiments, the antibody comprises a heavy chain variable region comprising a sequence having at least 85% sequence identity to SEQ ID NO:110 and/or a light chain variable region comprising a sequence having at least 85% sequence identity to SEQ ID NO:113.

In some embodiments, provided herein is an anti-NSP4 antibody comprising an HVR-H2, an HVR-H3, and an HVR-L3 sequence having at least 85% sequence identity to AWISPTGGNTYYADSVKG (SEQ ID NO:66) or AWIPTAGGNTYYADSVKG (SEQ ID NO:88), $X_1X_2X_3$FHNVAFDY (SEQ ID NO:91), wherein $X_1$ is K or R; $X_2$ is S, G, or V; and $X_3$ is L or F; and QQ$X_1X_2X_3X_4$PPT (SEQ ID NO:101), wherein $X_1$ is S, A, N, or T; $X_2$ is Y, N, or F; $X_3$ is T, S, or N; and $X_4$ is T, A, or S; respectively. In some embodiments, the antibody comprises an HVR-H2, an HVR-H3, and an HVR-L3 sequence having at least 85% sequence identity to AWISPTGGNTYYADSVKG (SEQ ID NO:66), KSLFHNVAFDY (SEQ ID NO:67), and QQSYTTPPT (SEQ ID NO:12), respectively. In some embodiments, the antibody comprises an HVR-H2, an HVR-H3, and an HVR-L3 sequence having at least 85% sequence identity to AWIPTAGGNTYYADSVKG (SEQ ID NO:88), KSLFHNVAFDY (SEQ ID NO:67), and QQSYTAPPT (SEQ ID NO:97), respectively. In some embodiments, the antibody comprises an HVR-H2, an HVR-H3, and an HVR-L3 sequence having at least 85% sequence identity to AWISPTGGNTYYADSVKG (SEQ ID NO:66), KSLFHNVAFDY (SEQ ID NO:67), and QQANSTPPT (SEQ ID NO:98), respectively. In some embodiments, the antibody comprises an HVR-H2, an HVR-H3, and an HVR-L3 sequence having at least 85% sequence identity to AWISPTGGNTYYADSVKG (SEQ ID NO:66), RGLFHNVAFDY (SEQ ID NO:89), and QQSYTAPPT (SEQ ID NO:97), respectively. In some embodiments, the antibody comprises an HVR-H2, an HVR-H3, and an HVR-L3 sequence having at least 85% sequence identity to AWISPTGGNTYYADSVKG (SEQ ID NO:66), RGLFHNVAFDY (SEQ ID NO:90), and QQNFSSPPT (SEQ ID NO:99), respectively. In some embodiments, the antibody comprises an HVR-H2, an HVR-H3, and an HVR-L3 sequence having at least 85% sequence identity to AWISPTGGNTYYADSVKG (SEQ ID NO:66), KSLFHNVAFDY (SEQ ID NO:67), and QQSYTAPPT (SEQ ID NO:97), respectively. In some embodiments, the antibody comprises an HVR-H2, an HVR-H3, and an HVR-L3 sequence having at least 85% sequence identity to AWISPTGGNTYYADSVKG (SEQ ID NO:66), RGLFHNVAFDY (SEQ ID NO:89), and QQTYNAPPT (SEQ ID NO:100), respectively.

In some embodiments, provided herein is an anti-NSP4 antibody comprising a heavy chain and a light chain, wherein
(a) the heavy chain comprises an HVR-H1, an HVR-H2, and an HVR-H3 sequence having at least 85% sequence identity to GFTFSGSWIS (SEQ ID NO:20), GTISPYNGSTYYADSVKG (SEQ ID NO:21), and RVLRPKVYASVMDY (SEQ ID NO:22), respectively; and/or
(b) the light chain comprises an HVR-L1, an HVR-L2, and an HVR-L3 sequence having at least 85% sequence identity to RASQDVS (SEQ ID NO:19), SASFLYS (SEQ ID NO:11), and QQSYTTPPT (SEQ ID NO:12), respectively.

In some embodiments, the antibody comprises a heavy chain variable region comprising a sequence having at least 85% sequence identity to SEQ ID NO:68 and/or a light chain variable region comprising a sequence having at least 85% sequence identity to SEQ ID NO:16.

In some embodiments, provided herein is an anti-NSP4 antibody comprising a heavy chain and a light chain, wherein
  (a) the heavy chain comprises an HVR-H1, an HVR-H2, and an HVR-H3 sequence having at least 85% sequence identity to GFTFSGYSIH (SEQ ID NO:23), AGISPTNGYTDYADSVKG (SEQ ID NO:24), and RLVFYRGVMDY (SEQ ID NO:25), respectively; and/or
  (b) the light chain comprises an HVR-L1, an HVR-L2, and an HVR-L3 sequence having at least 85% sequence identity to RASQDVS (SEQ ID NO:19), SASFLYS (SEQ ID NO:11), and QQSYTTPPT (SEQ ID NO:12), respectively.

In some embodiments, the antibody comprises a heavy chain variable region comprising a sequence having at least 85% sequence identity to SEQ ID NO:69 and/or a light chain variable region comprising a sequence having at least 85% sequence identity to SEQ ID NO:16.

In some embodiments, provided herein is an anti-NSP4 antibody comprising a heavy chain and a light chain, wherein
  (a) the heavy chain comprises an HVR-H1, an HVR-H2, and an HVR-H3 sequence having at least 85% sequence identity to GFTFSDNWIS (SEQ ID NO:26), GYIYPASGYTDYADSVKG (SEQ ID NO:27), and SDSPHAYWYAMDY (SEQ ID NO:28), respectively; and/or
  (b) the light chain comprises an HVR-L1, an HVR-L2, and an HVR-L3 sequence having at least 85% sequence identity to RASQDVS (SEQ ID NO:19), SASFLYS (SEQ ID NO:11), and QQSYTTPPT (SEQ ID NO:12), respectively.

In some embodiments, the antibody comprises a heavy chain variable region comprising a sequence having at least 85% sequence identity to SEQ ID NO:70 and/or a light chain variable region comprising a sequence having at least 85% sequence identity to SEQ ID NO:16.

In some embodiments, provided herein is an anti-NSP4 antibody comprising a heavy chain and a light chain, wherein
  (a) the heavy chain comprises an HVR-H1, an HVR-H2, and an HVR-H3 sequence having at least 85% sequence identity to GFTFTNNSIS (SEQ ID NO:29), GAISPNNGSTYYADSVKG (SEQ ID NO:30), and RNAWHYSWVGVMDY (SEQ ID NO:31), respectively; and/or
  (b) the light chain comprises an HVR-L1, an HVR-L2, and an HVR-L3 sequence having at least 85% sequence identity to RASQDVS (SEQ ID NO:19), SASFLYS (SEQ ID NO:11), and QQSYTTPPT (SEQ ID NO:12), respectively.

In some embodiments, the antibody comprises a heavy chain variable region comprising a sequence having at least 85% sequence identity to SEQ ID NO:71 and/or a light chain variable region comprising a sequence having at least 85% sequence identity to SEQ ID NO:16.

In some embodiments, provided herein is an anti-NSP4 antibody comprising a heavy chain and a light chain, wherein
  (a) the heavy chain comprises an HVR-H1, an HVR-H2, and an HVR-H3 sequence having at least 85% sequence identity to GFTFTDYSIH (SEQ ID NO:32), AEIYPYSGDTYYADSVKG (SEQ ID NO:33), and RDGDGWFDWAMDY (SEQ ID NO:34), respectively; and/or
  (b) the light chain comprises an HVR-L1, an HVR-L2, and an HVR-L3 sequence having at least 85% sequence identity to RASQDVS (SEQ ID NO:19), SASFLYS (SEQ ID NO:11), and QQSYTTPPT (SEQ ID NO:12), respectively.

In some embodiments, the antibody comprises a heavy chain variable region comprising a sequence having at least 85% sequence identity to SEQ ID NO:72 and/or a light chain variable region comprising a sequence having at least 85% sequence identity to SEQ ID NO:16.

In some embodiments, provided herein is an anti-NSP4 antibody comprising a heavy chain and a light chain, wherein
  (a) the heavy chain comprises an HVR-H1, an HVR-H2, and an HVR-H3 sequence having at least 85% sequence identity to GFTFSSTAIS (SEQ ID NO:35), GEIYPSDGYTDYADSVKG (SEQ ID NO:36), and RVKWAVSSLGVMDY (SEQ ID NO:37), respectively; and/or
  (b) the light chain comprises an HVR-L1, an HVR-L2, and an HVR-L3 sequence having at least 85% sequence identity to RASQDVS (SEQ ID NO:19), SASFLYS (SEQ ID NO:11), and QQSYTTPPT (SEQ ID NO:12), respectively.

In some embodiments, the antibody comprises a heavy chain variable region comprising a sequence having at least 85% sequence identity to SEQ ID NO:73 and/or a light chain variable region comprising a sequence having at least 85% sequence identity to SEQ ID NO:16.

In some embodiments, provided herein is an anti-NSP4 antibody comprising a heavy chain and a light chain, wherein
  (a) the heavy chain comprises an HVR-H1, an HVR-H2, and an HVR-H3 sequence having at least 85% sequence identity to GFTFTDSDIS (SEQ ID NO:38), AWISPSDGATDYADSVKG (SEQ ID NO:39), and HEASDDDYAIDY (SEQ ID NO:40), respectively; and/or
  (b) the light chain comprises an HVR-L1, an HVR-L2, and an HVR-L3 sequence having at least 85% sequence identity to RASQDVS (SEQ ID NO:19), SASFLYS (SEQ ID NO:11), and QQSYTTPPT (SEQ ID NO:12), respectively.

In some embodiments, the antibody comprises a heavy chain variable region comprising a sequence having at least 85% sequence identity to SEQ ID NO:74 and/or a light chain variable region comprising a sequence having at least 85% sequence identity to SEQ ID NO:16.

In some embodiments, provided herein is an anti-NSP4 antibody comprising a heavy chain and a light chain, wherein
  (a) the heavy chain comprises an HVR-H1, an HVR-H2, and an HVR-H3 sequence having at least 85% sequence identity to GFTFSDYWIS (SEQ ID NO:41), AGISPNNGDTYYADSVKG (SEQ ID NO:42), and REDDDERDYAMDY (SEQ ID NO:43), respectively; and/or (b) the light chain comprises an HVR-L1, an HVR-L2, and an HVR-L3 sequence having at least 85% sequence identity to RASQDVS (SEQ ID NO:19), SASFLYS (SEQ ID NO:11), and QQSYTTPPT (SEQ ID NO:12), respectively).

In some embodiments, the antibody comprises a heavy chain variable region comprising a sequence having at least 85% sequence identity to SEQ ID NO:75 and/or a light chain variable region comprising a sequence having at least 85% sequence identity to SEQ ID NO:16.

In some embodiments, provided herein is an anti-NSP4 antibody comprising a heavy chain and a light chain, wherein
  (a) the heavy chain comprises an HVR-H1, an HVR-H2, and an HVR-H3 sequence having at least 85% sequence identity to GFTFTGYGIS (SEQ ID NO:44), GWIYPASGATYYADSVKG (SEQ ID NO:45), and RHRAFDWYPYYIGSSVMDY (SEQ ID NO:46), respectively; and/or
  (b) the light chain comprises an HVR-L1, an HVR-L2, and an HVR-L3 sequence having at least 85% sequence identity to RASQDVS (SEQ ID NO:19), SASFLYS (SEQ ID NO:11), and QQSYTTPPT (SEQ ID NO:12), respectively.

In some embodiments, the antibody comprises a heavy chain variable region comprising a sequence having at least 85% sequence identity to SEQ ID NO:76 and/or a light chain variable region comprising a sequence having at least 85% sequence identity to SEQ ID NO:16.

In some embodiments, provided herein is an anti-NSP4 antibody comprising a heavy chain and a light chain, wherein
  (a) the heavy chain comprises an HVR-H1, an HVR-H2, and an HVR-H3 sequence having at least 85% sequence identity to GFTFSDYSIS (SEQ ID NO:47), GEINPAGGATYYADSVKG (SEQ ID NO:48), and RGDFPFWSDAYYVMDY (SEQ ID NO:49), respectively; and/or
  (b) the light chain comprises an HVR-L1, an HVR-L2, and an HVR-L3 sequence having at least 85% sequence identity to RASQDVS (SEQ ID NO:19), SASFLYS (SEQ ID NO:11), and QQSYTTPPT (SEQ ID NO:12), respectively).

In some embodiments, the antibody comprises a heavy chain variable region comprising a sequence having at least 85% sequence identity to SEQ ID NO:77 and/or a light chain variable region comprising a sequence having at least 85% sequence identity to SEQ ID NO:16.

In some embodiments, provided herein is an anti-NSP4 antibody comprising a heavy chain and a light chain, wherein
  (a) the heavy chain comprises an HVR-H1, an HVR-H2, and an HVR-H3 sequence having at least 85% sequence identity to GFTFSDNDIS (SEQ ID NO:50), GSISPDNGDTNYADSVKG (SEQ ID NO:51), and RDDVPAVFTSAMDY (SEQ ID NO:52), respectively; and/or
  (b) the light chain comprises an HVR-L1, an HVR-L2, and an HVR-L3 sequence having at least 85% sequence identity to RASQDVS (SEQ ID NO:19), SASFLYS (SEQ ID NO:11), and QQSYTTPPT (SEQ ID NO:12), respectively.

In some embodiments, the antibody comprises a heavy chain variable region comprising a sequence having at least 85% sequence identity to SEQ ID NO:78 and/or a light chain variable region comprising a sequence having at least 85% sequence identity to SEQ ID NO:16.

In some embodiments, provided herein is an anti-NSP4 antibody comprising a heavy chain and a light chain, wherein
  (a) the heavy chain comprises an HVR-H1, an HVR-H2, and an HVR-H3 sequence having at least 85% sequence identity to GFTFSGSDIS (SEQ ID NO:53), GEIYPSNGDTYYADSVKG (SEQ ID NO:54), and RSVRPSWWAMDY (SEQ ID NO:55), respectively; and/or
  (b) the light chain comprises an HVR-L1, an HVR-L2, and an HVR-L3 sequence having at least 85% sequence identity to RASQDVS (SEQ ID NO:19), SASFLYS (SEQ ID NO:11), and QQSYTTPPT (SEQ ID NO:12), respectively.

In some embodiments, the antibody comprises a heavy chain variable region comprising a sequence having at least 85% sequence identity to SEQ ID NO:79 and/or a light chain variable region comprising a sequence having at least 85% sequence identity to SEQ ID NO:16.

In some embodiments, provided herein is an anti-NSP4 antibody comprising a heavy chain and a light chain, wherein
  (a) the heavy chain comprises an HVR-H1, an HVR-H2, and an HVR-H3 sequence having at least 85% sequence identity to GFTFSSYDIS (SEQ ID NO:56), GTISPYDGYTDYADSVKG (SEQ ID NO:57), and RYIRRYSVHYGMDY (SEQ ID NO:58), respectively; and/or
  (b) the light chain comprises an HVR-L1, an HVR-L2, and an HVR-L3 sequence having at least 85% sequence identity to RASQDVS (SEQ ID NO:19), SASFLYS (SEQ ID NO:11), and QQSYTTPPT (SEQ ID NO:12), respectively.

In some embodiments, the antibody comprises a heavy chain variable region comprising a sequence having at least 85% sequence identity to SEQ ID NO:80 and/or a light chain variable region comprising a sequence having at least 85% sequence identity to SEQ ID NO:16.

In some embodiments, provided herein is an anti-NSP4 antibody comprising a heavy chain and a light chain, wherein
  (a) the heavy chain comprises an HVR-H1, an HVR-H2, and an HVR-H3 sequence having at least 85% sequence identity to GFTFTSTSIH (SEQ ID NO:59), AEITPHGGYTNYADSVKG (SEQ ID NO:60), and RGRTKWGWLYGMDY (SEQ ID NO:61), respectively; and/or
  (b) the light chain comprises an HVR-L1, an HVR-L2, and an HVR-L3 sequence having at least 85% sequence identity to RASQDVS (SEQ ID NO:19), SASFLYS (SEQ ID NO:11), and QQSYTTPPT (SEQ ID NO:12), respectively.

In some embodiments, the antibody comprises a heavy chain variable region comprising a sequence having at least 85% sequence identity to SEQ ID NO:81 and/or a light chain variable region comprising a sequence having at least 85% sequence identity to SEQ ID NO:16.

In some embodiments, provided herein is an anti-NSP4 antibody comprising a heavy chain and a light chain, wherein
  (a) the heavy chain comprises an HVR-H1, an HVR-H2, and an HVR-H3 sequence having at least 85% sequence identity to GFTFTNNSIH (SEQ ID NO:62), AEIAPDDGYTYYADSVKG (SEQ ID NO:63), and RGVIRYAYLYAMDY (SEQ ID NO:64), respectively; and/or (b) the light chain comprises an HVR-L1, an HVR-L2, and an HVR-L3 sequence having at least 85% sequence identity to RASQDVS (SEQ ID NO:19), SASFLYS (SEQ ID NO:11), and QQSYTTPPT (SEQ ID NO:12), respectively.

In some embodiments, the antibody comprises a heavy chain variable region comprising a sequence having at least 85% sequence identity to SEQ ID NO:82 and/or a light chain variable region comprising a sequence having at least 85% sequence identity to SEQ ID NO:16.

In some embodiments, provided herein is an anti-NSP4 antibody comprising a heavy chain and a light chain, wherein
(a) the heavy chain comprises an HVR-H1, an HVR-H2, and an HVR-H3 sequence having at least 85% sequence identity to GFTFSGSGIH (SEQ ID NO:65), AWISPTGGNTYYADSVKG (SEQ ID NO:66), and KSLFHNVAFDY (SEQ ID NO:67), respectively; and/or
(b) the light chain comprises an HVR-L1, an HVR-L2, and an HVR-L3 sequence having at least 85% sequence identity to RASQDVS (SEQ ID NO:19), SASFLYS (SEQ ID NO:11), and QQSYTTPPT (SEQ ID NO:12), respectively.

In some embodiments, the antibody comprises a heavy chain variable region comprising a sequence having at least 85% sequence identity to SEQ ID NO:83 and/or a light chain variable region comprising a sequence having at least 85% sequence identity to SEQ ID NO:16.

In some embodiments, provided herein is an anti-NSP4 antibody comprising a heavy chain and a light chain, wherein
(a) the heavy chain comprises an HVR-H1, an HVR-H2, and an HVR-H3 sequence having at least 85% sequence identity to GFTFSNTYIS (SEQ ID NO:1), GFIYPANGATYYADSVKG (SEQ ID NO:2), and RRYRLSFDY (SEQ ID NO:3), respectively; and/or
(b) the light chain comprises an HVR-L1, an HVR-L2, and an HVR-L3 sequence having at least 85% sequence identity to RASQDVS (SEQ ID NO:19), SASFLYS (SEQ ID NO:11), and QQSYTTPPT (SEQ ID NO:12), respectively.

In some embodiments, the antibody comprises a heavy chain variable region comprising a sequence having at least 85% sequence identity to SEQ ID NO:84 and/or a light chain variable region comprising a sequence having at least 85% sequence identity to SEQ ID NO:16.

In some embodiments, provided herein is an anti-NSP4 antibody comprising a heavy chain and a light chain, wherein
(a) the heavy chain comprises an HVR-H1, an HVR-H2, and an HVR-H3 sequence having at least 85% sequence identity to GFTFSGNDIS (SEQ ID NO:4), AGISPYGGSTYYADSVKG (SEQ ID NO:5), and RRVSFYSRHAGMDY (SEQ ID NO:6), respectively; and/or
(b) the light chain comprises an HVR-L1, an HVR-L2, and an HVR-L3 sequence having at least 85% sequence identity to RASQDVS (SEQ ID NO:19), SASFLYS (SEQ ID NO:11), and QQSYTTPPT (SEQ ID NO:12), respectively.

In some embodiments, the antibody comprises a heavy chain variable region comprising a sequence having at least 85% sequence identity to SEQ ID NO:85 and/or a light chain variable region comprising a sequence having at least 85% sequence identity to SEQ ID NO:16.

In some embodiments, provided herein is an anti-NSP4 antibody comprising a heavy chain and a light chain, wherein
(a) the heavy chain comprises an HVR-H1, an HVR-H2, and an HVR-H3 sequence having at least 85% sequence identity to GFTFTSYAIS (SEQ ID NO:7), AGISPSNGYTNYADSVKG (SEQ ID NO:8), and RAGRWTHSDIDY (SEQ ID NO:9), respectively; and/or
(b) the light chain comprises an HVR-L1, an HVR-L2, and an HVR-L3 sequence having at least 85% sequence identity to RASQDVS (SEQ ID NO:19), SASFLYS (SEQ ID NO:11), and QQSYTTPPT (SEQ ID NO:12), respectively.

In some embodiments, the antibody comprises a heavy chain variable region comprising a sequence having at least 85% sequence identity to SEQ ID NO:86 and/or a light chain variable region comprising a sequence having at least 85% sequence identity to SEQ ID NO:16.

In some embodiments that can be combined with any of the embodiments described above, the sequence identity can be at least 86%, 87%, 88%, 89%, 90%, 91%, 92%, 93%, 94%, 95%, 96%, 97%, 98%, 99%, or 100% sequence identity.

In some of the above embodiments, an anti-NSP4 antibody is an isolated antibody. In some of the above embodiments, an anti-NSP4 antibody is humanized. In one embodiment, an anti-NSP4 antibody comprises HVRs as in any of the above embodiments and HVRs (including HVRs comprising Kabat CDR, Chothia CDR, or Contact CDR sequences) of the antibodies described herein.

In certain embodiments, an anti-NSP4 antibody described herein comprises HVRs as defined by Kabat, e.g., an anti-NSP4 antibody comprising CDR-H1, CDR-H2, CDR-H3, CDR-L1, CDR-L2, and CDR-L3, wherein each of the CDRs is defined by Kabat as further described herein. In certain embodiments, an anti-NSP4 antibody described herein comprises HVRs as defined by Chothia, e.g., an anti-NSP4 antibody comprising CDR-H1, CDR-H2, CDR-H3, CDR-L1, CDR-L2, and CDR-L3, wherein each of the CDRs is defined by Chothia as further described herein. In certain embodiments, an anti-NSP4 antibody described herein comprises HVRs as defined by Contact CDR sequences, e.g., an anti-NSP4 antibody comprising CDR-H1, CDR-H2, CDR-H3, CDR-L1, CDR-L2, and CDR-L3, wherein each of the CDRs is defined by Contact CDR sequences as further described herein.

In another aspect, an anti-NSP4 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence selected from SEQ ID NO:16, 102, 103, 104, 106, 108, 109, 112, or 113. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-NSP4 antibody comprising that sequence retains the ability to bind to a NSP4. In certain embodiments, a total of 1, 2, 3, 4, 5, 6, 7, 8, 9, or 10 amino acids have been substituted, inserted and/or deleted in any of SEQ ID NO:16, 102, 103, 104, 106, 108, 109, 112, or 113. In certain embodiments, the substitutions, insertions, or deletions occur in regions outside the HVRs (i.e., in the FRs). Optionally, the anti-NSP4 antibody comprises the VL sequence of any of SEQ ID NO:16, 102, 103, 104, 106, 108, 109, 112, or 113, including post-translational modifications of those sequences. Optionally, the light chain contains a constant region with the sequence of SEQ ID NO:115.

In another aspect, an anti-NSP4 antibody comprises a heavy chain variable domain (VH) sequence having at least 90%, 91%, 92%, 93%, 94%, 95%, 96%, 97%, 98%, 99%, or 100% sequence identity to the amino acid sequence selected from SEQ ID NO:13-15, 68-86, 105, 107, 110, and 111. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-NSP4 antibody comprising that sequence retains the ability to bind to NSP4. In certain embodiments, a total of 1, 2, 3, 4, 5, 6, 7, 8, 9, or 10 amino acids have been substituted, inserted and/or deleted in any of SEQ ID NO:13-15, 68-86, 105, 107, 110, and 111. In certain embodiments, substitutions, insertions, or deletions occur in regions outside the HVRs (i.e., in the FRs). Optionally, the anti-NSP4 antibody comprises the VH sequence in any of SEQ ID NO:13-15, 68-86, 105, 107, 110, and 111, including post-translational modifications of those sequences. Optionally, the heavy chain contains a constant region with the sequence of SEQ ID NO:114.

In a further aspect of the invention, an anti-NSP4 antibody according to any of the above embodiments is a monoclonal antibody, including a chimeric, humanized or human antibody. In one embodiment, an anti-NSP4 antibody is an antibody fragment, e.g., a Fv, Fab, Fab', scFv, diabody, or F(ab')$_2$ fragment. In another embodiment, the antibody is a full length antibody, e.g., an intact IgG1 antibody or other antibody class or isotype (e.g., IgG$_2$, IgG$_3$, or IgG$_4$) as defined herein.

Amino acid sequences of NSP4 are known in the art. For example, a human NSP4 can have an amino acid sequence as shown in NCBI Accession number NP_999875.1, a non-human primate NSP4 can have an amino acid sequence as shown in NCBI Accession number XP_001146596.1 (chimpanzee NSP4), XP_002828403.1 (orangutan NSP4), EHH29398.1 (rhesus monkey NSP4), XP_003914595.1 (baboon NSP4), XP_002761565.1 (marmoset NSP4), or XP_003788878.1 (galago NSP4), a non-primate mammal can have an amino acid sequence as shown in NCBI Accession number NP_001036175.1 (mouse NSP4), Q6IE59.2 (rat NSP4), XP_004717061.1 (hedgehog NSP4), XP_001375784.7 (opossum NSP4), XP_542217.3 (dog NSP4), XP_593377.3 (cow NSP4) or XP_004009516.1 (sheep NSP4). In some embodiments, the anti-NSP4 antibody binds to human NSP4. In some embodiments, the anti-NSP4 antibody binds to mouse NSP4. In some embodiments, the anti-NSP4 antibody binds to both a human NSP4 and a mouse NSP4. In some embodiments, the anti-NSP4 antibody binds to an amino acid sequence of a NSP4 as shown in FIG. 1.

In a further aspect, an anti-NSP4 antibody according to any of the above embodiments may incorporate any of the features, singly or in combination, as described in Sections below:

Antibody Affinity

In certain embodiments, an antibody provided herein has a dissociation constant (Kd) of ≤1 µM, ≤150 nM, ≤100 nM, ≤50 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., J. Mol. Biol. 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications*, pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics such as the methods described in Example 3. Additional methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for a NSP4 and the other is for any other antigen. In certain embodiments, bispecific antibodies may bind to two different epitopes of a NSP4. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g. Gruber et al., *J. Immunol.*, 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to a NSP4 as well as another, different antigen (see, US 2008/0069820, for example).

Antibody Variants

In certain embodiments, amino acid sequence variants of the antibodies provided herein are contemplated. For example, it may be desirable to improve the binding affinity and/or other biological properties of the antibody Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes Amino acid substitutions may be introduced into an antibody of interest and the products screened for a desired activity, e.g., retained/improved antigen binding, decreased immunogenicity, or improved ADCC or CDC.

TABLE 1

Exemplary Substitutions.

| Original Residue | Exemplary Substitutions | Preferred Substitutions |
|---|---|---|
| Ala (A) | Val; Leu; Ile | Val |
| Arg (R) | Lys; Gln; Asn | Lys |

TABLE 1-continued

Exemplary Substitutions.

| Original Residue | Exemplary Substitutions | Preferred Substitutions |
|---|---|---|
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
 a. hydrophobic: Norleucine, Met, Ala, Val, Leu, Ile;
 b. neutral hydrophilic: Cys, Ser, Thr, Asn, Gln;
 c. acidic: Asp, Glu;
 d. basic: His, Lys, Arg;
 e. residues that influence chain orientation: Gly, Pro;
 f. aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e g, improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided comprising an Fc region wherein a carbohydrate structure attached to the Fc region has reduced fucose or lacks fucose, which may improve ADCC function. Specifically, antibodies are contemplated herein that have reduced fusose relative to the amount of fucose on the same antibody produced in a wild-type CHO cell. That is, they are characterized by having a lower amount of fucose than they would otherwise have if produced by native CHO cells (e.g., a CHO cell that produce a native glycosylation pattern, such as, a CHO cell containing a native FUT8 gene). In certain embodiments, the antibody is one wherein less than about 50%, 40%, 30%, 20%, 10%, or 5% of the N-linked glycans thereon comprise fucose. For example, the amount of fucose in such an antibody may be from 1% to 80%, from 1% to 65%, from 5% to 65% or from 20% to 40%. In certain embodiments, the antibody is one wherein none of the N-linked glycans thereon comprise fucose, i.e., wherein the antibody is completely without fucose, or has no fucose or is afucosylated. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

Antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); US 2005/0123546 (Umana et al.), and Ferrara et al., *Biotechnology and Bioengineering,* 93(5): 851-861 (2006). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

In certain embodiments, the antibody variants comprising an Fc region described herein are capable of binding to an FcγRIII. In certain embodiments, the antibody variants comprising an Fc region described herein have ADCC activity in the presence of human effector cells or have increased ADCC activity in the presence of human effector cells compared to the otherwise same antibody comprising a human wild-type IgG1Fc region.

Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues). In an exemplary embodiment, the anti-NSP4 antibody comprising the following amino acid substitutions in its Fc region: S298A, E333A, and K334A In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.)). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Recombinant Methods and Compositions

Antibodies may be produced using recombinant methods and compositions, e.g., as described in U.S. Pat. No. 4,816,567. In one embodiment, isolated nucleic acid encoding an anti-NSP4 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-NSP4 antibody is provided, wherein the method comprises culturing a host cell comprising a nucleic acid encoding the antibody, as provided above, under conditions suitable for expression of the antibody, and optionally recovering the antibody from the host cell (or host cell culture medium). Further provided herein are anti-NSP4 antibodies produced by such methods.

For recombinant production of an anti-NSP4 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

Assays

Anti-NSP4 antibodies provided herein may be identified, screened for, or characterized for their physical/chemical properties and/or biological activities by various assays known in the art.

Binding Assays and Other Assays

In one aspect, an antibody of the invention is tested for its antigen binding activity, e.g., by known methods such as ELISA, Western blot, etc.

In another aspect, competition assays may be used to identify an antibody that competes with one or more antibodies selected from 1-1, 1-2, 1-3, 1-5, 2-1, 2-2, 2-3, 2-4, 2-5, 3-2, 3-5, 4-2, 4-3, 4-4, 4-5, 5-1, 5-2, 5-3, 5-4, 35.WT, 35.14, 35.50, 35.62, 35.77, 51.WT, 51.30, 51.50, 51.51, 51.59, 51.72, and 51.82 for binding to a NSP4. In certain embodiments, such a competing antibody binds to the same epitope (e.g., a linear or a conformational epitope) that is bound by one or more antibodies selected from 1-1, 1-2, 1-3, 1-5, 2-1, 2-2, 2-3, 2-4, 2-5, 3-2, 3-5, 4-2, 4-3, 4-4, 4-5, 5-1, 5-2, 5-3, 5-4, 35.WT, 35.14, 35.50, 35.62, 35.77, 51.WT, 51.30, 51.50, 51.51, 51.59, 51.72, and 51.82. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized NSP4 is incubated in a solution comprising a first labeled antibody that binds to a NSP4 (e.g., a human NSP4 or a mouse NSP4) and a second unlabeled antibody that is being tested for its ability to compete with the first antibody for binding to NSP4. The second antibody may be present in a hybridoma supernatant. As a control, immobilized NSP4 is incubated in a solution comprising the first labeled antibody but not the second unlabeled antibody. After incubation under conditions permissive for binding of the first antibody to NSP4, excess unbound antibody is removed, and the amount of label associated with immobilized NSP4 is measured. If the amount of label associated with immobilized NSP4 is substantially reduced in the test sample relative to the control sample, then that indicates that the second antibody is competing with the first antibody for binding to NSP4. See Harlow and Lane (1988) *Antibodies: A Laboratory Manual* ch. 14 (Cold Spring Harbor Laboratory, Cold Spring Harbor, N.Y.).

In another aspect, biolayer interferometry may be used to determine the affinity of anti-NSP4 antibodies against a NSP4. In an exemplary assay, an anti-NSP4 antibody is immobilized onto anti-human Fc sensors, and incubated with increasing concentrations of NSP4 to obtain affinity measurements using an instrument such as, for example, the Octet System (ForteBio).

In another aspect, ELISA may be used to identify an antibody that binds to a complex of a NSP4 and a protease inhibitor (e.g., al-antitrypsin). In an exemplary assay, recombinant NSP4 is mixed with a protease inhibitor, such as a serine protease inhibitor, to allow complex formation. The NSP4 complexes are coated in nickel (Ni) plates via a His-tag present on the recombinant NSP4 and a capture ELISA is performed as previously described (see Kuhl et al., 2010, *J. Immunol.*, 185, 387-399) with the anti-NSP4 antibody. Binding of anti-NSP4 antibody to the NSP4 complexes as compared to an isotype antibody control identifies the antibody as binding to a complex of NSP4 and a protease inhibitor. See, e.g., Hinkofer et al., *J. Biol. Chem.*, 2013, 288:26635-26648.

In any of the embodiments herein, the NSP4 used in the assay can be a mature form or a precursor form of a NSP4.

Activity Assays

Assays known in the art and described herein (e.g., Example 3) can be used for identifying and testing biological activities of anti-NSP4 antibodies. In some embodiments, assays for testing anti-NSP4 antibodies for blocking NSP4 activity are provided. An exemplary test for biological activity may include, e.g., providing a NSP4 (e.g., a human NSP4) in a mixture with an anti-NSP4 antibody and incubating the mixture with one or more internally-quenched fluorogenic peptide substrate and measuring the fluorescence intensity with an instrument, such as, for example, a spectrophotometer. An increase in fluorescence in the presence of an anti-NSP4 antibody would indicate the anti-NSP4 antibody is unable to block NSP4 activity, while a lack of increase in fluorescence in the presence of an anti-NSP4 antibody would indicate the anti-NSP4 antibody blocks NSP4 activity. Exemplary fluorogenic peptide substrates that can used in assays described herein include, but are not limited to, a fluorogenic peptide substrate with the amino acid sequence $^1$IR{Arg(Me)}SSYSFKK$^{10}$ or $^1$IR{Arg}SSYSFKK$^{10}$.

In some embodiments, the anti-NSP4 antibody may block at least about any of 50%, 60%, 70%, 80%, 85%, 90%, 95% and 100% of NSP4 activity in any of these assays.

Assays for testing anti-NSP4 antibodies for blocking NSP4 activity are also provided. An exemplary method for assessing NSP4 activity may include providing granulocytes on a substrate, incubating the granulocytes with a NSP4 inhibitor, such as an anti-NSP4 antibody, followed by stimulation with a chemotactic factor (such as Complement C5a or interleukin-8), and measuring a change in chemotaxis or motility of the granulocytes in the presence of an anti-NSP4 antibody as compared to an isotype control, wherein a reduction in chemotaxis or motility indicates the anti-NSP4 antibody is blocking NSP4 activity.

In another exemplary assay, an in vivo animal model for a neutrophil-mediated disease can be used. For example, the neutrophil-dependent K/B×N serum transfer arthritis model can be used by administering an anti-NSP4 antibody prior to, concomitant with, or after administration of intravenous K/B×N serum. Vascular leakage, erythema, and edema in the paws of treated mice can be monitored using in vivo near-infrared fluorescence imaging as described in Example 2, wherein a reduction of any one of vascular leakage, erythema, or edema indicates the anti-NSP4 antibody blocks NSP4 activity.

Methods and Compositions for Diagnostics and Detection

In certain embodiments, any of the anti-NSP4 antibodies provided herein is useful for detecting the presence of a NSP4 protein in a biological sample. The term "detecting" as used herein encompasses quantitative or qualitative detection. In certain embodiments, a biological sample comprises a cell or tissue, such as neutrophils.

In one embodiment, an anti-NSP4 antibody for use in a method of diagnosis or detection is provided. In a further aspect, a method of detecting the presence of a NSP4 in a biological sample is provided. In certain embodiments, the method comprises contacting the biological sample with an anti-NSP4 antibody as described herein under conditions permissive for binding of the anti-NSP4 antibody to a NSP4, and detecting whether a complex is formed between the anti-NSP4 antibody and a NSP4. Such method may be an in vitro or in vivo method. In one embodiment, an anti-NSP4 antibody is used to select subjects eligible for therapy with an anti-NSP4 antibody, e.g. where a NSP4 is a biomarker for selection of patients.

Exemplary disorders that may be diagnosed using an antibody of the invention include stroke, diabetic retinopathy, edema, diabetic macular edema, hereditary angioedema, idiopathic angioedema, leakage of vasculature, cerebral ischemia, acute lung injury, asthma, chronic obstructive pulmonary disease (COPD), acute respiratory distress syndrome (ARDS), osteoarthritis, rheumatoid arthritis (e.g., juvenile rheumatoid arthritis), septic shock, chronic bronchitis, pulmonary emphysema, α-1 anti-trypsin deficiency, cystic fibrosis, idiopathic pulmonary fibrosis, systemic lupus erythematosus (SLE), autoimmune vasculitides, blistering skin diseases, cancer (e.g., lung cancer), a disease caused by a deficiency in a natural protease inhibitor (e.g., a serine protease inhibitor), and any other granulocyte-mediated disease or disorder (e.g., neutrophil-mediated disease or disorder) described and contemplated herein.

In certain embodiments, labeled anti-NSP4 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^3$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, (3-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

B. Pharmaceutical Compositions and Formulations

Also provided herein are pharmaceutical compositions and formulations comprising a NSP4 inhibitor described herein and a pharmaceutically acceptable carrier. In some embodiments, the NSP4 inhibitor may be an antibody described herein.

Pharmaceutical compositions and formulations as described herein can be prepared by mixing the NSP4 inhibitor (such as an antibody or a polypeptide) having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutralactive hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The composition and formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

C. Therapeutic Methods

Any of the NSP4 inhibitors (e.g., an anti-NSP4 antibody) provided herein may be used in therapeutic methods.

In one aspect, a NSP4 inhibitor (e.g., an anti-NSP4 antibody) for use as a medicament is provided. In further aspects, a NSP4 inhibitor (e.g., an anti-NSP4 antibody) for use in treating or preventing a disease or disorder mediated by granulocytes is provided. In certain embodiments, a NSP4 inhibitor (e.g., an anti-NSP4 antibody) for use in a method of treatment or prevention is provided. In certain embodiments, the invention provides a NSP4 inhibitor (e.g., an anti-NSP4 antibody) for use in a method of treating or preventing an individual having a disease or disorder mediated by granulocytes comprising administering to the individual an effective amount of the NSP4 inhibitor. In one such embodiment, the method further comprises administering to the individual an effective amount of at least one additional therapeutic agent. In some embodiments, the disease or disorder mediated by granulocytes is selected from the group consisting of vascular disease and inflammatory disease. An "individual" according to any of the above embodiments is preferably a human. In any of the embodiments herein, the disease or disorder mediated by granulocytes can be a disease described herein.

In certain embodiments, the invention provides an anti-NSP4 antibody for use in a method of treating or preventing an individual having a disease or disorder mediated by granulocytes comprising administering to the individual an effective amount of the anti-NSP4 antibody. In certain embodiments, the antibody specifically binds an NSP4 active site. In certain embodiments, the antibody inhibits catalytic activity of NSP4. In certain embodiments, the antibody specifically binds an NSP4 active site and inhibits catalytic activity of NSP4. In certain embodiments, the antibody specifically binds an NSP4 heparin binding site. In certain embodiments, the antibody competes with heparin for binding to NSP4. In certain embodiments, the antibody specifically binds an NSP4 heparin binding site and competes with heparin for binding to NSP4. In certain embodiments, an effective amount of an antibody that specifically binds an NSP4 active site and/or inhibits catalytic activity of NSP4 and an antibody that specifically binds an NSP4 heparin binding site and/or competes with heparin for binding to NSP4 is administered to the individual.

In a further aspect, the invention provides for the use of a NSP4 inhibitor (e.g., an anti-NSP4 antibody) in the manufacture or preparation of a medicament. In one embodiment, the medicament is for treatment or prevention of a disease or disorder mediated by granulocytes. In a further embodiment, the medicament is for use in a method of treating or preventing a disease or disorder mediated by granulocytes comprising administering to an individual having the disease or disorder an effective amount of the medicament. In one such embodiment, the method further comprises administering to the individual an effective amount of at least one additional therapeutic agent. In some embodiments, the disease or disorder mediated by granulocytes is selected from the group consisting of vascular disease and inflammatory disease. An "individual" according to any of the above embodiments may be a human. In any of the embodiments herein, the disease or disorder mediated by granulocytes can be a disease described herein.

In a further aspect, the invention provides a method for treating or preventing a disease or disorder mediated by granulocytes. In one embodiment, the method comprises administering to an individual having such disease or disorder an effective amount of a NSP4 inhibitor (e.g., an anti-NSP4 antibody). In one such embodiment, the method further comprises administering to the individual an effective amount of at least one additional therapeutic agent. In some embodiments, the disease or disorder mediated by granulocytes is selected from the group consisting of vascular disease and inflammatory disease. An "individual" according to any of the above embodiments may be a human. In any of the embodiments herein, the disease or disorder mediated by granulocytes can be a disease described herein.

In one aspect, a NSP4 inhibitor (e.g., an anti-NSP4 antibody) for use as a medicament is provided. In further aspects, a NSP4 inhibitor (e.g., an anti-NSP4 antibody) for use in treating neutrophil-mediated disease or disorder is provided. In certain embodiments, a NSP4 inhibitor (e.g., an anti-NSP4 antibody) for use in a method of treatment is provided. In certain embodiments, the invention provides a NSP4 inhibitor (e.g., an anti-NSP4 antibody) for use in a method of treating an individual having a neutrophil-mediated disease or disorder comprising administering to the individual an effective amount of the NSP4 inhibitor. In one such embodiment, the method further comprises administering to the individual an effective amount of at least one additional therapeutic agent. In some embodiments, the neutrophil-mediated disease or disorder is selected from the group consisting of vascular disease and inflammatory disease. An "individual" according to any of the above embodiments is preferably a human. In any of the embodiments herein, the neutrophil-mediated disease or disorder can be a disease described herein.

In a further aspect, the invention provides for the use of a NSP4 inhibitor (e.g., an anti-NSP4 antibody) in the manufacture or preparation of a medicament. In one embodiment, the medicament is for treatment of a neutrophil-mediated disease or disorder. In a further embodiment, the medicament is for use in a method of treating a neutrophil-mediated disease or disorder comprising administering to an individual having the disease or disorder an effective amount of the medicament. In one such embodiment, the method further comprises administering to the individual an effective amount of at least one additional therapeutic agent. In some embodiments, the neutrophil-mediated disease or disorder is selected from the group consisting of vascular disease and inflammatory disease. An "individual" according to any of the above embodiments may be a human. In any of the embodiments herein, the neutrophil-mediated disease or disorder can be a disease described herein.

In a further aspect, the invention provides a method for treating a neutrophil-mediated disease or disorder. In one embodiment, the method comprises administering to an individual having such disease or disorder an effective amount of a NSP4 inhibitor (e.g., an anti-NSP4 antibody). In one such embodiment, the method further comprises administering to the individual an effective amount of at least one additional therapeutic agent. In some embodiments, the neutrophil-mediated disease or disorder is selected from the group consisting of vascular disease and inflammatory disease. An "individual" according to any of the above embodiments may be a human. In any of the embodiments herein, the neutrophil-mediated disease or disorder can be a disease described herein.

Neutrophils, also known as polymorphonuclear leukocytes (PMN), are cells of the innate immune system that are involved in acute inflammation and phagocytosis of invading pathogens (e.g., bacteria). The anti-microbial activity of neutrophils is partially mediated by neutrophil serine proteases, such as neutrophil elastase, cathepsin G, and proteinase 3, which act intracellularly to destroy phagocytosed microorganisms or can be released by neutrophils to act extracellularly to contain and reduce pathogen proliferation at sites of infection. While neutrophil serine proteases that are released by neutrophils can serve a beneficial role in the innate immune system, these proteases may also contribute to the formation of neutrophil-mediated disease or disorders by causing, for example, aberrant tissue damage and inflammation. Studies have linked neutrophils as playing a contributory role in the pathology of several diseases such as, but not limited to, septic shock, acute respiratory distress syndrome, post-ischemic reperfusion, chronic obstructive pulmonary disease (COPD), rheumatoid arthritis, and cancer. See, e.g., Adams et al., *J Trauma-Injury Infect Crit Care.*, 2001, 51:452-456; Lindsey et al., *Circulation*, 2001, 103:2181-2187; Wright et al., *Rheumatology*, 2010, 49(9): 1618-1631; Magrone et al., *Pharm Des.*, 2012, 18(12):1609-19; and Vaguliene et al., *BMC Immunology.*, 2013, 6:14-36.

Neutrophil-mediated diseases or disorders include diseases characterized by inflammation (e.g., acute inflammation and/or chronic inflammation), increased vascular permeability, tissue damage, and/or other inflammatory processes in which neutrophils are known to play a role. In some embodiments, a neutrophil-mediated disease or disorder is a vascular disease selected from the group consisting of stroke, diabetic retinopathy, edema, diabetic macular edema, hereditary angioedema, idiopathic angioedema, leakage of vasculature, and cerebral ischemia. In some embodiments, a neutrophil-mediated disease or disorder is an inflammatory disease selected from the group consisting of acute lung injury, asthma, chronic obstructive pulmonary disease (COPD), acute respiratory distress syndrome (ARDS), osteoarthritis, rheumatoid arthritis (e.g., juvenile rheumatoid arthritis), and septic shock. In some embodiments, a neutrophil-mediated disease or disorder is a pulmonary disease selected from the group consisting of COPD, chronic bronchitis, pulmonary emphysema, α-1 anti-trypsin deficiency, cystic fibrosis, idiopathic pulmonary fibrosis, and ARDS. In some embodiments, a neutrophil-mediated disease or disorder is an autoimmune disease such as, but not limited to, systemic lupus erythematosus (SLE), autoimmune vasculitides, and blistering skin diseases. In some embodiments, the neutrophil-mediated disease or disorder is a cancer such as, but not limited to, lung cancer, breast cancer, colon cancer, lymphoma, pancreatic cancer, and brain cancer. In some embodiments, the cancer is metastatic cancer. In some embodiments, a neutrophil-mediated disease or disorder is a disease caused by a deficiency in a natural (i.e., host) protease inhibitor (e.g., a serine protease inhibitor) such as, but not limited to, α-1 anti-trypsin, antithrombin, C1 inhibitor, secretory leukocyte protease inhibitor, monocyte-neutrophil elastase inhibitor, and al-antichymotrypsin.

Granulocytes include neutrophils, eosinophils, and basophils. In some embodiments, the methods or medicaments described herein are useful for treating or preventing a disease or disorder mediated by granulocytes. For example, the disease or disorder that can be treated or prevented includes vascular diseases, inflammatory diseases, and autoimmune diseases. In some embodiments, the disease or disorder is selected from the group consisting of stroke, diabetic retinopathy, edema, diabetic macular edema, hereditary angioedema, idiopathic angioedema, leakage of vasculature, cerebral ischemia, acute lung injury, anaphylaxis, systemic anaphylaxis, allergic lung inflammation, asthma (e.g., allergic asthma, virus-induced asthma), chronic obstructive pulmonary disease (COPD), acute respiratory distress syndrome (ARDS), idiopathic pulmonary fibrosis, systemic lupus erythematosus (SLE), autoimmune vasculitides, blistering skin diseases (e.g., bullous pemphigoid), inflammatory skin diseases (e.g., atopic dermatitis, urticarial, eosinophilic cellutitis), cancer (e.g., lung cancer), kidney diseases (e.g., glomerulonephritis), osteoarthritis, rheumatoid arthritis, psoriatic arthritis, psoriasis, septic shock, inflammatory bowel disease (e.g., ulcerative colitis, Crohn's disease).

In a further aspect, the invention provides pharmaceutical compositions or formulations comprising any of the NSP4 inhibitors provided herein, e.g., for use in any of the above therapeutic methods. In one embodiment, a pharmaceutical composition or formulation comprises any of the NSP4 inhibitors (e.g., anti-NSP4 antibodies) provided herein and a pharmaceutically acceptable carrier. In another embodiment, a pharmaceutical composition or formulation comprises any of the NSP4 inhibitors provided herein and at least one additional therapeutic agent, e.g., as described below.

NSP4 inhibitors described herein can be used either alone or in combination with other agents in a therapy. For instance, a NSP4 inhibitor described herein may be co-administered with at least one additional therapeutic agent. Such combination therapies encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant.

A NSP4 inhibitor described herein (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

NSP4 inhibitors (e.g., antibodies) described herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The NSP4 inhibitor need not be, but is optionally formulated with one or more agents currently used to prevent or treat the disorder in question. The effective amount of such other agents depends on the amount of NSP4 inhibitor present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a NSP4 inhibitor (e.g., an anti-NSP4 antibody) (when used alone or in combination with one or more other additional therapeutic agents) will depend on the type of disease to be treated, the type of NSP4 inhibitor, the severity and course of the disease, whether the NSP4 inhibitor is administered for preventive or therapeutic purposes, previous therapy, the patient's clinical history and response to the treatment, and the discretion of the attending physician. The NSP4 inhibitor is suitably administered to the patient at one time or over a series of treatments.

For example, depending on the type and severity of the disease, about 1 µg/kg to 15 mg/kg (e.g. 0.1 mg/kg-10 mg/kg) of a NSP4 inhibitor (e.g., an anti-NSP4 antibody) can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the NSP4 inhibitor (e.g., an anti-NSP4 antibody) would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

III. Articles of Manufacture and Kits

In another aspect of the invention, an article of manufacture or a kit comprising one or more of the NSP4 inhibitors (e.g., anti-NSP4 antibodies) useful for the treatment, prevention and/or diagnosis of the disorders described above is provided. The article of manufacture or kit may further comprise a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a NSP4 inhibitor described herein. The label or package insert indicates that the composition is used for treating the condition of choice. In some embodiments, the condition of choice is a disease or disorder mediated by granulocytes. In some embodiments, the disease or disorder to be treated is selected from the group consisting of stroke, diabetic retinopathy, edema, diabetic macular edema, hereditary angioedema, idiopathic angioedema, leakage of vasculature, cerebral ischemia, acute lung injury, anaphylaxis, systemic anaphylaxis, allergic lung inflammation, asthma (e.g., allergic asthma, virus-induced asthma), chronic obstructive pulmonary disease (COPD), acute respiratory distress syndrome (ARDS), idiopathic pulmonary fibrosis, systemic lupus erythematosus (SLE), autoimmune vasculitides, blistering skin diseases (e.g., bullous pemphigoid), inflammatory skin diseases (e.g., atopic dermatitis, urticarial, eosinophilic cellutitis), cancer (e.g., lung cancer), kidney diseases (e.g., glomerulonephritis), osteoarthritis, rheumatoid arthritis, psoriatic arthritis, psoriasis, septic shock, inflammatory bowel disease (e.g., ulcerative colitis, Crohn's disease). In some embodiments, the condition of choice is a neutrophil-mediated disease or disorder such as, but not limited to, stroke, diabetic retinopathy, edema, diabetic macular edema, hereditary angioedema, idiopathic angioedema, leakage of vasculature, cerebral ischemia, acute lung injury, asthma, chronic obstructive pulmonary disease (COPD), acute respiratory distress syndrome (ARDS), osteoarthritis, rheumatoid arthritis (e.g., juvenile rheumatoid arthritis), septic shock, chronic bronchitis, pulmonary emphysema, α-1 anti-trypsin deficiency, cystic fibrosis, idiopathic pulmonary fibrosis, systemic lupus erythematosus (SLE), autoimmune vasculitides, blistering skin diseases, cancer (e.g., lung cancer), a disease caused by a deficiency in a natural protease inhibitor (e.g., a serine protease inhibitor), or any other neutrophil-mediated disease or disorder described and contemplated herein. Moreover, the article of manufacture or kit may comprise (a) a first container with a composition contained therein, wherein the composition comprises a NSP4 inhibitor described herein; and (b) a second container with a composition contained therein, wherein the composition comprises a second therapeutic agent. The article of manufacture or kit in this embodiment of the invention may further comprise a package insert indicating that the compositions can be used to treat a particular condition. Alternatively, or additionally, the article of manufacture or kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Although the foregoing invention has been described in some detail by way of illustration and example for purposes of clarity of understanding, the descriptions and examples should not be construed as limiting the scope of the invention.

The following are examples of methods and compositions of the invention. It is understood that various other embodiments may be practiced, given the general description provided above.

EXAMPLES

Example 1: Characterization of Substrate Recognition by Neutrophil Serine Protease 4 (NSP4)

Figure 2A:
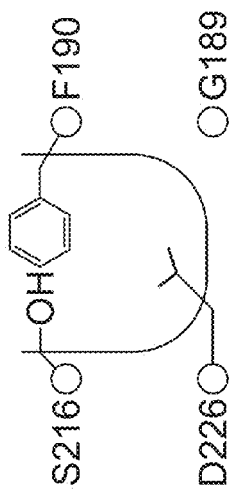
FIGS. 2A-2D demonstrate that NSP4 has an elastase-like active site with trypsin-like arginine specificity. A) Schematic of the NSP4 S1 pocket. B) Schematic of trypsin, chymotrypsin, and neutrophil elastase 51 pockets and their interactions with the preferred P1 residue. Trypsin-like proteases have a deep 51 pocket and form a salt bridge interaction between the substrate P1-arginine and the conserved D189 at the base of the S1 pocket (dashed lines). Chymotrypsin-like proteases have a large hydrophobic pocket to accommodate bulky P1 residues. Elastase-like proteases have a shallow S1 pocket, formed by residues at the 216 and 190 positions, to accommodate small aliphatic P1 residues. C) Profiling of NSP4 P1 substrate specificity by use of a fluorogenic peptide substrate panel with different P1 residues treated with recombinant wildtype (WT) or the inactive (S195A) NSP4 produced from insect (Baculovirus Expression vector systems; BEVS) or mammalian cells (Chinese Hamster Ovarian; CHO). P1-Arg peptide: WT (BEVS) $k_{cat}/K_M$=1.1×10$^4$±2.1×10$^3$ M$^{-1}$ s$^{-1}$ and WT (CHO) $k_{cat}/K_M$=7.5×10$^3$±1.1×10$^3$ M$^{-1}$ s$^{-1}$. D) Cleavage of fluorogenic peptide by NSP4 S1 pocket mutants. Activity is measured as nanomolar product formed per second (nM/s). Results are mean±standard deviation from at least three independent experiments.
Figure 2B:
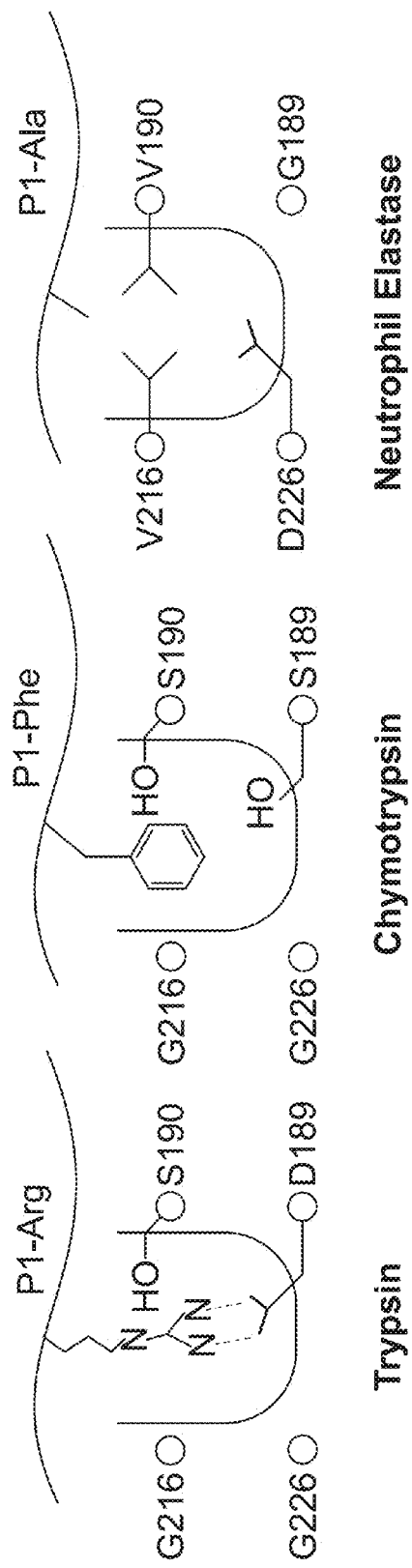

NSP4, a member of a family of neutrophil serine proteases characterized as trypsin-fold proteases, is stored in neutrophil azurophilic granules (Perera et al., *J Immunol.*, 2013), yet it is the least abundant of all NSPs (Perera et al., *Proc Natl Acad Sci USA*, 2012, 109:6229-6234) and its function remains unknown. NSP4 is highly conserved from bony fish to human (FIG. 1) and predates the evolutionary emergence of other NSPs (Perera et al., *Proc Natl Acad Sci USA*, 2012, 109:6229-6234; Perera et al., *Expert Rev Clin Immunol*, 2012, 8:501-503). NSP4, therefore, likely plays fundamental roles in neutrophil biology. While the relatively broad substrate specificity of neutrophil elastase (NE), cathepsin G (CG), and proteinase 3 (PR3) is well understood based on knowledge of their active site structures (Navia et al., *Proc Natl Acad Sci USA*, 1989, 86:7-11; Hof et al., *EMBO J*, 1996, 15:5481-5491; Fujinaga et al., *J Mol Biol*, 1996, 261:267-278), NSP4 poses a challenge in that it cleaves substrates after arginine residues (Perera et al., *Proc Natl Acad Sci USA*, 2012, 109:6229-6234; Perera et al., *J Immunol.*, 2013), but its primary sequence predicts a different elastase-like active site (FIG. 2A). Among trypsin-fold proteases, the active sites of trypsin, chymotrypsin, and elastase help define the three major classes of substrate specificities at the P1 position (Hedstrom et al, *Chem Rev*, 2002, 102:4501-4524) (FIG. 2B). Trypsin-like proteases, such as coagulation and complement factors, have a deep S1 pocket to accommodate the long arginine side chain that is stabilized by a salt bridge interaction with the highly conserved D189 (chymotrypsinogen numbering). In contrast, elastase-like proteases cannot accommodate a large arginine side chain owing to their shallow S1 pocket.

To investigate how NSP4 is able to achieve its arginine-specificity with an apparent elastase-like S1 pocket (FIGS. 2A and B), the atypical S1 pocket was characterized.

Methods
Recombinant Protein Expression and Purification

To produce human wild-type NSP4 for structural characterization, the DNA encoding human NSP4 from Ile34 (Ile16 in chymotrypsinogen numbering) to Ala283 was fused with an N-terminal $His_6$-tag and enteropeptidase cleavage site and cloned into pAcGP67 vector (BD Biosciences). The resulting baculovirus transfer vector was confirmed by DNA sequencing and co-transfected with BaculoGold linearized DNA (BD Biosciences) into Sf9 insect cells, and amplified three times to generate a high titer viral stock. For protein production, cells were cultured in shake flasks or in wave bags (GE Healthcare) at 27° C. with ESF921 medium (Expression Systems) for 72 hours post-infection and removed by centrifugation. The resulting supernatant was supplemented with 1 mM $NiCl_2$, 5 mM $CaCl_2$, in 50 mM Tris-HCl, pH 7.5. The protein in the supernatant was captured on a Ni-NTA column (Qiagen) by gravity flow, washed with 200 ml wash buffer (50 mM Tris pH 7.5, 300 mM NaCl, 10 mM imidazole), and eluted with elution buffer (50 mM Tris pH 7.5, 300 mM NaCl, 300 mM imidazole). Protein was concentrated and further purified on a size exclusion column (Superdex 200 HiLoad 16/60, GE Biosciences) equilibrated with 20 mM Tris pH 7.5, 150 mM NaCl.

To produce NSP4 mutants for biochemical characterization, the DNA encoding the human NSP4 fragment from Ile34 to Ala283 was cloned with an N-terminal FLAG tag and C-terminal $His_6$ tag in a modified pRK5 vector suitable for mammalian cell expression. The QuikChange mutagenesis kit (Agilent) was used to generate derivative expression constructs incorporating the desired single and double point mutants (in chymotrypsin numbering): F190A, S192A, S195A, S216G, F190A:S216G, and S192A:S216G. The constructs were expressed in Chinese Hamster Ovarian (CHO) cells by transient expression and after incubation the supernatant was harvested by centrifugation. The protein in the supernatant was captured on an anti-FLAG affinity resin by gravity flow, washed with 200 ml phosphate-buffered saline (PBS), eluted with elution buffer (50 mM sodium citrate pH 3.0, 150 mM NaCl), and immediately neutralized to pH 7 using 1M Tris pH 8.

Biochemical Assays

Both insect cell-derived and CHO cell-derived NSP4 were activated using enteropeptidase (Invitrogen) at 15 EU/ml of protein, and incubated overnight at 20° C. Completion of the cleavage reaction was monitored by SDS-PAGE and Liquid chromatography-mass spectrometry (LC-MS). A secondary purification with ion exchange was performed to remove enteropeptidase and purify NSP4 to homogeneity with a MonoS column (GE Healthcare) using a gradient elution with 20 mM Tris pH 7.5 from 0.05 M to 1.0 M NaCl.

Crystallization and Structure Determination

For apo-NSP4 and FFR:NSP4 crystals, insect cell-derived NSP4 was partially deglycosylated using Endo F3 at 1:100 Endo F3:NSP4 mass ratio in 100 mM sodium citrate pH 5.5, 300 mM NaCl for 3 hours at 37° C. and then overnight at 4° C. The deglycosylation reaction was verified using SDS-PAGE and LC-MS. For VLK:NSP4 crystals, the insect cell-derived NSP4 were fully glycosylated. To make FFR:NSP4 and VLK:NSP4 complexes, NSP4 was mixed with D-Phe-L-Phe-L-Arg-cmk (Bachem) or with D-Val-L-Leu-L-Lys-cmk (Bachem), respectively, at 20-fold molar excess for overnight at 20° C. The resulting FFR:NSP4 and VLK:NSP4 covalent complexes were verified using LC-MS. Apo-NSP4, FFR:NSP4, and VLK:NSP4 were all desalted using Superdex 5200 HiLoad 16/60 size exclusion chromatography column equilibrated using 20 mM Tris pH 7.5, 150 mM NaCl. The protein was concentrated to approximately 10 mg/ml and mixed 1:1 with the precipitant/buffer solution (mother liquor) for crystallization trials.

All crystals were obtained by sitting drop vapor diffusion method at 19° C., with the crystals appearing between 2 to 7 days. FFR:NSP4 crystallized in 20% PEG MME 2000, 0.1M Tris pH 8.5, 0.2M trimethylamine N-oxide. Apo-NSP4 (form 1) crystallized in 15-17% PEG-10,000, 0.1 M sodium acetate pH 4.4, 0.1 M ammonium acetate. Apo-NSP4 (form 2) crystallized in 22-25% PEG-3350, 0.1 M Bis-Tris pH 5.5, 0.2 M NaCl. VLK:NSP4 crystallized in 20% PEG-3350 0.2 M potassium acetate, with no additional buffer. The crystals were cryoprotected in mother liquor supplemented with 20% glycerol and flash frozen in liquid nitrogen.

Data collection experiments were performed using a synchrotron light source. Specifically, Apo (forms 1 and 2) and VLK-cmk datasets were collected at ALS beamline 5.0.1 at the wavelength of 0.9774 Å and temperature of 95 K (Advanced Light Source). The FFR-cmk dataset was collected at SSRL beamline 7-1 at the wavelength of 1.1271 Å and temperature of 100 K (Stanford Synchroton Radiation Light Source). Data was indexed and integrated using HKL2000 (Otwinowski et al., Methods in Enzymology, 1997, 276:307-326). The initial structure of NSP4 was solved using MrBUMP (Keegan et al., Acta Crystallogr D Biol Crystallogr, 2007, 63:447-457) to gain initial phases and rebuilt into maps created by simulated annealing using the PHENIX package (Adams et al., Acta Crystallogr D Biol Crystallogr, 2010, 66:213-221). The structures were refined using PHENIX with 97.0% (apo form 1), 95.4% (apo form 2), 96.5% (FFR-cmk), and 95.4% (VLK-cmk) of residues in the favored region of the Ramachandran plot and the rest in the allowed region. Data collection and refinement statistics are summarized in Table 2. All structural figures were generated using PyMol (Schrödinger, LLC).

Fluorogenic Peptide Cleavage Assay

Internally-quenched fluorogenic peptides with 7-methoxycourmain-4-acetate (Mca) and mini-PEG1 (8-amino-3,6-dioxaoctanoic acid) at the N-terminus and dinitrophenol (Dnp) attached to the penultimate lysine side chain near the C-terminus were synthesized using Fmoc solid-phase peptide synthesis (GenScript). The peptides were added to 50 nM NSP4 or 100 nM Factor Xa (Enzyme Research Laboratories) in 50 mM Tris pH 8.0, 150 mM NaCl, 2 mM $CaCl_2$ at 37° C. Enzyme kinetic measurements were done using SpectraMax M5 (MolecularDevices) with the excitation at 328 nm and emission at 393 nm Kinetic data were fitted using Prism5 (GraphPad Software) using the standard Michaelis-Menten kinetics model and a standard curve was generated to convert the rate of catalysis from the fluorescence measurements (RFU/s) to nanomolar products formed per second (nM/s). LC-MS was used to confirm the site of peptide cleavage using fluorogenic peptides that were incubated with 50 nM NSP4 or 200 nM Factor Xa in 50 mM Tris pH 8.0, 150 mM NaCl, 2 mM $CaCl_2$ at 37° C. for 1 hour. The peptide fragments were separated on a 5-60% acetonitrile:water reverse-phase gradient before analysis on a time-of-flight mass spectrometer (Agilent).

Heparin Binding Assays

Heparin binding was assessed using fluorescence polarization, where fluorescein-conjugated heparin (Invitrogen) was mixed with purified recombinant NSP4. Fluorescence polarization assays were performed in three independent measurements and read on a Victor 3 (Perkin Elmer) equipped with 485±30 nm excitation and 535±40 nm emission filters. To assess the reactions via electrophoretic mobility shift assay, an equal volume of 50% glycerol was added to NSP4:heparin mixture, which were then separated by polyacrylamide gel electrophoresis and fluorescence signal detected with a blue (488 nm) laser and a 526±20 nm emission filter using a Typhoon imager (GE Healthcare).

Characterization of $NSP4^{-/-}$ mice $NSP4^{-/-}$ mice were generated as previously described (Tang et al., Nat Biotechnol, 2010, 28:749-755) and backcrossed to C57/BL6 for more than 10 generations. Confirmation of NSP4 ablation and determination of neighboring protease gene expression in $NSP4^{-/-}$ mice were done using RT-PCR. RNA from total bone marrow cells of $NSP4^{-/-}$ mice or wild-type littermates were isolated using the RNeasy Mini kit (Qiagen) and the corresponding cDNA were synthesized using the iScript reverse transcriptase (Bio-Rad), all performed according to manufacturer instructions. qPCR were performed from cDNA samples using the TaqMan 2X PCR master mix (Applied Biosystems) with the following TaqMan primer/probe sets were obtained from Applied Biosystems, with the catalogue number in parenthesis: Prss57_1 (ABI Mm01144794_m1, spans exons 1-2), Prss57_2 (ABI Mm01144795_m1, spans exons 2-3), Prss57_3 (ABI Mm01144796_m1, spans exons 3-4), Cfd (ABI Mm01143935_g1, spans exons 4-5), Elane (ABI Mm01168928_g1, spans exons 1-2), Gzmm (ABI Mm00493150_m1, spans exons 2-3), Prtn3 (ABI Mm00478323_m1, spans exons 1-2), 18s rRNA (ABI 4333760F).

To quantify immune cell populations, cells from the femoral bone marrow of $NSP4^{-/-}$ mice or wild-type littermates were identified using standard flow cytometry protocols and the following antibody clones: anti-CD11b (M1/70); anti-CD11c (N418); anti-B220 (RA3-6B2); anti-Ly6C (HK1.4), anti-Ly6G (1A8). All antibodies were obtained from eBioscience. Viability was evaluated using Sytox Blue (Invitrogen). Stained cells were sorted using a FACSAria cell sorter (BD Biosciences). The following populations were sorted and counted: B cells, $B220^+$; total myeloid cells, $B220^-/CD11b^+$; monocytes, $B220^-/CD11b^+/Ly6C^{hi}$, and neutrophils, $B220^-/CD11b^+/Ly6G^{hi}$.

K/BxN Serum-Transfer Mouse Model

K/BxN serum-induced vascular permeability was monitored in vivo by non-invasive near-infrared fluorescence imaging (NIRF) of the mouse whole-paw. Mice were anesthetized by 2% isoflurane (Butler Schein, 1 L/min flow), implanted with a tail vein catheter, and immobilized with the paw secured by surgical tape on the imaging surface glass of the Kodak In-Vivo FX Pro 400 whole-animal NIRF imaging system (Carestream Health). Mice were injected through the tail vein catheter with 100 µl of the blood pool probe AngioSense 680 (PerkinElmer), imaged at 1 minute intervals (650 nm excitation/700 nm emission, 21.4 mm FOV, 10 second exposure, 2× binning) for 5 min to establish baseline fluorescence before tail vein catheter injection of 75 ul K/BxN serum and further imaging for another 25 min. The K/BxN serum used in this model was sourced from KRNx NOD F1 mice that exhibited severe arthritis. The average fluorescence intensities and the fold change in fluorescence intensities from the initial imaging time point within paws were quantified using custom routines in MatLab (MathWorks).

Arthritis was assessed daily for 8 days following vascular permeability analysis. Clinical scores range from 0 to 16 per animal, as assigned by combining the individual paw scores of 0 (normal joint appearance) to 4 (maximal erythema and edema). The following joints were analyzed for erythema and edema: tarsal or carpal joints, metatarsal or metacarpal joints, metatarsalphalangeal or metacarpalphalangeal joints, or phalanges.

Histological Examination of Mouse Arthritic Paws

Paws were fixed in neutral buffered formalin, decalcified and processed routinely to sagittal hemisections stained with hematoxylin and eosin. All 4 paws per animal were examined. Histological lesions were scored on an arbitrary scale from 0 (normal) to 5 (severe) for the following features: infiltration with inflammatory cells, fibroplasia including pannus formation, cartilage injury, and bone remodeling.

Results

Kinetic Characterization of NSP4 S1 Binding Pocket

Figure 2D:
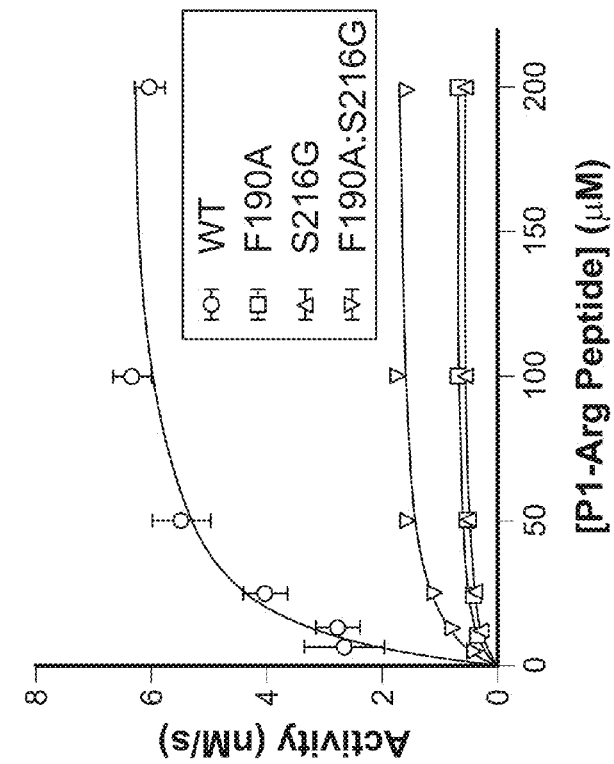
Figure 2C:
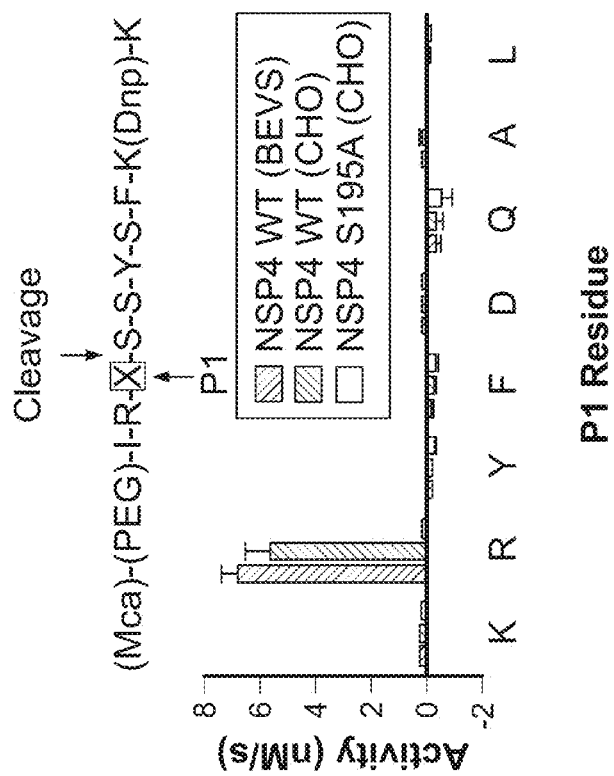

The ability of NSP4 to recognize a P1-arginine residue was investigated, particularly in light of the F190 and S216 residues in the NSP4 S1 binding pocket that appear poised to obstruct arginine binding (FIG. 2A). The NSP4 residues F190 and S216, situated on opposite sides of the opening to the S1 pocket, might act as a movable gate to allow access to the S1 pocket. If so, the P1-arginine side chain could be stabilized by D226 as a surrogate for D189 (G189 in NSP4) (FIG. 2A) (13, 14). To test this hypothesis, NSP4 variants were engineered having either a partially open (F190A or S216G) or fully open (F190A:S216G) "gate", all of which should increase enzyme activity if the hypothesis was correct. To measure effects on NSP4 activity, a fluorogenic peptide was synthesized that was specifically cleaved by NSP4 after arginine as the P1 residue $^1$IRR$^3$↓$^4$SSYSFKK$^{10}$ (FIG. 2C). The results showed that the single mutants (F190A or S216G) and the double mutant F190A:S216G had approximately 10-fold and 4-fold reduced activity ($k_{cat}/K_M$) compared to wild-type (FIG. 2D). These results did not support the movable gate hypothesis, but rather suggested that both F190 and S216 were critically important for positioning the substrate to enable catalysis.

Crystal Structures of NSP4

Figure 3A:
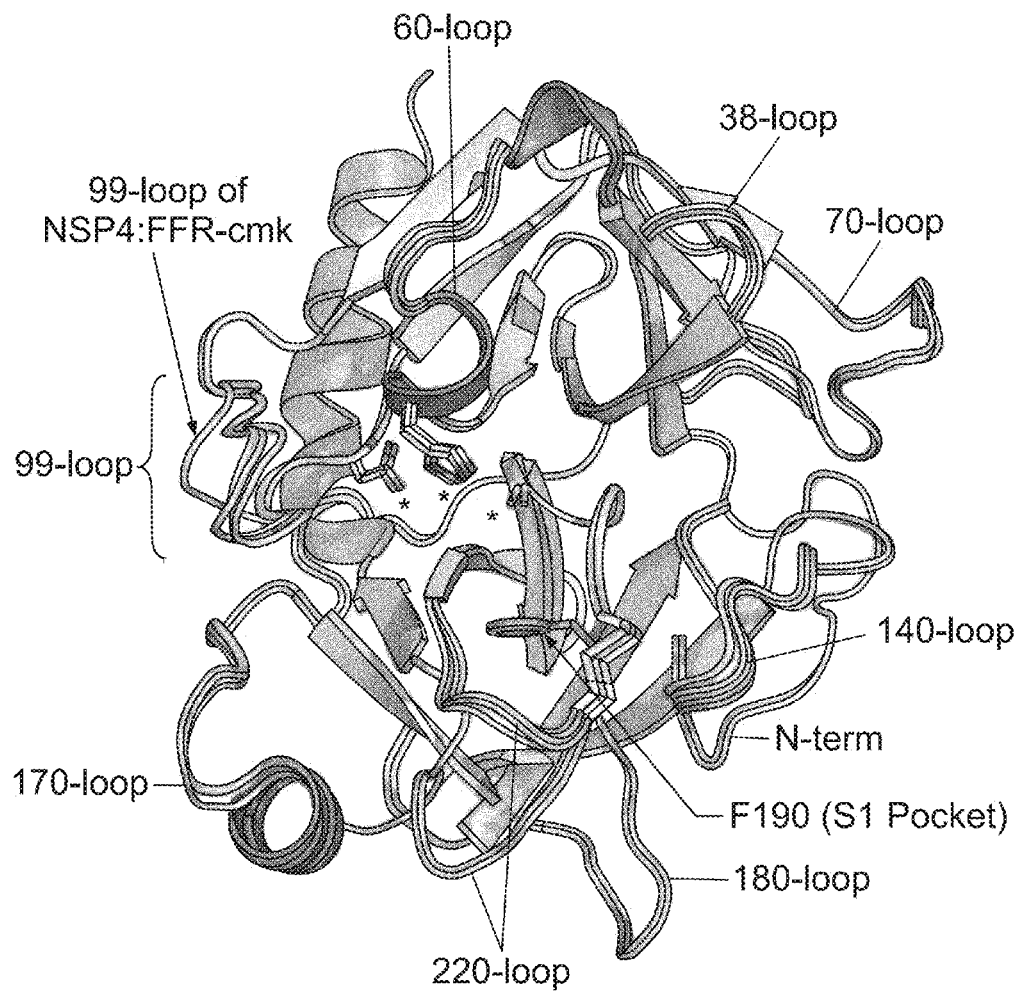
FIGS. 3A-3B demonstrate that NSP4 features an occluded S1 pocket and non-canonical interactions with P1-arginine. A) Superposition of NSP4 crystal structures: NSP4-apo form 1, NSP4-apo form 2, NSP4:FFR-cmk, and NSP4: VLK-cmk. Asterisks denote catalytic triad residues. B) Top left, FFR-cmk (sticks) bound to the canonical trypsin-like protease, factor VIIa, PDB 1DAN. Top right, FFR-cmk (sticks) bound to NSP4. Bottom left, side view of canonical S1 pockets with superposition of ten different P1-arginine ligands (sticks) bound to trypsin-like proteases (ribbons). Structures shown are 1DAN, 1SHH, 1ORF, 1AUT, 1PFX, 2FIR, 1LMW, 1BUI, 2B80, 1BDA. Bottom right, side view of FFR-cmk (sticks) bound to NSP4.

To elucidate the structural basis of the P1-arginine recognition mechanism, the X-ray crystal structure of NSP4 was determined with the covalently bound substrate mimic D-Phe-L-Phe-L-Arg chloromethyl ketone (FFR-cmk) at 1.40 Å resolution. In addition, two non-isomorphous structures of NSP4 in its apo-form at 2.55 Å and 2.70 Å resolutions (Table 2) were determined. All structures exhibited the double β-barrel and catalytic triad arrangement characteristic of trypsin-fold serine proteases (FIG. 3A). NSP4 also had an extended basic surface patch that may function to localize NSP4 to proteoglycans (FIG. 4A). Consistent with this view, NSP4 exhibited strong heparin binding in fluorescence polarization and electrophoretic mobility shift assays (FIG. 4B). Superposition of the NSP4 structures also showed that the 99-loop (FIG. 3A), which formed the S2/S4 substrate interaction sites, was labile and might be implicated in NSP4 allosteric regulation as demonstrated for other serine proteases (Ganesan et al., *Structure*, 2009, 17:1614-1624; Debela et al., *J Mol Biol*, 2007, 373:1017-1031).

TABLE 2

Data and refinement characteristics.

| | Apo (form 1) | Apo (form 2) | FFR-CMK | VLK-cmk |
|---|---|---|---|---|
| Data Collection | | | | |
| Space group | P4$_1$ | P6$_3$ | P2$_1$2$_1$2$_1$ | P6$_5$ |
| Cell Dimensions | | | | |
| a, b, c (Å) | 70.4, 70.4, 150.0 | 86.6, 86.6, 69.4 | 55.0, 64.5, 68.4 | 89.7, 89.7, 108.6 |
| α, β, γ (°) | 90, 90, 90 | 90, 90, 120 | 90, 90, 90 | 90, 90, 120 |
| Resolution (Å) | 50-2.55 | 50-2.70 | 35.69-1.40 | 50.0-3.08 |
| | (2.64-2.55) | (2.80-2.70) | (1.45-1.40) | (3.19-3.08) |
| R$_{symm}$ | 0.082 (0.494) | 0.149 (0.683) | 0.048 (0.765) | 0.154 (0.810) |
| <I/σI> | 14.1 (2.0) | 12.8 (2.7) | 34.3 (2.8) | 12.5 (2.4) |
| Completeness (%) | 99.3 (100) | 99.8 (100) | 93.8 (98.2) | 99.2 (99.8) |
| Redundancy | 3.8 (3.8) | 6.2 (6.3) | 7.0 (7.1) | 6.6 (6.6) |
| Reflections measured | 89593 | 50790 | 319648 | 60991 |
| Unique reflections | 23577 | 8192 | 45664 | 9241 |
| Wilson B (Å$^2$) | 62 | 52 | 18 | 81 |
| X-ray source | ALS 5.0.1 | ALS 5.0.1 | SSRL 7-1 | ALS 5.0.1 |
| Data reduction | HKL2000 | HKL2000 | HKL2000 | HKL2000 |
| Refinement | | | | |
| Resolution (Å) | 50-2.55 | 50-2.70 | 50-1.40 | 50-3.08 |
| Reflections (total) | 23565 | 8192 | 45530 | 9240 |
| Reflections in R$_{Free}$ | 1203 | 802 | 2276 | 423 |
| Molecules per asymmetric unit | 2 | 1 | 1 | 2 |
| R$_{work}$ | 0.197 | 0.187 | 0.192 | 0.185 |
| R$_{free}$ | 0.231 | 0.248 | 0.215 | 0.240 |
| Mean B-factor | 54 | 33 | 20 | 62 |
| Number TLS groups | 8 | 4 | 4 | 8 |
| No. atoms | 3775 | 1850 | 2136 | 3710 |
| Protein | 3572 | 1795 | 1811 | 3562 |
| Carbohydrate | 76 | 38 | 38 | 98 |
| Ligand | 0 | 0 | 34 | 50 |
| Solvent | 127 | 17 | 253 | 0 |
| R.m.s. deviations | | | | |
| Bond lengths (Å) | 0.009 | 0.008 | 0.008 | 0.009 |
| Bond angles (°) | 1.05 | 1.05 | 1.30 | 1.23 |
| Ramachandran (%) Preferred region | 97.0 | 95.4 | 96.5 | 95.4 |

*Values in parentheses are for highest-resolution shell.

Structural Basis of NSP4 Arginine Specificity

Figure 3B:
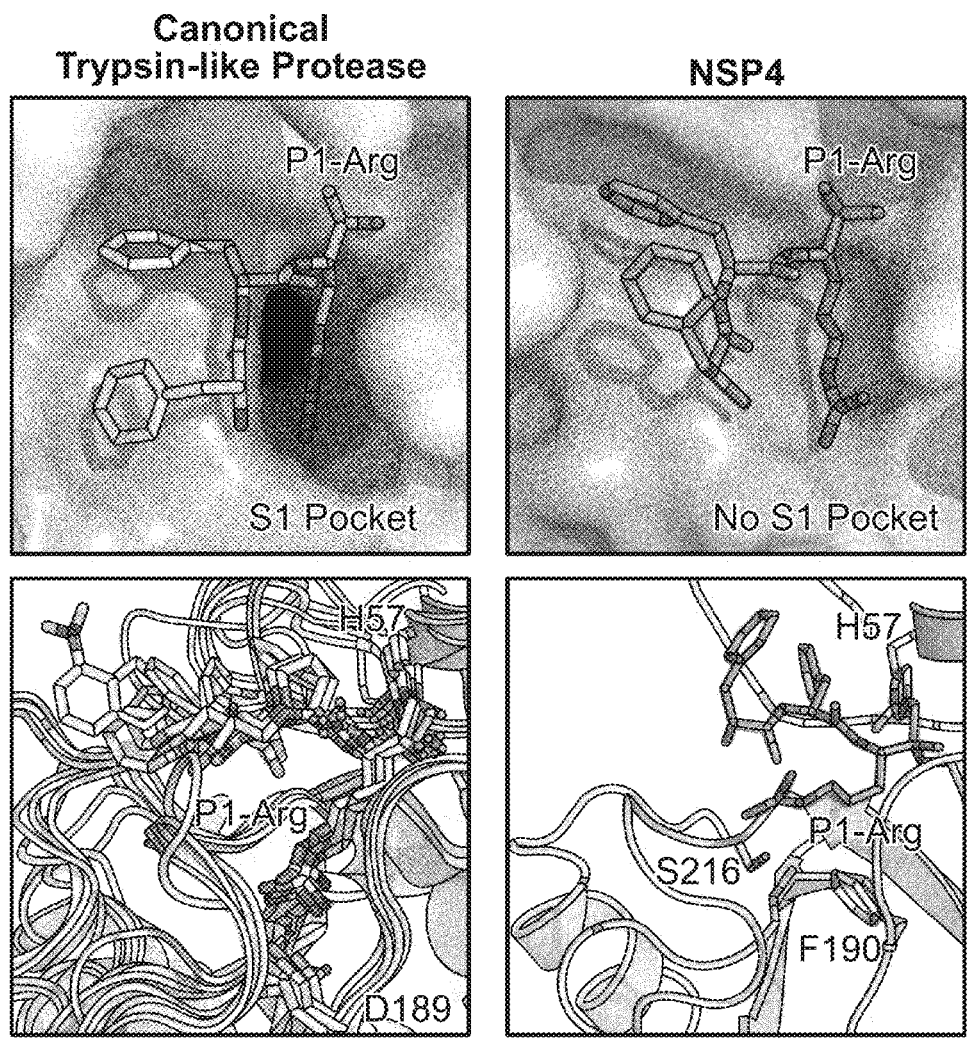
Figure 5:
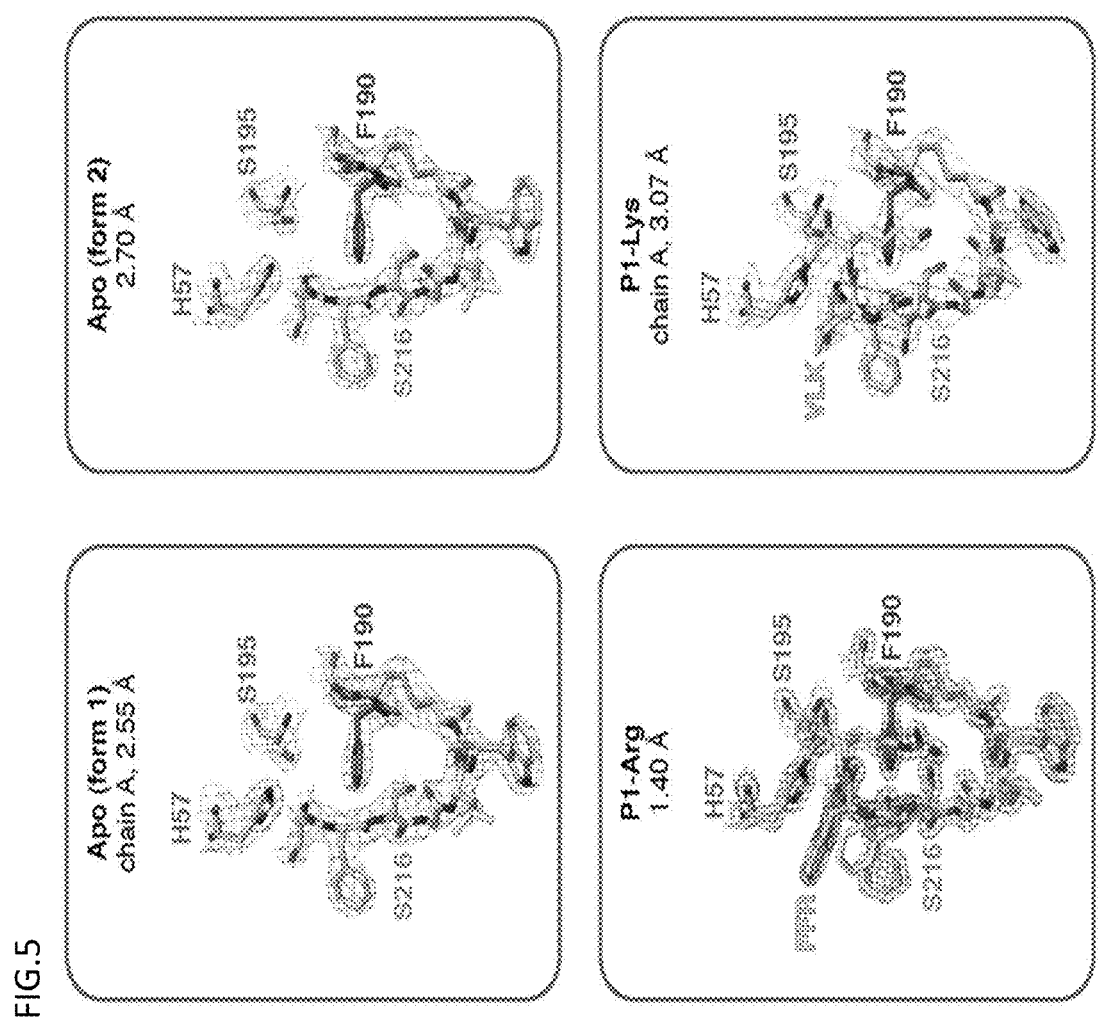
FIG. 5 shows the representative electron density at the NSP4 active site. σA-weighted 2mFo-DFc electron density map, contoured at 1.5σ, of the NSP4 active site. Shown are the 220-loop residues $^{214}SFSGLWC^{220}$, the 180-loop residues $^{190}FCS^{192}$, and the catalytic residues H57 and S195. The S216 and F190 residues, which occlude the S1 pocket, are shown as sticks. The bound FFR-cmk and VLK-cmk are shown as sticks.
Figure 6A:
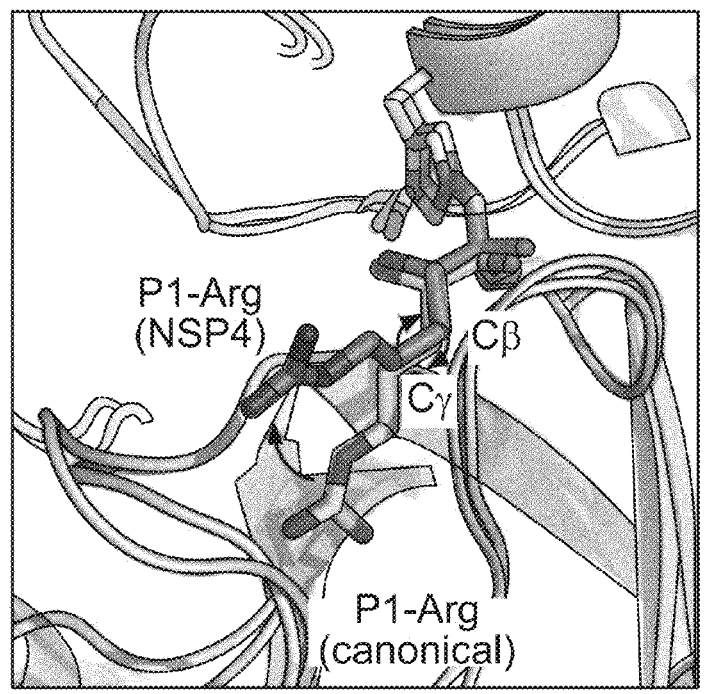
FIGS. 6A-6D demonstrate that the P1-arginine in the "up" confirmation is stabilized by a H-bond network. A) Structural superposition of P1-arginine in NSP4 and in Factor VIIa (PDB 1DAN). B) H-bond network around P1-arginine residue (P1-Arg) in NSP4. C) Cleavage of fluorogenic peptide by NSP4 hydrogen bond mutants. D) Cleavage of fluorogenic peptides with P1-arginine and P1-methylarginine by NSP4 or Factor Xa (FXa).
Figure 6B:
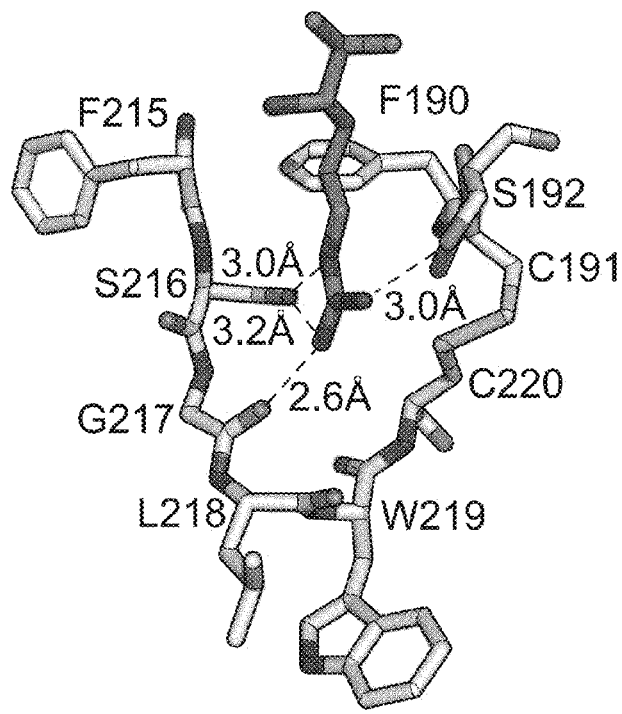
Figure 6C:
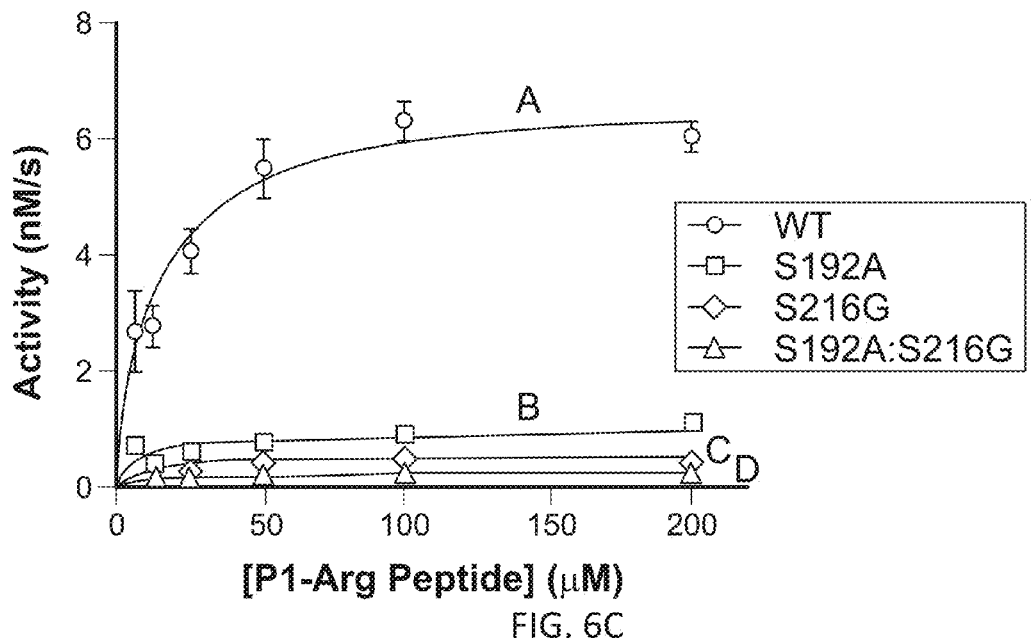

The structural details of the active site revealed an unprecedented mechanism by which the substrate P1-arginine was recognized and concurrently explained the NSP4 conundrum. The structures show that the canonical S1 pocket was non-existent, as it is completely occluded by F190 and S216 (FIG. 3B and FIG. 5). The F190 and S216 side chains were highly ordered, consistent with the absence of a 'gate' mechanism; instead, residues F190 and S216 formed the floor of a shallow groove above the occluded S1 pocket to accommodate the redirected arginine side chain (FIG. 3B). The arginine side chain movement from the canonical "down" to the new "up" position in NSP4 was accomplished by a rotation of the Cβ-Cγ bond (Chi2 angle) by 160° (FIG. 6A). Otherwise, the catalytic triad, the oxyanion hole, and the classical Cα trace of the FFR peptide, including the antiparallel main chain interactions between the protease 214-216 residues and the substrate P1-P3 residues, were all preserved. The "up" conformation of P1-arginine was supported by F190, which provided a hydrophobic platform that interacted favorably with the aliphatic portion of the P1-arginine side chain. In addition, the specificity for P1-arginine was conferred by a network of H-bonds involving the guanidinium group, coordinated by three H-bond acceptors—the S216 and S192 side chains and the G217 backbone carbonyl oxygen (FIG. 6B). Therefore, NSP4 replaced the predominant P1-arginine-stabilizing electrostatic interaction inside a typical trypsin-like S1 pocket with a new H-bond network situated on top of the occluded S1 pocket. The importance of this H-bond network for catalysis was examined by mutating the two H-bond acceptors S192 and S216. The single H-bond acceptor mutants showed 10-fold reduced activity, whereas removal of both H-bond acceptors (S192A:S216G) resulted in 20-fold reduction (FIG. 6C).

Figure 6D:
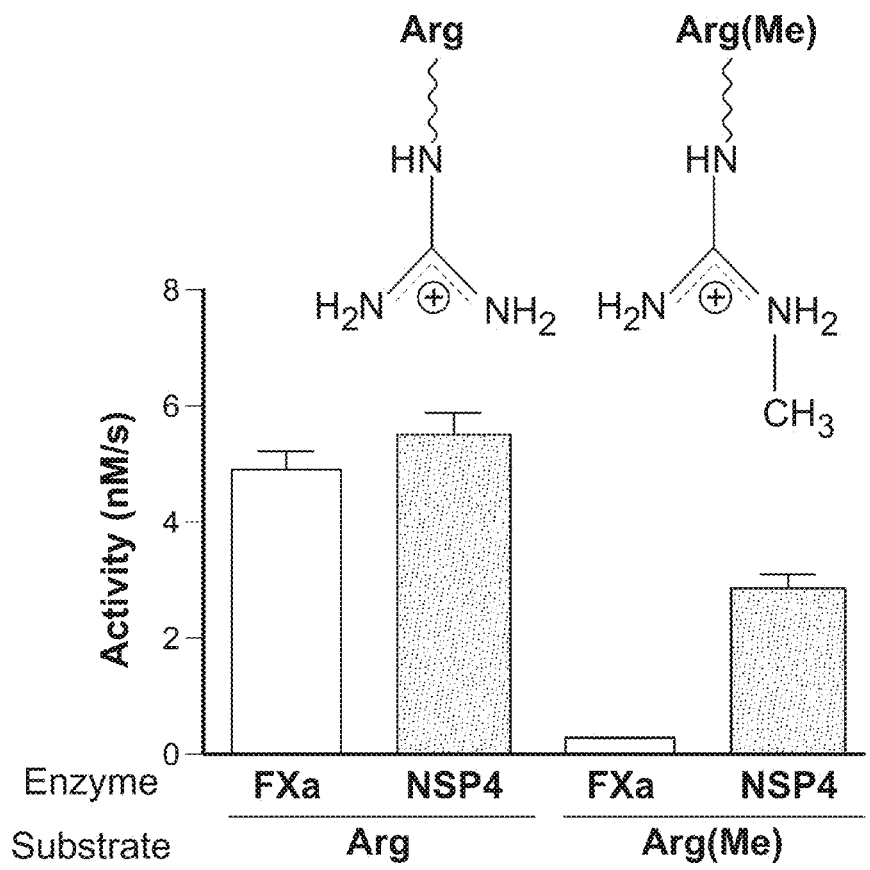
Figure 7:
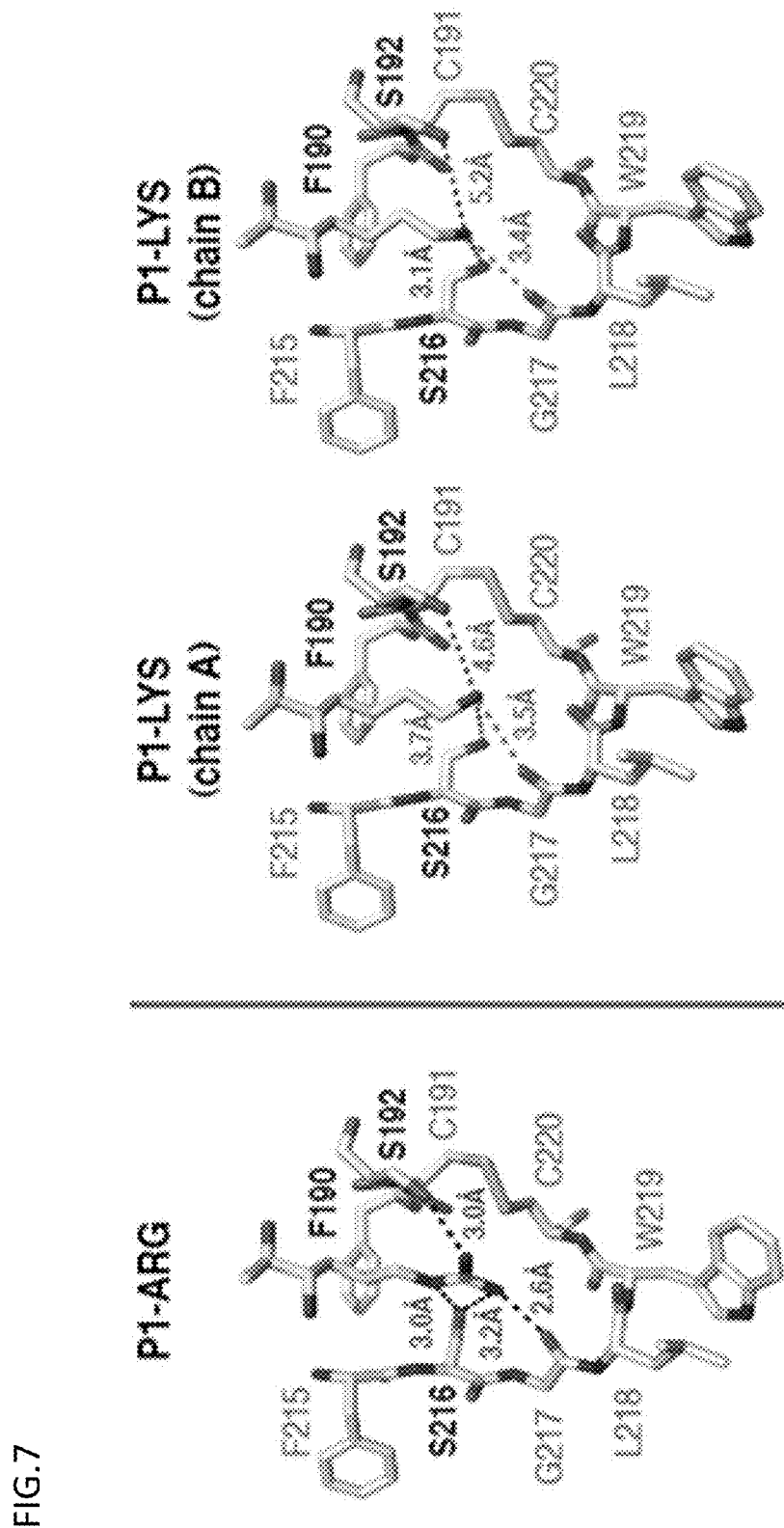
FIG. 7 demonstrates the structural basis for NSP4 preference for P1-arginine over P1-lysine. The P1-arginine in NSP4:FFR-cmk structure is stabilized by a network of H-bonds, coordinated by the H-bond acceptors S216 and S192 side chains and G217 backbone carbonyl oxygen. In contrast, the P1-lysine in NSP4:VLK-cmk structure does not engage the full complement of H-bond acceptors on NSP4.
Figure 8:
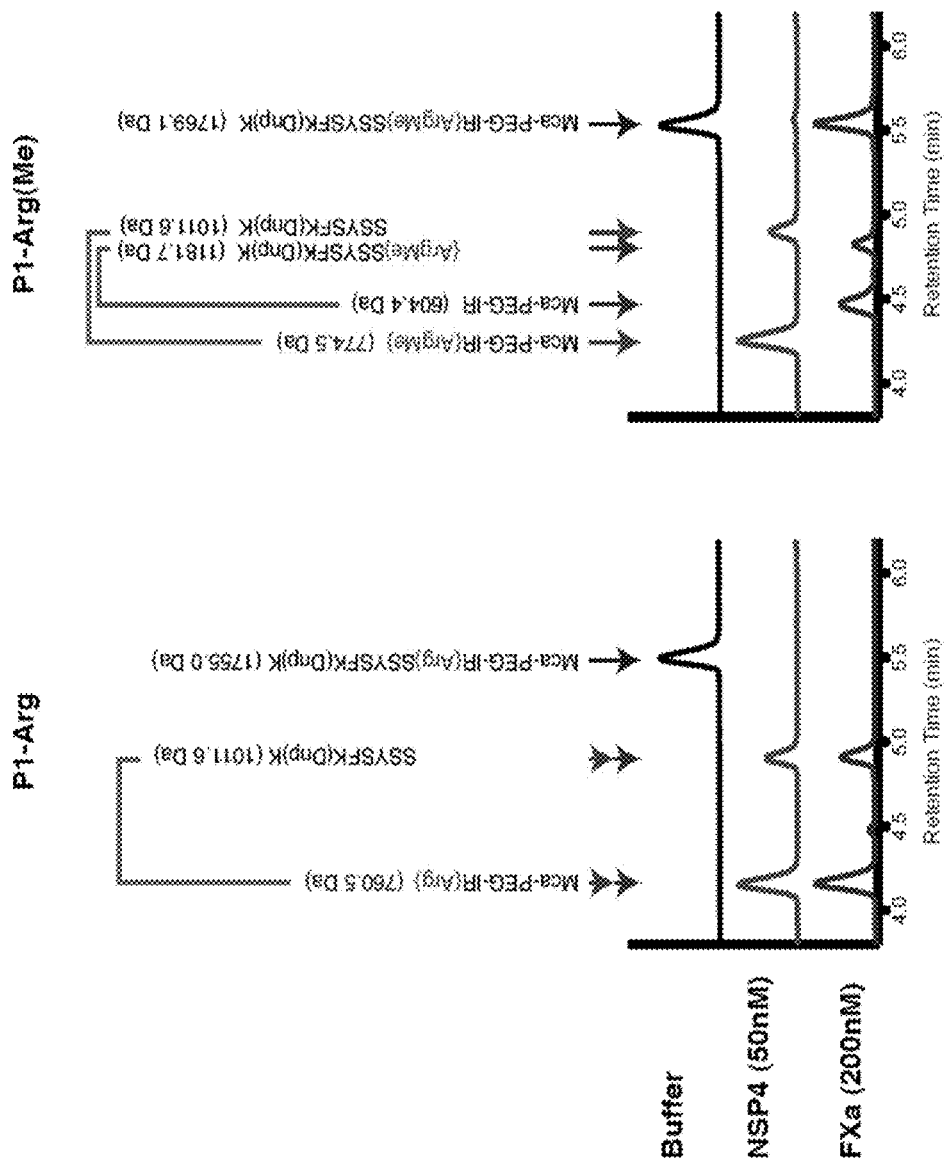
FIG. 8 shows confirmation of NSP4 or FXa cleavage of modified P1-arginine fluorogenic peptide substrates by liquid chromatography-mass spectrometry (LC-MS). Cleavage of P1-arginine (P1-Arg, left panel) or P1-methylarginine (P1-Arg(Me), right panel) fluorogenic peptide substrate by NSP4 (50 nM) or by factor Xa (FXa, 200 nM) was confirmed by use of LC-MS. The peaks, measured in total ion current, represents either full-length or hydrolyzed peptide fragments separated over reverse-phase HPLC. The identities of peptide fragments and their deduced mass are indicated. P1-Arg(Me) is refractory to FXa cleavage; the peaks observed in P1-Arg(Me) peptides for FXa represent a shifted P1 cleavage event occurring at $^1IR^2\downarrow^3\{Arg(Me)\}SSYS\text{-}FKK^{10}$ instead of the $^1IR\{Arg(Me)\}^3\downarrow^4SSYSFKK^{10}$ observed for NSP4.

Despite NSP4's poor activity towards P1-lysine (P1-Lys) substrates, it was possible to prepare a complex of NSP4 with the covalently bound lysine substrate mimic D-Val-L-Leu-L-Lys (VLK)-cmk and obtain a crystal structure at 3.08 Å resolution. It showed that the P1-lysine side chain adopted a conformation like that of P1-arginine (FIG. 7). However, unlike the longer P1-arginine side chain, the shorter P1-lysine side chain could not engage the full complement of H-bonds as the P1-arginine, thereby explaining the extremely poor cleavage after P1-lysine residues (FIG. 2C). NSP4 Processed Substrates With Modified Arginines In an orthogonal approach to validate the unique NSP4 active site, NSP4's activity towards peptide substrate with modified P1 arginine was examined. The naturally occurring arginine-derivative methylarginine is resistant to cleavage by trypsin-like proteases because the methylarginine side chain cannot be spatially accommodated inside the narrow S1 pocket (Baldwin et al., Science, 1971, 171:579-581; Asami et al., Bioorg Med Chem Lett, 2012, 22:6328-6332). This structural limitation did not apply to NSP4. Because the P1-arginine guanidinium group was solvent-exposed on NSP4, it was reasoned that NSP4 could accommodate modifications to the arginine guanidinium group such as an extra methyl group. Enzymatic assays with peptidic substrates demonstrated that NSP4 could indeed cleave after methylarginine, whereas the trypsin-like protease, factor Xa, with a canonical S1 pocket could only cleave unmodified P1-Arg substrate (FIG. 6D and FIG. 8).

Example 2: Determining the Biological Role of NSP4 Using NSP4-Deficient Mice

Figure 9A:
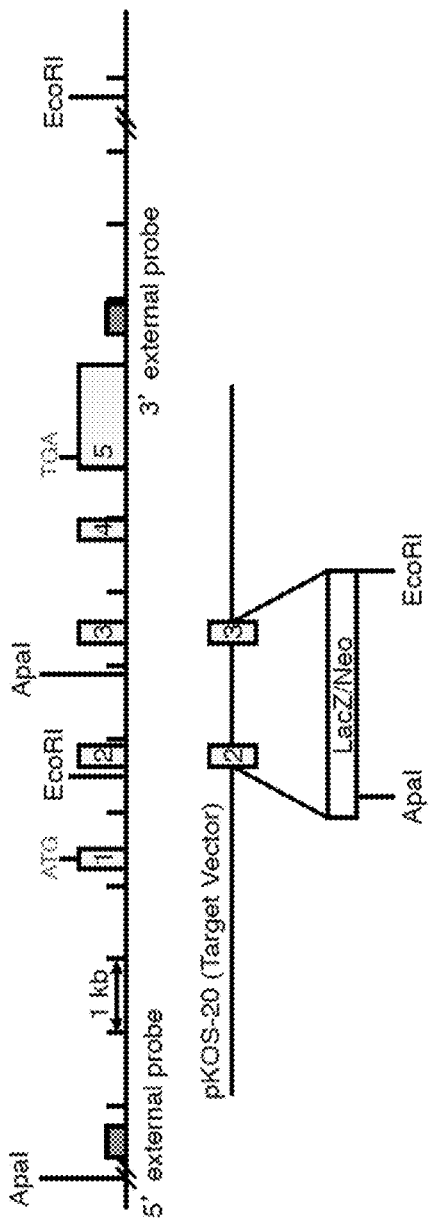
FIGS. 9A-9C show the characterization of NSP4$^{-/-}$ mice. A) Targeting strategy for generating NSP4$^{-/-}$ mice by homologous recombination, as previously described (Tang et al., Nat Biotechnol, 2010, 28:749-755). B) NSP4 ablation in NSP4$^{-/-}$ mice was confirmed by RT-qPCR from total bone marrow cells using three distinct NSP4 primers (PRSS57_1, PRSS57_2, PRSS57_3). The expression of neighboring protease genes, neutrophil elastase (Elane), granzyme M (Gzmm), proteinase 3 (Prtn3), and complement factor D (Cfd) were also analyzed. All gene expression levels are quantified by its relative abundance to mammalian 18S rRNA (dCt). C) Counting of viable total bone marrow cells and sorted B cells (B220$^+$), myeloid cells (B220$^-$/CD11b$^+$), monocytes (B220$^-$/CD11b$^+$/Ly6C$^{hi}$) and neutrophils (B220$^-$/CD11b$^+$/Ly6G$^{hi}$) cells.
Figure 9B:
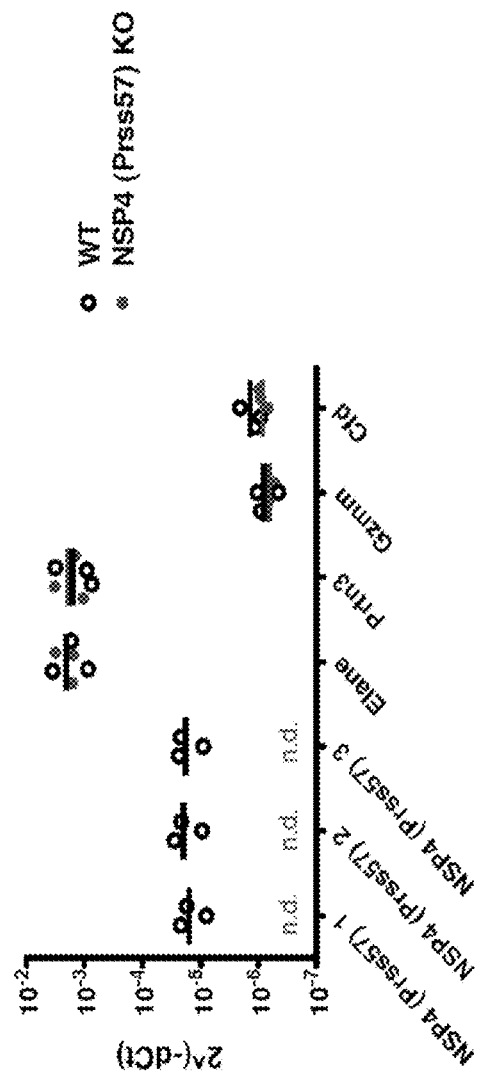
Figure 9C:
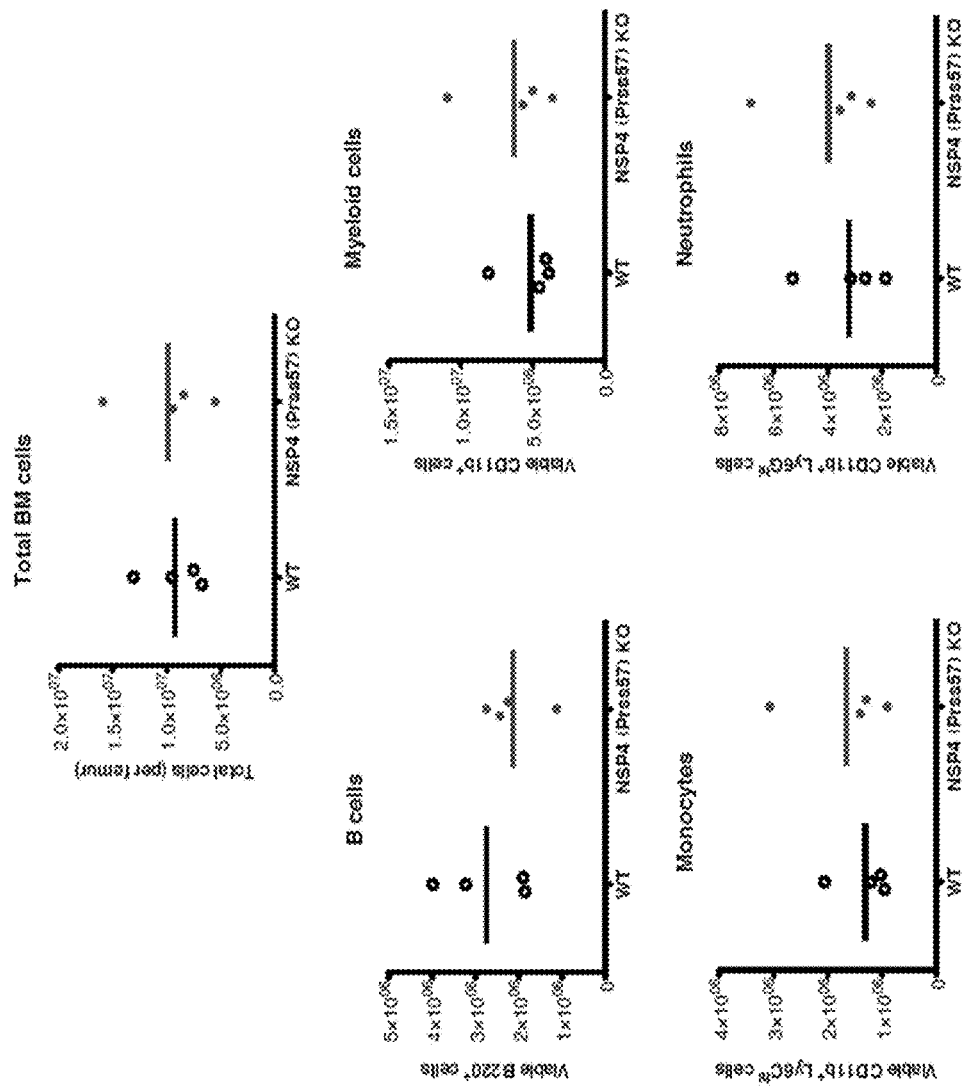

As a first step towards exploring the in vivo function of NSP4, the possible role of NSP4 in inflammation using the neutrophil-dependent K/BxN serum transfer arthritis model was investigated (Monach et al., Curr Protoc Immunol, 2008, Chapter 15:Unit 15.22). NSPs have been previously implicated in inflammatory arthritis, but required the combined deficiency of both NE and CG to achieve full protection in experimental arthritis models, suggesting functional redundancy among NSPs. However, given the unique arginine specificity of NSP4 and its evolutionary status, it was surmised that NSP4 might have essential functions in neutrophil-mediated inflammatory processes. To investigate the role of NSP4 in inflammation, NSP4-deficient mice were generated as previously described (Tang et al., Nat Biotechnol, 2010, 28:749-755) (FIG. 9A) and backcrossed to the C57BL/6 strain. Successful ablation of NSP4 in NSP4$^{-/-}$ mice was verified by RT-qPCR using different PCR primer/probe sets spanning three different NSP4 exon boundaries (FIG. 9B). In a similar manner, NSP4$^{-/-}$ mice were also analyzed for the expression of protease genes flanking NSP4 in this protease-rich locus. None of the neighboring protease genes, including the NSP members NE and PR3, were affected (FIG. 9B). The NSP4-deficient mice were viable and fertile, exhibited no notable abnormalities in comprehensive phenotypic screens (Henrich et al., Nat Struct Biol, 2003, 10:520-526), and had normal bone marrow cell, B cell, monocyte myeloid cell, and neutrophil counts (FIG. 9C).

Figure 10A:
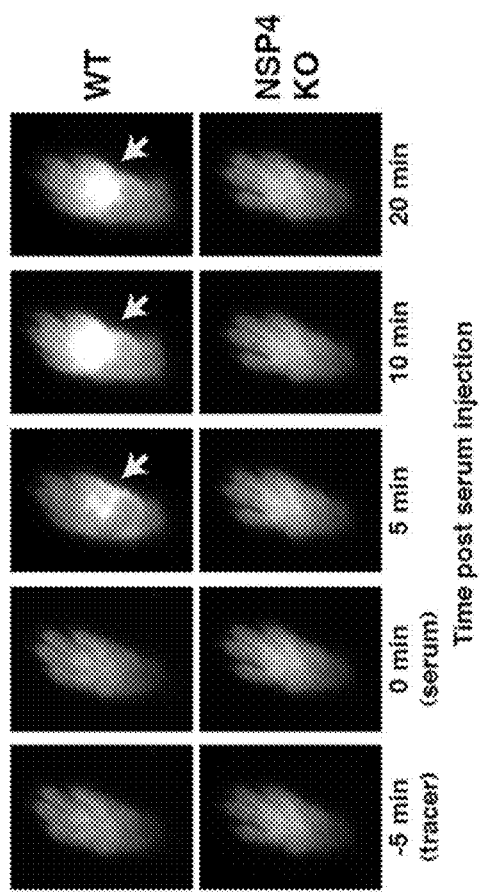
FIGS. 10A-10B show that NSP4 is required for K/BxN serum-induced vascular leakage. The fluorescence probe AngioSense 680 was injected intravenously via tail vein (at −5 min), allowed to equilibrate for 5 minutes, followed by intravenous injection of the K/BxN arthritic serum (at 0 min). A) Representative near-infrared fluorescence imaging of the forepaws from a wild-type and a NSP4$^{-/-}$ mouse. Vascular leakage could be observed in the wild-type mouse forepaw starting at 5 min (arrows). B) Individual quantification of the fold change in mean fluorescence intensity of wild-type mice or NSP4$^{-/-}$ mice, as labeled, n=5 mice per group.
Figure 10B:
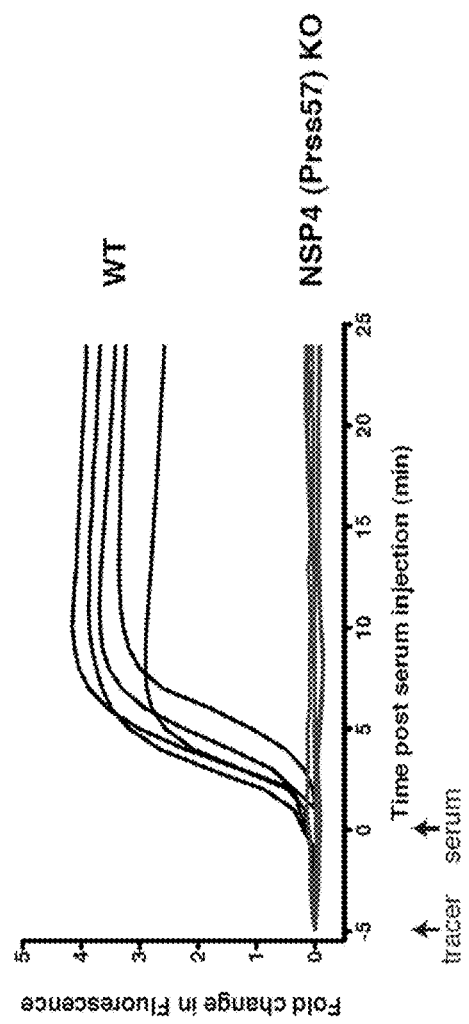

One major hallmark of the K/BxN model is the rapid onset of localized vascular edema in the mouse paws following intravenous K/BxN serum administration (Binstadt et al., Nat Immunol, 2006, 7:284-292). To monitor vascular leakage, a near-infrared fluorescence vascular probe was administered to both NSP4-deficient and wild-type mice 5 minutes prior to K/BxN serum injection and then visualized and quantified the subsequent vascular permeability changes by in vivo near-infrared fluorescence imaging (FIGS. 10A and B). Following intravenous administration of K/BxN serum, the wild-type mice, as expected, exhibited rapid extravasation of the vascular probe in the paws with reproducible severity and kinetics. In striking contrast, the fluorescence levels of NSP4$^{-/-}$ mice remained at baseline throughout the study (FIGS. 10A and B), suggesting that NSP4 played an indispensable role in mediating this immune complex-triggered vasopermeability response.

Figure 11C:
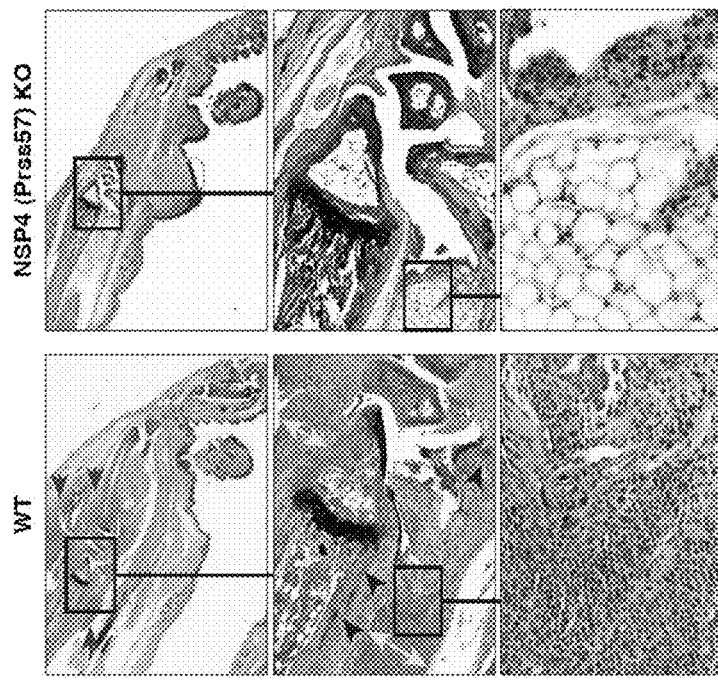
FIGS. 11A-11C show that NSP4 is required for K/BxN serum-induced arthritis. A) Clinical scores of mouse paws following systemic K/BxN serum injection in wild-type (circles) and NSP4$^{-/-}$ (squares) mice. The data is represented as mean±SEM, n=4 mice per group. B) Histological lesion scores of mouse paws at the experimental end point. All four paws of each mouse, n=4 mice per group, were examined as hemisections and scored for inflammation, fibroplasia, cartilage injury and bone remodeling on a scale of 0 (no lesions) to 5 (severe lesions). Wild-type mice had mild to moderate lesions (mean histological lesion scores of 3.4, 3.0, 2.1, 2.2), whereas NSP4$^{-/-}$ mice were essentially protected (mean histological lesion scores of 0.70, 0.80, 0.00, 0.78). Group-wise comparison on all four histological lesion score categories reached statistical significance with p<0.0001. C) Representative histological sections of wild-type (left) and NSP4$^{-/-}$ (right) mouse forepaws stained with hematoxylin and eosin. Top: wild-type mice had considerable soft tissue swelling with extensive periarticular inflammatory cell infiltration (arrows) and fibroplasia. Middle: wild-type paw lesions included intraarticular exudate (asterisk), periosteal osteolysis (arrowheads), and inflammatory cell infiltration (double arrows). Bottom: wild-type mice had dense periarticular inflammatory cell infiltration. NSP4$^{-/-}$ mice exhibited no tissue swelling (top), maintained normal joint architecture (middle), and had minimal cellular infiltrate (bottom).
Figure 11A:
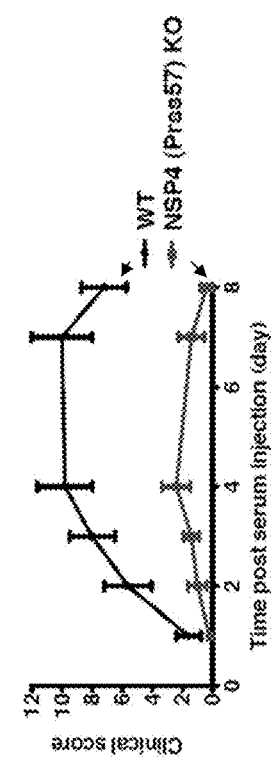
Figure 11B:
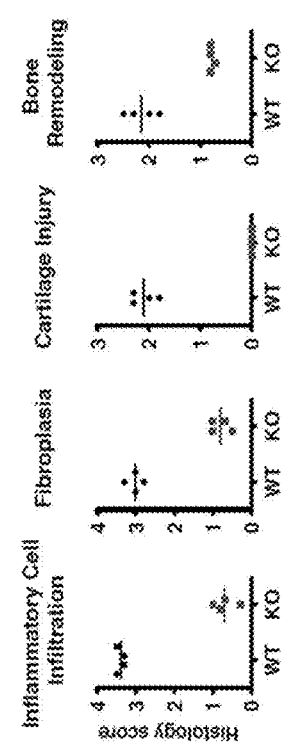

The initial induction of vascular leakage after K/BxN serum transfer in wild-type mice was followed by the development of erythema and edema, whereas NSP4$^{-/-}$ mice remained significantly protected during the 8-day post-induction period (FIG. 11A). Histological examination of the paws at the experimental end point showed mild to moderate polyarthritis in the wild-type control group while NSP4$^{-/-}$ mice were essentially devoid of lesions (FIGS. 11B and 11C). In the wild type mice, the polyarthritis observed was consistent with the K/BxN model and was characterized by infiltration with inflammatory cells, predominantly neutrophils, accompanied by mild fibroplasia, cartilage injury and bone remodeling (FIG. 11C). In contrast, the NSP4$^{-/-}$ mice had minimal pathological lesions (FIG. 11C, middle right), and virtually no inflammatory cell infiltration (FIG. 11C, bottom right). Taken together, these results indicated NSP4 played an indispensable pro-inflammatory role in this neutrophil-mediated disease model.

Example 3: Generation of Conformation-Specific and Species-Specific NSP4 Antibodies A panel of antibodies were generated and characterized for specificity against NSP4. Residues were numbered using the Kabat system (Kabat et al., Sequences of proteins of immunological interest, 5th Ed., Public Health Service, National Institutes of Health, Bethesda, Md. (1991)).

Methods

Generation of Recombinant Human and Mouse NSP4

Figure 12:
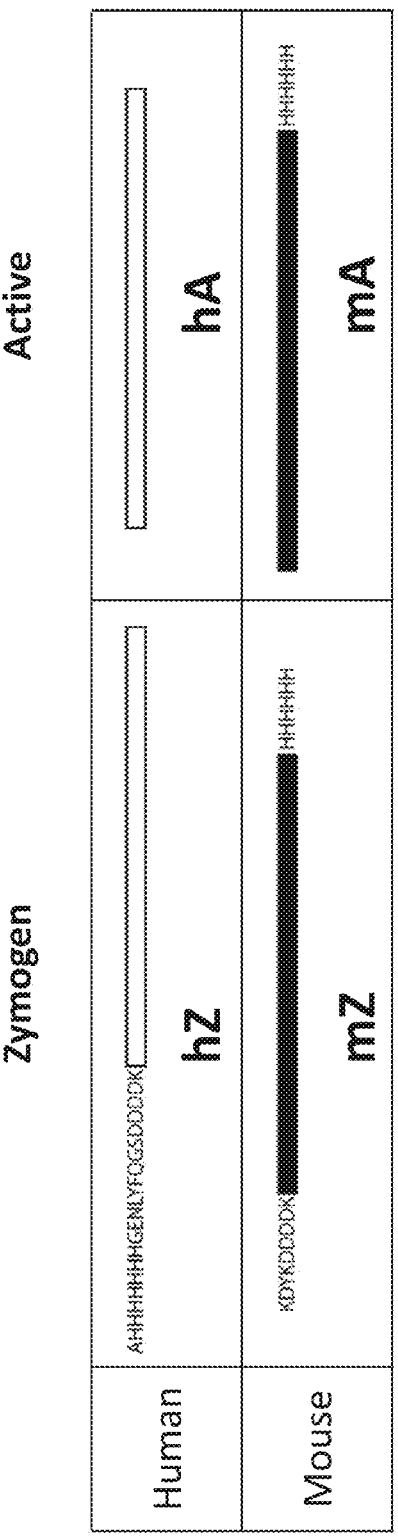
FIG. 12 is a diagram of a precursor form of NSP4 (zymogen) and mature form of NSP4 (active) used for generation of conformation-specific NSP4 antibodies by phage display. hZ indicates precursor form of human NSP4; mZ indicates precursor form of mouse NSP4; hA indicates mature form of human NSP4; and mA indicates mature form of mouse NSP4.

Recombinant human NSP4 and mouse NSP4 were generated as antigens for library sorting. NSP4 was produced as an inactive zymogen by engineering a cleavable epitope tag at the protein N-terminus to prevent premature activation and thus reduce cellular toxicity and increase protein expression in heterologous expression systems. A total of four NSP4 antigens were generated: human zymogen (hZ), human active (hA), mouse zymogen (mZ), and mouse active (mA). The hZ NSP4 was expressed in insect cells and purified by N-terminal 6His-tag using immobilized metal affinity chromatography. The mZ NSP4 was expressed in CHO cells and purified by N-terminal FLAG tag using anti-FLAG affinity chromatography. Both the hZ and mZ NSP4s were further purified using Superdex 200 size exclusion chromatography (GE Healthcare) and MonoS cation exchange chromatography (GE Healthcare). The catalytically active forms of these NSP4 (hA and mA) were generated by treating the purified zymogen forms (hZ and mZ) with EKmax enteropeptidase (Invitrogen) to remove the N-terminal epitope tag and were subsequently purified over another MonoS cation exchange chromatography (GE Healthcare) to homogeneity. Cleavage occurred on the C-terminal side of lysine following the amino acid sequence Asp-Asp-Asp-Asp-Lys. These four NSP4 antigens (hZ, hA, mZ, and mA) were used in parallel for phage library sorting and for screening conformational-specific and species-specific anti-NSP4 antibodies (FIG. 12).

Phagemid Vectors for Library Construction

Phage-displayed synthetic antibody libraries were generated using oligonucleotide-directed mutagenesis in the three heavy chain complementarity-determining regions (CDRs) on a modified h4D5-encoding phagemid, pV0350-4, as template, and described as Lib-3 (see Lee et al., 2004. *J Mol Biol* 340:1073-1093). For initial selection with the naïve libraries, hZ-, hA-, mZ, and mA-NSP4 were each immobilized separately on Maxisorp immunoplates (Nunc) and phage libraries were cycled through 4 rounds of binding selection (see Lee et al., *J Mol Biol*, 2004, 340:1073-1093) under high salt conditions in phosphate buffered saline supplemented with 1% BSA or casein (BSA at rounds 1 and 3, casein at rounds 2 and 4), 0.1% Tween-20, and an additional 0.5 M NaCl to reduce non-specific interaction between the positively charged NSP4 proteins and the negatively charged phage particles. Random clones selected from rounds 3 and 4 were picked and assayed to identify specific binders using phage enzyme-linked immunosorbent assay (ELISA). The VH regions of selected clones that bound to NSP4 were amplified by polymerase chain reaction (PCR) for sequencing.

Competition phage ELISA

Phage clones were propagated from single colonies by growing in 30 ml 2YT culture supplemented with carbenicillin and KO7 helper phage overnight at 30° C., purified, and assayed as described (see Lee et al., *J Mol Biol*, 2004, 340:1073-1093). Phage at sub-saturating concentrations were first incubated with increasing concentrations of target NSP4 antigen (either hZ, hA, mZ, or mA) for 1 to 2 hour(s), and then transferred to wells coated with the same NSP4 antigen to capture the unbound phage. The amount of phage bound was measured with anti-M13 antibody-horseradish peroxidase (HRP) conjugate (GE Healthcare), developed using the substrate tetramethylbenzidine (TMB) (Kirkegaard and Perry Laboratories) for approximately 5 min, quenched with 1.0 M H3PO4, and read with a spectrophotometer at 450 nm wavelength as previously described (see Lee et al., *J Mol Biol*, 2004, 340:1073-1093) Inhibitory concentration (IC50) values were calculated as the concentration of soluble antigen that inhibited 50% of the phage binding to the immobilized antigen.

Anti-NSP4 Antibody Production and Affinity Measurement

To generate IgG proteins for characterization, the variable domains of selected phage clones were cloned into pRK5-based plasmid with human light chain or heavy chain (human IgG1) constant domain for transient IgG expression in Chinese hamster ovary (CHO) cells, and purified using protein A affinity chromatography.

Biolayer interferometry measurements (ForteBio) were used to determine the affinity of anti-NSP4 antibodies against all four NSP4 antigens (hZ-, hA-, mZ-, and mA-NSP4). 5 µg/ml of each anti-NSP4 candidate was immobilized onto anti-human Fc sensors, and incubated with increasing concentrations of each NSP4 antigens to obtain affinity measurements. These antibody candidates were then binned to one of the following categories: 1) Conformation and species-specific: binds to either hZ, hA, or mA (no mZ-specific binders were identified); 2) Conformation-specific: binds to active (hA/mA) or zymogen (hZ/mZ) forms of NSP4; 3) Species-specific: binds to human (hZ/hA) or mouse (mZ/mA) forms of NSP4; and 4) Pan-NSP4: binds to all four forms of NSP4 (hZ/hA/mZ/mA).

Screening for NSP4 Blocking Antibodies

NSP4 fluorogenic activity assay was devised by screening a panel of internally-quenched fluorogenic peptide substrates (see Eigenbrot et al., *Structure*, 2012, 20:1040-1050) with NSP4. 50 nM of NSP4 was incubated with 2.5 uM of each fluorescence-quenched peptide substrate in 50 mM Tris pH 8.0, 200 mM NaCl, and 0.25% w/w CHAPS and the fluorescence intensity determined using the SpectraMax M5 spectrophotometer (MolecularDevices) with excitation at 328 nm and emission at 393 nm. The peptide substrate cleaved most efficiently by NSP4 was Mca-Ile-Arg-Arg-Ser-Tyr-Ser-Phe-Lys-[Dnp]-Lys, where Mca is 7-methoxycoumarin-4-acetate and Dnp is dinitrophenol. Incubation with NSP4 resulted in a specific cleavage resulting in two distinct fragments: Mca-Ile-Arg-Arg and Ser-Tyr-Ser-Phe-Lys [Dnp]-Lys.

To identify blocking anti-NSP4 antibody candidates, 10 nM of recombinant human or mouse NSP4 was incubated with 500 nM of each antibody candidate for 30 min at 37° C. This NSP4:antibody mixture was then mixed with 6.7 uM of the fluorogenic peptide substrate, incubated for 5 min at 37° C., and then read on the SpectraMax M5 spectrophotometer using the parameters described above.

Results

Figure 13:
FIG. 13 is a diagram of the CDR sequences of the heavy chain variable region of antibodies 5-2, 5-3, and 5-4. The sequences depicted in the figure are identified in the sequence listing as follows: CDRH1 for phage clone 5-2, SEQ ID NO:1; CDRH2 for phage clone 5-2, SEQ ID NO:2; CDRH3 for phage clone 5-2, SEQ ID NO:3; CDRH1 for phage clone 5-3, SEQ ID NO:4; CDRH2 for phage clone 5-3, SEQ ID NO:5; CDRH3 for phage clone 5-3, SEQ ID NO:6; CDRH1 for phage clone 5-4, SEQ ID NO:7; CDRH2 for phage clone 5-4, SEQ ID NO:8; and CDRH3 for phage clone 5-4, SEQ ID NO:9.
Figure 15:
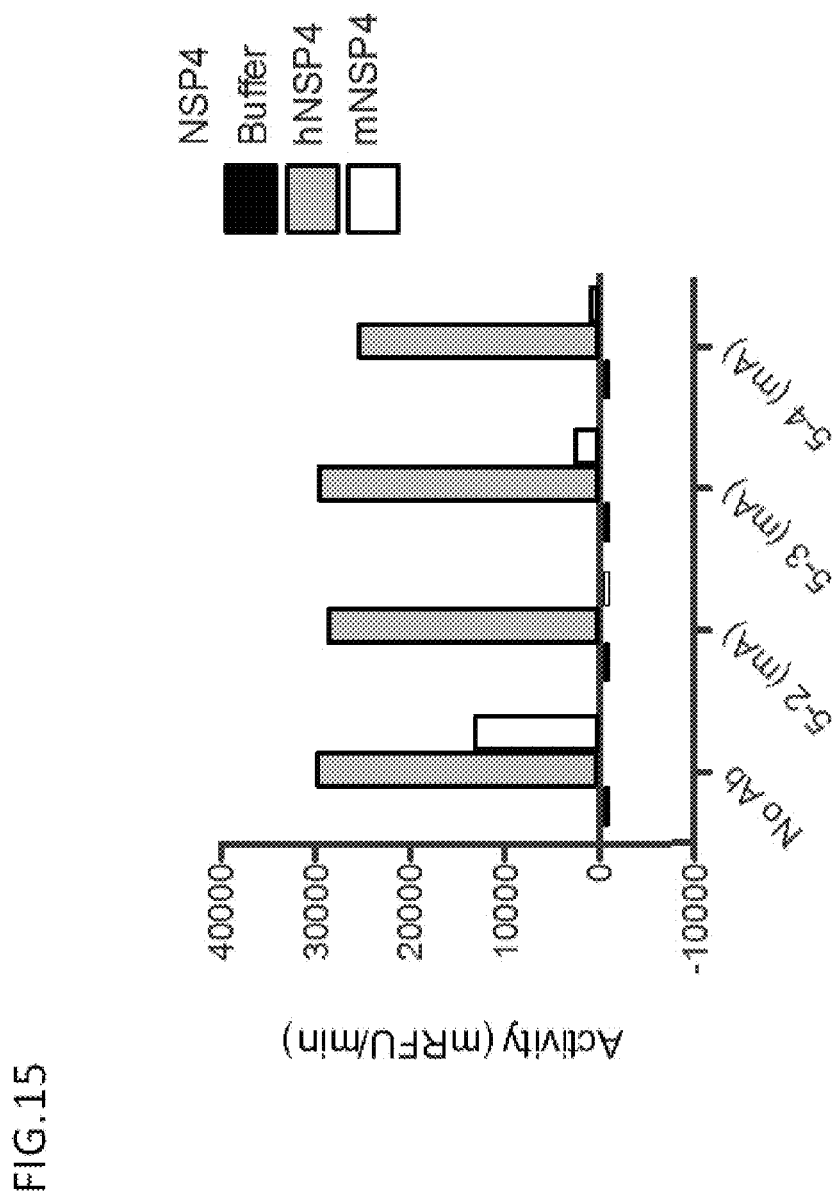
FIG. 15 is a graph demonstrating antibodies 5-2, 5-3, and 5-4 specifically blocked the protease activity of mouse NSP4 in a fluorogenic substrate assay. hNSP indicates mature human NSP4. mNSP4 indicates mature mouse NSP4.

Three antibody candidates that strongly bound to NSP4 during heavy chain variable domain (VH) library panning were isolated and used to generate IgG1 antibodies for further characterization (FIG. 13). Antibody candidates 5-2, 5-3, and 5-4 demonstrated a high degree of binding specificity against active mouse (mA) NSP4 antigen (FIGS. 14A, 14B, and 14C, respectively). Evaluation of the antibody candidates 5-2, 5-3, and 5-4 demonstrated their ability to block peptide cleavage activity of mouse NSP4 (FIG. 15). Furthermore, these antibodies did not block peptide cleavage activity of human NSP4, indicating that 5-2, 5-3, and 5-4 were species specific to mouse NSP4 (FIG. 15).

Antibodies against human NSP4 can be generated using the methods described herein.

ANTIBODY SEQUENCES

Heavy chain CDR1 for antibody 5-2'
(SEQ ID NO: 1)
GFTFSNTYIS

Heavy chain CDR2 for antibody 5-2'
(SEQ ID NO: 2)
GFIYPANGATYYADSVKG

Heavy chain CDR3 for antibody 5-2'
(SEQ ID NO: 3)
RRYRLSFDY

Heavy chain CDR1 for antibody 5-3'
(SEQ ID NO: 4)
GFTFSGNDIS

Heavy chain CDR2 for antibody 5-3'
(SEQ ID NO: 5)
AGISPYGGSTYYADSVKG

Heavy chain CDR3 for antibody 5-3'
(SEQ ID NO: 6)
RRVSFYSRHAGMDY

Heavy chain CDR1 for antibody 5-4'
(SEQ ID NO: 7)
GFTFTSYAIS

Heavy chain CDR2 for antibody 5-4'
(SEQ ID NO: 8)
AGISPSNGYTNYADSVKG

Heavy chain CDR3 for antibody 5-4'
(SEQ ID NO: 9)
RAGRWTHSDIDY

Light chain CDR1 for antibodies 5-2', 5-3', and 5-4'
(SEQ ID NO: 10)
RASQDVSTAVA Light chain CDR2 for antibodies 5-2', 5-3', and 5-4'
(SEQ ID NO: 11)
SASFLYS Light chain CDR3 for antibodies 5-2', 5-3', and 5-4'
(SEQ ID NO: 12)
QQSYTTPPT Heavy chain variable region for antibody 5-2'
(SEQ ID NO: 13)
EVQLVESGGGLVQPGGSLRLSCAASGFTFSNTYISWVRQAPGKGL

EWVGFIYPANGATYYADSVKGRFTISADTSKNTAYLQMNSLRAED

TAVYYCSRRYRLSFDYWGQGTLVTVSS

Heavy chain variable region for antibody 5-3'
(SEQ ID NO: 14)
EVQLVESGGGLVQPGGSLRLSCAASGFTFSGNDISWVRQAPGKGL

EWVAGISPYGGSTYYADSVKGRFTISADTSKNTAYLQMNSLRAED

TAVYYCSRRVSFYSRHAGMDYWGQGTLVTVSS

Heavy chain variable region for antibody 5-4'
(SEQ ID NO: 15)
EVQLVESGGGLVQPGGSLRLSCAASGFTFTSYAISWVRQAPGKGL

EWVAGISPSNGYTNYADSVKGRFTISADTSKNTAYLQMNSLRAED

TAVYYCSRAGRWTHSDIDYWGQGTLVTVSS

Light chain variable region for antibodies 5-2', 5-3', and 5-4'
(SEQ ID NO: 16)
DIQMTQSPSSLSASVGDRVTITCRASQDVSTAVAWYQQKPGKAPK

LLIYSASFLYSGVPSRFSGSGSGTDFTLTISSLQPEDFATYYCQQ

SYTTPPTFGQGTKVEIKR

Example 4: Characterization of NSP4 mRNA and Protein Expression Levels

Both mRNA and protein expression levels for NSP4 were measured in various mouse cell types to profile the cell types for the presence of NSP4.

Methods

RT-qPCR Measurement of NSP4 mRNA Levels.

To quantify the mRNA expression levels of NSP4 in immune cell populations from mouse femoral bone marrow, RT-qPCR analysis was performed Immune cell populations from mouse femoral bone marrow were identified using standard flow cytometry protocols and the following antibody clones: anti-CD11b (M1/70); anti-CD11c (N418); anti-B220 (RA3-6B2); (BM8); anti-Ly6C (HK1.4); anti-Ly6G (1A8); anti-Siglec F (E50-2440). All antibodies were obtained from eBioscience. Viability was evaluated using Sytox Blue (Invitrogen). Stained cells were sorted using a BD Biosciences FACSAria cell sorter. The following populations were sorted for downstream analysis: B cells, B220+ CD11b-; Monocytes, Ly6C+CD11b+; Neutrophils, Ly6G+ CD11b+; Eosinophils, Siglec F+CD11b+. Total RNA content was isolated from each cell type using RNeasy Mini kit (Qiagen) and the corresponding cDNA were synthesized using the iScript reverse transcriptase (Bio-Rad), all performed according to manufacturer instructions. qPCR measurements were performed from cDNA samples using the TaqMan 2X PCR master mix (Applied Biosystems) with the following three NSP4/Prss57 primer/probe sets (Applied Biosystems): Prss57_1 (ABI Mm01144794_m1), Prss57_2 (ABI Mm01144795_m1), and Prss57_3 (ABI Mm01144796_m1). Gene expression levels are expressed as $2^{(-dCt)}$ relative to mouse 18S rRNA control.

Western Blot Detection of NSP4 Protein.

To measure for the presence of NSP4 protein in immune cell populations from mouse femoral bone marrow, Western blot analysis was performed using rabbit anti-mouse NSP4 polyclonal antibody. Bone-marrow derived neutrophils were isolated from total bone marrow cells using the mouse neutrophil negative selection kit (Miltenyi Biotec) as performed according to manufacturer instructions. Bone marrow-derived eosinophils were isolated and cultured from bone marrow cells as described in Dyer et al., 2008. J Immunol 181(6):4004-4009. Bone marrow-derived mast cells were isolated and cultured from bone marrow cells as described in Lukacs et al., 1996, Blood 87(6):2262-2268. Bone marrow-derived macrophages were isolated from bone marrow cells as described in Zhang et al., 2008. Curr Protoc Immunol, Unit 14.1. Cell lysates were generated using SDS-Laemmli sample buffer (Bio-Rad) and the concentrations were determined using BCA protein assay (Pierce).

Results

RT-qPCR Measurement of NSP4 mRNA Levels.

Figure 16:
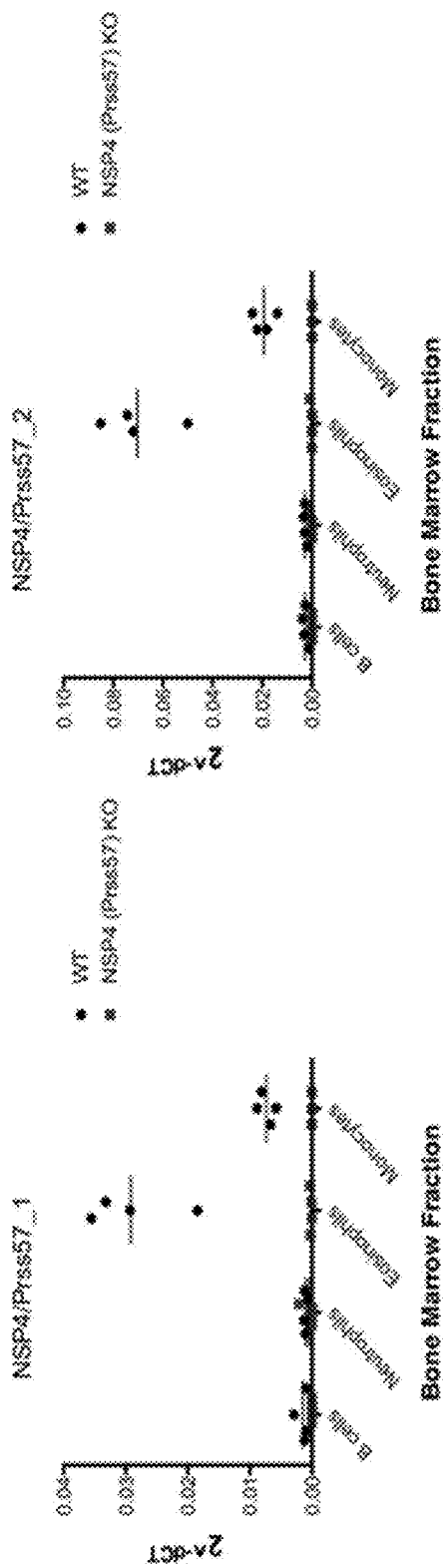

RT-qPCR analysis was performed to measure the mRNA expression levels of NSP4 in immune cell populations isolated from mouse femoral bone marrow. RT-qPCR measurements using three different NSP4/Prss57 primer/probe sets that span three different exon junctions corroborate NSP4 mRNA expression levels in B cells, neutrophils, eosinophils, and monocytes (FIG. 16). As indicated by FIG. 16A-C, NSP4 mRNA was very highly expressed in eosinophils and measurements indicated the presence of NSP4 mRNA expression in monocytes. NSP4 transcript was very low in fully differentiated neutrophils because transcription of NSP genes occur primarily during the premyelocytic stage and cease in fully differentiated neutrophils. See Theilgaard-Monch et al., *Blood* 105:1785-1796, 2005.

Western Blot Detection of NSP4 Protein.

Western blot analysis was performed using a rabbit anti-mouse NSP4 polyclonal antibody to measure the protein expression levels of NSP4 in neutrophils, eosinophils, mast cells and macrophages isolated and cultured from mouse femoral bone marrow (FIG. 17). As indicated, NSP4 protein (about 30 kD) was detected in neutrophils and eosinophils isolated from the wild-type mice, but NSP4 was not detected in mast cells or macrophages from wild-type mice. NSP4 was not detected in cells from NSP4-deficient mice.

Example 5: Neutrophil Recruitment Requires NSP4

In order to confirm the lack of neutrophil joint infiltration in NSP4$^{-/-}$ mice, neutrophil recruitment was monitored by luminol-based bioluminescence imaging in wild-type and NSP4$^{-/-}$ mice.

Methods

Luminol-Bioluminescence Imaging of Neutrophil Myeloperoxidase Activity in Mouse Paws.

Myeloperoxidase (MPO) activity was monitored in vivo through non-invasive bioluminescence imaging (BLI) of the mouse paws. Mice were anesthetized by 2% isoflurane (Butler Schein, 1 L/min flow), implanted with a tail vein catheter, and positioned on a heated stage inside the Photon Imager (Biospace Lab, Paris, France). Mice were injected through the tail vein catheter with a cocktail of 75 ul K/BxN serum and 150 ul MPO-sensitive luminol (Sigma-Aldrich). Light emission was recorded over 8 minutes post injection of the cocktail at 5 minute, 6 hour, and 24 hour intervals for each mouse. Bioluminescent pseudo-color images were shown superimposed on a gray-scale bright field image of the mouse, with the most intense signal being red and weakest signal blue. For quantitative analysis of the luminol signal, an elliptical region of interest (ROI) was drawn on the bioluminescent images over all four paws. The area of the ROI was kept constant and results expressed as photon counts per minute per cm$^2$ using the M3 Vision software (Biospace Lab).

To verify the expression of myeloperoxidase in NSP4-deficient mice, neutrophils from femoral bone marrow were isolated using the mouse neutrophil isolation kit (Miltenyi Biotec), and total cell lysates were made using 2x Laemmli buffer (Bio-Rad). Myeloperoxidase and actin were detected using anti-myeloperoxidase mouse monoclonal antibody (clone 392105; R&D Biosystems) and anti-beta-actin mouse monoclonal antibody (clone 8H10D10; Cell Signaling Technology), respectively.

Results

Luminol-based bioluminescence imaging of neutrophil myeloperoxidase (MPO) activity was performed to image neutrophils in mouse paws (FIG. 18A). NSP4-deficient neutrophils express normal levels of MPO (FIG. 18B), therefore luminol-bioluminescence levels can be used as a surrogate marker for monitoring neutrophil recruitment. See Gross et al., 2009, *Nat. Med.* 15::455-461. NSP4$^{-/-}$ mice exhibited a significantly reduced neutrophil myeloperoxidase activity 24 h after K/BxN serum transfer (FIG. 18C), suggesting a critical role for NSP4 in mediating neutrophil transmigration and joint infiltration in vivo. These optical imaging results are consistent with the lack of neutrophil infiltration observed in the histological examinations described above, thus confirming the lack of neutrophil joint infiltration in NSP4$^{-/-}$ mice.

Example 6: Affinity Improvement of Antibodies 3-5 and 5-1

Antibody clones 3-5 and 5-1 were affinity matured by optimizing their antibody light chain sequence to bind with higher affinity to NSP4.

Methods

Library Construction for Affinity Improvement of Clones 3-5 and 5-1 Derived from the VH Library.

Antibody clones Ab 3-5 (abbreviated Ab35) and Ab 5-1 (abbreviated Ab51) were selected for further affinity improvement. Phagemid pW0703 (derived from phagemid pV0350-2b (Lee et al., *J. Mol. Biol* 340, 1073-1093 (2004)), containing stop codon (TAA) in all CDR-L3 positions and displaying monovalent Fab on the surface of M13 bacteriophage served as the library template for grafting heavy chain variable domains (VH) of clones of interest from the VH library for affinity maturation. Both hard and soft randomization strategies were used for affinity maturation. For hard randomization, one light chain library with selected positions of the three light chain CDRs was randomized using amino acids designed to mimic natural human antibodies and the designed DNA degeneracy was as described in Lee et al. (*J. Mol. Biol* 340, 1073-1093 (2004)). For soft randomization, residues at positions 91-96 of CDR-L3, 30-33, 35 of CDR-H1, 50, 52, 53-54, 56, and 58 of CDR-H2, 95-100, 100A, and 100C of CDR-H3, were targeted; and three different combinations of CDR loops, H1/L3, H2/L3, and H3/L3, were selected for randomization. To achieve the soft randomization conditions, which introduced the mutation rate of approximately 50% at the selected positions, the mutagenic DNA was synthesized with 70-10-10-10 mixtures of bases favoring the wild type nucleotides (Gallop et al., *Journal of Medicinal Chemistry* 37:1233-1251 (1994)).

Phage Sorting Strategy to Generate Affinity Improvement.

For affinity improvement selection, phage libraries were subjected to one round of plate sorting followed by three additional rounds of solution sorting with increasing stringency. For round one, plate sorting strategy was used, where 3 OD/ml in 1% BSA and 0.05% Tween 20 of phage input were incubated with 5 ug/ml of mouse NSP4 at 100 ul/well buffer containing 1% BSA and 0.05% Tween-20 for 1.5 h at room temperature with gentle shaking. The wells were washed with PBS-0.05% Tween-20 ten times. Bound phage was eluted with 150 μl/well 50 mM HCl, 500 mM KCl for 30 minutes, and subsequently neutralized by 50 μl/well of 1M Tris pH 8, titered, and propagated for the next round. For rounds two through four, solution sorting strategies were used with increasing selection stringency. Specifically, biotinylated mouse NSP4 were used at 20 nM (round 2), 5 nM (round 3), and 0.5 nM with 500 nM unlabeled mNSP4 competitor (round 4) to select for improved on-rate and off-rate binders. To determine background binding, control wells containing phage were captured on neutravidin-coated plates. Bound phage captured on neutravidin-coated wells was eluted with 150 μl/well 50 mM HCl, 500 mM KCl for 30 minutes, and subsequently neutralized by 50 μl/well of 1M Tris pH8, titered, and propagated for the next round.

Epitope Mapping.

Recombinant mouse NSP4 was preincubated with buffer alone, NSP4 antibody 5-1 (Fab format), or with 10 ug/ml heparin sulfate (Sigma Aldrich) for 15 minutes at room temperature in phosphate buffered saline. 50 nM of this mouse NSP4 mixture was then incubated with optical sensors coated with NSP4 antibodies that were immobilized at 40 ug/ml in 1× Kinetic Buffer (Pall Corporation). The binding was measured using Octet biolayer interferometry (Pall Corporation).

Results

Multiple antibody clones were tested in a phage IC50 experiment to estimate their binding affinity to NSP4. Briefly, 2 ug/ml of NSP4 (hZ, hA, mZ, or mA variants) was coated on wells overnight at 4° C. in PBS supplemented with 0.5% BSA. Each individual phage clone (at 0.01 OD/ml) was purified and incubated with increasing concentrations of soluble NSP4 protein for 2 h at room temperature before being placed into wells coated with immobilized NSP4 protein for 15 min at room temperature. The wells were then washed with PBS supplemented with 0.05% Tween-20 for 10 times and developed using anti-M13 phage antibody conjugated with HRP (New England Biolabs). As shown in FIG. 19, higher affinity phage clones would more likely remain associated with the soluble antigen at lower antigen concentrations than lower affinity phage clones, resulting in less binding to the immobilized antigen coated on the wells during the 15 min incubation period. The soluble phage:antigen complex, with higher likelihood to be high-affinity phage clones, would thus be removed through successive washing steps, resulting in lower A450 signal at any given concentration of soluble antigen. Consequently, higher affinity phage clones would have a lower phage IC50 value, with a concomitant leftward-shift in the binding curves, compared to lower affinity phage clones. The HVR sequences for these clones are provided in Tables 3 and 4 below. Each of the antibodies in Tables 3 and 4 used the same light chain, which included a light chain variable region corresponding to SEQ ID NO: 16 and HVR-L1, HVR-L2, and HVR-L3 sequences corresponding to SEQ ID NO:19, 11, and 12, respectively.

TABLE 3

HC HVR Sequences for Anti-NSP4 Antibodies.

| Clone | HVR-H1 | SEQ ID | HVR-H2 | SEQ ID | HVR-H3 | SEQ ID |
|---|---|---|---|---|---|---|
| 1-1 | GFTFSGSWIS | 20 | GTISPYNGSTYYADSVKG | 21 | RVLRPKVYASVMDY | 22 |
| 1-2 | GFTFSGYSIH | 23 | AGISPTNGYTDYADSVKG | 24 | RLVFYRGVMDY | 25 |
| 1-3 | GFTFSDNWIS | 26 | GYIYPASGYTDYADSVKG | 27 | SDSPHAYWYAMDY | 28 |
| 1-5 | GFTFTNNSIS | 29 | GAISPNNGSTYYADSVKG | 30 | RNAWHYSWVGVMDY | 31 |
| 2-1 | GFTFTDYSIH | 32 | AEIYPYSGDTYYADSVKG | 33 | RDGDGWFDWAMDY | 34 |
| 2-2 | GFTFSSTAIS | 35 | GEIYPSDGYTDYADSVKG | 36 | RVKWAVSSLGVMDY | 37 |
| 2-3 | GFTFTDSDIS | 38 | AWISPSDGATDYADSVKG | 39 | HEASDDDYAIDY | 40 |
| 2-4 | GFTFSDYWIS | 41 | AGISPNNGDTYYADSVKG | 42 | REDDDERDYAMDY | 43 |
| 2-5 | GFTFTGYGIS | 44 | GWIYPASGATYYADSVKG | 45 | RHRAFDWYPYYIGSSVMDY | 46 |
| 3-2 | GFTFSDYSIS | 47 | GEINPAGGATYYADSVKG | 48 | RGDPPFWSDAYYVMDY | 49 |
| 3-5 | GFTFSDNDIS | 50 | GSISPDNGDTNYADSVKG | 51 | RDDVPAVFTSAMDY | 52 |
| 4-2 | GFTFSGSDIS | 53 | GEIYPSNGDTYYADSVKG | 54 | RSVRPSWWAMDY | 55 |
| 4-3 | GFTFSSYDIS | 56 | GTISPYDGYTDYADSVKG | 57 | RYIRRYSVHYGMDY | 58 |
| 4-4 | GFTFTSTSIH | 59 | AEITPHGGYTNYADSVKG | 60 | RGRTKWGWLYGMDY | 61 |
| 4-5 | GFTFTNNSIH | 62 | AEIAPDDGYTYYADSVKG | 63 | RGVIRYAYLYAMDY | 64 |
| 5-1 | GFTFSGSGIH | 65 | AWISPTGGNTYYADSVKG | 66 | KSLFHNVAFDY | 67 |
| 5-2 | GFTFSNTYIS | 1 | GFIYPANGATYYADSVKG | 2 | RRYRLSFDY | 3 |
| 5-3 | GFTFSGNDIS | 4 | AGISPYGGSTYYADSVKG | 5 | RRVSFYSRHAGMDY | 6 |
| 5-4 | GFTFTSYAIS | 7 | AGISPSNGYTNYADSVKG | 8 | RAGRWTHSDIDY | 9 |

TABLE 4

Heavy Chain Variable Region Sequences for Anti-NSP4 Antibodies.

| Clone | HC Variable Region Sequences | SEQ ID |
|---|---|---|
| 1-1 | EVQLVESGGGLVQPGGSLRLSCAAS<u>GFTFSGSWIS</u>WVRQAP GKGLEWV<u>GTISPYNGSTYYADSVKG</u>RFTISADTSKNTAYLQ MNSLRAEDTAVYYC<u>ARVLRPKVYASVMDY</u>WGQGTLVTSS | 68 |

TABLE 4-continued

Heavy Chain Variable Region Sequences for Anti-NSP4 Antibodies.

| Clone | HC Variable Region Sequences | SEQ ID |
|---|---|---|
| 1-2 | EVQLVESGGGLVQPGGSLRLSCAAS<u>GFTFSGYSIH</u>WVRQAP GKGLEWV<u>AGISPTNGYTDYADSVK</u>GRFTISADTSKNTAYLQ MNSLRAEDTAVYYCA<u>RLVFYRGVMDY</u>WGQGTLVTVSS | 69 |
| 1-3 | EVQLVESGGGLVQPGGSLRLSCAAS<u>GFTFSDNWIS</u>WVRQAP GKGLEWV<u>GYIYPASGYTDYADSVK</u>GRFTISADTSKNTAYLQ MNSLRAEDTAVYYCA<u>SDSPHAYWYAMDY</u>WGQGTLVTVSS | 70 |
| 1-5 | EVQLVESGGGLVQPGGSLRLSCAAS<u>GFTFTNNSIS</u>WVRQAP GKGLEWV<u>GAISPNNGSTYYADSVK</u>GRFTISADTSKNTAYLQ MNSLRAEDTAVYYCA<u>RNAWHYSWVGVMDY</u>WGQGTLVTVSS | 71 |
| 2-1 | EVQLVESGGGLVQPGGSLRLSCAAS<u>GFTFTDYSIH</u>WVRQAP GKGLEWV<u>AEIYPYSGDTYYADSVK</u>GRFTISADTSKNTAYLQ MNSLRAEDTAVYYCA<u>RDGDGWFDWAMDY</u>WGQGTLVTVSS | 72 |
| 2-2 | EVQLVESGGGLVQPGGSLRLSCAAS<u>GFTFSSTAIS</u>WVRQAP GKGLEWV<u>GEIYPSDGYTDYADSVK</u>GRFTISADTSKNTAYLQ MNSLRAEDTAVYYCA<u>RVKWAVSSLGVMDY</u>WGQGTLVTVSS | 73 |
| 2-3 | EVQLVESGGGLVQPGGSLRLSCAAS<u>GFTFTDSDIS</u>WVRQAP GKGLEWV<u>AWISPSDGATDYADSVK</u>GRFTISADTSKNTAYLQ MNSLRAEDTAVYYCA<u>HEASDDDYAIDY</u>WGQGTLVTVSS | 74 |
| 2-4 | EVQLVESGGGLVQPGGSLRLSCAAS<u>GFTFSDYWIS</u>WVRQAP GKGLEWV<u>AGISPNNGDTYYADSVK</u>GRFTISADTSKNTAYLQ MNSLRAEDTAVYYCA<u>REDDDERDYAMDY</u>WGQGTLVTVSS | 75 |
| 2-5 | EVQLVESGGGLVQPGGSLRLSCAAS<u>GFTFTGYGIS</u>WVRQAP GKGLEWV<u>GWIYPASGATYYADSVK</u>GRFTISADTSKNTAYLQ MNSLRAEDTAVYYCA<u>RHRAFDWYPYYIGSSVMDY</u>WGQGTLVTVSS | 76 |
| 3-2 | EVQLVESGGGLVQPGGSLRLSCAAS<u>GFTFSDYSIS</u>WVRQAP GKGLEWV<u>GEINPAGGATYYADSVK</u>GRFTISADTSKNTAYLQ MNSLRAEDTAVYYCA<u>RGDFPFWSDAYYVMDY</u>WGQGTLVTVSS | 77 |
| 3-5 | EVQLVESGGGLVQPGGSLRLSCAAS<u>GFTFSDNDIS</u>WVRQAP GKGLEWV<u>GSISPDNGDTNYADSVK</u>GRFTISADTSKNTAYLQ MNSLRAEDTAVYYCA<u>RDDVPAVFTSAMDY</u>WGQGTLVTVSS | 78 |
| 4-2 | EVQLVESGGGLVQPGGSLRLSCAAS<u>GFTFSGSDIS</u>WVRQAP GKGLEWV<u>GEIYPSNGDTYYADSVK</u>GRFTISADTSKNTAYLQ MNSLRAEDTAVYYCA<u>RSVRPSWWAMDY</u>WGQGTLVTVSS | 79 |
| 4-3 | EVQLVESGGGLVQPGGSLRLSCAAS<u>GFTFSSYDIS</u>WVRQAP GKGLEWV<u>GTISPYDGYTDYADSVK</u>GRFTISADTSKNTAYLQ MNSLRAEDTAVYYCA<u>RYIRRYSVHYGMDY</u>WGQGTLVTVSS | 80 |
| 4-4 | EVQLVESGGGLVQPGGSLRLSCAAS<u>GFTFTSTSIH</u>WVRQAP GKGLEWV<u>AEITPHGGYTNYADSVK</u>GRFTISADTSKNTAYLQ MNSLRAEDTAVYYCA<u>RGRTKWGWLYGMDY</u>WGQGTLVTVSS | 81 |
| 4-5 | EVQLVESGGGLVQPGGSLRLSCAAS<u>GFTFTNNSIH</u>WVRQAP GKGLEWV<u>AEIAPDDGYTYYADSVK</u>GRFTISADTSKNTAYLQ MNSLRAEDTAVYYCA<u>RGVIRYAYLYAMDY</u>WGQGTLVTVSS | 82 |
| 5-1 | EVQLVESGGGLVQPGGSLRLSCAAS<u>GFTFSGSGIH</u>WVRQAP GKGLEWV<u>AWISPTGGNTYYADSVK</u>GRFTISADTSKNTAYLQ MNSLRAEDTAVYYCA<u>KSLFHNVAFDY</u>WGQGTLVTVSS | 83 |
| 5-2 | EVQLVESGGGLVQPGGSLRLSCAAS<u>GFTFSNTYIS</u>WVRQAP GKGLEWV<u>GFIYPANGATYYADSVK</u>GRFTISADTSKNTAYLQ MNSLRAEDTAVYYCA<u>RRYRLSFDY</u>WGQGTLVTVSS | 84 |
| 5-3 | EVQLVESGGGLVQPGGSLRLSCAAS<u>GFTFSGNDIS</u>WVRQAP GKGLEWV<u>AGISPYGGSTYYADSVK</u>GRFTISADTSKNTAYLQ MNSLRAEDTAVYYCA<u>RRVSFYSRHAGMDY</u>WGQGTLVTVSS | 85 |
| 5-4 | EVQLVESGGGLVQPGGSLRLSCAAS<u>GFTFTSYAIS</u>WVRQAP GKGLEWV<u>AGISPSNGYTNYADSVK</u>GRFTISADTSKNTAYLQ MNSLRAEDTAVYYCA<u>RAGRWTHSDIDY</u>WGQGTLVTVSS | 86 |

CDR sequences are underlined.

FIG. 19 demonstrates the results of the phage IC50 experiments, which used soluble hZ-, hA-, mZ-, or mA-NSP4 as a competitor (as labeled). In these experiments, higher affinity clones were bound to soluble NSP4 at lower soluble NSP4 concentrations and thus have curves shifted to the left. Based on these results, individual antibodies were purified and expressed for further characterization. These results are summarized in the table below.

TABLE 8

Summary of phage IC50 values of NSP4-specific antibody phage clones.

| Ab clones | Soluble competitor used for IC50 (nM) | | | |
|---|---|---|---|---|
| | hZ (NSP4) | hA (NSP4) | mZ (NSP4) | mA (NSP4) |
| 1-series (panned against hZ-NSP4) | | | | |
| 1-1 | 154.70 | — | — | — |
| 1-2 | 22.08 | — | — | — |
| 1-3 | 52.05 | — | — | — |
| 1-5 | 114.50 | — | — | — |
| 2-series (panned against hZ-NSP4) | | | | |
| 2-1 | 7.62 | 3.81 | — | — |
| 2-2 | 10.42 | 10.11 | — | — |
| 2-3 | 3.07 | 4.96 | — | — |
| 2-4 | 2.30 | 1.63 | — | — |
| 2-5 | 21.98 | 5130.00 | — | — |
| 3-series (panned against mZ-NSP4) | | | | |
| 3-2 | — | — | 0.15 | — |
| 3-5 | — | — | 0.18 | — |
| 4-series (panned against hA-NSP4) | | | | |
| 4-2 | — | 84.76 | — | — |
| 4-3 | — | 1.58 | — | — |
| 4-4 | — | 1.48 | — | — |
| 5-series (panned against mA-NSP4) | | | | |
| 5-1 | — | — | — | 9.93 |
| 5-2 | — | — | — | 25.01 |
| 5-3 | — | — | — | 319.00 |
| 5-4 | — | — | — | 60.48 |

These antibodies were further characterized using biolayer interferometry measurements to estimate affinity (kD) to different NSP4 proteins (i.e., hZ, hA, mZ, and mA, as labeled). FIGS. 20A and B show the results for antibodies 1-1 and 1-2, respectively. FIGS. 21A and B show the results for antibodies 1-3 and 1-5, respectively. FIGS. 22A-D show the results for antibodies 2-1, 2-2, 2-3 and 2-4, respectively. FIG. 23 shows the results for antibody 2-5. FIGS. 24A and B show the results for antibodies 3-2 and 3-5, respectively. FIGS. 25A-C show the results for antibodies 4-2, 4-3 and 4-4, respectively. FIGS. 26A-D show the results for antibodies 5-1, 5-2, 5-3 and 5-4, respectively. These binding data suggest a panel of antibodies with distinct NSP4-binding characteristics, ranging from antibodies that are highly conformational-specific and species-specific (e.g., specific for one of hZ-NSP4, hA-NSP4, or mA-NSP4 such as antibodies 1-2, 4-3, and 5-3), to antibodies that are conformational-specific but not species-specific (e.g., specific for zymogen-NSP4 or active-NSP4 such as antibodies 2-2, 2-5, and 5-1), to antibodies that are species-specific but not conformational-specific (e.g., specific for human-NSP4 or mouse-NSP4 such as antibodies 3-2, 4-2, and 4-4), and finally to antibodies that are pan-NSP4 binders (e.g., bind to human and mouse NSP4 in their zymogen and active conformational states such as antibodies 2-1, 2-3, 2-4, and 3-5).

Antibodies were further tested for the ability to block NSP4 enzymatic activity. The ability to block human and mouse NSP4 was tested. FIG. 27 shows the effect of antibodies on zymogen NSP4. FIG. 28 shows the effect of antibodies on active NSP4. As shown in FIG. 28, antibodies 4-3 and 4-4 blocked human NSP4 activity, whereas each of the 5-series antibodies blocked mouse NSP4 activity. The in vitro properties of the antibodies are summarized in FIG. 29.

Without wishing to be bound to theory, it was hypothesized that the 5-series antibodies, due to their ability to block NSP4 enzyme activity and their preferential binding to the active form but not the zymogen form of NSP4, bound NSP4 proximal to the enzyme active site, a region that undergoes significant conformational change during the protease activation process. In contrast, it was hypothesized that the 3-series antibodies, due to their inability to block NSP4 enzyme activity and their conformational-insensitivity, bound NSP4 distal to the enzyme active site. This hypothesis on antibody epitopes was confirmed in a series of experiences depicted in FIGS. 30 and 31.

As shown in FIG. 30, Fab 5-1 interferes with Ab5-1, 5-2, and 5-4 binding, but not with Ab 3-2 or 3-5 binding, to mouse NSP4. Similarly, as shown in FIG. 31, heparin has little effect on Ab 5-1, 5-2, and 5-4 binding, but was able to significantly diminish binding of Ab 3-2 and 3-5 to NSP4. These results suggest that Ab 5-1, 5-2, 5-4 bind near the enzyme active site; in contrast, Ab 3-2 and 3-5 bind near the heparin binding site away from the enzyme active site.

Antibody clones 3-5 (referred to as Ab35 below) and 5-1 (referred to as Ab51 below) were chosen for further affinity improvement (carried out as described above). Ab35 was chosen due to its ability to bind to both human and mouse NSP4 and both zymogen and active conformations. Ab51 was chosen for its ability to inhibit mouse NSP4 catalytic activity with highest potency among the 5-series antibodies.

Tables 5 and 6 list affinity matured variants of antibody 3-5 (called 35.WT in the tables below), labeled as 35.XX, and affinity matured variants of antibody 5-1 (called 51.WT in the tables below), labeled as 51.XX. Heavy chain HVR sequences are listed in Table 5; light chain HVR sequences are listed in Table 6.

TABLE 5

HC HVR Sequences for Affinity Matured Anti-NSP4 Antibodies.

| Clone | HVR-H1 | SEQ ID | HVR-H2 | SEQ ID | HVR-H3 | SEQ ID |
|---|---|---|---|---|---|---|
| 35.WT | GFTFSDNDIS | 50 | GSISPDNGDTNYADSVKG | 51 | RDDVPAVFTSAMDY | 52 |
| 35.14 | GFTFSDNDIS | 50 | GSISPDNGDTNYADSVKG | 51 | RDDVPAVFTSAMDY | 52 |
| 35.50 | GFTFSDNDIS | 50 | GSISPDNGDTNYADSVKG | 51 | RDDVPAVFTSAMDY | 52 |
| 35.62 | GFTFSDNDIS | 50 | GSISPDNGDTNYADSVKG | 51 | RDDVPAVFTSAMDY | 52 |
| 35.77 | GFTFSGSGIH | 65 | AWISPTGGNTYYADSVKG | 66 | KRHLHNVAFDY | 87 |
| 51.WT | GFTFSGSGIH | 65 | AWISPTGGNTYYADSVKG | 66 | KSLFHNVAFDY | 67 |
| 51.30 | GFTFSGSGIH | 65 | AWIPTAGGNTYYADSVKG | 88 | KSLFHNVAFDY | 67 |
| 51.50 | GFTFSGSGIH | 65 | AWISPTGGNTYYADSVKG | 66 | KSLFHNVAFDY | 67 |
| 51.51 | GFTFSGSGIH | 65 | AWISPTGGNTYYADSVKG | 66 | RGLFHNVAFDY | 89 |
| 51.59 | GFTFSGSGIH | 65 | AWISPTGGNTYYADSVKG | 66 | RVFFHNVAFDY | 90 |
| 51.72 | GFTFSGSGIH | 65 | AWISPTGGNTYYADSVKG | 66 | KSLFHNVAFDY | 67 |
| 51.82 | GFTFSGSGIH | 65 | AWISPTGGNTYYADSVKG | 66 | RGLFHNVAFDY | 89 |
| Consensus | | | | | $X_1X_2X_3$FHNVAFDY | 91 |

TABLE 6

LC HVR Sequences for Affinity Matured Anti-NSP4 Antibodies.

| Clone | HVR-L1 | SEQ ID | HVR-L2 | SEQ ID | HVR-L3 | SEQ ID |
|---|---|---|---|---|---|---|
| 35.WT | RASQDVS | 19 | SASFLYS | 11 | QQSYTTPPT | 12 |
| 35.14 | RASQDVS | 19 | SASFLYS | 11 | QQSYGFPLT | 92 |
| 35.50 | RASQDVS | 19 | SASFLYS | 11 | QQSYDFPLT | 93 |
| 35.62 | RASQDVS | 19 | SASFLYS | 11 | QQSAGFPLT | 94 |
| Consensus | | | | | QQSX$_1$X$_2$X$_3$PX$_4$T | 95 |
| 35.77 | RASQDVS | 19 | SASFLYS | 11 | QQAYSAPPT | 96 |
| 51.WT | RASQDVS | 19 | SASFLYS | 11 | QQSYTTPPT | 12 |
| 51.30 | RASQDVS | 19 | SASFLYS | 11 | QQSYTAPPT | 97 |

TABLE 6-continued

LC HVR Sequences for Affinity Matured Anti-NSP4 Antibodies.

| Clone | HVR-L1 | SEQ ID | HVR-L2 | SEQ ID | HVR-L3 | SEQ ID |
|---|---|---|---|---|---|---|
| 51.50 | RASQDVS | 19 | SASFLYS | 11 | QQANSTPPT | 98 |
| 51.51 | RASQDVS | 19 | SASFLYS | 11 | QQSYTAPPT | 97 |
| 51.59 | RASQDVS | 19 | SASFLYS | 11 | QQNFSSPPT | 99 |
| 51.72 | RASQDVS | 19 | SASFLYS | 11 | QQSYTAPPT | 97 |
| 51.82 | RASQDVS | 19 | SASFLYS | 11 | QQTYNAPPT | 100 |
| Consensus | | | | | QQX$_1$X$_2$X$_3$X$_4$PPT | 101 |

Table 7 lists heavy chain and light chain variable region sequences for affinity matured variants of antibody 3-5 (called 35.WT in the table below), labeled as 35.XX, and affinity matured variants of antibody 5-1 (called 51.WT in the table below), labeled as 51.XX. Constant region sequences are provided below the table.

TABLE 7

HC and LC Variable Region Sequences for Affinity Matured Anti-NSP4 Antibodies.

| Clone | HC Variable Region Sequences | SEQ ID | LC Variable Region Sequences | SEQ ID |
|---|---|---|---|---|
| 35.WT | EVQLVESGGGLVQPGGSLRLSCAAS GFTFSDNDISWVRQAPGKGLEWVG SISPDNGDTNYADSVKGRFTISADTS KNTAYLQMNSLRAEDTAVYYCAR DDVPAVFTSAMDYWGQGTLVTVSS | 78 | DIQMTQSPSSLSASVGDRVTIT CRASQDVSTAVAWYQQKPGK APKLLIYSASFLYSGVPSRFSGS GSGTDFTLTISSLQPEDFATYY CQQSYTTPPTFGQGTKVEIKR | 16 |
| 35.14 | EVQLVESGGGLVQPGGSLRLSCAAS GFTFSDNDISWVRQAPGKGLEWVG SISPDNGDTNYADSVKGRFTISADTS KNTAYLQMNSLRAEDTAVYYCAR DDVPAVFTSAMDYWGQGTLVTVSS | 78 | DIQMTQSPSSLSASVGDRVTIT CRASQDVSTAVAWYQQKPGK APKLLIYSASFLYSGVPSRFSGS GSGTDFTLTISSLQPEDFATYY CQQSYGFPLTFGQGTKVEIKR | 102 |
| 35.50 | EVQLVESGGGLVQPGGSLRLSCAAS GFTFSDNDISWVRQAPGKGLEWVG SISPDNGDTNYADSVKGRFTISADTS KNTAYLQMNSLRAEDTAVYYCAR DDVPAVFTSAMDYWGQGTLVTVSS | 78 | DIQMTQSPSSLSASVGDRVTIT CRASQDVSTAVAWYQQKPGK APKLLIYSASFLYSGVPSRFSGS GSGTDFTLTISSLQPEDFATYY CQQSYDFPLTFGQGTKVEIKR | 103 |
| 35.62 | EVQLVESGGGLVQPGGSLRLSCAAS GFTFSDNDISWVRQAPGKGLEWVG SISPDNGDTNYADSVKGRFTISADTS KNTAYLQMNSLRAEDTAVYYCAR DDVPAVFTSAMDYWGQGTLVTVSS | 78 | DIQMTQSPSSLSASVGDRVTIT CRASQDVSTAVAWYQQKPGK APKLLIYSASFLYSGVPSRFSGS GSGTDFTLTISSLQPEDFATYY CQQSAGFPLTFGQGTKVEIKR | 104 |
| 35.77 | EVQLVESGGGLVQPGGSLRLSCAAS GFTFSGSGIHWVRQAPGKGLEWVA WISPTGGNTYYADSVKGRFTISADT SKNTAYLQMNSLRAEDTAVYYCA KRHLHNVAFDYWGQGTLVTVSS | 105 | DIQMTQSPSSLSASVGDRVTIT CRASQDVSTAVAWYQQKPGK APKLLIYSASFLYSGVPSRFSGS GSGTDFTLTISSLQPEDFATYY CQQAYSAPPTFGQGTKVEIKR | 106 |
| 51.WT | EVQLVESGGGLVQPGGSLRLSCAAS GFTFSGSGIHWVRQAPGKGLEWVA WISPTGGNTYYADSVKGRFTISADT SKNTAYLQMNSLRAEDTAVYYCA KSLFHNVAFDYWGQGTLVTVSS | 83 | DIQMTQSPSSLSASVGDRVTIT CRASQDVSTAVAWYQQKPGK APKLLIYSASFLYSGVPSRFSGS GSGTDFTLTISSLQPEDFATYY CQQSYTTPPTFGQGTKVEIKR | 16 |
| 51.30 | EVQLVESGGGLVQPGGSLRLSCAAS GFTFSGSGIHWVRQAPGKGLEWVA WIPTAGGNTYYADSVKGRFTISADT SKNTAYLQMNSLRAEDTAVYYCA KSLFHNVAFDYWGQGTLVTVSS | 107 | DIQMTQSPSSLSASVGDRVTIT CRASQDVSTAVAWYQQKPGK APKLLIYSASFLYSGVPSRFSGS GSGTDFTLTISSLQPEDFATYY CQQSYTAPPTFGQGTKVEIKR | 108 |
| 51.50 | EVQLVESGGGLVQPGGSLRLSCAAS GFTFSGSGIHWVRQAPGKGLEWVA WISPTGGNTYYADSVKGRFTISADT SKNTAYLQMNSLRAEDTAVYYCA KSLFHNVAFDYWGQGTLVTVSS | 83 | DIQMTQSPSSLSASVGDRVTIT CRASQDVSTAVAWYQQKPGK APKLLIYSASFLYSGVPSRFSGS GSGTDFTLTISSLQPEDFATYY CQQANSTPPTFGQGTKVEIKR | 109 |

TABLE 7-continued

HC and LC Variable Region Sequences for Affinity Matured Anti-NSP4 Antibodies.

| | | | | |
|---|---|---|---|---|
| 51.51 | EVQLVESGGGLVQPGGSLRLSCAAS<br>GFTFSGSGIHWVRQAPGKGLEWVA<br>WISPTGGNTYYADSVKGRFTISADT<br>SKNTAYLQMNSLRAEDTAVYYCAR<br>GLFHNVAFDYWGQGTLVTVSS | 110 | DIQMTQSPSSLSASVGDRVTIT<br>CRASQDVSTAVAWYQQKPGK<br>APKLLIYSASFLYSGVPSRFSGS<br>GSGTDFTLTISSLQPEDFATYY<br>CQQSYTAPPTFGQGTKVEIKR | 108 |
| 51.59 | EVQLVESGGGLVQPGGSLRLSCAAS<br>GFTFSGSGIHWVRQAPGKGLEWVA<br>WISPTGGNTYYADSVKGRFTISADT<br>SKNTAYLQMNSLRAEDTAVYYCAR<br>VFFHNVAFDYWGQGTLVTVSS | 111 | DIQMTQSPSSLSASVGDRVTIT<br>CRASQDVSTAVAWYQQKPGK<br>APKLLIYSASFLYSGVPSRFSGS<br>GSGTDFTLTISSLQPEDFATYY<br>CQQNFSSPPTFGQGTKVEIKR | 112 |
| 51.72 | EVQLVESGGGLVQPGGSLRLSCAAS<br>GFTFSGSGIHWVRQAPGKGLEWVA<br>WISPTGGNTYYADSVKGRFTISADT<br>SKNTAYLQMNSLRAEDTAVYYCA<br>KSLFHNVAFDYWGQGTLVTVSS | 83 | DIQMTQSPSSLSASVGDRVTIT<br>CRASQDVSTAVAWYQQKPGK<br>APKLLIYSASFLYSGVPSRFSGS<br>GSGTDFTLTISSLQPEDFATYY<br>CQQSYTAPPTFGQGTKVEIKR | 108 |
| 51.82 | EVQLVESGGGLVQPGGSLRLSCAAS<br>GFTFSGSGIHWVRQAPGKGLEWVA<br>WISPTGGNTYYADSVKGRFTISADT<br>SKNTAYLQMNSLRAEDTAVYYCAR<br>GLFHNVAFDYWGQGTLVTVSS | 110 | DIQMTQSPSSLSASVGDRVTIT<br>CRASQDVSTAVAWYQQKPGK<br>APKLLIYSASFLYSGVPSRFSGS<br>GSGTDFTLTISSLQPEDFATYY<br>CQQTYNAPPTFGQGTKVEIKR | 113 |

HC Constant Region Sequence (SEQ ID NO: 114)

ASTKGPSVYPLAPVCGDTTGSSVTLGCLVKGYFPEPVTLTWNSGSLSSGVHTFPAVL

QSDLYTLSSSVTVTSSTWPSQSITCNVAHPASSTKVDKKIEPRGPTIKPCPPCKCPA

PNLLGGPSVFIFPPKIKDVLMISLSPIVTCVVVAVSEDDPDVQISWFVNNVEVHTAQ

TQTHREDYASTLRVVSALPIQHQDWMSGKEFKCKVNNKDLPAPIERTISKPKGSVRA

PQVYVLPPPEEEMTKKQVTLTCMVTDFMPEDIYVEWTNNGKTELNYKNTEPVLDSDG

SYFMYSKLRVEKKNWVERNSYSCSVVHEGLHNHHTTKSFSRTPGK

LC Constant Region Sequence (SEQ ID NO: 115)

ADAAPTVSIFPPSSEQLTSGGASVVCFLNNFYPKDINVKWKIDGSERQNGVLNSWTD

QDSKDSTYSMSSTLTLTKDEYERHNSYTCEATHKTSTSPIVKSFNRNEC

CDR sequences are underlined.

The improvement of affinity-matured antibody clones was estimated in a series of phage IC50 experiments. FIG. 32 shows the affinities of affinity-matured antibody clones from Ab35 towards human and mouse NSP4. FIG. 33 shows the affinities of affinity-matured antibody clones from the Ab51 towards human NSP4. As shown, the affinities of the Ab35 clones were not improved as much as the Ab51 clones. Without wishing to be bound to theory, this could be due to the fact that the Ab35 started with higher affinity. In contrast, the affinities of the Ab51 improved significantly (over 500×).

Table 9 summarizes improvement of affinity-matured antibody clones as determined by their IC50 values in a phage competition binding assay.

TABLE 9

Affinity-matured antibodies.

| Ab Clones | mNSP4 IC50 (nM) | hNSP4 IC50 (nM) | Affinity improvement to mNSP4 |
|---|---|---|---|
| 35.WT | 0.131 | 32.79 | — |
| 35.14 | 0.048 | 23.41 | 2.7 |
| 35.50 | 0.075 | 22.75 | 1.7 |
| 35.62 | 0.206 | 25.69 | 0.6 |

TABLE 9-continued

Affinity-matured antibodies.

| Ab Clones | mNSP4 IC50 (nM) | hNSP4 IC50 (nM) | Affinity improvement to mNSP4 |
|---|---|---|---|
| 35.77 | 0.064 | — | 2.0 |
| 51.WT | 18.670 | — | — |
| 51.30 | 0.116 | — | 160.9 |
| 51.50 | 0.105 | — | 178.0 |
| 51.51 | 0.296 | — | 63.0 |
| 51.59 | 0.095 | — | 196.0 |
| 51.72 | 0.375 | — | 49.8 |
| 51.82 | 0.037 | — | 504.6 |

Ab35 and Ab51 were affinity improved up to 2.7-fold and 504.6-fold, respectively, over their parental clones by exploring and optimizing the CDR sequences on the antibody light chain for binding to NSP4. Both affinity matured Ab35 and Ab51 clones reached the targeted picomolar-affinity to NSP4 and bound to NSP4 with distinct epitopes. Without wishing to be bound to theory, it is thought that Ab35-derived clones bind to NSP4 at the heparin-binding site and Ab51-derived clones bind to NSP4 proximal to its enzyme active site.

Example 7: NSP4 Catalytic Activity In Vivo

To confirm that the enzymatic activity of NSP4 is associated with the disease phenotype observed in the K/BxN serum-transfer mouse model, the K/BxN model is compared in mice having wild-type NSP4, an NSP4 knockout and a catalytically dead NSP4 knockin (e.g., mice having an S224A mutation in their NSP4 protein sequence). In each of these three mouse strains, serum-induced vascular permeability is monitored in vivo using NIRF, luminol-bioluminescence imaging and histological examination. If the mouse expressing the catalytically dead NSP4 protein shows protection in the K/BxN model similar to the NSP4 knockout mouse, this result may indicate that the catalytic activity of NSP4 is associated with the disease phenotype and that inhibitors of NSP4 catalytic activity (e.g., an anti-NSP4 antibody such as antibody 51.WT, 51.30, 51.50, 51.51, 51.59, 51.72, 51.82) would be useful as therapeutic agents for various vascular and inflammatory disorders associated with NSP4 activity.

Example 8: Inhibition of NSP4 Activity NSP4 in a Mouse Model

Anti-NSP4 antibodies are tested in a mouse K/BxN model to confirm that antibody inhibition of NSP4 activity is protective of the disease phenotype observed in the wildtype NSP4 K/BxN model. K/BxN mice are challenged as described above either in the presence or absence of an anti-NSP4 antibody. NSP4 antibodies that either bind to the heparin binding site (e.g., the 35 series antibodies 35.WT, 35.14, 35.50, 35.62 and/or 35.77) or inhibit the catalytic activity of NSP4 (the 51 series antibodies 51.WT, 51.30, 51.50, 51.51, 51.59, 51.72, and/or 51.82) are tested in the K/BxN model. The results are compared to a control antibody (e.g., an antibody that does not bind to NSP4). If the mice treated with the anti-NSP4 antibodies show protection in the K/BxN model similar to the NSP4 knockout mouse, this result may indicate that the inhibition of NSP4 using an anti-NSP4 antibody would be useful as a therapeutic agent for various vascular and inflammatory disorders associated with NSP4 activity.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An anti-NSP4 antibody comprising a heavy chain and a light chain, wherein the light chain comprises an HVR-L1 comprising the sequence of SEQ ID NO:19, an HVR-L2 comprising the sequence of SEQ ID NO:11, and an HVR-L3 comprising the sequence of SEQ ID NO:12; and wherein the heavy chain comprises an HVR-H1 comprising the sequence of SEQ ID NO:56, an HVR-H2 comprising the sequence of SEQ ID NO:57, and an HVR-H3 comprising the sequence of SEQ ID NO:58.

2. The antibody of claim 1, wherein the light chain comprises a light chain variable region comprising the sequence of SEQ ID NO:16.

3. The antibody of claim 1, wherein the heavy chain comprises a heavy chain variable region comprising the sequence of SEQ ID NO: 80.

4. The antibody of claim 1, wherein the antibody is a monoclonal antibody.

5. The antibody of claim 1, wherein the antibody is an antibody fragment selected from the group consisting of a Fab, Fab'-SH, Fv, scFv, and (Fab')₂ fragment.

6. The antibody of claim 1, wherein the antibody comprises a constant region of human IgG1, IgG2, IgG3, or IgG4.

7. A pharmaceutical composition comprising the anti-NSP4 antibody of claim 1 and a pharmaceutically acceptable carrier.

8. An anti-NSP4 antibody comprising a heavy chain and a light chain, wherein the light chain comprises an HVR-L1 comprising the sequence of SEQ ID NO:19, an HVR-L2 comprising the sequence of SEQ ID NO:11, and an HVR-L3 comprising the sequence of SEQ ID NO:12; and wherein the heavy chain comprises an HVR-H1 comprising the sequence of SEQ ID NO:32, an HVR-H2 comprising the sequence of SEQ ID NO:33, and an HVR-H3 comprising the sequence of SEQ ID NO:34.

9. An anti-NSP4 antibody comprising a heavy chain and a light chain, wherein the light chain comprises an HVR-L1 comprising the sequence of SEQ ID NO:19, an HVR-L2 comprising the sequence of SEQ ID NO:11, and an HVR-L3 comprising the sequence of SEQ ID NO:12; and wherein the heavy chain comprises an HVR-H1 comprising the sequence of SEQ ID NO:38, an HVR-H2 comprising the sequence of SEQ ID NO:39, and an HVR-H3 comprising the sequence of SEQ ID NO:40.

10. An anti-NSP4 antibody comprising a heavy chain and a light chain, wherein the light chain comprises an HVR-L1 comprising the sequence of SEQ ID NO:19, an HVR-L2 comprising the sequence of SEQ ID NO:11, and an HVR-L3 comprising the sequence of SEQ ID NO:12; and wherein the heavy chain comprises an HVR-H1 comprising the sequence of SEQ ID NO:41, an HVR-H2 comprising the sequence of SEQ ID NO:42, and an HVR-H3 comprising the sequence of SEQ ID NO:43.

11. An anti-NSP4 antibody comprising a heavy chain and a light chain, wherein the light chain comprises an HVR-L1 comprising the sequence of SEQ ID NO:19, an HVR-L2 comprising the sequence of SEQ ID NO:11, and an HVR-L3 comprising the sequence of SEQ ID NO:12; and wherein the heavy chain comprises an HVR-H1 comprising the sequence of SEQ ID NO:53, an HVR-H2 comprising the sequence of SEQ ID NO:54, and an HVR-H3 comprising the sequence of SEQ ID NO:55.

12. An anti-NSP4 antibody comprising a heavy chain and a light chain, wherein the light chain comprises an HVR-L1 comprising the sequence of SEQ ID NO:19, an HVR-L2 comprising the sequence of SEQ ID NO:11, and an HVR-L3 comprising the sequence of SEQ ID NO:12; and wherein the heavy chain comprises an HVR-H1 comprising the sequence of SEQ ID NO:59, an HVR-H2 comprising the sequence of SEQ ID NO:60, and an HVR-H3 comprising the sequence of SEQ ID NO:61.

* * * * *

```
                        SEQUENCE LISTING

<160> NUMBER OF SEQ ID NOS: 115

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct

<400> SEQUENCE: 1

Gly Phe Thr Phe Ser Asn Thr Tyr Ile Ser
1               5                   10

<210> SEQ ID NO 2
<211> LENGTH: 18
<212> TYPE: PRT
<213> ORGANISM: Artificial Sequence
<220> FEATURE:
<223> OTHER INFORMATION: Synthetic Construct

<400> SEQUENCE: 2

Gly Phe Ile Tyr Pro Ala Asn Gly Ala Thr Tyr Tyr Ala Asp Ser Val
1               5                   10                  15

Lys Gly

<210> SEQ ID NO 3
<211> LENGTH: 9
<212> TYPE: PRT
<213> ORGANISM: Artificial Sequence
<220> FEATURE:
<223> OTHER INFORMATION: Synthetic Construct

<400> SEQUENCE: 3

Arg Arg Tyr Arg Leu Ser Phe Asp Tyr
1               5

<210> SEQ ID NO 4
<211> LENGTH: 10
<212> TYPE: PRT
```

```
<213> ORGANISM: Artificial Sequence
<220> FEATURE:
<223> OTHER INFORMATION: Synthetic Construct

<400> SEQUENCE: 4

Gly Phe Thr Phe Ser Gly Asn Asp Ile Ser
1               5                   10

<210> SEQ ID NO 5
<211> LENGTH: 18
<212> TYPE: PRT
<213> ORGANISM: Artificial Sequence
<220> FEATURE:
<223> OTHER INFORMATION: Synthetic Construct

<400> SEQUENCE: 5

Ala Gly Ile Ser Pro Tyr Gly Gly Ser Thr Tyr Tyr Ala Asp Ser Val
1               5                   10                  15

Lys Gly

<210> SEQ ID NO 6
<211> LENGTH: 14
<212> TYPE: PRT
<213> ORGANISM: Artificial Sequence
<220> FEATURE:
<223> OTHER INFORMATION: Synthetic Construct

<400> SEQUENCE: 6

Arg Arg Val Ser Phe Tyr Ser Arg His Ala Gly Met Asp Tyr
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic Construct

<400> SEQUENCE: 7

Gly Phe Thr Phe Thr Ser Tyr Ala Ile Ser
1               5                   10

<210> SEQ ID NO 8
<211> LENGTH: 18
<212> TYPE: PRT
<213> ORGANISM: Artificial Sequence
<220> FEATURE:
<223> OTHER INFORMATION: Synthetic Construct

<400> SEQUENCE: 8

Ala Gly Ile Ser Pro Ser Asn Gly Tyr Thr Asn Tyr Ala Asp Ser Val
1               5                   10                  15

Lys Gly

<210> SEQ ID NO 9
<211> LENGTH: 12
<212> TYPE: PRT
<213> ORGANISM: Artificial Sequence
<220> FEATURE:
<223> OTHER INFORMATION: Synthetic Construct

<400> SEQUENCE: 9

Arg Ala Gly Arg Trp Thr His Ser Asp Ile Asp Tyr
1               5                   10
```

```
<210> SEQ ID NO 10
<211> LENGTH: 11
<212> TYPE: PRT
<213> ORGANISM: Artificial Sequence
<220> FEATURE:
<223> OTHER INFORMATION: Synthetic Construct

<400> SEQUENCE: 10

Arg Ala Ser Gln Asp Val Ser Thr Ala Val Ala
 1               5                  10

<210> SEQ ID NO 11
<211> LENGTH: 7
<212> TYPE: PRT
<213> ORGANISM: Artificial Sequence
<220> FEATURE:
<223> OTHER INFORMATION: Synthetic Construct

<400> SEQUENCE: 11

Ser Ala Ser Phe Leu Tyr Ser
 1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic Construct

<400> SEQUENCE: 12

Gln Gln Ser Tyr Thr Thr Pro Pro Thr
 1               5

<210> SEQ ID NO 13
<211> LENGTH: 117
<212> TYPE: PRT
<213> ORGANISM: Artificial Sequence
<220> FEATURE:
<223> OTHER INFORMATION: Synthetic Construct

<400> SEQUENCE: 13

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Thr
            20                  25                  30

Tyr Ile Ser Trp Val Arg Gln Ala Pro Gly Lys Gly Leu Glu Trp Val
        35                  40                  45

Gly Phe Ile Tyr Pro Ala Asn Gly Ala Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Arg Tyr Arg Leu Ser Phe Asp Tyr Trp Gly Gln Gly Thr Leu
            100                 105                 110

Val Thr Val Ser Ser
        115

<210> SEQ ID NO 14
<211> LENGTH: 122
<212> TYPE: PRT
<213> ORGANISM: Artificial Sequence
<220> FEATURE:
<223> OTHER INFORMATION: Synthetic Construct
```

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Asn
            20                  25                  30

Asp Ile Ser Trp Val Arg Gln Ala Pro Gly Lys Gly Leu Glu Trp Val
        35                  40                  45

Ala Gly Ile Ser Pro Tyr Gly Ser Thr Tyr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Arg Val Ser Phe Tyr Ser Arg His Ala Gly Met Asp Tyr Trp
            100                 105                 110

Gly Gln Gly Thr Leu Val Thr Val Ser Ser
            115                 120

<210> SEQ ID NO 15
<211> LENGTH: 120
<212> TYPE: PRT
<213> ORGANISM: Artificial Sequence
<220> FEATURE:
<223> OTHER INFORMATION: Synthetic Construct

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ala Ile Ser Trp Val Arg Gln Ala Pro Gly Lys Gly Leu Glu Trp Val
        35                  40                  45

Ala Gly Ile Ser Pro Ser Asn Gly Tyr Thr Asn Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Ala Gly Arg Trp Thr His Ser Asp Ile Asp Tyr Trp Gly Gln
            100                 105                 110

Gly Thr Leu Val Thr Val Ser Ser
            115                 120

<210> SEQ ID NO 16
<211> LENGTH: 108
<212> TYPE: PRT
<213> ORGANISM: Artificial Sequence
<220> FEATURE:
<223> OTHER INFORMATION: Synthetic Construct

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Thr Thr Pro Pro
                 85                  90                  95

Thr Phe Gly Gln Gly Thr Lys Val Glu Ile Lys Arg
                100                 105

<210> SEQ ID NO 17
<211> LENGTH: 283
<212> TYPE: PRT
<213> ORGANISM: Homo sapiens

<400> SEQUENCE: 17

Met Gly Leu Gly Leu Arg Gly Trp Gly Arg Pro Leu Leu Thr Val Ala
 1               5                  10                  15

Thr Ala Leu Met Leu Pro Val Lys Pro Pro Ala Gly Ser Trp Gly Ala
                 20                  25                  30

Gln Ile Ile Gly Gly His Glu Val Thr Pro His Ser Arg Pro Tyr Met
             35                  40                  45

Ala Ser Val Arg Phe Gly Gly Gln His His Cys Gly Gly Phe Leu Leu
 50                  55                  60

Arg Ala Arg Trp Val Val Ser Ala Ala His Cys Phe Ser His Arg Asp
 65                  70                  75                  80

Leu Arg Thr Gly Leu Val Val Leu Gly Ala His Val Leu Ser Thr Ala
                 85                  90                  95

Glu Pro Thr Gln Gln Val Phe Gly Ile Asp Ala Leu Thr Thr His Pro
                100                 105                 110

Asp Tyr His Pro Met Thr His Ala Asn Asp Ile Cys Leu Leu Arg Leu
            115                 120                 125

Asn Gly Ser Ala Val Leu Gly Pro Ala Val Gly Leu Leu Arg Leu Pro
130                 135                 140

Gly Arg Arg Ala Arg Pro Pro Thr Ala Gly Thr Arg Cys Arg Val Ala
145                 150                 155                 160

Gly Trp Gly Phe Val Ser Asp Phe Glu Glu Leu Pro Pro Gly Leu Met
                165                 170                 175

Glu Ala Lys Val Arg Val Leu Asp Pro Asp Val Cys Asn Ser Ser Trp
                180                 185                 190

Lys Gly His Leu Thr Leu Thr Met Leu Cys Thr Arg Ser Gly Asp Ser
            195                 200                 205

His Arg Arg Gly Phe Cys Ser Ala Asp Ser Gly Gly Pro Leu Val Cys
210                 215                 220

Arg Asn Arg Ala His Gly Leu Val Ser Phe Ser Gly Leu Trp Cys Gly
225                 230                 235                 240

Asp Pro Lys Thr Pro Asp Val Tyr Thr Gln Val Ser Ala Phe Val Ala
                245                 250                 255

Trp Ile Trp Asp Val Val Arg Arg Ser Ser Pro Gln Pro Gly Pro Leu
                260                 265                 270

Pro Gly Thr Thr Arg Pro Pro Gly Glu Ala Ala
            275                 280

<210> SEQ ID NO 18
<211> LENGTH: 283
<212> TYPE: PRT

<213> ORGANISM: Homo sapiens

<400> SEQUENCE: 18

Met Gly Leu Gly Leu Arg Gly Trp Gly Arg Pro Leu Thr Val Ala
1               5                   10                  15

Thr Ala Leu Met Leu Pro Val Lys Pro Pro Ala Gly Ser Trp Gly Ala
            20                  25                  30

Gln Ile Ile Gly Gly His Glu Val Thr Pro His Ser Arg Pro Tyr Met
            35                  40                  45

Ala Ser Val Arg Phe Gly Gly Gln His His Cys Gly Gly Phe Leu Leu
        50                  55                  60

Arg Ala Arg Trp Val Val Ser Ala Ala His Cys Phe Ser His Arg Asp
65                  70                  75                  80

Leu Arg Thr Gly Leu Val Val Leu Gly Ala His Val Leu Ser Thr Ala
                85                  90                  95

Glu Pro Thr Gln Gln Val Phe Gly Ile Asp Ala Leu Thr Thr His Pro
            100                 105                 110

Asp Tyr His Pro Met Thr His Ala Asn Asp Ile Cys Leu Leu Arg Leu
        115                 120                 125

Asn Gly Ser Ala Val Leu Gly Pro Ala Val Gly Leu Leu Arg Pro Pro
130                 135                 140

Gly Arg Arg Ala Arg Pro Pro Thr Ala Gly Thr Arg Cys Arg Val Ala
145                 150                 155                 160

Gly Trp Gly Phe Val Ser Asp Phe Glu Glu Leu Pro Pro Gly Leu Met
                165                 170                 175

Glu Ala Lys Val Arg Val Leu Asp Pro Asp Val Cys Asn Ser Ser Trp
            180                 185                 190

Lys Gly His Leu Thr Leu Thr Met Leu Cys Thr Arg Ser Gly Asp Ser
        195                 200                 205

His Arg Arg Gly Phe Cys Ser Ala Asp Ser Gly Gly Pro Leu Val Cys
    210                 215                 220

Arg Asn Arg Ala His Gly Leu Val Ser Phe Ser Gly Leu Trp Cys Gly
225                 230                 235                 240

Asp Pro Lys Thr Pro Asp Val Tyr Thr Gln Val Ser Ala Phe Val Ala
                245                 250                 255

Trp Ile Trp Asp Val Val Arg Arg Ser Ser Pro Gln Pro Gly Pro Leu
            260                 265                 270

Pro Gly Thr Thr Arg Pro Pro Gly Glu Ala Ala
        275                 280

<210> SEQ ID NO 19
<211> LENGTH: 7
<212> TYPE: PRT
<213> ORGANISM: Artificial Sequence
<220> FEATURE:
<223> OTHER INFORMATION: Synthetic Construct

<400> SEQUENCE: 19

Arg Ala Ser Gln Asp Val Ser
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic Construct

```
<400> SEQUENCE: 20

Gly Phe Thr Phe Ser Gly Ser Trp Ile Ser
1               5                   10

<210> SEQ ID NO 21
<211> LENGTH: 18
<212> TYPE: PRT
<213> ORGANISM: Artificial Sequence
<220> FEATURE:
<223> OTHER INFORMATION: Synthetic Construct

<400> SEQUENCE: 21

Gly Thr Ile Ser Pro Tyr Asn Gly Ser Thr Tyr Tyr Ala Asp Ser Val
1               5                   10                  15

Lys Gly

<210> SEQ ID NO 22
<211> LENGTH: 14
<212> TYPE: PRT
<213> ORGANISM: Artificial Sequence
<220> FEATURE:
<223> OTHER INFORMATION: Synthetic Construct

<400> SEQUENCE: 22

Arg Val Leu Arg Pro Lys Val Tyr Ala Ser Val Met Asp Tyr
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic Construct

<400> SEQUENCE: 23

Gly Phe Thr Phe Ser Gly Tyr Ser Ile His
1               5                   10

<210> SEQ ID NO 24
<211> LENGTH: 18
<212> TYPE: PRT
<213> ORGANISM: Artificial Sequence
<220> FEATURE:
<223> OTHER INFORMATION: Synthetic Construct

<400> SEQUENCE: 24

Ala Gly Ile Ser Pro Thr Asn Gly Tyr Thr Asp Tyr Ala Asp Ser Val
1               5                   10                  15

Lys Gly

<210> SEQ ID NO 25
<211> LENGTH: 11
<212> TYPE: PRT
<213> ORGANISM: Artificial Sequence
<220> FEATURE:
<223> OTHER INFORMATION: Synthetic Construct

<400> SEQUENCE: 25

Arg Leu Val Phe Tyr Arg Gly Val Met Asp Tyr
1               5                   10

<210> SEQ ID NO 26
<211> LENGTH: 10
<212> TYPE: PRT
<213> ORGANISM: Artificial Sequence
```

```
<220> FEATURE:
<223> OTHER INFORMATION: Synthetic Construct

<400> SEQUENCE: 26

Gly Phe Thr Phe Ser Asp Asn Trp Ile Ser
1               5                   10

<210> SEQ ID NO 27
<211> LENGTH: 18
<212> TYPE: PRT
<213> ORGANISM: Artificial Sequence
<220> FEATURE:
<223> OTHER INFORMATION: Synthetic Construct

<400> SEQUENCE: 27

Gly Tyr Ile Tyr Pro Ala Ser Gly Tyr Thr Asp Tyr Ala Asp Ser Val
1               5                   10                  15

Lys Gly

<210> SEQ ID NO 28
<211> LENGTH: 13
<212> TYPE: PRT
<213> ORGANISM: Artificial Sequence
<220> FEATURE:
<223> OTHER INFORMATION: Synthetic Construct

<400> SEQUENCE: 28

Ser Asp Ser Pro His Ala Tyr Trp Tyr Ala Met Asp Tyr
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthetic Construct

<400> SEQUENCE: 29

Gly Phe Thr Phe Thr Asn Asn Ser Ile Ser
1               5                   10

<210> SEQ ID NO 30
<211> LENGTH: 18
<212> TYPE: PRT
<213> ORGANISM: Artificial Sequence
<220> FEATURE:
<223> OTHER INFORMATION: Synthetic Construct

<400> SEQUENCE: 30

Gly Ala Ile Ser Pro Asn Asn Gly Ser Thr Tyr Tyr Ala Asp Ser Val
1               5                   10                  15

Lys Gly

<210> SEQ ID NO 31
<211> LENGTH: 14
<212> TYPE: PRT
<213> ORGANISM: Artificial Sequence
<220> FEATURE:
<223> OTHER INFORMATION: Synthetic Construct

<400> SEQUENCE: 31

Arg Asn Ala Trp His Tyr Ser Trp Val Gly Val Met Asp Tyr
1               5                   10

<210> SEQ ID NO 32
```

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 32

Gly Phe Thr Phe Thr Asp Tyr Ser Ile His
1               5                   10

<210> SEQ ID NO 33
<211> LENGTH: 18
<212> TYPE: PRT
<213> ORGANISM: Artificial Sequence
<220> FEATURE:
<223> OTHER INFORMATION: Synthetic Construct

<400> SEQUENCE: 33

Ala Glu Ile Tyr Pro Tyr Ser Gly Asp Thr Tyr Tyr Ala Asp Ser Val
1               5                   10                  15

Lys Gly

<210> SEQ ID NO 34
<211> LENGTH: 13
<212> TYPE: PRT
<213> ORGANISM: Artificial Sequence
<220> FEATURE:
<223> OTHER INFORMATION: Synthetic Construct

<400> SEQUENCE: 34

Arg Asp Gly Asp Gly Trp Phe Asp Trp Ala Met Asp Tyr
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic Construct

<400> SEQUENCE: 35

Gly Phe Thr Phe Ser Ser Thr Ala Ile Ser
1               5                   10

<210> SEQ ID NO 36
<211> LENGTH: 18
<212> TYPE: PRT
<213> ORGANISM: Artificial Sequence
<220> FEATURE:
<223> OTHER INFORMATION: Synthetic Construct

<400> SEQUENCE: 36

Gly Glu Ile Tyr Pro Ser Asp Gly Tyr Thr Asp Tyr Ala Asp Ser Val
1               5                   10                  15

Lys Gly

<210> SEQ ID NO 37
<211> LENGTH: 14
<212> TYPE: PRT
<213> ORGANISM: Artificial Sequence
<220> FEATURE:
<223> OTHER INFORMATION: Synthetic Construct

<400> SEQUENCE: 37

Arg Val Lys Trp Ala Val Ser Ser Leu Gly Val Met Asp Tyr
1               5                   10
```

<210> SEQ ID NO 38
<211> LENGTH: 10
<212> TYPE: PRT
<213> ORGANISM: Artificial Sequence
<220> FEATURE:
<223> OTHER INFORMATION: Synthetic Construct

<400> SEQUENCE: 38

Gly Phe Thr Phe Thr Asp Ser Asp Ile Ser
 1               5                  10

<210> SEQ ID NO 39
<211> LENGTH: 18
<212> TYPE: PRT
<213> ORGANISM: Artificial Sequence
<220> FEATURE:
<223> OTHER INFORMATION: Synthetic Construct

<400> SEQUENCE: 39

Ala Trp Ile Ser Pro Ser Asp Gly Ala Thr Asp Tyr Ala Asp Ser Val
 1               5                  10                  15

Lys Gly

<210> SEQ ID NO 40
<211> LENGTH: 12
<212> TYPE: PRT
<213> ORGANISM: Artificial Sequence
<220> FEATURE:
<223> OTHER INFORMATION: Synthetic Construct

<400> SEQUENCE: 40

His Glu Ala Ser Asp Asp Asp Tyr Ala Ile Asp Tyr
 1               5                  10

<210> SEQ ID NO 41
<211> LENGTH: 10
<212> TYPE: PRT
<213> ORGANISM: Artificial Sequence
<220> FEATURE:
<223> OTHER INFORMATION: Synthetic Construct

<400> SEQUENCE: 41

Gly Phe Thr Phe Ser Asp Tyr Trp Ile Ser
 1               5                  10

<210> SEQ ID NO 42
<211> LENGTH: 18
<212> TYPE: PRT
<213> ORGANISM: Artificial Sequence
<220> FEATURE:
<223> OTHER INFORMATION: Synthetic Construct

<400> SEQUENCE: 42

Ala Gly Ile Ser Pro Asn Asn Gly Asp Thr Tyr Tyr Ala Asp Ser Val
 1               5                  10                  15

Lys Gly

<210> SEQ ID NO 43
<211> LENGTH: 13
<212> TYPE: PRT
<213> ORGANISM: Artificial Sequence
<220> FEATURE:
<223> OTHER INFORMATION: Synthetic Construct

<400> SEQUENCE: 43

Arg Glu Asp Asp Asp Glu Arg Asp Tyr Ala Met Asp Tyr
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthetic Construct

<400> SEQUENCE: 44

Gly Phe Thr Phe Thr Gly Tyr Gly Ile Ser
1               5                   10

<210> SEQ ID NO 45
<211> LENGTH: 18
<212> TYPE: PRT
<213> ORGANISM: Artificial Sequence
<220> FEATURE:
<223> OTHER INFORMATION: Synthetic Construct

<400> SEQUENCE: 45

Gly Trp Ile Tyr Pro Ala Ser Gly Ala Thr Tyr Tyr Ala Asp Ser Val
1               5                   10                  15

Lys Gly

<210> SEQ ID NO 46
<211> LENGTH: 19
<212> TYPE: PRT
<213> ORGANISM: Artificial Sequence
<220> FEATURE:
<223> OTHER INFORMATION: Synthetic Construct

<400> SEQUENCE: 46

Arg His Arg Ala Phe Asp Trp Tyr Pro Tyr Tyr Ile Gly Ser Ser Val
1               5                   10                  15

Met Asp Tyr

<210> SEQ ID NO 47
<211> LENGTH: 10
<212> TYPE: PRT
<213> ORGANISM: Artificial Sequence
<220> FEATURE:
<223> OTHER INFORMATION: Synthetic Construct

<400> SEQUENCE: 47

Gly Phe Thr Phe Ser Asp Tyr Ser Ile Ser
1               5                   10

<210> SEQ ID NO 48
<211> LENGTH: 18
<212> TYPE: PRT
<213> ORGANISM: Artificial Sequence
<220> FEATURE:
<223> OTHER INFORMATION: Synthetic Construct

<400> SEQUENCE: 48

Gly Glu Ile Asn Pro Ala Gly Gly Ala Thr Tyr Tyr Ala Asp Ser Val
1               5                   10                  15

Lys Gly

<210> SEQ ID NO 49
<211> LENGTH: 16
<212> TYPE: PRT

```
<213> ORGANISM: Artificial Sequence
<220> FEATURE:
<223> OTHER INFORMATION: Synthetic Construct

<400> SEQUENCE: 49

Arg Gly Asp Phe Pro Phe Trp Ser Asp Ala Tyr Tyr Val Met Asp Tyr
1               5                   10                  15

<210> SEQ ID NO 50
<211> LENGTH: 10
<212> TYPE: PRT
<213> ORGANISM: Artificial Sequence
<220> FEATURE:
<223> OTHER INFORMATION: Synthetic Construct

<400> SEQUENCE: 50

Gly Phe Thr Phe Ser Asp Asn Asp Ile Ser
1               5                   10

<210> SEQ ID NO 51
<211> LENGTH: 18
<212> TYPE: PRT
<213> ORGANISM: Artificial Sequence
<220> FEATURE:
<223> OTHER INFORMATION: Synthetic Construct

<400> SEQUENCE: 51

Gly Ser Ile Ser Pro Asp Asn Gly Asp Thr Asn Tyr Ala Asp Ser Val
1               5                   10                  15

Lys Gly

<210> SEQ ID NO 52
<211> LENGTH: 14
<212> TYPE: PRT
<213> ORGANISM: Artificial Sequence
<220> FEATURE:
<223> OTHER INFORMATION: Synthetic Construct

<400> SEQUENCE: 52

Arg Asp Asp Val Pro Ala Val Phe Thr Ser Ala Met Asp Tyr
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthetic Construct

<400> SEQUENCE: 53

Gly Phe Thr Phe Ser Gly Ser Asp Ile Ser
1               5                   10

<210> SEQ ID NO 54
<211> LENGTH: 18
<212> TYPE: PRT
<213> ORGANISM: Artificial Sequence
<220> FEATURE:
<223> OTHER INFORMATION: Synthetic Construct

<400> SEQUENCE: 54

Gly Glu Ile Tyr Pro Ser Asn Gly Asp Thr Tyr Tyr Ala Asp Ser Val
1               5                   10                  15

Lys Gly
```

```
<210> SEQ ID NO 55
<211> LENGTH: 12
<212> TYPE: PRT
<213> ORGANISM: Artificial Sequence
<220> FEATURE:
<223> OTHER INFORMATION: Synthetic Construct

<400> SEQUENCE: 55

Arg Ser Val Arg Pro Ser Trp Trp Ala Met Asp Tyr
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Synthetic Construct

<400> SEQUENCE: 56

Gly Phe Thr Phe Ser Ser Tyr Asp Ile Ser
1               5                   10

<210> SEQ ID NO 57
<211> LENGTH: 18
<212> TYPE: PRT
<213> ORGANISM: Artificial Sequence
<220> FEATURE:
<223> OTHER INFORMATION: Synthetic Construct

<400> SEQUENCE: 57

Gly Thr Ile Ser Pro Tyr Asp Gly Tyr Thr Asp Tyr Ala Asp Ser Val
1               5                   10                  15

Lys Gly

<210> SEQ ID NO 58
<211> LENGTH: 14
<212> TYPE: PRT
<213> ORGANISM: Artificial Sequence
<220> FEATURE:
<223> OTHER INFORMATION: Synthetic Construct

<400> SEQUENCE: 58

Arg Tyr Ile Arg Arg Tyr Ser Val His Tyr Gly Met Asp Tyr
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Synthetic Construct

<400> SEQUENCE: 59

Gly Phe Thr Phe Thr Ser Thr Ser Ile His
1               5                   10

<210> SEQ ID NO 60
<211> LENGTH: 18
<212> TYPE: PRT
<213> ORGANISM: Artificial Sequence
<220> FEATURE:
<223> OTHER INFORMATION: Synthetic Construct

<400> SEQUENCE: 60

Ala Glu Ile Thr Pro His Gly Gly Tyr Thr Asn Tyr Ala Asp Ser Val
1               5                   10                  15
```

Lys Gly

<210> SEQ ID NO 61
<211> LENGTH: 14
<212> TYPE: PRT
<213> ORGANISM: Artificial Sequence
<220> FEATURE:
<223> OTHER INFORMATION: Synthetic Construct

<400> SEQUENCE: 61

Arg Gly Arg Thr Lys Trp Gly Trp Leu Tyr Gly Met Asp Tyr
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Synthetic Construct

<400> SEQUENCE: 62

Gly Phe Thr Phe Thr Asn Asn Ser Ile His
1               5                   10

<210> SEQ ID NO 63
<211> LENGTH: 18
<212> TYPE: PRT
<213> ORGANISM: Artificial Sequence
<220> FEATURE:
<223> OTHER INFORMATION: Synthetic Construct

<400> SEQUENCE: 63

Ala Glu Ile Ala Pro Asp Asp Gly Tyr Thr Tyr Tyr Ala Asp Ser Val
1               5                   10                  15
Lys Gly

<210> SEQ ID NO 64
<211> LENGTH: 14
<212> TYPE: PRT
<213> ORGANISM: Artificial Sequence
<220> FEATURE:
<223> OTHER INFORMATION: Synthetic Construct

<400> SEQUENCE: 64

Arg Gly Val Ile Arg Tyr Ala Tyr Leu Tyr Ala Met Asp Tyr
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthetic Construct

<400> SEQUENCE: 65

Gly Phe Thr Phe Ser Gly Ser Gly Ile His
1               5                   10

<210> SEQ ID NO 66
<211> LENGTH: 18
<212> TYPE: PRT
<213> ORGANISM: Artificial Sequence
<220> FEATURE:
<223> OTHER INFORMATION: Synthetic Construct

<400> SEQUENCE: 66

```
Ala Trp Ile Ser Pro Thr Gly Gly Asn Thr Tyr Tyr Ala Asp Ser Val
 1               5                  10                  15

Lys Gly

<210> SEQ ID NO 67
<211> LENGTH: 11
<212> TYPE: PRT
<213> ORGANISM: Artificial Sequence
<220> FEATURE:
<223> OTHER INFORMATION: Synthetic Construct

<400> SEQUENCE: 67

Lys Ser Leu Phe His Asn Val Ala Phe Asp Tyr
 1               5                  10

<210> SEQ ID NO 68
<211> LENGTH: 122
<212> TYPE: PRT
<213> ORGANISM: Artificial Sequence
<220> FEATURE:
<223> OTHER INFORMATION: Synthetic Construct

<400> SEQUENCE: 68

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Gly Ser
            20                  25                  30

Trp Ile Ser Trp Val Arg Gln Ala Pro Gly Lys Gly Leu Glu Trp Val
        35                  40                  45

Gly Thr Ile Ser Pro Tyr Asn Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Val Leu Arg Pro Lys Val Tyr Ala Ser Val Met Asp Tyr Trp
            100                 105                 110

Gly Gln Gly Thr Leu Val Thr Val Ser Ser
        115                 120

<210> SEQ ID NO 69
<211> LENGTH: 119
<212> TYPE: PRT
<213> ORGANISM: Artificial Sequence
<220> FEATURE:
<223> OTHER INFORMATION: Synthetic Construct

<400> SEQUENCE: 69

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Gly Tyr
            20                  25                  30

Ser Ile His Trp Val Arg Gln Ala Pro Gly Lys Gly Leu Glu Trp Val
        35                  40                  45

Ala Gly Ile Ser Pro Thr Asn Gly Tyr Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

```
Ala Arg Leu Val Phe Tyr Arg Gly Val Met Asp Tyr Trp Gly Gln Gly
            100                 105                 110

Thr Leu Val Thr Val Ser Ser
        115

<210> SEQ ID NO 70
<211> LENGTH: 121
<212> TYPE: PRT
<213> ORGANISM: Artificial Sequence
<220> FEATURE:
<223> OTHER INFORMATION: Synthetic Construct

<400> SEQUENCE: 70

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Asn
             20                  25                  30

Trp Ile Ser Trp Val Arg Gln Ala Pro Gly Lys Gly Leu Glu Trp Val
         35                  40                  45

Gly Tyr Ile Tyr Pro Ala Ser Gly Tyr Thr Asp Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Ser Asp Ser Pro His Ala Tyr Trp Tyr Ala Met Asp Tyr Trp Gly
            100                 105                 110

Gln Gly Thr Leu Val Thr Val Ser Ser
        115                 120

<210> SEQ ID NO 71
<211> LENGTH: 122
<212> TYPE: PRT
<213> ORGANISM: Artificial Sequence
<220> FEATURE:
<223> OTHER INFORMATION: Synthetic Construct

<400> SEQUENCE: 71

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asn Asn
             20                  25                  30

Ser Ile Ser Trp Val Arg Gln Ala Pro Gly Lys Gly Leu Glu Trp Val
         35                  40                  45

Gly Ala Ile Ser Pro Asn Asn Gly Ser Thr Tyr Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Asn Ala Trp His Tyr Ser Trp Val Gly Val Met Asp Tyr Trp
            100                 105                 110

Gly Gln Gly Thr Leu Val Thr Val Ser Ser
        115                 120

<210> SEQ ID NO 72
<211> LENGTH: 121
<212> TYPE: PRT
```

```
<213> ORGANISM: Artificial Sequence
<220> FEATURE:
<223> OTHER INFORMATION: Synthetic Construct

<400> SEQUENCE: 72

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
             20                  25                  30

Ser Ile His Trp Val Arg Gln Ala Pro Gly Lys Gly Leu Glu Trp Val
         35                  40                  45

Ala Glu Ile Tyr Pro Tyr Ser Gly Asp Thr Tyr Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Asp Gly Asp Gly Trp Phe Asp Trp Ala Met Asp Tyr Trp Gly
            100                 105                 110

Gln Gly Thr Leu Val Thr Val Ser Ser
        115                 120

<210> SEQ ID NO 73
<211> LENGTH: 122
<212> TYPE: PRT
<213> ORGANISM: Artificial Sequence
<220> FEATURE:
<223> OTHER INFORMATION: Synthetic Construct

<400> SEQUENCE: 73

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Thr
             20                  25                  30

Ala Ile Ser Trp Val Arg Gln Ala Pro Gly Lys Gly Leu Glu Trp Val
         35                  40                  45

Gly Glu Ile Tyr Pro Ser Asp Gly Tyr Thr Asp Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Val Lys Trp Ala Val Ser Ser Leu Gly Val Met Asp Tyr Trp
            100                 105                 110

Gly Gln Gly Thr Leu Val Thr Val Ser Ser
        115                 120

<210> SEQ ID NO 74
<211> LENGTH: 120
<212> TYPE: PRT
<213> ORGANISM: Artificial Sequence
<220> FEATURE:
<223> OTHER INFORMATION: Synthetic Construct

<400> SEQUENCE: 74

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Ser
             20                  25                  30
```

```
Asp Ile Ser Trp Val Arg Gln Ala Pro Gly Lys Gly Leu Glu Trp Val
            35                  40                  45

Ala Trp Ile Ser Pro Ser Asp Gly Ala Thr Asp Tyr Ala Asp Ser Val
 50                  55                  60

Lys Gly Arg Phe Thr Ile Ser Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala His Glu Ala Ser Asp Asp Tyr Ala Ile Asp Tyr Trp Gly Gln
                100                 105                 110

Gly Thr Leu Val Thr Val Ser Ser
            115                 120
```

<210> SEQ ID NO 75
<211> LENGTH: 121
<212> TYPE: PRT
<213> ORGANISM: Artificial Sequence
<220> FEATURE:
<223> OTHER INFORMATION: Synthetic Construct

<400> SEQUENCE: 75

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
             20                  25                  30

Trp Ile Ser Trp Val Arg Gln Ala Pro Gly Lys Gly Leu Glu Trp Val
            35                  40                  45

Ala Gly Ile Ser Pro Asn Asn Gly Asp Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Glu Asp Asp Asp Glu Arg Asp Tyr Ala Met Asp Tyr Trp Gly
                100                 105                 110

Gln Gly Thr Leu Val Thr Val Ser Ser
            115                 120
```

<210> SEQ ID NO 76
<211> LENGTH: 127
<212> TYPE: PRT
<213> ORGANISM: Artificial Sequence
<220> FEATURE:
<223> OTHER INFORMATION: Synthetic Construct

<400> SEQUENCE: 76

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Gly Tyr
             20                  25                  30

Gly Ile Ser Trp Val Arg Gln Ala Pro Gly Lys Gly Leu Glu Trp Val
            35                  40                  45

Gly Trp Ile Tyr Pro Ala Ser Gly Ala Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
```

```
                     85                  90                  95
Ala Arg His Arg Ala Phe Asp Trp Tyr Pro Tyr Tyr Ile Gly Ser Ser
                100                 105                 110

Val Met Asp Tyr Trp Gly Gln Gly Thr Leu Val Thr Val Ser Ser
        115                 120                 125

<210> SEQ ID NO 77
<211> LENGTH: 124
<212> TYPE: PRT
<213> ORGANISM: Artificial Sequence
<220> FEATURE:
<223> OTHER INFORMATION: Synthetic Construct

<400> SEQUENCE: 77

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Ser Ile Ser Trp Val Arg Gln Ala Pro Gly Lys Gly Leu Glu Trp Val
        35                  40                  45

Gly Glu Ile Asn Pro Ala Gly Gly Ala Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Asp Phe Pro Phe Trp Ser Asp Ala Tyr Tyr Val Met Asp
                100                 105                 110

Tyr Trp Gly Gln Gly Thr Leu Val Thr Val Ser Ser
        115                 120

<210> SEQ ID NO 78
<211> LENGTH: 122
<212> TYPE: PRT
<213> ORGANISM: Artificial Sequence
<220> FEATURE:
<223> OTHER INFORMATION: Synthetic Construct

<400> SEQUENCE: 78

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Asn
            20                  25                  30

Asp Ile Ser Trp Val Arg Gln Ala Pro Gly Lys Gly Leu Glu Trp Val
        35                  40                  45

Gly Ser Ile Ser Pro Asp Asn Gly Asp Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Asp Val Pro Ala Val Phe Thr Ser Ala Met Asp Tyr Trp
                100                 105                 110

Gly Gln Gly Thr Leu Val Thr Val Ser Ser
        115                 120

<210> SEQ ID NO 79
<211> LENGTH: 120
```

```
<212> TYPE: PRT
<213> ORGANISM: Artificial Sequence
<220> FEATURE:
<223> OTHER INFORMATION: Synthetic Construct

<400> SEQUENCE: 79

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Gly Ser
            20                  25                  30

Asp Ile Ser Trp Val Arg Gln Ala Pro Gly Lys Gly Leu Glu Trp Val
        35                  40                  45

Gly Glu Ile Tyr Pro Ser Asn Gly Asp Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Val Arg Pro Ser Trp Trp Ala Met Asp Tyr Trp Gly Gln
            100                 105                 110

Gly Thr Leu Val Thr Val Ser Ser
        115                 120

<210> SEQ ID NO 80
<211> LENGTH: 122
<212> TYPE: PRT
<213> ORGANISM: Artificial Sequence
<220> FEATURE:
<223> OTHER INFORMATION: Synthetic Construct

<400> SEQUENCE: 80

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Asp Ile Ser Trp Val Arg Gln Ala Pro Gly Lys Gly Leu Glu Trp Val
        35                  40                  45

Gly Thr Ile Ser Pro Tyr Asp Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Ile Arg Arg Tyr Ser Val His Tyr Gly Met Asp Tyr Trp
            100                 105                 110

Gly Gln Gly Thr Leu Val Thr Val Ser Ser
        115                 120

<210> SEQ ID NO 81
<211> LENGTH: 122
<212> TYPE: PRT
<213> ORGANISM: Artificial Sequence
<220> FEATURE:
<223> OTHER INFORMATION: Synthetic Construct

<400> SEQUENCE: 81

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Ser Thr
```

```
                20                  25                  30
Ser Ile His Trp Val Arg Gln Ala Pro Gly Lys Gly Leu Glu Trp Val
            35                  40                  45
Ala Glu Ile Thr Pro His Gly Gly Tyr Thr Asn Tyr Ala Asp Ser Val
        50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Gly Arg Thr Lys Trp Gly Trp Leu Tyr Gly Met Asp Tyr Trp
            100                 105                 110
Gly Gln Gly Thr Leu Val Thr Val Ser Ser
        115                 120

<210> SEQ ID NO 82
<211> LENGTH: 122
<212> TYPE: PRT
<213> ORGANISM: Artificial Sequence
<220> FEATURE:
<223> OTHER INFORMATION: Synthetic Construct

<400> SEQUENCE: 82

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Thr Asn Asn
                20                  25                  30
Ser Ile His Trp Val Arg Gln Ala Pro Gly Lys Gly Leu Glu Trp Val
            35                  40                  45
Ala Glu Ile Ala Pro Asp Asp Gly Tyr Thr Tyr Tyr Ala Asp Ser Val
        50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Gly Val Ile Arg Tyr Ala Tyr Leu Tyr Ala Met Asp Tyr Trp
            100                 105                 110
Gly Gln Gly Thr Leu Val Thr Val Ser Ser
        115                 120

<210> SEQ ID NO 83
<211> LENGTH: 119
<212> TYPE: PRT
<213> ORGANISM: Artificial Sequence
<220> FEATURE:
<223> OTHER INFORMATION: Synthetic Construct

<400> SEQUENCE: 83

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Gly Ser
                20                  25                  30
Gly Ile His Trp Val Arg Gln Ala Pro Gly Lys Gly Leu Glu Trp Val
            35                  40                  45
Ala Trp Ile Ser Pro Thr Gly Gly Asn Thr Tyr Tyr Ala Asp Ser Val
        50                  55                  60
Lys Gly Arg Phe Thr Ile Ser Ala Asp Thr Ser Lys Asn Thr Ala Tyr
65                  70                  75                  80
```

-continued

```
Leu Gln Met Asn Ser Leu Arg Ala Glu Asp Thr Ala Val Tyr Tyr Cys
                85                  90                  95

Ala Lys Ser Leu Phe His Asn Val Ala Phe Asp Tyr Trp Gly Gln Gly
        100                 105                 110

Thr Leu Val Thr Val Ser Ser
        115
```

<210> SEQ ID NO 84
<211> LENGTH: 117
<212> TYPE: PRT
<213> ORGANISM: Artificial Sequence
<220> FEATURE:
<223> OTHER INFORMATION: Synthetic Construct

<400> SEQUENCE: 84

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Thr
        20                  25                  30

Tyr Ile Ser Trp Val Arg Gln Ala Pro Gly Lys Gly Leu Glu Trp Val
        35                  40                  45

Gly Phe Ile Tyr Pro Ala Asn Gly Ala Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Tyr Arg Leu Ser Phe Asp Tyr Trp Gly Gln Gly Thr Leu
        100                 105                 110

Val Thr Val Ser Ser
        115
```

<210> SEQ ID NO 85
<211> LENGTH: 122
<212> TYPE: PRT
<213> ORGANISM: Artificial Sequence
<220> FEATURE:
<223> OTHER INFORMATION: Synthetic Construct

<400> SEQUENCE: 85

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Gly Asn
        20                  25                  30

Asp Ile Ser Trp Val Arg Gln Ala Pro Gly Lys Gly Leu Glu Trp Val
        35                  40                  45

Ala Gly Ile Ser Pro Tyr Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Val Ser Phe Tyr Ser Arg His Ala Gly Met Asp Tyr Trp
        100                 105                 110

Gly Gln Gly Thr Leu Val Thr Val Ser Ser
        115                 120
```

<210> SEQ ID NO 86

```
<211> LENGTH: 120
<212> TYPE: PRT
<213> ORGANISM: Artificial Sequence
<220> FEATURE:
<223> OTHER INFORMATION: Synthetic Construct

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ala Ile Ser Trp Val Arg Gln Ala Pro Gly Lys Gly Leu Glu Trp Val
        35                  40                  45

Ala Gly Ile Ser Pro Ser Asn Gly Tyr Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala Gly Arg Trp Thr His Ser Asp Ile Asp Tyr Trp Gly Gln
            100                 105                 110

Gly Thr Leu Val Thr Val Ser Ser
        115                 120

<210> SEQ ID NO 87
<211> LENGTH: 11
<212> TYPE: PRT
<213> ORGANISM: Artificial Sequence
<220> FEATURE:
<223> OTHER INFORMATION: Synthetic Construct

<400> SEQUENCE: 87

Lys Arg His Leu His Asn Val Ala Phe Asp Tyr
1               5                   10

<210> SEQ ID NO 88
<211> LENGTH: 18
<212> TYPE: PRT
<213> ORGANISM: Artificial Sequence
<220> FEATURE:
<223> OTHER INFORMATION: Synthetic Construct

<400> SEQUENCE: 88

Ala Trp Ile Pro Thr Ala Gly Gly Asn Thr Tyr Tyr Ala Asp Ser Val
1               5                   10                  15

Lys Gly

<210> SEQ ID NO 89
<211> LENGTH: 11
<212> TYPE: PRT
<213> ORGANISM: Artificial Sequence
<220> FEATURE:
<223> OTHER INFORMATION: Synthetic Construct

<400> SEQUENCE: 89

Arg Gly Leu Phe His Asn Val Ala Phe Asp Tyr
1               5                   10

<210> SEQ ID NO 90
<211> LENGTH: 11
<212> TYPE: PRT
<213> ORGANISM: Artificial Sequence
<220> FEATURE:
```

<223> OTHER INFORMATION: Synthetic Construct

<400> SEQUENCE: 90

Arg Val Phe Phe His Asn Val Ala Phe Asp Tyr
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = K or R
<220> FEATURE:
<221> NAME/KEY: VARIANT
<222> LOCATION: 2
<223> OTHER INFORMATION: Xaa = S, G, or V
<220> FEATURE:
<221> NAME/KEY: VARIANT
<222> LOCATION: 3
<223> OTHER INFORMATION: Xaa = L or F

<400> SEQUENCE: 91

Xaa Xaa Xaa Phe His Asn Val Ala Phe Asp Tyr
1               5                   10

<210> SEQ ID NO 92
<211> LENGTH: 9
<212> TYPE: PRT
<213> ORGANISM: Artificial Sequence
<220> FEATURE:
<223> OTHER INFORMATION: Synthetic Construct

<400> SEQUENCE: 92

Gln Gln Ser Tyr Gly Phe Pro Leu Thr
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic Construct

<400> SEQUENCE: 93

Gln Gln Ser Tyr Asp Phe Pro Leu Thr
1               5

<210> SEQ ID NO 94
<211> LENGTH: 9
<212> TYPE: PRT
<213> ORGANISM: Artificial Sequence
<220> FEATURE:
<223> OTHER INFORMATION: Synthetic Construct

<400> SEQUENCE: 94

Gln Gln Ser Ala Gly Phe Pro Leu Thr
1               5

<210> SEQ ID NO 95
<211> LENGTH: 9
<212> TYPE: PRT
<213> ORGANISM: Artificial Sequence
<220> FEATURE:
<223> OTHER INFORMATION: Synthetic Construct
<220> FEATURE:

```
<221> NAME/KEY: VARIANT
<222> LOCATION: 4
<223> OTHER INFORMATION: Xaa = Y or A
<220> FEATURE:
<221> NAME/KEY: VARIANT
<222> LOCATION: 5
<223> OTHER INFORMATION: Xaa = T, G, or D
<220> FEATURE:
<221> NAME/KEY: VARIANT
<222> LOCATION: 6
<223> OTHER INFORMATION: Xaa = T or F
<220> FEATURE:
<221> NAME/KEY: VARIANT
<222> LOCATION: 8
<223> OTHER INFORMATION: Xaa = P or L

<400> SEQUENCE: 95

Gln Gln Ser Xaa Xaa Xaa Pro Xaa Thr
 1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic Construct

<400> SEQUENCE: 96

Gln Gln Ala Tyr Ser Ala Pro Pro Thr
 1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic Construct

<400> SEQUENCE: 97

Gln Gln Ser Tyr Thr Ala Pro Pro Thr
 1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic Construct

<400> SEQUENCE: 98

Gln Gln Ala Asn Ser Thr Pro Pro Thr
 1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic Construct

<400> SEQUENCE: 99

Gln Gln Asn Phe Ser Ser Pro Pro Thr
 1               5

<210> SEQ ID NO 100
<211> LENGTH: 9
<212> TYPE: PRT
<213> ORGANISM: Artificial Sequence
<220> FEATURE:
```

<223> OTHER INFORMATION: Synthetic Construct

<400> SEQUENCE: 100

Gln Gln Thr Tyr Asn Ala Pro Pro Thr
1               5

<210> SEQ ID NO 101
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = S, A, N, or T
<220> FEATURE:
<221> NAME/KEY: VARIANT
<222> LOCATION: 4
<223> OTHER INFORMATION: Xaa = Y, N, or F
<220> FEATURE:
<221> NAME/KEY: VARIANT
<222> LOCATION: 5
<223> OTHER INFORMATION: Xaa = T, S, or N
<220> FEATURE:
<221> NAME/KEY: VARIANT
<222> LOCATION: 6
<223> OTHER INFORMATION: Xaa = T, A, or S

<400> SEQUENCE: 101

Gln Gln Xaa Xaa Xaa Xaa Pro Pro Thr
1               5

<210> SEQ ID NO 102
<211> LENGTH: 108
<212> TYPE: PRT
<213> ORGANISM: Artificial Sequence
<220> FEATURE:
<223> OTHER INFORMATION: Synthetic Construct

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Gly Phe Pro Leu
                85                  90                  95

Thr Phe Gly Gln Gly Thr Lys Val Glu Ile Lys Arg
            100                 105

<210> SEQ ID NO 103
<211> LENGTH: 108
<212> TYPE: PRT
<213> ORGANISM: Artificial Sequence
<220> FEATURE:
<223> OTHER INFORMATION: Synthetic Construct

<400> SEQUENCE: 103

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asp Phe Pro Leu
                85                  90                  95

Thr Phe Gly Gln Gly Thr Lys Val Glu Ile Lys Arg
            100                 105
```

<210> SEQ ID NO 104
<211> LENGTH: 108
<212> TYPE: PRT
<213> ORGANISM: Artificial Sequence
<220> FEATURE:
<223> OTHER INFORMATION: Synthetic Construct

<400> SEQUENCE: 104

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ala Gly Phe Pro Leu
                85                  90                  95

Thr Phe Gly Gln Gly Thr Lys Val Glu Ile Lys Arg
            100                 105
```

<210> SEQ ID NO 105
<211> LENGTH: 119
<212> TYPE: PRT
<213> ORGANISM: Artificial Sequence
<220> FEATURE:
<223> OTHER INFORMATION: Synthetic Construct

<400> SEQUENCE: 105

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Ser
            20                  25                  30

Gly Ile His Trp Val Arg Gln Ala Pro Gly Lys Gly Leu Glu Trp Val
        35                  40                  45

Ala Trp Ile Ser Pro Thr Gly Gly Asn Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Lys Arg His Leu His Asn Val Ala Phe Asp Tyr Trp Gly Gln Gly
```

-continued

```
                100                 105                 110
Thr Leu Val Thr Val Ser Ser
        115

<210> SEQ ID NO 106
<211> LENGTH: 108
<212> TYPE: PRT
<213> ORGANISM: Artificial Sequence
<220> FEATURE:
<223> OTHER INFORMATION: Synthetic Construct

<400> SEQUENCE: 106

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Ser Thr Ala
             20                  25                  30

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Tyr Ser Ala Pro Pro
             85                  90                  95

Thr Phe Gly Gln Gly Thr Lys Val Glu Ile Lys Arg
        100                 105

<210> SEQ ID NO 107
<211> LENGTH: 119
<212> TYPE: PRT
<213> ORGANISM: Artificial Sequence
<220> FEATURE:
<223> OTHER INFORMATION: Synthetic Construct

<400> SEQUENCE: 107

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Gly Ser
             20                  25                  30

Gly Ile His Trp Val Arg Gln Ala Pro Gly Lys Gly Leu Glu Trp Val
         35                  40                  45

Ala Trp Ile Pro Thr Ala Gly Gly Asn Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
             85                  90                  95

Ala Lys Ser Leu Phe His Asn Val Ala Phe Asp Tyr Trp Gly Gln Gly
        100                 105                 110

Thr Leu Val Thr Val Ser Ser
        115

<210> SEQ ID NO 108
<211> LENGTH: 108
<212> TYPE: PRT
<213> ORGANISM: Artificial Sequence
<220> FEATURE:
<223> OTHER INFORMATION: Synthetic Construct

<400> SEQUENCE: 108
```

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                      55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ala Pro Pro
                85                  90                  95

Thr Phe Gly Gln Gly Thr Lys Val Glu Ile Lys Arg
            100                 105
```

<210> SEQ ID NO 109
<211> LENGTH: 108
<212> TYPE: PRT
<213> ORGANISM: Artificial Sequence
<220> FEATURE:
<223> OTHER INFORMATION: Synthetic Construct

<400> SEQUENCE: 109

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                      55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Thr Pro Pro
                85                  90                  95

Thr Phe Gly Gln Gly Thr Lys Val Glu Ile Lys Arg
            100                 105
```

<210> SEQ ID NO 110
<211> LENGTH: 119
<212> TYPE: PRT
<213> ORGANISM: Artificial Sequence
<220> FEATURE:
<223> OTHER INFORMATION: Synthetic Construct

<400> SEQUENCE: 110

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Gly Ser
            20                  25                  30

Gly Ile His Trp Val Arg Gln Ala Pro Gly Lys Gly Leu Glu Trp Val
        35                  40                  45

Ala Trp Ile Ser Pro Thr Gly Gly Asn Thr Tyr Tyr Ala Asp Ser Val
50                      55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
```

```
                    85                  90                  95
Ala Arg Gly Leu Phe His Asn Val Ala Phe Asp Tyr Trp Gly Gln Gly
            100                 105                 110

Thr Leu Val Thr Val Ser Ser
        115

<210> SEQ ID NO 111
<211> LENGTH: 119
<212> TYPE: PRT
<213> ORGANISM: Artificial Sequence
<220> FEATURE:
<223> OTHER INFORMATION: Synthetic Construct

<400> SEQUENCE: 111

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Gly Ser
            20                  25                  30

Gly Ile His Trp Val Arg Gln Ala Pro Gly Lys Gly Leu Glu Trp Val
        35                  40                  45

Ala Trp Ile Ser Pro Thr Gly Gly Asn Thr Tyr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Val Phe Phe His Asn Val Ala Phe Asp Tyr Trp Gly Gln Gly
            100                 105                 110

Thr Leu Val Thr Val Ser Ser
        115

<210> SEQ ID NO 112
<211> LENGTH: 108
<212> TYPE: PRT
<213> ORGANISM: Artificial Sequence
<220> FEATURE:
<223> OTHER INFORMATION: Synthetic Construct

<400> SEQUENCE: 112

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Phe Ser Ser Pro Pro
                85                  90                  95

Thr Phe Gly Gln Gly Thr Lys Val Glu Ile Lys Arg
            100                 105

<210> SEQ ID NO 113
<211> LENGTH: 108
<212> TYPE: PRT
<213> ORGANISM: Artificial Sequence
<220> FEATURE:
```

<223> OTHER INFORMATION: Synthetic Construct

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Asn Ala Pro Pro
                85                  90                  95

Thr Phe Gly Gln Gly Thr Lys Val Glu Ile Lys Arg
            100                 105

<210> SEQ ID NO 114
<211> LENGTH: 330
<212> TYPE: PRT
<213> ORGANISM: Artificial Sequence
<220> FEATURE:
<223> OTHER INFORMATION: Synthetic Construct

<400> SEQUENCE: 114

Ala Ser Thr Lys Gly Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Ala Val Ser Glu Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Ala Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

```
Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
                260                 265                 270

Asn Tyr Lys Asn Thr Glu Pro Val Leu Asp Ser Asp Gly Ser Tyr Phe
            275                 280                 285

Met Tyr Ser Lys Leu Arg Val Glu Lys Lys Asn Trp Val Glu Arg Asn
        290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 115
<211> LENGTH: 106
<212> TYPE: PRT
<213> ORGANISM: Artificial Sequence
<220> FEATURE:
<223> OTHER INFORMATION: Synthetic Construct

<400> SEQUENCE: 115

Ala Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
                20                  25                  30

Pro Lys Asp Ile Asn Val Lys Trp Lys Ile Asp Gly Ser Glu Arg Gln
            35                  40                  45

Asn Gly Val Leu Asn Ser Trp Thr Asp Gln Asp Ser Lys Asp Ser Thr
        50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

Ile Val Lys Ser Phe Asn Arg Asn Glu Cys
                100                 105
```